United States Patent
Newman et al.

(10) Patent No.: US 12,427,188 B2
(45) Date of Patent: Sep. 30, 2025

(54) PYOCYANINE DEMETHYLASES AND RELATED PHENAZINE DEGRADING AGENTS COMPOSITIONS, METHODS AND SYSTEMS FOR INTERFERING WITH VIABILITY OF BACTERIA

(71) Applicants: CALIFORNIA INSTITUTE OF TECHNOLOGY, Pasadena, CA (US); YEDA RESEARCH & DEVELOPMENT CO. LTD. AT THE WEIZMANN INSTITUTE OF SCIENCE, Rehovot (IL)

(72) Inventors: Dianne K Newman, Pasadena, CA (US); Chelsey M VanDrisse, Pasadena, CA (US); Rosalie Lipsh-Sokolik, Rehovot (IL); Olga Khersonsky, Rehovot (IL); Sarel J Fleishman, Rehovot (IL)

(73) Assignees: CALIFORNIA INSTITUTE OF TECHNOLOGY, Pasadena, CA (US); YEDA RESEARCH & DEVELOPMENT CO LTD. AT THE WEIZMANN INSTITUTE OF SCIENCE, Rehovot (IL)

( * ) Notice: Subject to any disclaimer, the term of this patent is extended or adjusted under 35 U.S.C. 154(b) by 0 days.

(21) Appl. No.: 17/520,345

(22) Filed: Nov. 5, 2021

(65) Prior Publication Data
US 2022/0175892 A1 Jun. 9, 2022

Related U.S. Application Data

(60) Provisional application No. 63/110,246, filed on Nov. 5, 2020.

(51) Int. Cl.
*A61K 38/44* (2006.01)
*A61K 31/7036* (2006.01)
*A61P 31/04* (2006.01)
*C12N 9/02* (2006.01)

(52) U.S. Cl.
CPC .......... *A61K 38/44* (2013.01); *A61K 31/7036* (2013.01); *A61P 31/04* (2018.01); *C12N 9/0004* (2013.01)

(58) Field of Classification Search
CPC ...... A61K 38/44; A61K 38/00; C12N 9/0004; C12N 9/0026; A01N 63/50
See application file for complete search history.

(56) References Cited

U.S. PATENT DOCUMENTS

| | | | |
|---|---|---|---|
| 5,223,409 A | 6/1993 | Ladner et al. | |
| 6,004,438 A | 12/1999 | Woodson | |
| 9,926,526 B2 | 3/2018 | Newman et al. | |
| 9,926,562 B2 | 3/2018 | Chatziantoniou et al. | |
| 10,406,211 B2 | 9/2019 | Newman et al. | |
| 10,689,613 B2 | 6/2020 | Newman et al. | |
| 10,689,713 B2 | 6/2020 | Chelliserry et al. | |
| 10,913,936 B2* | 2/2021 | Newman | A61K 45/06 |
| 11,820,973 B2 | 11/2023 | Newman et al. | |
| 11,827,944 B2 | 11/2023 | Ismagilov et al. | |
| 12,241,094 B2 | 3/2025 | Newman et al. | |
| 2002/0102628 A1 | 8/2002 | Phibbs et al. | |
| 2003/0022349 A1 | 1/2003 | Ausubel et al. | |
| 2008/0075730 A1 | 3/2008 | Storey et al. | |
| 2010/0035992 A1 | 2/2010 | Bhushan et al. | |
| 2010/0124554 A1 | 5/2010 | Newman et al. | |
| 2011/0189260 A1 | 8/2011 | Herr et al. | |
| 2013/0022578 A1 | 1/2013 | Newman et al. | |
| 2013/0095184 A1 | 4/2013 | Lyczak et al. | |
| 2015/0073491 A1 | 3/2015 | Ehrensberger et al. | |
| 2016/0058843 A1 | 3/2016 | Newman et al. | |
| 2017/0266215 A1 | 9/2017 | Newman et al. | |
| 2017/0275597 A1* | 9/2017 | Newman | A61K 45/06 |
| 2017/0283763 A1 | 10/2017 | Newman et al. | |
| 2019/0142864 A1 | 5/2019 | Newman et al. | |
| 2020/0362299 A1 | 11/2020 | Newman et al. | |
| 2021/0032603 A1 | 2/2021 | Newman et al. | |
| 2021/0322462 A1 | 10/2021 | Newman et al. | |
| 2025/0058002 A1 | 2/2025 | Newman et al. | |

FOREIGN PATENT DOCUMENTS

| | | |
|---|---|---|
| CN | 115297895 A | 11/2022 |
| EP | 2702141 B1 | 3/2018 |
| KR | 2014014059 7 A | 12/2014 |

(Continued)

OTHER PUBLICATIONS

Merriam-Webster, "demethylate", https://www.merriam-webster.com/dictionary/demethylate, 2023 (Year: 2023).*
Uniprot Entry No. A0A1G9T5F4_ALLAB, published Jan. 18, 2017 (Year: 2017).*
Costa et al. Pyocyanin degradation by a tautomerizing demethylase inhibits Pseudomonas aeruginosa biofilms, Science 355, 170-173 (2017) (Year: 2017).*
Advisory Action for U.S. App. No. 15/394,138, filed Dec. 29, 2016, on behalf of California Institute of Technology. Mail Date: Sep. 22, 2022. 8 Pages.
Alekshun, M.N. "New advances in antibiotic development and discovery." *Expert Opinion on Investigational Drugs* 14(2). 2005. pp. 117-134. 18 Pages.

(Continued)

*Primary Examiner* — Louise W Humphrey
*Assistant Examiner* — Alexander M Duryee
(74) *Attorney, Agent, or Firm* — Steinfl + Bruno LLP

(57) ABSTRACT

Provided herein are engineered pyocyanin demethylases having replacements in in positions A53, I73, A87, T91, M99, A129 and K141 of pyocyanin demethylase PodA of SEQ ID NO: 1 or a derivative thereof and related phenazine degrading agents, compositions, methods and systems, as well as a combined administration of one or more pyocyanin demethylases and antibiotics and/or antibiotics resulting in a synergic inhibition of viability of phenazine producing bacteria, and related phenazine degrading agents, compositions, methods and systems.

24 Claims, 23 Drawing Sheets

Specification includes a Sequence Listing.

(56) References Cited

FOREIGN PATENT DOCUMENTS

| WO | 93/21511 A1 | 10/1993 |
| WO | 2012/149058 A2 | 11/2012 |
| WO | 2017/165578 A1 | 9/2017 |
| WO | 2019/097241 A1 | 5/2019 |
| WO | 2022/09902 4 A1 | 5/2022 |
| WO | 2024/226835 A1 | 10/2024 |

OTHER PUBLICATIONS

Google Scholar Search for "Treatment with Fluoroshikimate Antibiotics + Phenazine Inhibitor Treats Bacterial Infection," 2 Pages.

Griffin A.S., et al., "Cooperation and Competition in Pathogenic Bacteria," Nature, Aug. 26, 2004, vol. 430 (7003), 1024-1027 4 pages.

Gutteridge et al. "Understanding nature's catalytic toolkit" *TRENDS in Biochemical Sciences, Elsevier*. Nov. 2005. vol. 30, No. 11. pp. 622-629. 8 pages.

Haas D., et al., "Biological Control of Soil-borne Pathogens by Fluorescent Pseudomonads," Nature Reviews Microbiology, Apr. 2005, vol. 3 (4), 13 pages.

Hagel et al. "Biochemistry and occurrence of O-demethylation in plant metabolism" *frontiers in Physiology, Frontiers Media S.A.* Jul. 2010. vol. 1, No. 14. pp. 1-7. 7 pages.

Hare N.J., et al., "Proteomic Profiling of Pseudomonas Aeruginosa AES-1 R, PA01 and PA14 Reveals Potential Virulence Determinants Associated with a Transmissible Cystic Fibrosis-associated Strain," BMC Microbiology, 2012, vol. 12:16, 14 pages.

Harrison F., "Microbial Ecology of the Cystic Fibrosis Lung," Microbiology, Apr. 2007, vol. 153 (Pt 4), 917-923. 7 pages.

Hassan et al. "Mechanism of the Antibiotic Action of Pyocyanine" *Journal of Bacteriology, American Society of Microbiology*. Jan. 1980. vol. 141, No. 1. pp. 156-163. 8 pages.

Hassan H.M., et al., "Intracellular Production of Superoxide Radical and of Hydrogen Peroxide by Redox Active Compounds," Archives of Biochemistry and Biophysics, Sep. 1979, vol. 196 (2), 385-395. 11 pages.

Hassett D.J., et al., "Pseudomonas Aeruginosa sodA and sodB Mutants Defective in Manganese- and Iron-cofactored Superoxide Dismutase Activity Demonstrate the Importance of the Iron-cofactored Form in Aerobic Metabolism," Journal of Bacteriology, Nov. 1995, vol. 177 (22), 6330-6337. 10 pages.

Hassett D.J., et al., "Response of Pseudomonas Aeruginosa to Pyocyanin: Mechanisms of Resistance, Antioxidant Defenses, and Demonstration of a Manganese-cofactored Superoxide Dismutase," Infection and Immunity, Feb. 1992, vol. 60 (2), 328-336. 9 pages.

Headd et al. "Use of knowledge-based restraints in phenix.refine to improve macromolecular refinement at low resolution" *Acta Crystallographica Section D: Biological Crystallography, International Union of Crystallography*. Apr. 2012. vol. 68 (part 4). pp. 381-390. 17 pages.

Heeb, S., et al. "Regulatory Roles of the GacS/GacA two-component system in plantassociated and other Gram-negative bacteria", MPMI vol. 14, No. 12, 2001, pp. 1351-1363, submitted Jul. 18, 2001 (13 pages).

Hentzer M., et al., "Attenuation of Pseudomonas Aeruginosa Virulence by Quorum Sensing Inhibitors," The EMBO Journal, Aug. 2003, vol. 22 (15), 3803-3815. 13 pages.

Hernandez M.E., et al., "Extracellular Electron Transfer,"Cellular and Molecular Life Sciences, Oct. 2001, vol. 58 (11), 1562-1571. 10 pages.

Hernandez M.E., et al., "Phenazines and Other Redox-active Antibiotics Promote Microbial Mineral Reduction," Applied and Environmental Microbiology, Feb. 2004, vol. 70 (2), 8 pages.

Heydorn A., et al., "Quantification of Biofilm Structures by the Novel Computer Program COMSTAT," Microbiology, Oct. 2000, vol. 146 (Pt 10), 13 pages.

Hidalgo E., et al., "The Redox-regulated soxR Protein Acts From a Single DNA Site as a Repressor and an Allosteric Activator," The EMBO Journal, May 1998, vol. 17 (9), 2629-2636. 8 pages.

Hill D., et al., "Antibiotic Susceptibilities of Pseudomonas aeruginosa Isolates Derived from Patients with Cystic Fibrosis under Aerobic, Anaerobic, and Biofilm Conditions," Journal of Clinical Microbiology, Oct. 2005, vol. 43 (10), 6 pages.

Hirakata Y., et al., "Efflux Pump Inhibitors Reduce the Invasiveness of Pseudomonas Aeruginosa," International Journal of Antimicrobial Agents, Oct. 2009, vol. 34 (4), 4 pages.

Hoiby et al. "Pseudomonas aeruginosa biofilms in cystic fibrosis" *Future Microbiology, Future Medicine Ltd*. Nov. 2010. vol. 5, No. 11. pp. 1663-1674. 18 pages.

Hou M.H., et al., "Mithramycin Forms a Stable Dimeric Complex by Chelating With Fe(II): DNA-interacting Characteristics, Cellular Permeation and Cytotoxicity," Nucleic Acids Research, Mar. 2005, vol. 33 (4), 10 pages.

Houghten R.A., et al., "The Use of Synthetic Peptide Combinatorial Libraries for the Identification of Bioactive Peptides," Biotechniques, Sep. 1992, vol. 13 (3), 10 pages.

Huang J., et al., "Global Analysis of Growth Phase Responsive Gene Expression and Regulation of Antibiotic Biosynihetic Pathways in Streptomyces Coelicolof Using DNA Microarrays," Genes & Development, Dec. 2001, vol. 15 (23), 10 pages.

Hunter et al. "Ferrous Iron is a Significant Component of Bioavailable Iron in Cystic Fibrosis Airways" *mBio, American Society of Microbiology*. Jul./Aug. 2013. vol. 4, No. 4. pp. 1-8. 8 pages.

Hunter R.C., et al., "Fe(II) is Abundant in Cystic Fibrosis Sputum: Implications for Rational Drug Design," Feb. 14, 2012, Science, Submitted Manuscript, 10 pages.

Hunter R.C., et al., "Phenazine Content in the Cystic Fibrosis Respiratory Tract Negatively Correlates With Lung Function and Microbial Complexity," American Journal of Respiratory Cell and Molecular Biology, Dec. 2012, vol. 47 (6), 8 pages.

Im, et al., "Interference of ferric ions with ferrous iron quantification using the ferrozine assay", Journal of Microbiological Methods, 2013, 95(3):p. 366-367.

Ingledew W.M., et al., "A New Resuspension Medium for Pyocyanine Production,"Canadian Journal of Microbiology, Jun. 1969, vol. 15 (6), 4 pages.

International Preliminary Report on Patentability for Application No. PCT/US2012/035052, Mail Date: Nov. 7, 2013, 9 pages.

International Preliminary Report on Patentability for International Application No. PCT/US2017/023688 filed on Mar. 22, 2017 on behalf of California Institute of Technology Mail Date: Sep. 25, 2018 15 pages.

International Search Report and Written Opinion for Application No. PCT/US2012/035052, Mail Date: Oct. 31, 2012. 14 pages.

International Search Report and Written Opinion for International PCT Application No. PCT/US2021/058275 filed on Nov. 5, 2021, on behalf of California Institute of Technology. Mail Date: Mar. 3, 2022. 13 Pages.

International Search Report for International Application No. PCT/US2017/023688, filed on Mar. 22, 2017, on behalf of California Institute of Technology. Mail Date: Jun. 30, 2017. 6 pages.

Ito A., et al., "Increased Antibiotic Resistance of *Escherichia coli* in Mature Biofilms," Applied and Environmental Microbiology, Jun. 2009, vol. 75 (12), 9 pages.

Jo, J., et al., "Interdependency of respiratory metabolism and phenazine-associated physiology in Pseudomonas aeruginosa PA14." *Journal of bacteriology*, 2020. 202(4): p. e00700-19.

Johansen H.K., et al., "Pseudomonas Aeruginosa and Burkholderia Cepacia Infection in Cystic Fibrosis Patients Treated in Toronto and Copenhagen," Pediatric Pulmonology, Aug. 1998, vol. 26 (2), 8 pages.

Johnson et al. "Hidden Markov model speed heuristic and iterative HMM search procedure" *BMC Bioinformatics, BioMed Central Ltd*. 2010. vol. 11, No. 431. pp. 1-8. 8 pages.

Jolley K.A., et al., "2-oxoacid Dehydrogenase Multienzyme Complexes in the Halophilic Archaea? Gene Sequences and Protein Structural Predictions," Microbiology, May 2000, vol. 146 (Pt 5), 9 pages.

(56) References Cited

OTHER PUBLICATIONS

Jones et al. "Determination of Submicromolar Concentrations of Formaldehyde by Liquid Chromatography" *Analytical Chemistry, American Chemical Society*. Sep. 15, 1999. vol. 71, No. 18. pp. 4030-4033. 4 pages.

Jones et al. "Mycobacteria Isolated From Soil" *Canadian Journal of Microbiology, National Research Council of Canada*. Apr. 1965. vol. 11, No. 2. pp. 127-133. 9 pages.

Kabsch, Wolfgang. "Integration, scaling, space-group assignment and post-refinement" *Acta Crystallographica Section D—Biological Crystallography, International Union of Crystallography*. 2010. vol. D66. pp. 133-144. 12 pages.

Kabsch, Wolfgang. "XDS" *Acta Crystallographica Section D—Biological Crystallography*, International Union of Crystallography. 2010. vol. D66. pp. 125-132. 9 pages.

Kaneko Y., et al., "The Transition Metal Gallium Disrupts Pseudomonas Aeruginosa Iron Metabolism and has Antimicrobial and Antibiofilm Activity," The Journal of Clinical Investigation, Apr. 2007, vol. 117 (4), 12 pages.

Karasulu et al. "Photoinduced Intramolecular Charge Transfer in an Electronically Modified Flavin Derivative: Roseoflavin" *The Journal of Physical Chemistry, American Chemical Society B*. 2015. vol. 119. pp. 928-943. 17 pages.

Kelley et al. "The Phyre2 web portal for protein modeling, prediction and analysis" *Nature Protocols, Nature America Inc*. 2015. vol. 10, No. 6. pp. 845-858. 14 pages.

Kemmer et al. "Nonlinear least-squares data fitting in Excel spreadsheets" *Nature Protocols, Nature Publishing Group*. 2010. vol. 5, No. 2. pp. 267-281. 15 pages.

Kerbarh O., et al., "Mechanistic and Inhibition Studies of Chorismate-utilizing Enzymes," Biochemical Society Transactions, Aug. 2005, vol. 33 (Pt 4), 4 pages.

Kern et al. "Ch. 25—Measurement of Phenazines in Bacterial Cultures" *Editors: Filloux and Ramos, Methods in Molecular Biology—Pseudomonas Methods and Protocols*, Springer Science+Business Media. 2014. vol. 1149.pp. 303-310. 9 pages.

Kerr J.R., et al., "Pseudomonas Aeruginosa Pyocyanin and 1-hydroxyphenazine Inhibit Fungal Growth," Journal of Clinical Pathology, May 1999, vol. 52 (5), 4 pages.

Khersonsky, O., et al., "Automated design of efficient and functionally diverse enzyme repertoires." Molecular cell, 2018. 72(1): p. 178-186. e5.

Kidani et al. "Studies on Metal Chelate Compounds of Phenazine Derivatives. I. Spectrophotometric Studies on Copper Chelate Compounds of I-Hydroxyphenazine and its Di-N-oxide" *Chemical and Pharmaceutical Bulletin, Pharmaceutical Society of Japan*. 1958. vol. 6, No. 5. pp. 556-562. 7 pages.

Kidani et al. "Studies on Metal Chelate Compounds of Phenazine Derivatives. VIII. Metal Complexes of I-Hydroxyphenazine"—Abstract Only *Yakugaku Zasshi, Pharmaceutical Society of Japan*. 1973. vol. 93, No. 9. pp. 1089-1093. 5 pages.

Kim E.J., et al., "Expression of the quorum-sensing regulatory protein LasR is strongly affected by iron and oxygen concentrations in cultures of Pseudomonas aeruginosa irrespective of cell density," Microbiology, Apr. 2005, vol. 151 (Pt 4), 12 pages.

Kim et al. "Protein structure prediction and analysis using the Robetta server" *Nucleic Acids Research, Oxford University Press*. 2004. vol. 32. pp. W526-W531. 6 pages.

Kim et al. "Tolerance of dormant and active cells in Pseudomonas aeruginosa PA01 biofilm to antimicrobial agents" *Journal of Antimicrobial Chemotherapy , Oxford University Press*. 2009. vol. 63. pp. 129-135. 7 pages.

King E.O., et al., "Two Simple Media for the Demonstration of Pyocyanin and Fluorescin," Journal of Laboratory and Clinical Medicine, Aug. 1954, vol. 44 (2), 7 pages.

Kito N., et al., "Reduction by a Model of NAD(P)H: Construction of Electron Bridges," Chemistry Letters, 1974, vol. 3 (4), 4 pages.

Klepac-Ceraj V., et al., "Relationship Between Cystic Fibrosis Respiratory Tract Bacterial Communities and Age, Genotype, Antibiotics and Pseudomonas Aeruginosa," Environmental Microbiology, May 2010, vol. 12(5), 11 pages.

Knudson R.J., et al., "The Maximal Expiratory Flow-volume Curve. Normal Standards, Variability, and Effects of Age," The American Review of Respiratory Disease, May 1976, vol. 113 (5), 13 pages.

Kobayashi K., et al., "Activation of SoxR-dependent Transcription in Pseudomonas Aeruginosa," Journal of Biochemistry, Nov. 2004, vol. 136 (5), 9 pages.

Koch B., et al., "A Panel of Tn7-based Vectors for Insertion of the Gfp Marker Gene or for Delivery of Cloned DNA Into Gram-negative Bacteria at a Neutral Chromosomal Site," Journal of Microbiological Methods, Jul. 2001, vol. 45 (3), pp. 187-195. 9 pages.

Koley D., et al., "Discovery of a Biofilm Electrocline Using Real-time 3D Metabolite Analysis," Proceedings of the National Academy of Sciences of the United States of America, Dec. 2011, vol. 108 (50), 6 pages.

Kolter R., et al., "The Stationary Phase of the Bacterial Life Cycle," Annual Review of Microbiology, 1993, vol. 47, 20 pages.

Komadel P., "Quantitative Assay of Minerals for Fe2+ and Fe3+ Using 1,10-Phenanthroline: III. A Rapid Photochemical Method," Clays and Clay Minerals, Jan. 1988, vol. 36 (4), 3 pages.

Konings A.F., et al., "Pseudomonas Aeruginosa Uses Multiple Pathways to Acquire Iron During Chronic Infection in Cystic Fibrosis Lungs," Infection and Immunity, Aug. 2013, vol. 81 (8), 8 pages.

Kopf et al. "Ligand-Enhanced Abiotic Iron Oxidation and the Effects of Chemical versus Biological Iron Cycling in Anoxic Environments" Environmental Science & Technology, American Chemical Society. 2013. vol. 47. pp. 2602-2611. 10 pages.

Kragh et al. "Role of Multicellular Aggregates in Biofilm Formation" *mBio, American Society for Microbiology*. 2016. vol. 7, No. 2. pp. 1-11. 11 pages.

Kreamer et al. "The Ferrous Iron-Responsive BqsRS Two-Component System Activates Genes That Promote Cationic Stress Tolerance" *mBio, American Society of Microbiology*. Mar./Apr. 2015. vol. 6, No. 2. pp. 1-12. 12 pages.

Kreamer N.N., et al., "BqsR/BqsS Constitute a Two-component System That Senses Extracellular Fe(II) in Pseudomonas Aeruginosa," Journal of Bacteriology, Mar. 2012, vol. 194 (5), 10 pages.

Krogh et al. "Predicting Transmembrane Protein Topology with a Hidden Markov Model: Application to Complete Genomes" *Journal of Molecular Biology, Academic Press*. 2001. vol. 305. pp. 567-580. 14 pages.

Kummerli et al. "Viscous medium promotes cooperation in pathogenic bacterium Pseudomonas aeruginosa" *Proceedings of the Royal Society B, The Royal Society*. 2009. vol. 276. pp. 3531-3538. 8 pages.

Lam K.S., et al., "Application of Combinatorial Library Methods in Cancer Research and Drug Discovery," Anti-cancer Drug Design, Apr. 1997, vol. 12 (3), 145-167.24 pages.

Lambertsen L., et al., "Mini-Tn7 Transposons for Site-specific Tagging of Bacteria with Fluorescent Proteins," Environmental Microbiology, Jul. 2004, vol. 6 (7), 7 pages.

Lau G.W., et al., "Pseudomonas Aeruginosa Pyocyanin Is Critical for Lung Infection in Mice," Infection and Immunity, Jul. 2004, vol. 72 (7), 5 pages.

Lau G.W., et al., "The Role of Pyocyanin in Pseudomonas Aeruginosa Infection," Trends in Molecular Medicine, Dec. 2004, vol. 10 (12), 8 pages.

Laursen J.B., et al., "Phenazine Natural Products: Biosynthesis, Synthetic Analogues, and Biological Activity," Chemical Reviews, Mar. 2004, vol. 104 (3), 24 pages.

Learoyd S.A., et al., "An Investigation of Dye Reduction by Food-borne Bacteria, " The Journal of Applied Bacteriology, Jun. 1992, vol. 72 (6), 7 pages.

Lehner B., et al., "How to Use RNA Interference," Briefings in Functional Genomics, Apr. 2004, vol. 3 (1), 16 pages.

Lehtinen J., "Improvements in the Assessment of Bacterial Viability and Killing," Astronomica-Chemica-Physica-Mathematica, 2007, 72 pages.

(56) References Cited

OTHER PUBLICATIONS

Li Q.A., et al., "Ligand Binding Induces an Ammonia Channel in 2-amino-2-desoxyisochorismate (Adic) Synthase Phze," The Journal of Biological Chemistry, May 2011, vol. 286 (20), 9 pages.

Li X.Z., et al., "Influence of the MexA-MexB-oprM Multidrug Efflux System on Expression of the MexC-MexD-oprJ and MexE-MexF-oprN Multidrug Efflux Systems in Pseudomonas Aeruginosa," The Journal of Antimicrobial Chemotherapy, Dec. 2000, vol. 46 (6), 9 pages.

Liberati N.T., et al., "An Ordered, Nonredundant Library of Pseudomonas Aeruginosa Strain PA14 Transposon Insertion Mutants," Proceedings of the National Academy of Sciences of the United States of America, Feb. 2006, vol. 103 (8), 7 pages.

Lies D.P., et al., "Shewanella Oneidensis MR-1 uses Overlapping Pathways for Iron Reduction at a Distance and by Direct Contact Under Conditions Relevant for Biofilms," Applied and Environmental Microbiology, Aug. 2005, vol. 71 (8), 14 pages.

Lim, Y.W., et al., "Metagenomics and Metatranscriptomics: Windows on CF-associated Viral and Microbial Communities," Journal of Cystic Fibrosis, Mar. 2013, vol. 12 (2), 11 pages.

Lin M.H., et al., "Involvement of Iron in Biofilm Formation by *Staphylococcus aureus*," PLoS One, Mar. 2012, vol. 7 (3), 7 pages.

Liochev S.I., et al., "Induction of the soxRS Regulon of *Escherichia coli* by Superoxide," The Journal of Biological Chemistry, Apr. 1999, vol. 274 (14), 4 pages.

Liu Y., et al., "Synergistic Activities of an Efflux Pump Inhibitor and Iron Chelators Against Pseudomonas Aeruginosa Growth and Biofilm Formation," Antimicrobial Agents and Chemotherapy, Sep. 2010, vol. 54 (9), pp. 3960-3963. 4 pages.

Livak K.J., et al., "Analysis of Relative Gene Expression Data Using Real-time Quantitative PCR and the 2(-delta Delta C(T)) Method," Methods, Dec. 2001, vol. 25 (4), 7 pages.

Look D.C., et al., "Pyocyanin and Its Precursor Phenazine-1-carboxylic Acid Increase IL-8, and Intercellular Adhesion Molecule-1 Expression in Human Airway Epithelial Cells by Oxidant-dependent Mechanisms," Journal of Immunology, Sep. 2005, vol. 175 (6), 8 pages.

Lovley D.R., et al., "Humic Substances as Electron Acceptors for Microbial Respiration," Nature, Aug. 1996, vol. 382, pp. 445-448. 4 pages.

Lovley D.R., et al., "Rapid Assay for Microbially Reducible Ferric Iron in Aquatic Sediments," Applied and Environmental Microbiology, Jul. 1987, vol. 53 (7), 6 pages.

Lyczak J.B., et al., "Lung Infections Associated with Cystic Fibrosis," Clinical Microbiology Reviews, Apr. 2002, vol. 15 (2), 30 pages.

Maddula V.S.R.K., et al., "Altering the Ratio of Phenazines in Pseudomonas Chlororaphis (aureofaciens) Strain 30-84: Effects on Biofilm Formation and Pathogen Inhibition," Journal of Bacteriology, Apr. 2008, vol. 190 (8), 9 pages.

Maddula V.S.R.K., et al., "Quorum Sensing and Phenazines Are Involved in Biofilm Formation by Pseudomonas Chlororaphis (Aureofaciens) Strain 30-84," Microbial Ecology, Aug. 2006, vol. 52 (2), 289-301. 13 pages.

Mah et al. "A genetic basis for Pseudomonas aeruginosa biofilm antibiotic resistance" Nature, Nature Publishing Group. Nov. 20, 2003. vol. 426. pp. 306-310. 5 pages.

Mahajan-Miklos S., et al., "Molecular Mechanisms of Bacterial Virulence Elucidated Using a Pseudomonas aeruginosa-Caenorhabditis elegans Pathogenesis Model," Cell, Jan. 1999, vol. 96 (1), 10 pages.

Malasarn et al. "Characterization of the Arsenate Respiratory Reductase from *Shewanella* sp. Strain ANA-3" *Journal of Bacteriology, American Society for Microbiology*. Jan. 2008. vol. 190, No. 1. pp. 135-142. 8 pages.

Marshall B., et al., "Citrate-Mediated Iron Uptake in Pseudomonas Aeruginosa: Involvement of the Citrate-Inducible FecA Receptor and the FeoB Ferrous Iron Transporter," Microbiology, Jan. 2009, vol. 155, 11 pages.

Marsili E., et al., "Shewanella Secretes Flavins That Mediate Extracellular Electron Transfer," Proceedings of the National Academy of Sciences of the United States of America, Mar. 2008, vol. 105 (10), 6 pages.

Conway T., "The Entner-Doudoroff Pathway: History, Physiology and Molecular Biology," FEMS Microbiology Letters, Sep. 1992, vol. 103 (1), 27 pages.

Corkery K., "Inhalable Drugs for Systemic Therapy," Respiratory Care, Jul. 2000, vol. 45 (7), p. 831-835. 5 pages.

Cornelis P., et al., "Iron Uptake Regulation in Pseudomonas Aeruginosa," Biometals, Feb. 2009, vol. 22 (1), 8 pages.

Cornforth, D.M., et al., "Quantitative framework for model evaluation in microbiology research using Pseudomonas aeruginosa and cystic fibrosis infection as a test case." MBio, 2020. 11(1): p. e03042-19.

Corrected Notice of Allowance Action for U.S. Appl. No. 15/466,839, filed Mar. 22, 2017, on behalf of California Institute of Technology. Date: Sep. 23, 2020. 10 Pages.

Costa et al. "Enzymatic Degradation of Phenazines Can Generate Energy and Protect Sensitive Organisms from Toxicity" *mBio, American Society of Microbiology*. Nov. 2015. vol. 6, No. 6. pp. 1-10. 10 pages.

Costa et al. "Pyocyanin degradation by a tautomerizing demethylase inhibits Pseudomonas aeruginosa biofilms" Science, American Association for the Advancement of Science. Jan. 13, 2017. vol. 355, No. 6321. pp. 170-173. 5 pages.

Costerton J.W., et al., "Bacterial Biofilms: A Common Cause of Persistent Infections," Science, May 1999, vol. 284 (5418), 6 pages.

Cowley E.S., et al., "Pediatric Cystic Fibrosis Sputum can be Chemically Dynamic, Anoxic, and Extremely Reduced due to Hydrogen Sulfide Formation," mBio, Jul. 2015, vol. 6 (4), 19 pages.

Cox C.D., et al., "Role of Pyocyanin in the Acquisition of Iron from Transferrin," Infection and Immunity, Apr. 1986, vol. 52 (1), 8 pages.

Cronan J.E., et al., " Function, Attachment and Synthesis of Lipoic Acid in *Escherichia coli*," Advances in Microbial Physiology, 2005, vol. 50, 44 pages.

Cull M.G., et al., "Screening for Receptor Ligands using Large Libraries of Peptides Linked to the C Terminus of the Lac Repressor," Proceedings of the National Academy of Sciences of the United States of America, 1992, vol. 89 (5), 5 pages.

Cundliffe E., "How Antibiotic-Producing Organisms Avoid Suicide," Annual Review of Microbiology, 1989, vol. 43, 27 pages.

Cwirla S.E., et al., "Peptides on Phage: A Vast Library of Peptides for Identifying Ligands," Proceedings of the National Academy of Sciences of the United States of America, Aug. 1990, vol. 87 (16), 5 pages.

Czarnik A.W, "Encoding Methods for Combinatorial Chemistry," Current Opinion in Chemical Biology, Jun. 1997, vol. 1 (1), 7 pages.

Das et al. "Phenazine production enhances extracellular DNA release via hydrogen peroxide generation in Pseudomonas aeruginosa" *Communicative and Integrative Biology, Landes Bioscience*. May 2013. vol. 6, No. 3. pp. e23570-1-e23570-4. 4 pages.

Das et al. "Phenazine virulence factor binding to extracellular DNA is important for Pseudomonas aeruginosa biofilm formation" *Scientific Reports, Nature Publishing Group*. Feb. 11, 2015. vol. 5, No. 8398. pp. 1-9. 9 pages.

Das et al. "Pyocyanin Facilitates Extracellular DNA Binding to Pseudomonas aeruginosa Influencing Cell Surface Properties and Aggregation" *PLOS One, Public Library of Science*. Mar. 11, 2013. vol. 8, No. 3. 11 pages.

Das et al. "Pyocyanin Promotes Extracellular DNA Release in Pseudomonas aeruginosa" *PLOS One, Public Library of Science*. Oct. 2012. vol. 7, No. 10. pp 1-9. 9 pages.

Dasgupta et al. "Expression Systems for Study of Mycobacterial Gene Regulation and Development of Recombinant BCG Vaccines" *Biochemical and Biophysical Research Communications, Academic Press*. 1998. vol. 246. pp. 797-804. 8 pages.

Dashper S.G., et al., "A Novel Porphyromonas Gingivalis FeoB Plays a Role in Manganese Accumulation," The Journal of Biological Chemistry, Jul. 29, 2005, vol. 280 (30), 9 pages.

(56) References Cited

OTHER PUBLICATIONS

Davies D.G., et al., "The Involvement of Cell-to-cell Signals in the Development of a Bacterial Biofilm," Science, Apr. 1998, vol. 280 (5361), 4 pages.

Davis G., et al., "Free Radical Production from the Aerobic Oxidation of Reduced Pyridine Nucleotides Catalyzed by Phenazine Derivatives," Biochimica et Biophysica Acta, Sep. 1983, vol. 724 (3), 9 pages.

De Graef M.R., et al., "The Steady-state Internal Redox State (NADH/NAD) Reflects the External Redox State and is Correlated with Catabolic Adaptation in *Escherichia coli*," Journal of Bacteriology, Apr. 1999, vol. 181 (8), 8 pages.

De Kok A., et al., "The Pyruvate Dehydrogenase Complex From Gram-negative Bacteria," Biochimica et Biophysica Acta, Jun. 1998, vol. 1385 (2), 14 pages.

De La Fuente-Nunez et al. "Bacterial biofilm development as a multicellular adaptation: antibiotic resistance and new therapeutic strategies" *Current Opinion in Microbiology, Elsevier*. 2013. vol. 16. pp. 580-589. 9 pages.

De Vos D., et al., "Direct Detection and Identification of Pseudomonas aeruginosa in Clinical Samples Such as Skin Biopsy Specimens and Expectorations by Multiplex PCR Based on Two Outer Membrane Lipoprotein Genes, opri and oprL," Journal of Clinical Microbiology, Jun. 1997, vol. 35 (6), 5 pages.

De Vos D., et al., "Study of Pyoverdine Type and Production by Pseudomonas Aeruginosa Isolated From Cystic Fibrosis Patients: Prevalence of Type II Pyoverdine Isolates and Accumulation of Pyoverdine-negative Mutations," Archives of Microbiology, May 2001, vol. 175 (5), 5 pages.

Dehio C., et al., "Maintenance of Broad-host-range Incompatibility Group P and Group Q Plasmids and Transposition of Tn5 in Bartonella Henselae Following Conjugal Plasmid Transfer From *Escherichia coli*," Journal of Bacteriology, Jan. 1997, vol. 179 (2), 4 pages.

Delaney S.M. et al., "phzO, a Gene for Biosynthesis of 2-Hydroxylated Pnenazine Compounds in Pseudomonas aureofaciens 30-84", Journal of Bacteriology, 2001, vol. 183, No. 1, pp. 318-327. (Year: 2001).

Devlin J.J., et al., "Random Peptide Libraries: A Source of Specific Protein Binding Molecules," Science, Jul. 1990, vol. 249 (4967), 3 pages.

DeWitt S.H., et al., "Diversomers: An Approach to Nonpeptide, Nonoligomeric Chemical Diversity," Proceedings of the National Academy of Sciences of the United States of America, Aug. 1993, vol. 90 (15), 5 pages.

Deziel E., et al., "RhlA is Required for the Production of a Novel Biosurfactant Promoting Swarming Motility in Pseudomonas Aeruginosa: 3-(3-hydroxyalkanoyloxy)alkanoic Acids (HAAs), the Precursors of Rhamnolipids," Microbiology, Aug. 2003, vol. 149 (Pt 8), 9 pages.

Dhall et al. "Generating and Reversing Chronic Wounds in a Diabetic Mice by Manipulating Wound Redox Parameters" *Journal of Diabetes Research, Hindawi Publishing Corporation*. Dec. 2014. vol. 2014, No. 562625. pp. 1-18. 19 pages.

Dias M.V., et al., "Chorimate Synthase: An Attractive Target for Drug Development Against Orphan Diseases," Current Drug Targets, 2007, vol. 8 (3), 8 pages.

Dietrich et al. "Bacterial Community Morphogenesis Is Intimately Linked to the Intracellular Redox State" *Journal of Bacteriology, American Society of Microbiology*. Apr. 2013. vol. 195, No. 7. pp. 1371-1380. 10 pages.

Dietrich et al. "The phenazine pyocyanin is a terminal signalling factor in the quorum sensing network of Pseudomonas aeruginosa" *Molecular Microbiology, Blackwell Publishing Ltd*. 2006. vol. 61, No. 5. pp. 1308-1321. 14 pages.

Dietrich L.E., et al., "Redox-active Antibiotics Control Gene Expression and Community Behavior in Divergent Bacteria," Science, Aug. 2008, vol. 321 (5893), 5 pages.

Dietrich L.E., et al., "The Phenazine Pyocyanin Is a Terminal Signalling Factor in the Quorum Sensing Network of Pseudomonas Aeruginosa," Molecular Microbiology, Sep. 2006, vol. 61 (5), 14 pages.

Diggle et al. "The Pseudomonas aeruginosa quinolone signal molecule overcomes the cell density-dependency of the quorum sensing hierarchy, regulates rhi-dependent genes at the onset of stationary phase and can be produced in the absence of LasR" *Molecular Microbiology, Blackwell Publishing Ltd*. 2003, vol. 50, No. 1. pp 29-43. 15 pages.

Ding et al. "The Redox State of the [2Fe-2S] Clusters in SoxR Protein Regulates Its Activity as a Transcription Factor" *The Journal of Biological Chemistry, American Society for Biochemistry and Molecular Biology Inc*. Dec. 27, 1996. vol. 271, No. 52. pp. 33173-33175. 4 pages.

Donlan R.M., et al., "Biofilms: Survival Mechanisms of Clinically Relevant Microorganisms," Clinical Microbiology Reviews, Apr. 2002, vol. 15 (2), 27 pages.

Driscoll et al. "The Epidemiology, Pathogenesis, and Treatment of Pseudomonas aeruginosa Infections" *Drugs, Adis Data Information BV*. 2007. vol. 67, No. 3. pp. 351-368. 18 pages.

Eiamphungporn W., et al., "Agrobacterium tumefaciens soxR is Involved in Superoxide Stress Protection and also Directly Regulates Superoxide-Inducible Expression of itself and a Target Gene," Journal of Bacteriology, Dec. 2006, vol. 188 (24), 5 pages.

Elble R., "A Simple and Efficient Procedure of Transformation of Yeasts," Biotechniques, Jul. 1992, vol. 13 (1), 3 pages.

Elhassanny A.E., et al., "The Ferrous Iron Transporter FtrABCD is Required for the Virulence of Brucella Abortus 2308 in Mice," Molecular Microbiology, Jun. 2013, vol. 88 (6), 13 pages.

Emde R.A., et al., "Anaerobic Oxidation of Glycerol by *Escherichia coli* in an Amperometric Poised-potential Culture System," Applied Microbiology and Biotechnology, Dec. 1989, vol. 32 (2), 6 pages.

Emde R.A., et al., "Oxidation of Glycerol, Lactate, and Propionate by Propionibacterium Freudenreichii in a Poised-potential Amperometric Culture System," Archives of Microbiology, Apr. 1990, vol. 153 (5), 506-512. 7 pages.

Emerson et al. "Pseudomonas Aeruginosa and Other Predictors of Mortality and Morbidity in Young Children with Cystic Fibrosis" *Pediatric Pulmonology, Wiley-Liss Inc*. 2002. vol. 34, pp. 91-100. 10 pages.

Emsley et al. "Features and development of Coot" *Acta Crystallographica Section D—Biological Crystallography, International Union of Crystallography*. 2010. vol. D66. pp. 486-501. 16 pages.

EP Decision to grant for EP Application No. 12775958.7 filed on Apr. 25, 2012. Mailing Date: Feb. 15, 2018. 1 Page.

Erb E., et al., "Recursive Deconvolution of Combinatorial Chemical Libraries," Proceedings of the National Academy of Sciences of the United States of America, Nov. 1994, vol. 91 (24), 5 pages.

Eschbach M., et al., "Long-term Anaerobic Survival of the Opportunistic Pathogen Pseudomonas Aeruginosa via Pyruvate Fermentation," Journal of Bacteriology, Jul. 2004, vol. 186 (14), 10 pages.

European Examination Report mailed on Jan. 29, 2016 for European Application No. 12775958.7 filed on Apr. 25, 2012, 8 pages.

European Examination Report mailed on Nov. 14, 2016 for European Application No. 12775958.7 filed on Apr. 25, 2012, 6 pages.

Evans et al. "How good are my data and what is the resolution?" *Acta Crystallographica Section D—Biological Crystallography, International Union of Crystallography*. 2013. vol. D69. pp. 1204-1214. 12 pages.

Evans, Philip. "Scaling and assessment of data quality" *Acta Crystallographica Section D—Biological Crystallography, International Union of Crystallography*. 2006. vol. D62. pp. 72-82. 11 pages.

Evans, Philip R. "An introduction to data reduction: space-group determination, scaling and intensity statistics" *Acta Crystallographica Section D—Biological Crystallography. International Union of Crystallography*. 2011. vol. D67. pp. 282-292. 11 pages.

Extended European Search Report for European Application No. 12775958.7, Mail Date: Dec. 5, 2014, 8 pages.

(56) References Cited

OTHER PUBLICATIONS

Felici F., et al., "Selection of Antibody Ligands from a Large Library of Oligopeptides Expressed on a Multivalent Exposition Vector," Journal of Molecular Biology, Nov. 1991, vol. 222 (2), 10 pages.

Fernandes P.B., "Technological Advances in High-throughput Screening," Current Opinion in Chemical Biology, Oct. 1998, vol. 2 (5), 7 pages.

Final Office Action for U.S. Appl. No. 12/548,362. Mail Date: Dec. 5, 2012, 9 pages.

Final Office Action for U.S. Appl. No. 12/548,362. Mail Date: Sep. 10, 2015, 30 pages.

Final Office Action for U.S. Appl. No. 13/456,172, filed Apr. 25, 2012. Mail Date: Dec. 8, 2015. 19 pages.

Final Office Action for U.S. Appl. No. 13/456,172. Mail Date: Aug. 21, 2014, 20 pages.

Final Office Action for U.S. Appl. No. 15/394,138, filed Dec. 29, 2016, on behalf of California Institute of Technology. Mail Date: Mar. 24, 2022. 10 Pages.

Final Office Action for U.S. Appl. No. 15/394,138, filed Dec. 29, 2016 on behalf of California Institute of Technology. Mail Date: Jul. 2, 2020. 10 Pages.

Final Office Action for U.S. Appl. No. 15/466,839, filed Mar. 22, 2017 on behalf of California Institute of Technology Mail Date: Jun. 12, 2019 27 pages.

Final Office Action for U.S. Appl. No. 14/830,673, filed Aug. 19, 2015, on behalf of California Institute of Technology. Mail Date: Mar. 16, 2018. 23 pages.

Fischbach M.A., et al., "How Pathogenic Bacteria Evade Mammalian Sabotage in the Battle for Iron," Nature Chemical Biology, Mar. 2006, vol. 2 (3), 7 pages.

Floriano B., et al., "AfsR is a Pleiotropic but Conditionally Required Regulatory Gene for Antibiotic Production in Streptomyces Coelicolor A3(2)," Molecular MicroBiology, Jul. 1996, vol. 21 (2), 12 pages.

Flume P.A., et al., "Cystic Fibrosis Pulmonary Guidelines Chronic Medications for Maintenance of Lung Health," American Journal of Respiratory and Critical Care Medicine, Nov. 2007, vol. 176 (10), 13 pages.

Fodor S.P., et al., "Multiplexed Biochemical Assays with Biological Chips," Nature, Aug. 1993, vol. 364 (6437), 2 pages.

Folschweiller N., et al., "The Interaction Between Pyoverdin and its Outer Membrane Receptor in Pseudomonas Aeruginosa Leads to Different Conformers: a Time-resolved Fluorescence Study," Biochemistry, Dec. 2002, vol. 41 (49), 11 pages.

Fothergill J.L., et al., "Widespread Pyocyanin Over-production Among Isolates of a Cystic Fibrosis Epidemic Strain," BMC Microbiology, May 2007, vol. 7, 10 pages.

Friedheim E., et al., "Pyocyanin, an Accessory Respiratory Enzyme," The Journal of Experimental Medicine, Jul. 1931, vol. 54 (2), 15 pages.

Friedheim E.A., "Potentiometric Study of Pyocyanine," The Journal of Biological Chemistry, Feb. 1931, vol. 91, 14 pages.

Friedman L., et al., "Genes Involved in Matrix Formation in Pseudomonas Aeruginosa PA14 Biofilms," Molecular MicroBiology, Feb. 2004, vol. 51 (3), 16 pages.

Fritsche T.R., et al., "Comparative Antimicrobial Characterization of LBM415 (NVP PDF-713), a New Peptide Deformylase Inhibitor of Clinical Importance, Antimicrobial Agents and Chemotherapy," Antimicrobial Agents and Chemotherapy, Apr. 2005, vol. 49 (4), 10 pages.

Fuhrer T., et al., "Experimental Identification and Quantification of Glucose Metabolism in Seven Bacterial Species,"Journal of Bacteriology, Mar. 2005, vol. 187 (5), 11 pages.

Fultz M.L., et al., "Mediator Compounds for the Electrochemical Study of Biological Redox Systems: A Compilation," Analytical Chimical Acta, Mar. 1982, vol. 140, 18 pages.

Gallagher L.A., et al., "Functions Required for Extracellular Quinolone Signaling by Pseudomonas Aeruginosa," Journal of Bacteriology, Dec. 2002, vol. 184 (23), 10 pages.

Gallagher L.A., et al., "Pseudomonas Aeruginosa PA01 Kills Caenorhabditis Elegans by Cyanide Poisoning," Journal of Bacteriology, Nov. 2001, vol. 183 (21), 8 pages.

Galli F., et al., "Oxidative Stress and Antioxidant Therapy in Cystic Fibrosis," Biochimica et Biophysica Acta, May 2012, vol. 1822 (5), 24 pages.

Gallop M.A., et al., "Applications of Combinatorial Technologies to Drug Discovery. 1. Background and Peptide Combinatorial Libraries," Journal of Medical Chemistry, Apr. 1994, vol. 37 (9), 19 pages.

Galloway, N.R., et al., "Rapid cloning for protein crystallography using type HIS restriction enzymes." *Crystal growth & design*, 2013. 13(7): p. 2833-2839.

Gammaproteobacteria, Wikipedia entry retrieved on Mar. 23, 2020 from https://en.wikipedia.org/wiki/Gammaproteobacteria . 3 Pages.

Gardner P.R., et al., "Superoxide Production by the Mycobacterial and Pseudomonad Quinoid Pigments Phthiocol and Pyocyanine in Human Lung Cells," Archives of Biochemistry and Biophysics, Sep. 1996, vol. 333 (1), 8 pages.

Garg S., et al., "Superoxide Mediated Reduction of Organically Complexed Iron(III): Comparison of Non-Dissociative and Dissociative Reduction Pathways," Environmental Science & Technology, May 2007, vol. 41 (9), 8 pages.

Garske L.A., et al., "Sub-inhibitory Concentrations of Ceftazidime and Tobramycin Reduce the Quorum Sensing Signals of Pseudomonas Aeruginosa," Pathology, Dec. 2004, vol. 36 (6), 5 pages.

Gaudu P., et al., "SoxR, a [2Fe-2S] Transcription Factor, Is Active Only in its Oxidized Form," Proceedings of the National Academy of Sciences of the United States of America, Sep. 1996, vol. 93 (19), 10094-10098. 5 pages.

Gene Bridges: DNA Engineering Specialists, Red/ET Recombination, "Quick & Easy *E.coli* Gene Deletion Kit," Technical Protocol, Cat. No.K006, Jan. 2007, Version 2.0, 40 pages.

Ghio A.J., et al., "Iron Accumulates in the Lavage and Explanted Lungs of Cystic Fibrosis Patients," Journal of Cystic Fibrosis : Official Journal of the European Cystic Fibrosis Society, Jul. 2013, vol. 12 (4), 9 pages.

Ghosh S., et al., "Periodic Iron Nanomineralization in Human Serum Transferrin Fibrils," Angewandte Chemie-International Edition, 2008, vol. 47 (12), 5 pages.

Gibbs C.R., et al., "Characterization and Application of Ferrozine Iron Reagent as a Ferrous Iron Indicator," Analytical Chemistry, Jul. 1976, vol. 48 (8), 5 pages.

Gifford A.H., et al., "Iron Homeostasis during Cystic Fibrosis Pulmonary Exacerbation," Clinical and Translational Science, Aug. 2012, vol. 5 (4), 6 pages.

Glasser et al. "Phenazine redox cycling enhances anaerobic survival in Pseudomonas aeruginosa by facilitating generation of ATP and a proton-motive force" *Molecular Microbiology, John Wiley & Sons Ltd*. 2014. vol. 92, No. 2. pp. 399-412. 14 pages.

Gohain N., "Studies on the Structure and Function of Phenazine Modifying Enzymes PhzM and PhzS Involved in the Biosynthesis of Pyocyanin," Ph.D. Thesis Dissertation submitted in 2008 to Max Planck Institute for Molecular Physiology & Department of Chemistry, University of Dortmund, Germany, 2008, 143 pages.

Goldenzweig et al. "Automated Structure- and Sequence-Based Design of Proteins for High Bacterial Expression and Stability" *Molecular Cell, Cell Press*. 2016. vol. 63. pp. 337-346. 11 pages.

Goodwin J. F., et al., "Chelation of Ferrous Sulphate Solutions by Desferrioxamine B," Nature, Jan. 1965, vol. 205, 3 pages.

Govan J.R., et al., "Microbial Pathogenesis in Cystic Fibrosis: Mucoid Pseudomonas Aeruginosa and Burkholderia Cepacia," Microbiological reviews, Sep. 1996, vol. 60 (3), 36 pages.

Grahl et al. "Ch 3.—The Yin and Yang of Phenazine Physiology" *Editors: Chincholkar and Thomashow, Microbial Phenazines, Springer-Verlag Berlin Heidelberg*. 2013. pp. 43-69. 28 pages.

Martell, et al., "Critical stability constants", vol. 6: Second Supplement. 1989: Springer. 643 pages.

Martin L.W., et al., "Pseudomonas Siderophores in the Sputum of Patients With Cystic Fibrosis," Biometals, Dec. 2011, vol. 24 (6), 9 pages.

Mashburn L.M., et al., "*Staphylococcus aureus* Serves as an Iron Source for Pseudomonas Aeruginosa During in Vivo Coculture," Journal of Bacteriology, Jan. 2005, vol. 187 (2), 14 pages.

(56) References Cited

OTHER PUBLICATIONS

Mateos F., et al., "Iron Metabolism in the Lower Respiratory Tract," Thorax, Jul. 1998, vol. 53 (7), 8 pages.

Mavrodi, D.V et al., "A Seven-Gene Locus for Synthesis of Phenazine-1-Carboxylic Acid by Psuedomonas fluorescens 2-79", (May 1998), J. Bacteriol., vol. 180, No. 9, pp. 2541-2548.

Mavrodi D.V., et al., "Functional Analysis of Genes for Biosynthesis of Pyocyanin and Phenazine-1-carboxamide From Pseudomonas Aeruginosa PAO1," Journal of Bacteriology, Nov. 2001, vol. 183 (21), 13 pages.

Mavrodi D.V., et al., "Phenazine Compounds in Fluorescent *Pseudomonas* spp. Biosynthesis and Regulation," Annual Review of Phytopathology, Sep. 2006, vol. 44, 29 pages.

Mavrodi et al. "Irrigation Differentially Impacts Populations of Indigenous Antibiotic-Producing *Pseudomonas* spp. in the Rhizosphere of Wheat" *Applied and Environmental Microbiology, American Society of Microbiology*. May 2012. vol. 78, No. 9. pp. 3214-3220. 7 pages.

Maynard, Adam et al. "Antibiotic Korormicin A Kills Bacteria by Producing Reactive Oxygen Species" Journal of Bacteriology, vol. 201, Issue 11, 300718-18, Jun. 2019. pp. 1-11.

Mazzola M., et al., "Contribution of Phenazine Antibiotic Biosynthesis to the Ecological Competence of Fluorescent Pseudomonads in Soil Habitats," Applied and Environmental Microbiology, Aug. 1992, vol. 58 (8), 9 pages.

McCoy et al. "Phaser crystallographic software" *Journal of Applied Crystallography, International Union of Crystallography*. 2007. vol. 40. pp. 658-674. 17 pages.

McDonald, M. et al. "Phenazine Biosynthesis in Pseudomonas fluorescens: Branchpoint from the Primary Shikimate Biosynthetic Pathway and Role of Phenazine-1,6-dicarboxylic Acid", J. Am. Chem. Soc., 2001, 123, 38, pp. 9459-9460.

McIlwain et al. "359. The Phenazine Series. Part VI. Reactions of Alkyl Phenazonium Salts; the Phenazyls" *Journal of the Chemical Society, Royal Society of Chemistry*. 1937. pp. 1704-1711. 9 pages.

McKinlay J.B., et al., "Extracellular Iron Reduction Is Mediated in Part by Neutral Red and Hydrogenase in *Escherichia coli*," Applied and Environmental Microbiology, Jun. 2004, vol. 70 (6), 9 pages.

Mehra S., et al., "A Framework to Analyze Multiple Time Series Data: A Case Study With Streptomyces Coelicolor," Journal of Industrial Microbiology and Biotechnology, Feb. 2006, vol. 33 (2), 14 pages.

Meirelles, L.A. and D.K. Newman, "Both toxic and beneficial effects of pyocyanin contribute to the lifecycle of Pseudomonas aeruginosa." *Molecular microbiology*, 2018. 110(6): p. 995-1010.

Meirelles, L.A., et al., "Bacterial defenses against a natural antibiotic promote collateral resilience to clinical antibiotics." *PLoS biology*, 2021. 19(3): p. e3001093.

Mentel M., et al., "Of Two Make One: The Biosynthesis of Phenazines," Chembiochem, Sep. 2009, vol. 10 (14), 10 pages.

Merriam-Webster entry for "pathway," as available Apr. 25, 2009, retrieved Oct. 16, 2022 from the WayBackMachine.com (1 page).

Merritt P.A., et al., "Motility and Chemotaxis in Agrobacterium Tumefaciens Surface Attachment and Biofilm Formation," Journal of Bacteriology, Nov. 2007, vol. 189 (22), 11 pages.

Meylan, S., et al., "Carbon sources tune antibiotic susceptibility in Pseudomonas aeruginosa via tricarboxylic acid cycle control." *Cell chemical biology*, 2017. 24(2): p. 195-206.

Michaelis et al. "Potentiometric Studies on Semiquinones" *Journal of the American Chemical Society, American Chemical Society*. Apr. 1933. vol. 55. pp. 1481-1494. 14 pages.

Michaelis et al. "The Viologen Indicators" *The Journal of General Physiology, Rockefeller University Press*. 1933. vol. 16, No. 6. pp. 859-873. 15 pages.

Miller M.R., et al., "General Considerations for Lung Function Testing," European Respiratory Journal, Jul. 2005, vol. 26 (1), pp. 153-161. 9 pages.

Miller R.A., et al., "Protease-cleaved Iron-transferrin Augments Oxidant-mediated Endothelial Cell Injury via Hydroxyl Radical Formation," Journal of Clinical Investigation, Jun. 1995, vol. 95 (6), 10 pages.

Miroux, B. et al., "Over-production of proteins in Escherichia coli: mutant hosts that allow synthesis of some membrane proteins and globular proteins at high levels." *Journal of molecular biology*, 1996. 260(3): p. 289-298.

Moker N., et al., "Pseudomonas Aeruginosa Increases Formation of Multidrug-tolerant Persister Cells in Response to Quorum-sensing Signaling Molecules," Journal of Bacteriology, Apr. 2010, vol. 192 (7), 1946-1955. 11 pages.

Moreau-Marquis, S, et al., "Pseudomonas aeruginosa biofilm formation in the cystic fibrosis airway", Pulmonary Pharmacology & Therapeutics, 2008, 21(4):p. 595-599.

Moreau-Marquis S., et al., "The DeltaF508-CFTR Mutation Results in Increased Biofilm Formation by Pseudomonas Aeruginosa by Increasing Iron Availability," American Journal of Physiology Lung Cellular and Molecular Physiology, Mar. 21, 2008, vol. 295 (1), 14 pages.

Moreau-Marquis S., et al., "Tobramycin and FDA-Approved Iron Chelators Eliminate Pseudomonas Aeruginosa Biofilms on Cystic Fibrosis Cells," American Journal of Respiratory Cell and Molecular Biology, Sep. 2009, vol. 41(3), 9 pages.

Moree et al. "Interkingdom metabolic transformations captured by microbial imaging mass spectrometry" *Proceedings of the National Academy of Sciences, National Academy of Sciences*. Aug. 21, 2012. vol. 109, No. 35. pp. 13811-13816. 6 pages.

Morel F.M, et al. "Principles and Applications of Aquatic Chemistry," John Wiley & Sons, Inc, 1993, Table of Contents, 2 pages.

Moriarty et al. "Electronic Ligand Builder and Optimization Workbench (eLBOW): a tool for ligand coordinate and restraint generation" *Acta Crystallographica Section D—Biological Crystallography, International Union of Crystallography*. 2009. vol. D65. pp. 1074-1080. 7 pages.

Morrison et al. "Flavin Model Systems. I. The Electrochemistry of 1-Hydroxyphenazine and Pyocyanine in Aprotic Solvents" *Journal of the American Chemical Society, American Chemical Society*. 1978. vol. 100, No. 1. pp. 207-211. 5 pages.

Mossner E., et al., "Importance of Redox Potential for the in Vivo Function of the Cytoplasmic Disulfide Reductant Thioredoxin From *Escherichia coli*," Journal of Biological Chemistry, Sep. 1999, vol. 274 (36), 6 pages.

Muh U., et al., "A Structurally Unrelated Mimic of a Pseudomonas Aeruginosa acyl-homoserine Lactone Quorum-sensing Signal," Proceedings of the National Academy of Sciences of the United States of America, Nov. 2006, vol. 103 (45), 5 pages.

Musk D.J., et al., "Iron Salts Perturb Biofilm Formation and Disrupt Existing Biofilms of Pseudomonas Aeruginosa," Chemistry and Biology, Jul. 2005, vol. 12 (7), 8 pages.

Naikare H., et al., "Major Role for FeoB in Campylobacter Jejuni Ferrous Iron Acquisition, Gut Colonization, and Intracellular Survival," Infection and Immunity, Oct. 2006, vol. 74 (10), 12 pages.

Nancollas et al. "Guidelines for the Determination of Stability Constants" *Pure and Applied Chemistry, International Union of Pure and Applied Chemistry*. 1982. vol. 54, No. 12. pp. 2675-2692. 18 pages.

Nash, T. "The Colorimetric Estimation of Formaldehyde by Means of the Hantzsch Reaction" *Biochemical Journal, Portland Press*. 1953. vol. 55. pp. 416-421. 6 pages.

NCBI "GenBank accession No. AL125546.1—hypothetical protein XA26_16990 [*Mycobacterium fortuitum*]" *National Center for Biotechnology Information*. Apr. 2017.1 page.

Netzer, R., et al., "Ultrahigh specificity in a network of computationally designed protein interaction pairs." *Nature communications*, 2018. 9(1): p. 1-13.

Neubauer et al. "Lipid remodeling in Rhodopseudomonas palustris TIE-1 upon loss of hopanoids and hopanoid methylation" *Geobiology, John Wiley & Sons Ltd*. 2015. Vol. 13, No. 5. pp 1-11. 11 pages.

Newman D.K., et al., "A Role for Excreted Quinones in Extracellular Electron Transfer," Nature, May 2000, vol. 405 (6782), 4 pages.

(56) References Cited

OTHER PUBLICATIONS

Newman D.K., et al., "A Role for Excreted Quinones in Extracellular Electron Transfer," Nature, May 2000, vol. 405 (6782), 4 pages.
Non-Final Office Action for U.S. Appl. No. 12/548,362. Mail Date: Aug. 28, 2014, 9 pages.
Non-Final Office Action for U.S. Appl. No. 12/548,362. Mail Date: Mar. 27, 2012, 7 pages.
Non-Final Office Action for U.S. Appl. No. 13/456,172, filed Apr. 25, 2012. Mail Date: Mar. 10, 2017. 21 pages.
Non-Final Office Action for U.S. Appl. No. 13/456,172, filed Apr. 25, 2012. Mail Date: May 31, 2016. 28 pages.
Non-Final Office Action for U.S. Appl. No. 13/456,172. Mail Date: Mar. 23, 2015, 25 pages.
Non-Final Office Action for U.S. Appl. No. 13/456,172. Mail Date: Nov. 18, 2013, 31 pages.
Non-Final Office Action for U.S. Appl. No. 14/830,673, filed Aug. 19, 2015, on behalf of California Institute of Technology. Mail Date: Oct. 15, 2018. 18 pgs.
Non-Final Office Action for U.S. Appl. No. 14/830,673, filed Aug. 19, 2015, on behalf of California Institute of Technology. Mail Date: Aug. 8, 2017.13 pgs.
Non-Final Office Action for U.S. Appl. No. 15/394,138, filed Dec. 29, 2016, on behalf of California Institute of Technology. Mail Date: Sep. 16, 2021. 11 Pages.
Non-Final Office Action for U.S. Appl. No. 15/394,138, filed Dec. 29, 2016 on behalf of California Institute of Technology. Mail Date: Apr. 2, 2019. 5 pages.
Non-Final Office Action for U.S. Appl. No. 15/466,839, filed Mar. 22, 2017, on behalf of California Institute of Technology. Mail Date: Dec. 11, 2018. 34 pages.
Non-Final Office Action for U.S. Appl. No. 16/885,131, filed May 27, 2020 on behalf of California Institute of Technology Mail Date: Sep. 2, 2022 18 pages.
Non-Final Office Action for U.S. Appl. No. 15/394,138, filed Dec. 29, 2016 on behalf of California Institute of Technology. Mail Date: Nov. 13, 2019.23 pages.
Non-Final Office Action for U.S. Appl. No. 15/420,022, filed Jan. 30, 2017 on behalf of California Institute of Technology. Mail Date: Aug. 6, 2019.17 pages.
Non-Final Office Action issued for U.S. Appl. No. 12/548,362, filed Aug. 26, 2009 on behalf of California Institute of Technology. Mail Date: Jun. 29, 2016. 10 pages.
Norman et al. "Effect of Pyocyanin on a Crude-Oil-Degrading Microbial Community" *Applied and Environmental Microbiology, American Society for Microbiology*. Jul. 2004. vol. 70, No. 7. pp. 4004-4011. 8 pages.
Nosanchuk J., et al., "The Contribution of Melanin to Microbial Pathogenesis," Cellular Microbiology, Apr. 2003, vol. 5 (4), 21 pages.
Notice of Allowance for U.S. Appl. No. 13/456,172, filed Apr. 25, 2012. Mail Date: Aug. 29, 2017. 9 pages.
Notice of Allowance for U.S. Appl. No. 14/830,673, filed Aug. 19, 2015 on behalf of California Institute of Technology Mail Date: Apr. 19, 2019 29 pages.
Notice of Allowance for U.S. Appl. No. 15/420,022, filed Jan. 30, 2017 on behalf of California Institute of Technology. Mail date: Feb. 24, 2020. 23 pages.
Notice of Allowance for U.S. Appl. No. 15/466,839, filed Mar. 22, 2017 on behalf of California Institute of Technology. Mail Date: Jan. 21, 2020. 27 pages.
Notice of Allowance for U.S. Appl. No. 15/466,839, filed Mar. 22, 2017 on behalf of California Institute of Technology. Mail date: Oct. 10, 2019. 12 pages.
Notice of Allowance for U.S. Appl. No. 15/466,839, filed Mar. 22, 2017 on behalf of California Institute of Technology. Mail Date: Jun. 4, 2020. 11 Pages.
Ochsner U.A., et al., " Genetics and Regulation of Two Distinct Haem-uptake Systems, phu and has, in Pseudomonas Aeruginosa," Microbiology, Jan. 2000, vol. 146 (Pt 1), 14 pages.

O'Malley Y.Q., et al., "Pseudomonas Aeruginosa Pyocyanin Directly Oxidizes Glutathione and Decreases Its Levels in Airway Epithelial Cells," American Journal of Physiology Lung Cellular and Molecular Physiology, Jul. 2004, vol. 287 (1), 10 pages.
O'Malley Y.Q., et al., "The Pseudomonas Secretory Product Pyocyanin Inhibits Catalase Activity in Human Lung Epithelial Cells," American Journal of Physiology Lung Cellular and Molecular Physiology, Nov. 2003, vol. 285 (5), 11 pages.
O'May C.Y., et al., "Iron-Binding Compounds Impair Pseudomonas Aeruginosa Biofilm Formation, Especially Under Anaerobic Conditions," Journal of Medical Microbiology, Jun. 2009, vol. 58 (Pt 6), 9 pages.
Orr-Weaver T.L., et al., "Yeast Recombination—The Association Between Double-strand Gap Repair and Crossing-Over," Proceedings of the National Academy of Sciences of the United States of America, Jul. 1983, vol. 80 (14), 5 pages.
O'Toole G.A., et al., "Flagellar and Twitching Motility are Necessary for Pseudomonas Aeruginosa Biofilm Development," Molecular Microbiology, Oct. 1998, vol. 30 (2), 10 pages.
O'Toole G.A., et al., "Genetic Approaches to Study of Biofilms," Methods in Enzymology, 1999, vol. 310, 19 pages. O'Toole, G.A., "Microtiter dish biofilm formation assay." Journal of visualized experiments: JOVE, 2011(47).
O'Toole, G.A., "Microtiter dish biofilm formation assay." *Journal of visualized experiments, JoVE*, 2011(47).
O'Toole, George A. "To Build a Biofilm" *Journal of Bacteriology, American Society for Microbiology*. May 2003. vol. 185, No. 9. pp. 2687-2689. 3 pages.
Padilla et al. "A statistic for local intensity differences: robustness to anisotropy and pseudo-centering and utility for detecting twinning" *Acta Crystallographica Section D—Biological Crystallography, International Union of Crystallography*. 2003. vol. D59. pp. 1124-1130. 7 pages.
Palma M., et al., "Pseudomonas aeruginosa SoxR Does Not Conform to the Archetypal Paradignm for SoxR-Dependent Regulation of the Bacterial Oxidative Stress Adaptive Response," Infection And Immunity, May 2005, vol. 73 (5), 9 pages.
Palmer K.L., et al., "Cystic Fibrosis Sputum Supports Growth and Cues Key Aspects of Pseudomonas aeruginosa Physiology," Journal of Bacteriology, Aug. 2005, vol. 187 (15), 11 pages.
Palmer K.L., et al., "Nutritional Cues Control Pseudomonas aeruginosa Multicellular Behavior in Cystic Fibrosis Sputum," Journal of Bacteriology, Nov. 2007, vol. 189 (22), 10 pages.
Pamp S.J., et al., "Tolerance to the Antimicrobial Peptide Colistin in Pseudomonas Aeruginosa Biofilms is Linked to Metabolically Active Cells, and Depends on the Pmr and mexAB-oprM Genes," Molecular Microbiology, Apr. 2008, vol. 68 (1), 18 pages.
Panter S.S., "Release of Iron from Hemoglobin," Methods in Enzymology, Feb. 1994, vol. 231, 13 pages.
Pao S.S., et al., "Major Facilitator Superfamily," Microbiology and Molecular Biology Reviews, Mar. 1998, vol. 62 (1), 35 pages.
Park W., et al., "Regulation of Superoxide Stress in Pseudomonas Putida KT2440 Is Different From the SoxR Paradigm in *Escherichia coli*," Biochemical and Biophysical Research Communications, Mar. 2006, vol. 341(1), 6 pages.
Parsons et al. "Structural and Functional Analysis of the Pyocyanin Biosynthetic Protein PhzM from Pseudomonas aeruginosa" *Biochemistry, American Chemical Society*. Feb. 20, 2007. vol. 46, No. 7. pp. 1821-1828. 20 pages.
Parsons J.F., et al., "Structure of the Phenazine Biosynthesis Enzyme PhzG," Acta crystallographica, Section D, Biological crystallography, Nov. 2004, vol. 60 (Pt 11), 4 pages.
Patriquin G.M., et al., "Influence of Quorum Sensing and Iron on Twitching Motility and Biofilm Formation in Pseudomonas Aeruginosa," Journal of Bacteriology, Jan. 2008, vol. 190 (2), 11 pages.
Pearson et al. "Improved Tools for Biological Sequence Comparison" *Proceedings of the National Academy of Sciences, National Academy of Sciences*. Apr. 15, 1988. vol. 85, No. 8. pp. 2444-2448. 6 pages.
Pearson, William R. "Searching Protein Sequence Libraries: Comparison to the Sensitivity and Selectivity of the Smith-Waterman and FASTA Algorithms" *Genomics, Academic Press Inc*. 1991. vol. 11. pp. 635-650. 16 pages.

(56) References Cited

OTHER PUBLICATIONS

Pezzulo A., et al., "Reduced Airway Surface pH Impairs Bacterial Killing in the Porcine Cystic Fibrosis Lung," Nature, Jul. 2012, vol. 487 (7405), 7 pages.
Pierre J.L., et al., "Chemistry for an Essential Biological Process: The Reduction of Ferric Iron," Biometals, Dec. 2002, vol. 15 (4), 6 pages.
Pierson et al. "Metabolism and function of phenazines in bacteria: impacts on the behavior of bacteria in the environment and biotechnological processes" *Applied Microbiology and Biotechnology, Springer Science+Business Media*. 2010. vol. 86. pp. 1659-1670. 12 pages.
Pierson III, L.S. et al., "Molecular analysis of genes encoding phenazine biosynthesis in the biological control bacterium Pseudomonas aureofaciens 30-84", (Dec. 1995) FEMS Microbiol. Lett., vol. 134, Issue 2-3, pp. 299-307.
Pierson III, L.S., et al., "Phenazine Antibiotic Biosynthesis in Pseudomonas Aureofaciens 30-84 is Regulated by PhzR in Response to Cell Density," Journal of Bacteriology, Jul. 1994, vol. 176 (13), pp. 3966-3974. 10 pages.
Pillai B., et al., "Structural Insights Into Stereochemical Inversion by Diaminopimelate Epimerase: An Antibacterial Drug Target," Proceedings of the National Academy of Sciences of the United States of America, Jun. 2006, vol. 103 (23), 6 pages.
Pomposiello P.J., et al., "Identification of SoxS-Regulated Genes in *Salmonella enterica* Serovar Typhimurium," Journal of Bacteriology, Jan. 2000, vol. 182 (1), 7 pages.
Poole K., et al., "Iron Acquisition and Its Control in Pseudomonas Aeruginosa: Many Roads Lead to Rome," Frontiers in Bioscience, May 2003, vol. 8, 26 pages.
Price-Whelan A., et al., "Pyocyanin Alters Redox Homeostasis and Carbon Flux through Central Metabolic Pathways in Pseudomonas Aeruginosa PA14," Journal of Bacteriology, Sep. 2007, vol. 189 (17), 10 pages.
Price-Whelan A., et al., "Rethinking 'Secondary' Metabolism: Physiological Roles for Phenazine Antibiotics," Nature Chemical Biology, Feb. 2006, vol. 2 (2), 8 pages.
Price-Whelan et al. "Corrigendum: Rethinking "secondary" metabolism: physiological roles for phenazine antibiotics" *Nature Chemical Biology, Nature Publishing Group*. Apr. 2006. vol. 2, No. 4. pp. 221. 2 pages.
Printout from Merriam-Webster for the entry "selecting" as of Apr. 22, 2009. 1 page.
Printout from Merriam-Webster for the entry "selectivity" as of Apr. 22, 2009. 1 page.
Printout from Merriam-Webster for the entry "specificity" as of Apr. 22, 2009. 1 page.
Pseudomonas, Wikipedia entry retrieved on Mar. 23, 2020 from https://en.wikipedia.org/wiki/Pseudomonas. 12 Pages.
Aanaes K., et al., "Decreased Mucosal Oxygen Tension in the Maxillary Sinuses in Patients With Cystic Fibrosis," Journal of Cystic Fibrosis, Mar. 2011, vol. 10 (2), 7 pages.
Abdul Rahim S., et al., "Studies of Binary Complexes of Metal Ions with 2,2-Bipyridyl by Potentiometry," Chemical Science Transactions, 2015, vol. 4 (1), 5 pages.
Adams et al. "PHENIX: a comprehensive Python-based system for macromolecular Structure solution" *Acta Crystallographica Section D—Biological Crystallography, International Union of Crystallography*. 2010. vol. D66. pp. 213-221. 9 pages.
Aendekerk S., et al., "The MexGHI-OpmD Multidrug Efflux Pump Controls Growth, Antibiotic Susceptibility and Virulence in Pseudomonas Aeruginosa via 4-Quinolone-Dependent Cell-to-Cell Communication," Microbiology, Apr. 2005, vol. 151 (Pt 4), 13 pages.
Afonine et al. "Towards automated crystallographic structure refinement with phenix refine" *Acta Crystallographica Section D, International Union of Crystallography*. 2012. vol. D68. pp. 352-367. 16 pages.

Aisen P., "Transferrin, the Transferrin Receptor, and the Uptake of Iron by Cells," Metal Ions in Biological Systems, 1998, vol. 35, 47 pages.
Albrecht-Gary A.M., et al., "Bacterial Iron Transport-Coordination Properties of Pyoverdin PaA, a Peptidic Siderophore of Pseudomonas Aeruginosa," Inorganic Chemistry, 1994, vol. 33 (26), 12 pages.
Alibert-Franco et al., "Efflux Mechanism, an Attractive Target to Combat Multidrug Resistant Plasmodium Falciparum and Pseudomonas Aeruginosa," Current Medicinal Chemistry, 2009, vol. 16 (3), pp. 301-317. 17 pages.
Altschul et al. "Gapped BLAST and PSI-BLAST: a new generation of protein database search programs" *Nucleic Acids Research, Oxford University Press*, 1997. vol. 25, No. 17. pp. 3389-3402. 14 pages.
Alvarez-Ortega C., et al., "Responses of Pseudomonas Aeruginosa to Low Oxygen Indicate that Growth in the Cystic Fibrosis Lung is by Aerobic Respiration," Molecular microbiology, Jul. 2007, vol. 65 (1), 13 pages.
Amornrit W., et al., "Elevated Intracellular Levels of Iron in Host Cells Promotes Burkholderia Pseudomallei Infection," Asian Biomedicine, Jun. 2012, vol. 6 (3), 7 pages.
Anand et al. "Structure and Mechanism of Lysine-specific Demethylase Enzymes" *Journal of Biological Chemistry, The American Society for Biochemistry and Molecular Biology Inc*. Dec. 7, 2007. vol. 282, No. 49. pp. 35425-35429. 6 pages.
Anastacio, et al., "Limitations of the ferrozine method for quantitative assay of mineral systems for ferrous and total iron", Geochimica et Cosmochimica Acta, 2008, 72(20):p. 5001-5008.
Askoura M., et al., "Efflux Pump Inhibitors (EPIs) as New Antimicrobial Agents Against Pseudomonas Aeruginosa," The Libyan Journal of Medicine, May 2011, vol. 6, 8 pages.
Aslund F., et al., "Redox Potentials of Glutaredoxins and Other Thioldisulfide Oxidoreductases of the Thioredoxin Superfamily Determined by Direct Protein-Protein Redox Equilibria," The Journal of Biological Chemistry, Dec. 1997, vol. 272 (49), 7 pages.
Avery A.M., et al., "Iron Blocks the Accumulation and Activity of Tetracyclines in Bacteria," Antimicrobial Agents and Chemotherapy, May 2004, vol. 48 (5), pp. 1892-1894. 3 pages.
Babic F., et al., "Tobramycin at Subinhibitory Concentration Inhibits the RhlI/R Quorum Sensing System in a Pseudomonas Aeruginosa Environmental Isolate," BMC Infectious Diseases, 2010, vol. 10, 148. 12 pages.
Babin et al. "SutA is a bacterial transcription factor expressed during slow growth in Pseudomonas aeruginosa" *Proceedings of the National Academy of Sciences, National Academy of Sciences*. Jan. 19, 2016. vol. 113, No. 5. pp. E597-E605. 9 pages.
Baker E.N., et al., "Three-Dimensional Structure of Lactoferrin in Various Functional States," Advances in Experimental Medicine and Biology, 1994, vol. 357, 12 pages.
Ball J.W., et al., "A New Method for the Direct Determination of Dissolved Fe(III) Concentration in Acid Mine Waters," U.S. Geological Survey, 1999, 10 pages.
Bange et al. "Recovery of Mycobacteria from Patients with Cystic Fibrosis" *Journal of Clinical Microbiology, American Society for Microbiology*. Nov. 1999. vol. 37, No. 11. pp. 3761-3763. 3 pages.
Banin E., et al., "Chelator-Induced Dispersal and Killing of Pseudomonas Aeruginosa Cells in a Biofilm," Applied and Environmental Microbiology, Mar. 2006, vol. 72 (3), 6 pages.
Banin E., et al., "Iron and Pseudomonas Aeruginosa Biofilm Formation," Proceedings of the National Academy of Sciences of the United States of America, Aug. 2005, vol. 102 (31), p. 11076-11081. 6 pages.
Banin E., et al., "The Potential of Desferrioxamine-Gallium as an Anti-Pseudomonas Therapeutic Agent," Proceedings of the National Academy of Sciences of the United States of America, Oct. 2008, vol. 105 (43), 6 pages.
Bao Y., et al., "An Improved Tn7-Based System for the Single-Copy Insertion of Cloned Genes into Chromosomes of Gram-Negative Bacteria," Gene, Dec. 1991, vol. 109 (1), 2 pages.
Bard, A. J., and L. R. Faulkner. 2001. Electrochemical Methods: Fundamentals and Applications. 2nd Edition. John Wiley, New York. 850 pages.

(56) References Cited

OTHER PUBLICATIONS

Baron S.S., et al., "Antibiotic Action of Pyocyanin," Antimicrobial Agents and Chemotherapy, Dec. 1981, vol. 20 (6), 8 pages.

Baron S.S., et al., "Molecular Mechanism of the Antimicrobial Action of Pyocyanin," Current Microbiology, Apr. 1989, vol. 18 (4), 8 pages.

BARUA p. K., et al., "Effect of Iron Limitation on Bacteroids Gingivalis," Oral Microbiology and Immunology, Oct. 1990, vol. 5 (5), pp. 263-268. 8 pages.

Bashiri et al. "Production of recombinant proteins in Mycobacterium smegmatis for structural and functional studies" Protein Science, The Protein Society. 2015. vol. 24, No. 1. pp. 1-10. 10 pages.

Baudin A., et al., "A Simple and Efficient Method for Direct Gene Deletion in Saccharomyces Cerevisiae," Nucleic Acids Research, Jul. 1993, vol. 21 (14), 2 pages.

Baxendale, et al., "Equilibria in solutions of ferrous ions and aa-dipyridyl", Aug. 15, 1949, pp. 55-63.

Baxendale J.H., et al., "The Kinetics of Formation and Dissociation of the Ferrous Trisdipyridyl lon," Transactions of the Faraday Society, 1950, vol. 46, 9 pages.

Baynes R. D., et al., "Effects of Ferrous and Ferric Chelators on Transferrin-Iron-Macrophage Interactions," American Journal of Hematology, Sep. 1988, vol. 29 (1), pp. 27-32. Abstract only, 1 page.

Beifuss U., et al., "Methanophenazine and Other Natural Biologically Active Phenazines," Part of the Topics in Current Chemistry Book Series, Natural Products Synthesis II, Jan. 2005, vol. 244, 37 pages.

Bellin, D.L., et al., "Electrochemical camera chip for simultaneous imaging of multiple metabolites in biofilms." Nature communications, 2016. 7(1): p. 1-10.

Benz M., et al., "Humic Acid Reduction by Propionibacterium freudenreichii and Other Fermenting Bacteria," Applied and Environmental Microbiology, Dec. 1998, vol. 64 (11), 7 pages.

Berardinis V., et al., "A Complete Collection of Single-Gene Deletion Mutants of Acinetobacter Baylyi ADP1," Molecular Systems Biology, 2008, vol. 4, article 174, 15 pages.

Berlutti F., et al., "Iron Availability Influences Aggregation, Biofilm, Adhesion and Invasion of Pseudomonas Aeruginosa and Burkholderia Cenocepacia," International Journal of Immunopathology and Pharmacology, Oct.-Dec. 2005, vol. 18 (4), 10 pages.

Bernofsky C., et al., "An Improved Cycling Assay for Nicotinamide Adenine Dinucleotide," Analytical Biochemistry, Jun. 1973, vol. 53 (2), 7 pages.

Bessette P. H., et al., "Efficient Folding of Proteins With Multiple Disulfide Bonds in the Escherichia coli Cytoplasm," Proceedings of the National Academy of Sciences of the United States of America, Nov. 1999, vol. 96 (24), 6 pages.

Binding selectivity, Wikipedia, Retrieved from "http://en.wikipedia.org/wiki/Binding selectivity" Feb. 13, 2012, 4 pages.

Bjarnsholt et al. "Pseudomonas aeruginosa tolerance to tobramycin, hydrogen peroxide and polymorphonuclear leukocytes is quorum-sensing dependent" Microbiology, Microbiological Society. 2005. vol. 151. pp. 373-383. 11 pages.

Bjarnsholt et al. "The in-vivo biofilm" Trends in Microbiology, Cell Press. Sep. 2013.vol. 21, No. 9. pp. 466-474. 9 pages.

Bjarnsholt T., et al., "Pseudomonas Aeruginosa Biofilms in the Respiratory Tract of Cystic Fibrosis Patients," Pediatric Pulmonology, Jun. 2009, vol. 44 (6), 12 pages.

Bland J.M., et al., "Calculating Correlation Coefficients With Repeated Obsverations: Part 2-correlation Between Subjects," BMJ (Clinical research ed.), Mar. 1995, vol. 310 (6980), 1 page.

Blankenfeldt W., et al., "Structure and Function of the Phenazine Biosynthetic Protein PhzF From Pseudomonas Fluorescens," Proceedings of the National Academy of Sciences of the United States of America, Nov. 2004, vol. 101 (47), 6 pages.

Blommel, P. G., et al., "Enhanced bacterial protein expression during auto-induction obtained by alteration of lac repressor dosage and medium composition." Biotechnology progress, 2007. 23(3): p. 585-598.

Bolte et al. "A guided tour into subcellular colocalization analysis in light microscopy. " Journal of Microscopy, The Royal Microscopical Society. Dec. 2006. vol. 224 (Pt 3). pp. 213-232. 20 pages.

Borriello et al. "Oxygen Limitation Contributes to Antibiotic Tolerance of Pseudomonas aeruginosa in Biolfilms" Antimicrobial Agents and Chemotherapy, American Society for Microbiology. Jul. 2004. vol. 48, No. 7. pp. 2659-2664. 6 pages.

Bouchara J.P., et al., "Development of an Oligonucleotide Array for Direct Detection of Fungi in Sputum Samples From Patients With Cystic Fibrosis," Journal of Clinical Microbiology, Jan. 2009, vol. 47 (1), 11 pages.

Boyer E., et al., "Acquisition of Mn(II) in Addition to Fe(II) Is Required for Full Virulence of Salmonella Enterica Serovar Typhimurium," Infection and Immunity, Nov. 2002, vol. 70 (11), 11 pages.

Bradford et al. "A Rapid and Sensitive Method for the Quantitation of Microgram Quantities of Protein Utilizing the Principle of Protein-Dye Binding" Analytical Biochemistry, Academic Press Inc. 1976. vol. 72. pp. 248-254. 7 pages.

Brandon et al. "The determination of the stability constant for the iron(II) complex of the biochelator pyridine-2,6-bis(monothiocarboxylic acid) " Biodegradation, Kluwer Academic Publishers. 2003. vol. 14. pp. 73-82. 10 pages.

Breuer W., et al., "Iron Acquired From Transferrin by K562 Cells Is Delivered Into a Cytoplasmic Pool of Chelatable Iron(II)," The Journal of Biological Chemistry, Oct. 1995, vol. 270 (41), 8 pages.

Briard et al. "Pseudomonas aeruginosa manipulates redox and iron homeostasis of its microbiota partner Aspergillus fumigatus via phenazines" Scientific Reports, Nature Publishing Group. Feb. 10, 2015. vol. 5, No. 8220. pp. 1-13. 13 pages.

Brickman T.J., et al., "Differential Expression of Bordetella Pertussis Iron Transport System Genes During Infection," Molecular Microbiology, Oct. 2008, vol. 70 (1), 12 pages.

Brickman T.J., et al., "Iron and ph-responsive FtrABCD Ferrous Iron Utilization System of Bordetella Species," Molecular Microbiology, Nov. 2012, vol. 86 (3), 14 pages.

Brown C.T., et al., "Evolutionary Comparisons Suggest Many Novel cAMP Response Protein Binding Sites in Escherichia coli," Proceedings of the National Academy of Sciences of the United States of America, Feb. 2004, vol. 101 (8), 6 pages.

Brown J.X., et al., "Identification of Small Molecule Inhibitors that Distinguish Between Non-transferrin Bound Iron Uptake and Transferrin-mediated Iron Transport," Chemistry & Biology, Mar. 2004, vol. 11 (3), 10 pages.

Buckett P.D., et al., "Small Molecule Inhibitors of Divalent Metal Transporter-1," American Journal of Physiology Gastrointestinal and Liver Physiology, Apr. 2009, vol. 296 (4), 8 pages.

Bultreys A., et al., "High-Performance Liquid Chromatography Analyses of Pyoverdin Siderophores Differentiate Among Phytopathogenic Fluorescent Pseudomonas Species," Applied and Environmental Microbiology, Feb. 2003, vol. 69 (2), 12 pages.

Bunik V.I., et al., "Inactivation of the 2-oxo Acid Dehydrogenase Complexes Upon Generation of Intrinsic Radical Species," European Journal of Biochemistry, Oct. 2002, vol. 269 (20), 12 pages.

Bus J.S., et al., "Paraquat: Model for Oxidant-initiated Toxicity," Environmental Health Perspectives, Apr. 1984, vol. 55, 10 pages.

Byng G.S., et al., "Biosynthesis of Phenazine Pigments in Mutant and Wildtype Cultures of Pseudomonas Aeruginosa," Journal of Bacteriology, Jun. 1979, vol. 138 (3), 8 pages.

Carrell T., et al., "A Solution-Phase Screening Procedure for the Isolation of Active Compounds from a Library of Molecules," Angewandte Chemie International Edition in English, Nov. 1994, vol. 33 (20), 4 pages.

Cartron M.L., et al., "Feo-Transport of Ferrous Iron Into Bacteria," Biometals, Apr. 2006, vol. 19, 15 pages.

Chang P. C., et al., "Simultaneous Production of Three Phenazine Pigments by Pseudomonas Aeruginosa Mac 436," Canadian Journal of Microbiology, May 1969, vol. 15 (5), pp. 439-444. 6 pages.

Chater K.F., "Streptomyces Inside-out: A New Perspective on the Bacteria that Provide us with Antibiotics," Philosophical Transactions of the Royal Society of London. Series B, Biological Sciences, May 2006, vol. 361 (1469), 8 pages.

(56) References Cited

OTHER PUBLICATIONS

Chatfield C.H., et al., "The Secreted Pyomelanin Pigment of Legionella pneumophila Confers Ferric Reductase Activity," Infection and Immunity, Aug. 2007, vol. 75 (8), 10 pages.

Cheluvappa, R., "Standardized chemical synthesis of Pseudomonas aeruginosa pyocyanin." MethodsX, 2014. 1: p. 67-73.

Chen K., et al., "Metabolic Degradation of Phenazine-1-Carboxylic Acid by the Strain *Sphingomonas* sp. DP58: The Identification of Two Metabolites," Biodegradation, Sep. 2008, vol. 19 (5), 9 pages.

Chen X., et al., "Role of Electrostatic Interactions in Cohesion of Bacterial Biofilms," Applied Microbiology and Biotechnology, Sep. 2002, vol. 59 (6), 3 pages.

Chin-A-Woeng, T.F.C et al., "Introduction of the phzH gene of Pseudomonas chlororaphis PCL1391 extends the range of biocontrol ability of phenazine-1-carboxylic acid-producing *Pseudomonas* spp. Strains", (2001) Mol. Plant-Microbe Interact., vol. 14, No. 8, pp. 1006-1015.

Cho C.Y., et al., "An Unnatural Biopolymer," Science, Sep. 1993, vol. 261 (5126), 3 pages.

Choi H.M.T., et al., "Programmable in Situ Amplification for Multiplexed Imaging of mRNA Expression," Nature Biotechnology, 2010, vol. 28 (11), 7 pages.

CLARK Jr., L.C., et al., "Continuous Recording of Blood Oxygen Tensions by Polarography," Journal of Applied Physiology, Sep. 1953, vol. 6 (3), 5 pages.

Cloos et al. "Erasing the methyl mark: histone demethylases at the center of cellular differentiation and disease" *Genes and Development, Cold Spring Harbor Laboratory Press.* 2008. vol. 22. pp. 1115-1140. 27 pages.

Cohen et al. "Oligoribonuclease is a central feature of cyclic diguanylate signaling in Pseudomonas aeruginosa" *Proceedings of the National Academy of Sciences, National Academy of Sciences.* Sep. 8, 2015. vol. 112, No. 36. pp. 11359-11364. 6 pages.

Notice of Allowance for U.S. Appl. No. 15/466,839, filed Mar. 22, 2017 on behalf of California Institute of Technology. Mail Date: Sep. 11, 2020. 8 Pages.

Aisen P., Leibman A. 1968; "The stability constant of the Fe3+ conalbumin complexes". Biochemical and Biophysical Research Communications, vol. 30, No. 4:407-413.

Angehrn, Peter, et al. "New antibacterial agents derived from the DNA gyrase inhibitor cyclothialidine." Journal of medicinal chemistry, vol. 47, No. 6 (2004): 1487-1513.

Danzer, K., "Selectivity and specificity in analytical chemistry. General considerations and attempt of a definition and quantification," Fresenius J Anal Chem 369, pp. 397-402. Mar. 2001. Website: doi.org/10.1007/s002160000684.

He, Ze, and Michael D. Toney. "Direct detection and kinetic analysis of covalent Intermediate formation in the 4-amino-4-deoxychorismate synthase catalyzed reaction." Biochemistry 45.15 (2006): 5019-5028.

Hedstrom, L., "Enzyme Specificity and Selectivity," In eLS, (Ed.). Feb. 15, 2010. 8 pages. Website: doi.org/10.1002/9780470015902. a0000716.pub2.

International Preliminary Report on Patentability for International PCT Application No. PCT/US2021/058275 filed on Nov. 5, 2021, on behalf of California Institute of Technology. Mail Date: May 19, 2023. 7 Pages.

Lam K.S., et al., "A New Type of Synthetic Peptide Library for Identifying Ligand-binding Activity," Nature, Nov. 7, 1991, vol. 354 (6348), pp. 82-84.

Levin, Anna S., et al. "Intravenous colistin as therapy for nosocomial infections caused by multidrug-resistant Pseudomonas aeruginosa and Acinetobacter baumannii." Clinical Infectious Diseases 28.5 (1999): 1008-1011.

Non-Final Office Action for U.S. Appl. No. 15/394,138, filed Dec. 29, 2016 on behalf of California Institute of Technology et al. Mailing date Jun. 16, 2023. 41 pages.

Non-Final Office Action for U.S. Appl. No. 17/027,587, filed Sep. 21, 2020 on behalf of California Institute of Technology. Mailed on May 8, 2023. 31 pages.

Non-Final Office Action issued by the USPTO for U.S. Appl. No. 15/394,138, mailing date Nov. 10, 2022, 15 pages.

Notice of Allowance for U.S. Appl. No. 15/394,138, filed Dec. 29, 2016 on behalf of California Institute of Technology et al. Mailing date Apr. 4, 2023. 9 pages.

Notice of Allowance for U.S. Appl. No. 16/885,131, filed May 27, 2020 on behalf of California Institute of Technology. Mail Date: Jul. 25, 2023. 8 pages.

Notice of Allowance for U.S. Appl. No. 16/885,131, filed May 27, 2020 on behalf of California Institute of Technology. Mail Date: Mar. 27, 2023. 20 pages.

Notification of Reopening of Prosecution Due to Consideration of an Information Disclosure Statement Filed After Mailing of a Notice of Allowance for U.S. Appl. No. 15/394,138, filed Dec. 29, 2016 on behalf of California Institute of Technology et al. Mailing date May 16, 2023. 4 pages.

Ohara, Hiroshi, and Toyozo Terasima. "Lethal effect of mitomycin-C on cultured mammalian cells." GANN Japanese Journal of Cancer Research 63.3 (Jun. 1972): 317-327.

Printout of Merriam Webster's definition of "disrupt" 2005 (1 pg). Downloaded through the Wayback Machine.

Rabaey K., et al., "Microbial Phenazine Production Enhances Electron Transfer in Biofuel Cells," Environmental Science and Technology, May 2005, vol. 39 (9), 8 pages.

Rahme L.G., et al., "Common Virulence Factors for Bacterial Pathogenicity in Plants and Animals," Science, Jun. 1995, vol. 268 (5219), 4 pages.

Rajan S., et al., "Pulmonary Infections in Patients with Cystic Fibrosis," Seminars in Respiratory Infections, Mar. 2002, vol. 17 (1), 10 pages.

Raman et al. "Structure prediction for CASP8 with all-atom refinement using Rosetta" Proteins, Wiley-Liss Inc. 2009. Vol. 77. pp 89-99. 11 pages.

Ramos I et al., "Phenazines Affect Biofilm Formation by Pseudomonas Aeruginosa in Similar Ways at Various Scales," Research Microbiology, Apr. 2010, vol. 161 (3), 5 pages.

Ran H., et al., "Human Targets of Pseudomonas Aeruginosa Pyocyanin," Proceedings of the National Academy of Sciences of the United States of America, Nov. 2003, vol. 100 (24), 6 pages.

Rashid M.H., et al., "Inorganic Polyphosphate is needed for Swimming, Swarming, and Twitching Motilities of Pseudomonas Aeruginosa," Proceedings of the National Academy of Sciences of the United States of America, Apr. 25, 2000, vol. 97(9), 6 pages.

Ratledge C., et al., "Iron Metabolism in Pathogenic Bacteria," Annual Review of Microbiology, 2000, vol. 54, 70 pages.

Recinos D.A., et al., "Redundant Phenazine Operons in Pseudomonas Aeruginosa Exhibit Environment-Dependent Expression and Differential Roles in Pathogenicity," Proceedings of the National Academy of Sciences of the United States of America, Nov. 20, 2012, vol. 109(47), 21 pages.

Reid D.W., et al., "Increased Airway Iron as a Potential Factor in the Persistence of Pseudomonas Aeruginosa Infection in Cystic Fibrosis," The European Respiratory Journal, Aug. 2007, vol. 30 (2), 7 pages.

Reid D.W., et al., "Iron Chelation Directed against Biofilms as an Adjunct to Conventional Antibiotics," American Journal of Physiology-Lung Cellular and Molecular Physiology, Apr. 28, 2009, vol. 296(5), L857-L858. 2 pages.

Reid D.W., et al., "Role of Lung Iron in Determining the Bacterial and Host Struggle in Cystic Fibrosis," American Journal of Physiology Lung Cellular and Molecular Physiology, Nov. 2009, vol. 297 (5), 9 pages.

Reimmann C., et al., "Dihydroaeruginoic Acid Synthetase and Pyochelin Synthetase, Products of the pchEF Genes, are Induced by Extracellular Pyochelin in Pseudomonas Aeruginosa," Microbiology, Nov. 1998, vol. 144 ( Pt 11), 14 pages.

Reimmann, C. et al., "The global activator GacA of Pseudomonas aeruginosa PAO positively controls the production of the autoinducer N-butryryl-homoserine lactone and the formation of the virulence factors pyocyanin, cyanide, and lipase", Molecular Microbiology (1997), 24(2), 309-319.

(56) References Cited

OTHER PUBLICATIONS

Response to Rule 312 Communication for U.S. Appl. No. 16/885,131, filed May 27, 2020 on behalf of California Institute of Technology. Mail Date: Jun. 13, 2023. 2 pages.
Response to Rule 312 Communication for U.S. Appl. No. 16/885,131, filed May 27, 2020 on behalf of California Institute of Technology Mail Date: May 5, 2023. 3 pages.
Restriction Requirement for U.S. Appl. No. 12/548,362. Mail Date: Nov. 29, 2011, 6 pages.
Restriction Requirement for U.S. Appl. No. 13/456,172, filed Apr. 25, 2012. Mail Date: Feb. 12, 2013, 10 pages.
Restriction Requirement for U.S. Appl. No. 15/394,138, filed Dec. 29, 2016, on behalf of the California Institute of Technology. Mail Date: Oct. 1, 2018. 5 pgs.
Restriction Requirement for U.S. Appl. No. 15/420,022, filed Jan. 30, 2017, on behalf of California Institute of Technology. Mail Date: Mar. 13, 2019. 8 pages.
Restriction Requirement for U.S. Appl. No. 15/466,839, filed Mar. 22, 2017, on behalf of California Institute of Technology. Mail Date: May 1, 2018. 10 pages.
Restriction Requirement for U.S. Appl. No. 14/830,673, filed Aug. 19, 2015 on behalf of California Institute of Technology Mail Date: Jan. 4, 2017. 7 pages.
Restriction Requirement issued by the USPTO for U.S. Appl. No. 17/027,587, mailing date Jan. 12, 2023, 9 pages.
Reszka K.J. et al., "Oxidation of Pyocyanin, a Cytotoxic Product from Pseudomonas Aeruginosa, by Microperoxidase 11 and Hydrogen Peroxide," Free Radical Biology and Medicine, Jun. 1, 2004, vol. 36(11), 12 pages.
Ribeiro C.C., et al., "The Effect of Iron on *Streptococcus mutans* Biofilm and on Enamel Demineralization," Brazilian Oral Research, Jul.-Aug. 2012, vol. 26(4), 6 pages.
Robey M., et al., "Legionella Pneumophila feoAB Promotes Ferrous Iron Uptake and Intracellular Infection," Infection & Immunity, Oct. 2002, vol. 70(10), 11 pages.
Rocha E.R., et al., "Effect of Ferric and Ferrous Iron Chelators on Growth of Bacteroides Fragilis under Anaerobic Conditions," FEMS Microbiology Letters, Nov. 1, 1991, vol. 84, pp. 45-50. 6 pages.
Rogan M.P., et al., "Loss of Microbicidal Activity and Increased Formation of Biofilm due to Decreased Lactoferrin Activity in Patients with Cystic Fibrosis," Journal of Infectious Diseases, Oct. 1, 2004, vol. 190(7), 10 pages.
Rogers G.B., et al., "Studying Bacterial Infections Through Culture-independent Approaches," Journal of Medical Microbiology, Nov. 2009, vol. 58 (Pt 11), 18 pages.
Rozen S., et al., "Primer3 on the WWW for General Users and for Biologist Programmers," Methods in Molecular Biology, 2000, vol. 132, 22 pages.
Ruby E.G., et al., "Pyruvate Production and Excretion by the Luminous Marine Bacteria," Applied and Environmental Microbiology, Aug. 1977, vol. 34(2), 7 pages.
Ruddy, J., et al., "Sputum tobramycin concentrations in cystic fibrosis patients with repeated administration of inhaled tobramycin." Journal of aerosol medicine and pulmonary drug delivery, 2013. 26(2): p. 69-75.
Ruiz et al. "Relationship between Clinical and Environmental Isolates of Pseudomonas aeruginosa in a Hospital Setting" Archives of Medical Research, Elsevier. 2004. vol. 35. pp. 251-257. 7 pages.
San K.Y., et al., "Metabolic Engineering through Cofactor Manipulation and its Effects on Metabolic Flux Redistribution in *Escherichia coli*," Metabolic Engineering, Apr. 2002, vol. 4(2), 11 pages.
Saunders, S.H., et al., "Extracellular DNA promotes efficient extracellular electron transfer by pyocyanin in Pseudomonas aeruginosa biofilms." Cell, 2020. 182(4): p. 919-932. e19.
Schalk I.J., "Metal Trafficking via Siderophores in Gram-Negative Bacteria: Specificities and Characteristics of the Pyoverdine Pathway," Journal of Inorganic Biochemistry, May-Jun. 2008, vol. 102(5-6), 11 pages.

Schiessl, K.T., et al., "Phenazine production promotes antibiotic tolerance and metabolic heterogeneity in Pseudomonas aeruginosa biofilms." Nature communications, 2019. 10(1): p. 1-10.
Schneider et al. "NIH Image to ImageJ: 25 years of Image Analysis" Natural Methods, Nature Publishing Group. Jul. 2012. Vol. 9, No. 7. pp 671-675. 12 pages.
Schneider T.L., et al., "Portability of Oxidase Domains in Nonribosomal Peptide Synthetase Modules," Biochemistry, Dec. 21, 2004, vol. 43(50), 10 pages.
Schreiber K., et al., "Anaerobic Survival of Pseudomonas Aeruginosa by Pyruvate Fermentation Requires an Usp-type Stress Protein," Journal of Bacteriology, Jan. 2006, vol. 188(2), 11 pages.
Scott J.K., et al., "Searching for Peptide Ligands with an Epitope Library," Science, Jul. 27, 1990, vol. 249(4967), 5 pages.
Saenz Y., et al., "Effect of the Efflux Pump Inhibitor Phe-Arg-beta-naphthylamide on the MIC Values of the Quinolones, Tetracycline and Chloramphenicol, in *Escherichia coli* Isolates of Different Origin," Journal of Antimicrobial Chemotherapy, Feb. 4, 2004, vol. 53(3), 2 pages.
Sezonov, G., D. Joseleau-Petit, and R. d'Ari, "*Escherichia coli* physiology in Luria-Bertani broth." Journal of bacteriology, 2007. 189(23): p. 8746-8749.
Shanks R.M.Q., et al., "*Saccharomyces cerevisiae*-Based Molecular Tool Kit for Manipulation of Genes from Gram-Negative Bacteria," Applied and Environmental Microbiology, Jul. 2006, vol. 72 (7), 11 pages.
Shapiro J.A., "The Use of Mudlac Transposons as Tools for Vital Staining to Visualize Clonal and Non-clonal Patterns of Organization in Bacterial Growth on Agar Surfaces," Journal of General Microbiology, May 1984, vol. 130 (5), 13 pages.
Shih et al. "Self-cleavage of fusion protein in vivo using TEV protease to yield native protein" Protein Science, Cold Spring Harbor Laboratory Press. 2005. vol. 14. pp. 936-941. 6 pages.
Shyu et al. "Protective Role of tolC in Efflux of the Electron Shuttle Anthraquinone-2, 6-Disulfonate" Journal of Bacteriology, American Society for Microbiology. Mar. 2002. vol. 184, No. 6. pp. 1806-1810. 5 pages.
Sikora A.L., et al., "Kinetic and Inhibition Studies of Dihydroxybenzoate-AMP Ligase from *Escherichia coli*," Biochemistry, May 2010, vol. 49 (17), 28 pages.
Singh P.K., et al., "A Component of Innate Immunity Prevents Bacterial Biofilm Development," Nature, May 2002, vol. 417 (6888), 4 pages.
Singh P.K., et al., "Quorum-sensing Signals Indicate That Cystic Fibrosis Lungs Are Infected with Bacterial Biofilms," Nature, Oct. 2000, vol. 407 (6805), 762-764. 3 pages.
Singh P.K., "Iron Sequestration by Human Lactoferrin Stimulates P. Aeruginosa Surface Motility and Blocks Biofilm Formation," Biometals, Jun. 2004, vol. 17 (3), 4 pages.
Skaar E.P., "The Battle for Iron Between Bacterial Pathogens and Their Vertebrate Hosts," PLoS Pathogens, Aug. 2010, vol. 6 (8), 4 pages.
Smith E.E., et al., "Genetic Adaptation by Pseudomonas Aeruginosa to the Airways of Cystic Fibrosis Patients," Proceedings of the National Academy of Sciences of the United States of America, May 2006, vol. 103 (22), 6 pages.
Smith et al. "Identification of Common Molecular Subsequences" Journal of Molecular Biology, Academic Press Inc. 1981. Vol. 147. pp 195-197. 4 pages.
Song et al. "High-Resolution Comparative Modeling with RosettaCM" Structure, Cell Press. Oct. 8, 2013. vol. 21. pp. 1735-1742. 8 pages.
Spero, M.A. and D.K. Newman, "Chlorate specifically targets oxidant-starved, antibiotictolerant populations of Pseudomonas aeruginosa biofilms." MBio, 2018. 9(5): p. e01400-18.
Staab J.F., et al., "EntG Activity of Escherichia coli Enterobactin Synthetase," Journal of Bacteriology, Nov. 1990, vol. 172 (11), 8 pages.
Stams A.J., et al., "Exocellular Electron Transfer in Anaerobic Microbial Communities," Environmental Microbiology, Mar. 2006, vol. 8 (3), 12 pages.

(56) References Cited

OTHER PUBLICATIONS

Steele K., et al., "Characterization of a Ferrous Iron-Responsive Two-Component System in Nontypeable Haemophilus Influenzae," Journal of Bacteriology, Nov. 2012, vol. 194 (22), 12 pages.

Stewart, Philip S. "Biofilm Accumulation Model That Predicts Antibiotic Resistance of Pseudomonas aeruginosa Biofilms" Antimicrobial Agents and Chemotherapy, American Society for Microbiology. May 1994. Vol. 38, No. 5. pp 1052-1058. 7 pages.

Stewart, P.S., "Diffusion in biofilms." Journal of bacteriology, 2003. 185(5): p. 1485-1491.

Stewart-Tull D.E., et al., "The Effect of 1-Hydroxyphenazine and Pyocyanin From Pseudomonas Aeruginosa on Mammalian Cell Respiration," Journal of Medical Microbiology, 1971, vol. 5 (1), 7 pages.

Stites S.W., et al., "Increased Iron and Ferrition Content of Sputum from Patients with Cystic Fibrosis or Chronic Bronchitis," Clinical Investigations, Sep. 1998, vol. 114 (3), 6 pages.

Stookey L.L., et al., "Ferrozine-a New Spectrophotometric Reagent for Iron," Analytical Chemistry, Jun. 1970, vol. 42 (7), 3 pages.

Studer, R.A. et al. Review Article: Residue mutations and their impact on protein structure and function: detecting beneficial and pathogenic changes. Biochem J. (2013) 449, 581-594.

Studier et al. "Use of Bacteriophage T7 RNA Polymerase to Direct Selective High-level Expression of Cloned Genes" Journal of Molecular Biology, Academic Press Inc. 1986. vol. 189. pp 113-130. 18 pages.

Su J.H., et al., "Ferrous Iron-binding Protein Omb of *Salmonella enterica* Serovar Choleraesuis Promotes Resistance to Hydrophobic Antibiotics and Contributes to Its Virulence," Microbiology, Jul. 2009, vol. 155 (Pt 7), 10 pages.

Sullivan N.L., et al., "Quantifying the Dynamics of Bacterial Secondary Metabolites by Spectral Multi photon Microscopy," ACS Chemical Biology, Sep. 2011, vol. 6 (9), 7 pages.

Summers et al. "Novel, Highly Specific N-Demethylases Enable Bacteria To Live on Caffeine and Related Purine Alkaloids" Journal of Bacteriology, American Society for Microbiology. Apr. 2012. vol. 194, No. 8. pp. 2041-2049. 9 pages.

Sundberg S.A., et al., "High-throughput and Ultra-high-throughput Screening: Solution- and Cell-based Approaches," Current Opinion in Biotechnology, Feb. 2000, vol. 11 (1), 7 pages.

Supplemental Non-Final Office Action for U.S. Appl. No. 15/420,022, filed Jan. 30, 2017 on behalf of California Institute of Technology. Mail Date: Aug. 8, 2019. 17 pages.

Sweet W.J., et al., "Changes in Cytochrome Content and Electron Transport Patterns in Pseudomonas Putida as a Function of Growth Phase," Journal of Bacteriology, Jan. 1978, vol. 133 (1), 9 pages.

System—Definition by Merriam-Webster, Dated: Dec. 6, 2010. 2 pages.

Tabatabaie T., et al., "Reactive Oxygen Species-mediated Inactivation of Pyruvate Dehydrogenase," Archives of Biochemistry and Biophysics, Dec. 1996, vol. 336 (2), 7 pages.

Taga et al. "BluB cannibalizes flavin to form the lower ligand of vitamin B12" Nature, Nature Publishing Group. Mar. 22, 2007. vol. 446, No. 7134. pp. 449-453. 11 pages.

Tahlan K., et al., "Initiation of Actinorhodin Export in Streptomyces Coelicolor," Molecular Microbiology, Feb. 2007, vol. 63 (4), 11 pages.

Tamura et al. "MEGA6: Molecular Evolutionary Genetics Analysis Version 6.0" Molecular Biology and Evolution, Oxford University Press. 2013. vol. 30, No. 12. pp. 2725-2729. 5 pages.

Tang, X.X., et al., "Acidic pH increases airway surface liquid viscosity in cystic fibrosis." The Journal of clinical investigation, 2016. 126(3): p. 879-891.

Teal et al. "Spatiometabolic Stratification of Shewanella oneidensis Biofilms" Applied and Environmental Microbiology, American Society for Microbiology. Nov. 2006. vol. 72, No. 11. pp. 7324-7330. 7 pages.

Terwilliger et al. "Automated ligand fitting by core-fragment fitting and extension into density" Acta Crystallographica Section D—Biological Crystallography, International Union of Crystallography. 2006. vol. D62. pp. 915-922. 8 pages.

Terwilliger et al. "Iterative model building, structure refinement and density modification with the PHENIX AutoBuild wizard" Acta Crystallographica Section D—Biological Crystallography, International Union of Crystallography. 2008. vol. D64. pp. 61-69. 9 pages.

Terwilliger et al. "Ligand identification using electron-density map correlations" Acta Crystallographica Section D—Biological Crystallography, International Union of Crystallography. Jan. 2007. vol. 63—Part 1. pp. 101-107. 8 pages.

Thauer R.K., et al., "Energy Conservation in Chemotrophic Anaerobic Bacteria," Bacteriological Reviews, Mar. 1977, vol. 41 (1), 81 pages.

Thomashow L.S., et al., "Role of a Phenazine Antibiotic from Pseudomonas Fluorescens in Biological Control of Gaeumannomyces Graminis Var. Tritici," Journal of Bacteriology, Aug. 1988, vol. 170 (8), 11 pages.

Thomsen M.C.F et al., "Seq2Logo: a method for construction and visualization of amino acid binding motifs and sequence profiles including sequence weighting, pseudo counts and two-sided representation of amino acid enrichment and depletion" Nucleic acids research, 2012. 40(W1): p. W281-W287.

Timms-Wilson et al. "Chromosomal Insertion of Phenazine-1-Carboxylic Acid Biosynthetic Pathway Enhances Efficacy of Damping-off Disease Control by Pseudomonas fluorescens" Molecular Plant-Microbe Interactions, The American Phytopathological Society. 2000. vol. 13, No. 12. pp. 1293-1300. 8 pages.

Tipton et al. "QapR (PA5506) Represses on Operon That Negatively Affects the Pseudomonas Quinolone Signal in Pseudomonas aeruginosa" Journal of Bacteriology, American Society for Microbiology. Aug. 2013. vol. 195, No. 15. pp. 3433-3441. 9 pages.

To T.B., et al., "New Method for the Direct Determination of Dissolved Fe(III) Concentration in Acid Mine Waters," Environmental Science & Technology, 1999, vol. 33 (5), pp. 807-813. 7 pages.

Tomlin K.L., et al., "Quorum-sensing Mutations Affect Attachment and Stability of Burkholderia Cenocepacia Biofilms," Applied and Environmental Microbiology, Sep. 2005, vol. 71 (9), 12 pages.

Torti S.V., et al., "Tumor Cell Cytotoxicity of a Novel Metal Chelator," Blood, Aug. 1998, vol. 92 (4), 7 pages.

Trutko S.M., et al., "Physiological Role of Pyocyanin Synthesized by Pseudomonas Aeruginosa, " Microbiologya, 1989, vol. 57, 8 pages.

Trutko S.M., et al., "The Physiological Role of Phenazine Pigments Synthesized by the Bacteria Pseudomonas Aureofaciens," Biochemistry, 1989, vol. 54, 7 pages.

Tsaneva I.R., et al., "soxR, a Locus Governing a Superoxide Response Regulon in *Escherichia coli* K-12," Journal of Bacteriology, Aug. 1990, vol. 172 (8), 9 pages.

Turick C.E., et al., "Melanin Production and Use as a Soluble Electron Shuttle for Fe(III) Oxide Reduction and as a Terminal Electron Acceptor by Shewanella algae BrY," Applied and Environmental Microbiology, May 2002, vol. 68 (5), 9 pages.

Turner et al. "Occurrence, Biochemistry and Physiology of Phenazine Pigment Production" Advances in Microbial Physiology, Academic Press. 1986. vol. 27. pp. 211-275. 65 pages.

Tuschl T., et al., "Targeted mRNA Degradation by Double-stranded RNA in Vitro," Genes and Development, Dec. 1999, vol. 13 (24), 7 pages.

Vandrisse, C. et al., "New high-cloning-efficiency vectors for complementation studies and recombinant protein overproduction in *Escherichia coli* and *Salmonella enterica*." Plasmid, 2016. 86: p. 1-6.

Vandrisse C. M. et al., "Computationally designed pyocyanin demethylase acts synergistically with tobramycin to kill recalcitrant Pseudomonas aeruginosa biofilms" PNAS, vol. 118 No. 12, Oct. 2020, pp. 1-10.

Vandrisse C. M. et al., "Leveraging the soil-clinic axis for the development of novel microbial therapeutics", Poster. The Weizmann-Caltech Symposium on the Carbon Cycle. Rehovot, Israel, Feb. 2020.

Vanitha et al. "Bio Control Potential of Pseudomonas fluorescens against Coleus Root Rot Disease" Journal of Plant Pathology and Microbiology, OMICS International. 2014. vol. 5, No. 1. 4 pages.

(56) References Cited

OTHER PUBLICATIONS

Vasil M.L., et al., "The Response of Pseudomonas Aeruginosa to Iron: Genetics, Biochemistry and Virulence," Molecular Microbiology, Nov. 1999, vol. 34 (3), 15 pages.

Vecchione J.J., et al., "Two Distinct Major Facilitator Superfamily Drug Efflux Pumps Mediate Chloramphenicol Resistance in Streptomyces Coelicolor," Antimicrobial Agents and Chemotherapy, Nov. 2009, vol. 53 (11), 6 pages.

Velayudhan J., et al., "Iron Acquisition and Virulence in Helicobacter Pylori: A Major Role for FeoB, a High-Affinity Ferrous Iron Transporter," Molecular Microbiology, Jul. 2000, vol. 37 (2), 13 pages.

Vessman, J., et al., "Selectivity in analytical chemistry (IUPAC Recommendations 2001)," Pure and Applied Chemistry, vol. 73, No. 8, 2001, pp. 1381-1386. 6 Pages. https://doi.org/10.1351/pac200173081381.

Visca P., et al., "Cloning and Nucleotide Sequence of the pvdA Gene Encoding the Pyoverdin Biosynthetic Enzyme L-Ornithine N5-Oxygenase in Pseudomonas Aeruginosa," Bacteriology, Feb. 1994, vol. 176 (4), 14 pages.

Wade D.S., et al., "Regulation of Pseudomonas Quinolone Signal Synthesis in Pseudomonas Aeruginosa," Bacteriology, Jul. 2005, vol. 187 (13), 10 pages.

Wallace JR et al. "Spectrum of Disease Due to Rapidly Growing Mycobacteria" Reviews of Infectious Diseases, University of Chicago. Jul./Aug. 1983. vol. 5, No. 4. pp. 657-679. 24 pages.

Walsh et al. "Flavoenzymes: Versatile Catalysts in Biosynthetic Pathways" Natural Product Reports, Royal Society of Chemistry. Jan. 2013. vol. 30, No. 1. pp. 1-53. 53 pages.

Walters III, M.C., et al., "Contributions of antibiotic penetration, oxygen limitation, and low metabolic activity to tolerance of Pseudomonas aeruginosa biofilms to ciprofloxacin and tobramycin." Antimicrobial agents and chemotherapy, 2003. 47(1): p. 317-323.

Wang, Dongping, et al., "Roles of the Gac-Rsm pathway in the regulation of phenazine biosynthesis in Pseudomonas chlororaphis 30-84", MicrobiologyOpen 2013, 2(3): 505-524

Wang et al. "Phenazine-1-Carboxylic Acid Promotes Bacterial Biofilm Development via Ferrous Iron Acquisition" Journal of Bacteriology, American Society for Microbiology. Jul. 2011. vol. 193, No. 14. pp. 3606-3617. 12 pages.

Wang Y., et al., "Endogenous Phenazine Antibiotics Promote Anaerobic Survival of Pseudomonas Aeruginosa via Extracellular Electron Transfer," Journal of Bacteriology, Jan. 2010, vol. 192 (1), 6 pages.

Wang Y., et al., "Redox Reactions of Phenazine Antibiotics With Ferric (Hydr)Oxides and Molecular Oxygen," Environmental Science & Technology, Apr. 2008, vol. 42 (7), 7 pages.

Wang Z., et al., "Oxidase Activity of a Flavin-Dependent Thymidylate Synthase," FEBS Journal, May 2009, vol. 276 (10), 10 pages.

Warszawski, S., et al., "Optimizing antibody affinity and stability by the automated design of the variable light-heavy chain interfaces." PLoS computational biology, 2019. 15(8): p. e1007207.

Weaver V. B., et al., "Burkholderia Spp. Alter Pseudomonas Aeruginosa Physiology Through Iron Sequestration," Journal of Bacteriology, Apr. 2004, vol. 186 (8), 10 pages.

Webb M, "Pyruvate Accumulation in Growth-Inhibited Cultures of Aerobacter Aerogenes," Biochemical Journal, Jan. 1968, vol. 106 (2), 6 pages.

Whitchurch et al. "Extracellular DNA Required for Bacterial Biofilm Formation" Science, American Association for the Advancement of Science. Feb. 22, 2002. vol. 295. pp. 1487. 2 pages.

Whiteley M., et al., "Identification of Genes Controlled by Quorum Sensing in Pseudomonas Aeruginosa," Proceedings of the National Academy of Sciences, Nov. 1999, vol. 96 (24), 6 pages.

Wikipedia entry for "Proteobacteria," as published Oct. 25, 2007, retrieved Dec. 31, 2020 from the WayBack Machine, online: //web.archive.org (3 pages).

Wikipedia entry for "Protozoa," as published Nov. 29, 2007, retrieved Dec. 31, 2020 from the WayBackMachine.com (2 pages).

Williams D.R., et al., "Denitrifying Pseudomonas Aeruginosa: Some Parameters of Growth and Active Transport," Applied and Environmental Microbiology, Aug. 1978, vol. 36 (2), 8 pages.

Williams H.D., et al., "Oxygen, Cyanide and Energy Generation in the Cystic Fibrosis Pathogen Pseudomonas Aeruginosa," Advances in Microbial Physiology, 2007, vol. 52, 72 pages.

Williams R.P., et al., "Symposium on Bacterial Pigments," Bacteriological Reviews, Dec. 1956, vol. 20 (4), 3 pages.

Wilson R., et al., "Measurement of Pseudomonas Aeruginosa Phenazine Pigments in Sputum and Assessment of Their Contribution to Sputum Sol Toxicity for Respiratory Epithelium," Infection and Immunity, Sep. 1988, vol. 56 (9), 4 pages.

Wimpenny J.W., et al., "Levels of Nicotinamide Adenine Dinucleotide and Reduced Nicotinamide Adenine Dinucleotide in Facultative Bacteria and the Effect of Oxygen," Journal of Bacteriology, Jul. 1972, vol. 111 (1), 10 pages.

Winn et al. "Overview of the CCP4 suite and current developments" Acta Crystallogrpahica Section D—Biological Crystallography, International Union of Crystallography. 2011. vol. D67. pp. 235-242. 8 pages.

Winn et al. "Use of TLS parameters to model anisotropic displacements in macromolecular refinement" Acta Crystallographica Section D—Biological Crystallography, International Union of Crystallography. 2001. vol. D57. pp. 122-133. 12 pages.

Wiren V.N., et al., "Nicotianamine Chelates both FeIII and FeII. Implications for Metal Transport in Plants," Plant Physiology, Mar. 1999, vol. 119 (3), 8 pages.

Wolfgang M.C., et al., "Pseudomonas Aeruginosa Regulates Flagellin Expression as Part of a Global Response to Airway Fluid from Cystic Fibrosis Patients," Proceedings of the National Academy of Sciences, Apr. 2004, vol. 101 (17), 5 pages.

Worlitzsch D., et al., "Effects of Reduced Mucus Oxygen Concentration in Airway Pseudomonas Infections of Cystic Fibrosis Patients," The Journal of Clinical Investigation, Feb. 2002, vol. 109 (3), 9 pages.

Worst D.J., et al., "Helicobacter Pylori ribBA-Mediated Riboflavin Production Is Involved in Iron Acquisition," Bacteriology, Mar. 1998, vol. 180 (6), 8 pages.

Written Opinion for International Application No. PCT/US2017/023688, filed on Mar. 22, 2017, on behalf of California Institute of Technology. Mail Date: Jun. 30, 2017. 14 pages.

Wu et al. "Quantitative hopanoid analysis enables robust pattern detection and comparison between laboratories" Geobiology, John Wiley & Sons Ltd. 2015. vol. 13, No. 4. pp 391-407. 17 pages.

Wyckoff E.E., et al., "Genetics and Environmental Regulation of Shigella Iron Transport Systems," Biometals, Feb. 2009, vol. 22 (1), 9 pages.

Xu K.D., et al., "Spatial Physiological Heterogeneity in Pseudomonas Aeruginosa Biofilm Is Determined by Oxygen Availability," Applied and Environmental Microbiology, Oct. 1998, vol. 64 (10), 6 pages.

Yaeger, R.G. Excerpts of Medical Microbiology, "Chapter 77 Protozoa: Structure, Classification, Growth, and Development," published 1996 (7 pages).

Yanagihara K., et al., "Effects of Short Interfering RNA against Methicillin-Resistant *Staphylococcus aureus* Coagulase in Vitro and In Vivo," Journal of Antimicrobial Chemotherapy, 2005, vol. 57 (1), 5 pages.

Yang L., et al., "Microbial Ecology and Adaptation in Cystic Fibrosis Airways," Environmental Microbiology, Jul. 2011, vol. 13 (7), 8 pages.

Yang Z.J., et al., "Isolation, Identification, and Degradation Characteristics of Phenazine-1-Carboxylic Acid-Degrading Strain *Sphingomonas* Sp. DP58," Current Microbiology, Oct. 2007, vol. 55 (4), 4 pages.

Yim G., et al., "Antibiotics as Signalling Molecules," Philosophical Transactions of the Royal Society of London, Jul. 2007, vol. 362 (1483), 6 pages.

Youard Z.A., et al., "Pseudomonas Fluorescens CHAO Produces Enantio-Pyochelin, the Optical Antipode of the Pseudomonas Aeruginosa Siderophore Pyochelin," Journal of Biological Chemistry, Dec. 2007, vol. 282 (49), 8 pages.

(56) References Cited

OTHER PUBLICATIONS

Zamri A., et al., "An Improved Stereocontrolled Synthesis of Pyochelin, Siderophore of Pseudomonas Aeruginosa and Burkholderia Cepacia," Tetrahedron, Jan. 2000, vol. 56 (2), 8 pages.

Zhao Q., et al., "Differential Effects of Mutations in tonB1 on Intrinsic Multidrug Resistance and Iron Acquisition in Pseudomonas Aeruginosa," Bacteriology, Apr. 2002, vol. 184 (7), 6 pages.

Zhu, K., et al., "Universal antibiotic tolerance arising from antibiotic-triggered accumulation of pyocyanin in Pseudomonas aeruginosa." PLoS biology, 2019. 17(12): p. e3000573.

Zuckermann R.N., et al., "Discovery of Nanomolar Ligands for 7-transmembrane G-protein-coupled Receptors From a Diverse N-(Substituted)glycine Peptoid Library," Journal of Medicinal Chemistry, Aug. 1994, vol. 37 (17), 8 pages.

Armstrong, S. and C. Ruckley, Use of a fibrous dressing in exuding leg ulcers. Journal of Wound Care, Jul. 1997. 6(7): p. 322-324.

Bockris, J.M. and L. Oldfield, The oxidation-reduction reactions of hydrogen peroxide at inert metal electrodes and mercury cathodes. Transactions of the faraday society, 1955. 51: p. 249-259.

Fisher, R.A., B. Gollan, and S. Helaine, Persistent bacterial infections and persister cells. Nature Reviews Microbiology, May 2017. 15(8): p. 453-464.

Gaur, Priyanka, et al. Interpretation of Antimicrobial Susceptibility Testing Using European Committe on Antimicrobial Susceptibility Testing (EUCAST) and Clinical and Laboratory Standards Institute (CLSI) Breakpoints: Analysis of Agreement. Cureus, Mar. 31, 2023, 15 (3): e36977. 8 pages.

Hareendran, A., et al., Measuring the impact of venous leg ulcers on quality of life. Journal of Wound Care, Feb. 2005. 14(2): p. 53-57.

Krasner, D., et al., The ABCs of wound care dressings. wound management, 1993. 66: pp. 66, 68-69, 72, 74-76, 78-86. 16 pages.

Niepa, T.H., J.L. Gilbert, and D. Ren, Controlling Pseudomonas aeruginosa persister cells by weak electrochemical currents and synergistic effects with tobramycin. Biomaterials, Oct. 2012. 33(30): p. 7356-7365.

Okshevsky, M. and R.L. Meyer, Evaluation of fluorescent stains for visualizing extracellular DNA in biofilms. Journal of Microbiological Methods, Oct. 2014. 105: p. 102-104.

Urban, MV et al. (Nov. 16, 2017) "Hydrogen peroxide (H2O2): a review of its use in surgery." Wien Med Wochenschr 169: 222-225. DOI: 10.1007/s10354-017-0610-2.

A0AON9Y7W5_MYCFO. UniProtKB/TrEMBL Database. Jan. 20, 2016. 1 page.

Armstrong, S. and C. Ruckley, Use of a fibrous dressing in exuding leg ulcers. Journal of Wound Care, Jul. 1997. 6(7): p. 322-324. Abstract Only.

Boateng, U.S., et al., Wound healing dressings and drug delivery systems: a review. Journal of pharmaceutical sciences, Aug. 2008. 97(8): p. 2892-2923.

Bolton, L. and L. Van Rijswijk, Wound dressings: meeting clinical and biological needs. Dermatology nursing, Jul. 1991. 3(3): p. 146-161. 16 pages.

Bosire, E.M. and M.A. Rosenbaum, Electrochemical potential influences phenazine production, electron transfer and consequently electric current generation by Pseudomonas aeruginosa. Frontiers in Microbiology, May 2017. vol. 8, Article 892: p. 260405. 11 pages.

Chica, R.A. et al. "Semi-rational approaches to engineering enzyme activity: Combining the benefits of directed evolution and rational design" Curr. Opin. Biotechnol., 2005, 16 (4), 378-384. An Excerpt. 23 pages.

Choi, Yongwook et al., "PROVEAN web server: a tool to predict the fuctional effect of amino acid substitutions and indels", Bioinformatics, vol. 31, Issue 16, Aug. 2015, pp. 2745-2747.

Ciemniecki, J.A. and D.K. Newman, NADH dehydrogenases are the predominant phenazine reductases in the electron transport chain of Pseudomonas aeruginosa. Molecular Microbiology, May 2023. 119(5): p. 560-573. 25 pages.

Cornell, WC et al. (Dec. 2020) Phenazine oxidation by a distal electrode modulates biofilm morphogenesis. Biofilm, 2: 100025. 6 pages.

Csernatony, Z., et al., Metal implants and MRI: A mythbuster study. Glob. Imaging Insights, May 7, 2021. 6: p. 1-4.

Dahlem Junior, M.A., et al., Quinones as an efficient molecular scaffold in the antibacterial/antifungal or antitumoral arsenal. International Journal of Molecular Sciences, Nov. 2022. 23(22): p. 14108. 16 pages. DOI: 10.3390/ijms232214108.

Dar, D., et al., Global landscape of phenazine biosynthesis and biodegradation reveals species-specific colonization patterns in agricultural soils and crop microbiomes. eLife, Sep. 15, 2020. 9: p. e59726. 23 pages.

Doucet, Nicolas. Thesis for University of Montreal, Mutagenese semi-aleatoire et analyse dynamique de Beta-lactamase TEM-1 de *Escherichia coli*. Dec. 2006. 315 pages.

Final Office Action for U.S. Appl. No. 17/027,587, filed Sep. 21, 2020 on behalf of California Institute of Technology. Mailed on Feb. 14, 2024. 30 pages.

Fisher, R.A., B. Gollan, and S. Helaine, Persistent bacterial infections and persister cells. Nature Reviews Microbiology, May 2017. 15(8): p. 453-464. Abstract Only.

Franza, T. and P. Gaudu, Quinones: more than electron shuttles. Research in Microbiology, 2022. 173(6-7): p. 103953. 10 pages.

Gilliland, E.L., et al., Bacterial colonisation of leg ulcers and its effect on the success rate of skin grafting. Annals of the Royal College of Surgeons of England, 1988. 70(2): p. 105-108.

Gimeno, M., et al., A controlled antibiotic release system to prevent orthopedic-implant associated infections: An in vitro study. European Journal of Pharmaceutics and Biopharmaceutics, 2015. 96: p. 264-271.

Glasser, N.R., S.H. Saunders, and D.K. Newman, The colorful world of extracellular electron shuttles. Annual review of microbiology, Jul. 21, 2017. 71: p. 731-751. 28 pages.

Hareendran, A., et al., Measuring the impact of venous leg ulcers on quality of life. Journal of Wound Care, Feb. 2005. 14(2): p. 53-57. Abstract Only.

International Search Report and Written Opinion for International Application No. PCT/US2024/026318 filed on Apr. 25, 2024 on behalf of California Institute of Technology. Mailed on Aug. 16, 2024. 13 pages.

Kang, J., Y.-H. Cho, and Y. Lee, Pyocyanin and 1-Hydroxyphenazine promote anaerobic killing of Pseudomonas aeruginosa via single-electron transfer with ferrous iron. Microbiology Spectrum, Nov. 2, 2022. 10(6): p. e02312-22. 14 pages.

Keogh, D., et al., Extracellular electron transfer powers Enterococcus faecalis biofilm metabolism. MBio, Mar./Apr. 2018. 9(2): p. 10.1128/mbio. 00626-17. 16 pages.

Laskowski, R.A. et al. "PROCHECK: a program to check the stereochemical quality of protein structures", J Appl Cryst. 1993; 26:283-291.

Lazarus, G.S., et al., Reprint of: Definitions and guidelines for assessment of wounds and evaluation of healing. Arch Dermatol, 1994. 130(4): p. 489-493.

Light, S.H., et al., A flavin-based extracellular electron transfer mechanism in diverse Gram-positive bacteria. Nature, Oct. 2018. 562(7725): p. 140-144. 27 pages.

Mathura, V. et al. "APDbase: Amino acid Physico-chemical properties Database", Bioinformation, 1, 1, Mar. 12, 2005, pp. 2-4. Biomedical Informatics Publishing Group.

Mevers, E. et al. "An elusive electron shuttle from a facultative anaerobe" eLife, (Jun. 24, 2019), 8:e48054.15 pages. DOI: elifesciences. org/articles/4805.

Mohamed, A. et al. "Hydrogen peroxide-producing electrochemical bandage controlled by a wearable potentiostat for treatment of wound infections", Biotechnol Bioeng, (Jul. 2021), 118 (7), 2815-2821. 11 pages. Website: www.ncbi.nlm.nih.gov/pmc/articles/PMC8653773/.

Niepa, T.H., J.L. Gilbert, and D. Ren, Controlling Pseudomonas aeruginosa persister cells by weak electrochemical currents and synergistic effects with tobramycin. Biomaterials, Oct. 2012. 33(30): p. 7356-7365. Abstract Only.

Okshevsky, M. and R.L. Meyer, Evaluation of fluorescent stains for visualizing extracellular DNA in biofilms. Journal of Microbiological Methods, Oct. 2014. 105: p. 102-104. Abstract Only.

(56) References Cited

OTHER PUBLICATIONS

Otero, Fernand Jimenez et al. "Pyocyanin-dependent electrochemical inhibition of Pseudomonas aeruginosa biofilms is synergistic with antibiotic treatment", American Society for Microbiology, mBio, (Jun. 14, 2023), vol. 14, Issue 4. 7 pp. 10-1128/mbio.00702-23.

Park, H.Y., et al., Comparison of two fluorescent probes in preclinical non-invasive imaging and image-guided debridement surgery of Staphylococcal biofilm implant infections. Scientific reports, Jan. 15, 2021. 11(1): p. 1622. 13 pages.

PROCHECK and PROCHECK-NMR. Available on Feb. 26, 2016 through the Way Back Machine. 2 pages. Website: www.ebi.ac.uk/thornton-srv/software/PROCHECK/.

PROVEAN on J. Craig Venter Institute website, Available on Feb. 23, 2016 through the Way Back Machine. 1 page. Website: provean.jcvi.org/index.php.

Raval, Y.S., et al., Hydrogen peroxide-generating electrochemical scaffold activity against trispecies biofilms. Antimicrobial agents and chemotherapy, Mar. 24, 2020. 64(4): p. 10.1128/aac. 02332-19. 6 pages.

Reetz, M.T. et al., Iterative saturation mutagenesis (ISM) for rapid directed evolution of functional enzymes. Nature Protocols, (Published online Apr. 12, 2007), vol. 2, No. 4, pp. 891-903.

Rosenbaum, F.P. and V. Müller, Energy conservation under extreme energy limitation: the role of cytochromes and quinones in acetogenic bacteria. Extremophiles, Nov. 2021. 25(5): p. 413-424. Doi: 10.1007/s00792-021-01241-0.

Schroth, M.N., et al., Epidemiology of Pseudomonas aeruginosa in agricultural areas. Journal of Medical Microbiology, Aug. 2018. 67(8): p. 1191-1201.

Siloto, Rodrigo M.P. et al., Site saturation mutagenesis: Methods and Applications in protein engineering. Biocatalysis and Agricultural Biotechnology. (Online Apr. 5, 2012). 1, pp. 181-189.

Skerman, V., V. McGowan, and P. Sneath, Approved lists of bacterial names (amended). Washington (DC), ASM Press 1989. Excerpt only. 2 pages.

Smith, D.J. et al., "Effect of intravenous or oral sodium chlorate administration on the fecal shedding of *Escherichia coli* in sheep". Journal Animal Science, 2013, 91: 5962-5969. Dod:10.2527/jas2013-6796.

Sultana, S.T., et al., Electrochemical scaffold generates localized, low concentration of hydrogen peroxide that inhibits bacterial pathogens and biofilms. Scientific reports, Oct. 14, 2015. 5(1): p. 1-10.

Urban, MV et al. (Jun. 2019) "Hydrogen peroxide (H2O2): a review of its use in surgery." Wien Med Wochenschr 169: 222-225. DOI: 10.1007/s10354-017-0610-2. Abstract Only.

Van Beilen, J.W. and K.J. Hellingwerf, All three endogenous quinone species of Escherichia coli are involved in controlling the activity of the aerobic/anaerobic response regulator ArcA. Frontiers in microbiology, Sep. 2016. 7: p. 208925. 11 pages. DOI: 10.3389/fmicb.2016.01339.

Wikipedia—Standard Electrode Potential (data page). Last updated Apr. 15, 2024. 16 pages. Website: en.wikipedia.org/wiki/Standard_electrode_potential_(data_page).

Wikipedia: Nerst Equation. Last updated: Dec. 27, 2023. Downloaded through the Wayback Machine on for Feb. 27, 2024. 16 page. en.wikipedia.org/wiki/Nernst_equation.

Wikipedia, "Pourbaix Diagram". Downloaded Jun. 4, 2024. Last edited Mar. 21, 2024. 11 pages. Website: en.wikipedia.org/wiki/Pourbaix_diagram.

Xi, W., et al., Point-of-care antimicrobial coating protects orthopaedic implants from bacterial challenge. Nature communications, Sep. 16, 2021. 12(1): p. 5473. 15 pages.

Zoller, S.D., et al., Evading the host response: *Staphylococcus* "hiding" in cortical bone canalicular system causes increased bacterial burden. Bone Research, Dec. 19, 2020. 8(1): p. 43. 11 pages.

Notice of Allowance for U.S. Appl. No. 17/027,587, filed Sep. 21, 2020 on behalf of California Institute of Technology. Mailed on Oct. 30, 2024. 15 pages.

Supplemental Notice of Allowability for U.S. Appl. No. 17/027,587, filed Sep. 21, 2020 on behalf of California Institute of Technology. Mailed on Dec. 5, 2024. 6 pages.

* cited by examiner

SEQUENCE LISTING

```
<160> NUMBER OF SEQ ID NOS: 10

<210> SEQ ID NO 1
<211> LENGTH: 162
<212> TYPE: PRT
<213> ORGANISM: Mycobacterium fortuitum

<400> SEQUENCE: 1

Met Thr Gly Lys Thr Lys Pro Ala Ile Ile Gly Gly Val Ala Ile Thr
1               5                   10                  15

Ala Leu Ala Ala Ala Gly Leu Gly Val Trp Leu Phe Thr Asp Gly Arg
            20                  25                  30

Gly Gly Arg Ser Thr Thr Glu Pro Val Thr Met Thr Leu Asp Val Lys
        35                  40                  45

Asn Asp Gln Val Ala Lys His Asp Phe Gly Lys Pro Gly Met Asp Val
    50                  55                  60

Gly Asp Met Asp Ile Phe Ser Asp Ile Leu Ser Val Asp Gly Lys Gln
65                  70                  75                  80

Val Gly Tyr Asp Gly Gly Ala Cys Phe Phe Thr Asn Val Thr Pro Asp
                85                  90                  95

Asn Pro Met Thr Tyr Cys Glu Leu Thr Ile His Leu Asp Ala Gly Glu
            100                 105                 110

Ile Phe Ala Arg Ser Leu Thr Pro His Thr Leu Ala Pro Phe Thr Met
        115                 120                 125

Ala Ile Thr Gly Gly Thr Gly Glu Tyr Ala Asn Ser Lys Gly Glu Leu
    130                 135                 140

Thr Val Ser Gly Val Ala Thr Pro Asp Glu Lys Tyr Glu Leu Lys Leu
145                 150                 155                 160

Thr Lys

<210> SEQ ID NO 2
<211> LENGTH: 141
<212> TYPE: PRT
<213> ORGANISM: Artificial Sequence
<220> FEATURE:
<223> OTHER INFORMATION: Sybthetic Polypeptide
```

```
<400> SEQUENCE: 2

Met Asp Gly Arg Gly Gly Arg Ser Thr Thr Glu Pro Val Thr Met Thr
1               5                   10                  15

Leu Asp Val Lys Asn Asp Gln Val Ala Lys His Asp Phe Gly Lys Pro
            20                  25                  30

Gly Met Asp Val Gly Asp Met Asp Ile Phe Ser Asp Ile Leu Ser Val
        35                  40                  45

Asp Gly Lys Gln Val Gly Tyr Asp Gly Gly Ala Cys Phe Phe Thr Asn
    50                  55                  60

Val Thr Pro Asp Asn Pro Met Thr Tyr Cys Glu Leu Thr Ile His Leu
65                  70                  75                  80

Asp Ala Gly Glu Ile Phe Ala Arg Ser Leu Thr Pro His Thr Leu Ala
                85                  90                  95

Pro Phe Thr Met Ala Ile Thr Gly Gly Thr Glu Tyr Ala Asn Ser
            100                 105                 110

Lys Gly Glu Leu Thr Val Ser Gly Val Ala Thr Pro Asp Glu Lys Tyr
        115                 120                 125

Glu Leu Lys Leu Thr Lys Ala Glu Asn Leu Tyr Phe Gln
    130                 135                 140

<210> SEQ ID NO 3
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 3

Val Thr Met Thr Leu Asp Val Lys Asn Asp Gln Val Ala Lys His Asp
1               5                   10                  15

Phe Gly Lys Pro Gly Met Asp Val Gly Asp Met Asp Ile Phe Ser Asp
            20                  25                  30

Ile Leu Ser Val Asp Gly Lys Gln Val Gly Tyr Asp Gly Gly Ala Cys
        35                  40                  45

Phe Phe Thr Asn Val Thr Pro Asp Asn Pro Met Thr Tyr Cys Glu Leu
    50                  55                  60

Thr Ile His Leu Asp Ala Gly Glu Ile Phe Ala Arg Ser Leu Thr Pro
65                  70                  75                  80

His Thr Leu Ala Pro Phe Thr Met Ala Ile Thr Gly Gly Thr Gly Glu
                85                  90                  95

Tyr Ala Asn Ser Lys Gly Glu Leu Thr Val Ser Gly Val Ala Thr Pro
            100                 105                 110

Asp Glu Lys Tyr Glu Leu Lys Leu Thr Lys
        115                 120

<210> SEQ ID NO 4
<211> LENGTH: 123
<212> TYPE: PRT
<213> ORGANISM: Artificial Sequence
<220> FEATURE:
<223> OTHER INFORMATION: Synthetic polynucleotide

<400> SEQUENCE: 4

Met Val Thr Met Thr Leu Asp Val Lys Asn Asp Gln Val Asn Lys His
1               5                   10                  15

Asp Phe Gly Lys Pro Gly Met Asp Val Gly Asp Met Asp Ile Phe Ser
            20                  25                  30
```

Asp Thr Leu Ser Val Asp Gly Lys Gln Val Gly Tyr Asp Gly Gly Val
         35                  40                  45

Cys Phe Phe Thr Asn Val Thr Pro Asp Asn Pro Val Thr Tyr Cys Glu
 50                  55                  60

Leu Thr Ile His Leu Asp Ala Gly Glu Ile Phe Ala Arg Ser Leu Thr
 65                  70                  75                  80

Pro Ala Thr Leu Ala Pro Phe Thr Met Thr Ile Thr Gly Gly Thr Gly
                 85                  90                  95

Glu Tyr Ala Asn Ser Lys Gly Glu Leu Thr Val Ser Gly Val Ala Thr
                100                 105                 110

Pro Asp Glu Lys Tyr Glu Leu Lys Leu Thr Lys
        115                 120

<210> SEQ ID NO 5
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 5
nngctcttcn ttcatggacg gtcgcggcgg ccggagtaca a                41

<210> SEQ ID NO 6
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 6
nngctcttcn taatcatttc gtcagtttca attcgtactt ctc              43

<210> SEQ ID NO 7
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 7
gccctgaaaa tacaggtttt cactagttg                              29

<210> SEQ ID NO 8
<211> LENGTH: 25
<212> TYPE: DNA
<213> ORGANISM: Artificial Sequence
<220> FEATURE:
<223> OTHER INFORMATION: Synthetic polynucleotide

```
<400> SEQUENCE: 8
taagaattct cgagctcccg ggatc                                          25

<210> SEQ ID NO 9
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 9
attacgatat cccaactagt gaaaacctgt attttcaggg c                        41

<210> SEQ ID NO 10
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 10
tgctcagcgg ccgcggatcc cgggagctcg agaattctta                          40
```

PYOCYANINE DEMETHYLASES AND RELATED PHENAZINE DEGRADING AGENTS COMPOSITIONS, METHODS AND SYSTEMS FOR INTERFERING WITH VIABILITY OF BACTERIA

CROSS-REFERENCE TO RELATED APPLICATION

The present application claims priority to U.S. Provisional Application No. 63/110,246 entitled "Phenazine Degrading Agents and Related Compositions, Methods, Systems for Interfering with Viability of Bacteria" filed on Nov. 5, 2020, the content of which is incorporated herein by reference in their entirety. The present applications may also be related to U.S. Non-Provisional application Ser. No. 15/466,839 entitled "Phenazine Degrading Agents And Related Compositions, Methods And Systems For Interfering With Viability Of Bacteria" filed on Mar. 22, 2017 and granted on Feb. 9, 2019 with US patent number U.S. Pat. No. 10,913,936, herein also incorporated herein by reference in its entirety.

STATEMENT OF GOVERNMENT GRANT

This invention was made with government support under Grant No(s). AI127850 & HL152190 awarded by the National Institutes of Health. The government has certain rights in the invention.

FIELD

The present disclosure relates to methods and systems for interfering with the viability of bacteria and related compounds and compositions. In particular, the present disclosure relates to a pyocyanin demethylase and related phenazine degrading agents, compositions, methods and systems for interfering with the viability of bacteria.

BACKGROUND

Phenazines are bacteria produced compounds which have been shown to be important for viability of phenazine producing bacteria Whether for medical application or for fundamental biology studies, several methods are commonly used for the detection of and interference with the viability of bacteria. in particular when aimed at therapeutic or diagnostic applications.

Although methods, systems and compositions have been developed to interfere with, and in particular, to reduce bacterial viability through phenazine degradation, development of more efficacious phenazine degraders able to effectively inhibit bacterial viability is still particularly challenging.

SUMMARY

Provided herein, are pyocyanin demethylases, related phenazine degrading agents, effective phenazine degrading agents' amounts, as well as related methods, systems and compositions that in several embodiments are configured for effective reduction of antibiotic resistance and/or survivability of phenazine producing bacteria.

In particular, provided herein are engineered pyocyanin demethylases which are based on the surprising identification of replacement in in positions A53, I73, A87, T91, M99, A129 and K141 of pyocyanin demethylase PodA having sequence (SEQ ID NO: 1)
$M_1T_2G_3K_4T_5K_6P_7A_8I_9I_{10}G_{11}G_{12}V_{13}A_{14}I_{15}T_{16}A_{17}L_{18}$
$A_{19}A_{20}A_{21}G_{22}L_{23}G_{24}V_{25}W_{26}L_{27}F_{28}T_{29}D_{30}G_{31}R_{32}G_{33}$
$G_{34}R_{35}S_{36}T_{37}T_{38}E_{39}P_{40}V_{41}T_{42}M_{43}T_{44}L_{45}D_{46}V_{47}K_{48}$
$N_{49}D_{50}Q_{51}V_{52}A_{53}K_{54}H_{55}D_{56}F_{57}G_{58}K_{59}P_{60}G_{61}M_{62}D_{63}$
$V_{64}G_{65}D_{66}M_{67}D_{68}I_{69}F_{70}S_{71}D_{72}I_{73}L_{74}S_{75}V_{76}D_{77}G_{78}$
$K_{79}Q_{80}V_{81}G_{82}Y_{83}D_{84}G_{85}G_{86}A_{87}C_{88}F_{89}F_{90}T_{91}N_{92}V_{93}$
$T_{94}P_{95}D_{96}N_{97}P_{98}M_{99}T_{100}Y_{101}C_{102}E_{103}L_{104}T_{105}I_{106}$
$H_{107}L_{108}D_{109}A_{110}G_{111}E_{112}I_{113}F_{114}A_{115}R_{116}S_{117}$
$L_{118}T_{119}P_{120}H_{121}T_{122}L_{123}A_{124}P_{125}F_{126}T_{127}M_{128}$
$A_{129}I_{130}T_{131}G_{132}G_{133}T_{134}G_{135}E_{136}Y_{137}A_{138}N_{139}$
$S_{140}K_{141}G_{142}E_{143}L_{144}T_{145}V_{146}S_{147}G_{148}V_{149}A_{150}$
$T_{151}P_{152}D_{153}E_{154}K_{155}Y_{156}E_{157}L_{158}K_{159}L_{160}T_{161}$
$K_{162}$, which can increase stability, yield and/or activity of the pyocyanin demethylase in SEQ ID NO: 1 or portions thereof, as well as combined administration of natural occurring and/or engineered pyocyanin demethylases and antibiotics resulting in a synergic inhibition of viability of phenazine producing bacteria.

According to a first aspect, an engineered pyocyanin demethylase or a derivative thereof are described, the pyocyanin demethylase comprising sequence (SEQ ID NO: 1)
$M_1T_2G_3K_4T_5K_6P_7A_8I_9I_{10}G_{11}G_{12}V_{13}A_{14}I_{15}T_{16}A_{17}L_{18}$
$A_{19}A_{20}A_{21}G_{22}L_{23}G_{24}V_{25}W_{26}L_{27}F_{28}T_{29}D_{30}G_{31}R_{32}G_{33}$
$G_{34}R_{35}S_{36}T_{37}T_{38}E_{39}P_{40}V_{41}T_{42}M_{43}T_{44}L_{45}D_{46}V_{47}K_{48}$
$N_{49}D_{50}Q_{51}V_{52}A_{53}K_{54}H_{55}D_{56}F_{57}G_{58}K_{59}P_{60}G_{61}M_{62}D_{63}$
$V_{64}G_{65}D_{66}M_{67}D_{68}I_{69}F_{70}S_{71}D_{72}I_{73}L_{74}S_{75}V_{76}D_{77}G_{78}$
$K_{79}Q_{80}V_{81}G_{82}Y_{83}D_{84}G_{85}G_{86}A_{87}C_{88}F_{89}F_{90}T_{91}N_{92}V_{93}$
$T_{94}P_{95}D_{96}N_{97}P_{98}M_{99}T_{100}Y_{101}C_{102}E_{103}L_{104}T_{105}I_{106}$
$H_{107}L_{108}D_{109}A_{110}G_{111}E_{112}I_{113}F_{114}A_{115}R_{116}S_{117}$
$L_{118}T_{119}P_{120}H_{121}T_{122}L_{123}A_{124}P_{125}F_{126}T_{127}M_{128}$
$A_{129}I_{130}T_{131}G_{132}G_{133}T_{134}G_{135}E_{136}Y_{137}A_{138}N_{139}$
$S_{140}K_{141}G_{142}E_{143}L_{144}T_{145}V_{146}S_{147}G_{148}V_{149}A_{150}$
$T_{151}P_{152}D_{153}E_{154}K_{155}Y_{156}E_{157}L_{158}K_{159}L_{160}$
$T_{161}K_{162}$, the pyocyanin demethylase further modified to include at least two replacements in SEQ ID NO: 1 selected from
  A53 with L, N, or V
  I73 with I, E, K, L, Q, R, T or V
  A87 with C, I, T or V
  T91 with V
  M99 with M, C, F, I, K, R, V or Y
  A129 with A, C, S, T, or V
  K141 with K, S or T and configured to be capable of the engineered pyocyanin demethylase or a derivative thereof to demethylate pyocyanin and/or a pyocyanin-like phenazines of formula (III)

$$\text{(III)}$$

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

—O⁻.

According to a second and preferred aspect, an engineered pyocyanin demethylase PodA$_{30-162}$ or a derivative thereof are described, the pyocyanin demethylase comprising sequence (SEQ ID NO: 2)
$D_1G_2R_3G_4G_5R_6S_7T_8T_9E_{10}P_{11}V_{12}T_{13}M_{14}T_{15}L_{16}D_{17}$ $VI_8K_{19}N_{20}D_{21}Q_{22}V_{23}A_{24}K_{25}H_{26}D_{27}F_{28}G_{29}K_{30}P_{31}$ $G_{32}M_{33}D_{34}V_{35}G_{36}D_{37}M_{38}D_{39}I_{40}F_{41}S_{42}D_{43}I_{44}L_{45}$ $S_{46}V_{47}D_{48}G_{49}K_{50}Q_{51}A_{52}G_{53}Y_{54}D_{55}G_{56}G_{57}A_{58}C_{59}$ $F_{60}F_{61}T_{62}N_{63}V_{64}T_{65}P_{66}D_{67}N_{68}P_{69}M_{70}T_{71}Y_{72}C_{73}$ $E_{74}L_{75}T_{76}I_{77}H_{78}L_{79}D_{80}A_{81}G_{82}E_{83}I_{84}F_{85}A_{86}R_{87}$ $S_{88}L_{89}T_{90}P_{91}H_{92}T_{93}L_{94}A_{95}P_{96}F_{97}T_{98}M_{99}A_{100}$ $I_{101}T_{102}G_{103}G_{104}T_{105}G_{106}E_{107}Y_{108}A_{109}N_{110}$ $S_{111}K_{112}G_{113}E_{114}L_{115}T_{116}V_{117}S_{118}G_{119}V_{120}$ $A_{121}T_{122}P_{123}D_{124}E_{125}K_{126}Y_{127}E_{128}L_{129}K_{130}$ $L_{131}T_{132}K_{133}A_{134}E_{135}N_{136}L_{137}Y_{138}F_{139}Q_{140}$, the pyocyanin demethylase further modified to include at least two replacements in SEQ ID NO: 2 selected from A24 with L, N, or V I44 with I, E, K, L, Q, R, T or V A58 with C, I, T or V T62 with V M70 with M, C, F, I, K, R, V or Y A100 with A, C, S, T, or V K112 with K, S or T and configured to be capable of the engineered pyocyanin demethylase or a derivative thereof to demethylate pyocyanin and/or a pyocyanin-like phenazines of formula (III)

$$\text{(III)}$$

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

—O⁻.

According to a third and further preferred aspect, an engineered pyocyanin demethylase PodA$_{41-162}$ or a derivative thereof are described, the pyocyanin demethylase comprising sequence (SEQ ID NO: 3)
$V_1T_2M_3T_4L_5D_6V_7K_8N_9D_{10}Q_{11}V_{12}A_{13}K_{14}H_{15}D_{16}F_{17}$ $G_{18}K_{19}P_{20}G_{21}M_{22}D_{23}V_{24}G_{25}D_{26}M_{27}D_{28}I_{29}F_{30}S_{31}$ $D_{32}I_{33}L_{34}S_{35}V_{36}D_{37}G_{38}K_{39}Q_{40}V_{41}G_{42}Y_{43}D_{44}G_{45}$ $G_{46}A_{47}C_{48}F_{49}F_{50}T_{51}N_{52}V_{53}T_{54}P_{55}D_{56}N_{57}P_{58}M_{59}$ $T_{60}Y_{61}C_{62}E_{63}L_{64}T_{65}I_{66}H_{67}L_{68}D_{69}A_{70}G_{71}E_{72}I_{73}$ $F_{74}A_{75}R_{76}S_{77}L_{78}T_{79}P_{80}H_{81}T_{82}L_{83}A_{84}P_{85}F_{86}T_{87}$ $M_{88}A_{89}I_{90}T_{91}G_{92}G_{93}T_{94}G_{95}E_{96}Y_{97}A_{98}N_{99}S_{100}$ $K_{101}G_{102}E_{103}L_{104}T_{105}V_{106}S_{107}G_{108}V_{109}A_{110}$ $T_{111}P_{112}D_{113}E_{114}K_{115}Y_{16}E_{117}L_{118}K_{119}L_{120}$ $T_{121}K_{122}$, the pyocyanin demethylase further modified to include at least two replacements in SEQ ID NO: 3 selected from A13 with L, N, or V I33 with I, E, K, L, Q, R, T or V A47 with C, I, T or V T51 with V M59 with M, C, F, I, K, R, V or Y A89 with A, C, S, T, or V K101 with K, S or T and configured to be capable of the engineered pyocyanin demethylase or a derivative thereof to demethylate pyocyanin and/or a pyocyanin-like phenazines of formula (III)

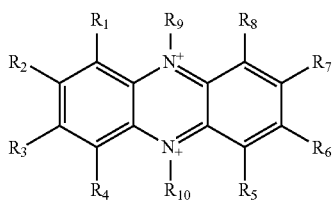

(III)

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

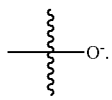

According to a fourth aspect, a phenazine degrading agent is described, comprising an engineered pyocyanin demethylase of the present disclosure and/or a derivative thereof.

According to a fifth aspect, a method and a system to interfere with viability of phenazine producing bacteria are described. The method comprises
    contacting the phenazine producing bacteria with an engineered pyocyanin demethylase of the present disclosure and/or a derivative thereof, alone or in combination with an antibiotic and/or other antimicrobial for a time and under conditions to reduce survivability and/or antibiotic resistance of the bacteria.

In some embodiments contacting the engineered pyocyanin demethylase of the present disclosure and/or a derivative thereof, can be further performed in combination with other phenazine degrading agents possibly within a phenazine degrading agent according to the second aspect of the present disclosure.

The system comprises one or more engineered pyocyanin demethylase of the present disclosure and/or a derivative thereof, one or more phenazine degrading agents of the present disclosure, one or more antibiotics and/or one or more other antimicrobials. In some embodiments of the methods and systems, the bacteria comprise persister cells.

According to a sixth aspect, a method and a system are described for treating and/or preventing a bacterial infection by a phenazine producing bacteria in an individual. The method comprises
    administering to the individual an effective amount of one or more an engineered pyocyanin demethylase of the present disclosure and/or a derivative thereof, alone or in combination with an antibiotic and/or another antimicrobial. In particular, in some embodiments, administering of an engineered pyocyanin demethylase of the present disclosure and/or a derivative thereof can be performed in combination with one or more antibiotics and/or other antimicrobials.

In some embodiments contacting the engineered pyocyanin demethylase of the present disclosure and/or a derivative thereof, can be further performed in combination with other phenazine degrading agents possibly within a phenazine degrading agent according to the second aspect of the present disclosure.

The system comprises one or more engineered pyocyanin demethylase of the present disclosure and/or a derivative thereof, one or more phenazine degrading agents, one or more-antibiotics and/or one or more other antimicrobials. In some embodiments of methods and systems, the bacteria comprise persister cells.

According to a seventh aspect, a method and a system to interfere with viability of phenazine producing bacteria are described. The method comprises
    contacting the phenazine producing bacteria with
        a phenazine degrading agent comprising a pyocyanin demethylase in an amount of at least 0.01 uM, preferably at least 0.2 uM and more preferably at least 0.5 uM and higher alone or more preferably in combination with
        an antibiotic at a concentration of at least 2.0 ug mL, at least 10.0 ug mL-1, at least 25.0 ug mL-1, at least 50.0 ug mL-1, and at least 100.0 ug m the contacting performed for a time and under conditions to reduce survivability and/or antibiotic resistance of the bacteria.

In most preferred embodiments the phenazine degrading agent comprising a pyocyanin demethylase in an amount of at least 5 uM and possibly between 5 uM and 20 uM, and the antibiotic is preferably an aminoglycoside In some embodiments, the phenazine degrading agent comprises or consists of at least one engineered pyocyanin demethylase of the present disclosure and/or a derivative thereof, The system comprises one or more phenazine degrading agents in an amount of at least 0.01 uM, preferably at least 0.2 uM and more preferably at least 0.5 uM and higher and in most preferred embodiments at least 5 uM and possibly between 5 uM and 20 uM, and one or more antibiotics in an amount of at least 0.5 ug mL preferably from 40-60 ug mL depending on the MIC of the antibiotics as will be understood by a skilled person and/or one or more other antimicrobials. In some embodiments of the methods and systems, the bacteria comprise persister cells.

According to a eighth aspect, a method and a system are described for treating and/or preventing a bacterial infection by a phenazine producing bacteria in an individual. The method comprises
    administering to the individual an effective amount of with phenazine degrading agent in an amount of at least 0.01 uM, preferably at least 5 uM and possibly between 5 uM and 20 uM alone or in combination with an antibiotic and/or other antimicrobials.

In some embodiments, the phenazine degrading agent comprises or consists of at least one engineered pyocyanin demethylase of the present disclosure and/or a derivative thereof, The system comprises one or more phenazine degrading agents in an amount of at least 0.01 uM, preferably at least 5 uM and possibly between 5 uM and 20 uM one or more phenazine degrading agents, one or more antibiotics and/or one or more other antimicrobials. In some embodiments of methods and systems, the bacteria comprise persister cells.

According to a ninth aspect, an antimicrobial is described. The antimicrobial comprises one or more phenazine degrading agents herein described in an amount of at least 0.01 uM, preferably at least 5 uM and possibly between 5 uM and 20 uM and/or at least one engineered pyocyanin demethylase of the present disclosure and/or a derivative thereof.

In particular, the at least one engineered pyocyanin demethylase of the present disclosure and/or a derivative thereof are comprised in the antimicrobial in an amount suitable to reduce antibiotic resistance and/or survivability of phenazine producing bacteria and preferably in an amount of at least 0.01 uM, preferably at least 5 uM and possibly between 5 uM and 20 uM.

In some embodiments, the antimicrobial comprises a compatible vehicle, which can be a vehicle for effective administrating and/or delivering of the one or more agents to an individual. In some embodiments of the methods and systems, the bacteria comprise persister cells.

According to a tenth aspect, a composition is described. The composition comprises one or more phenazine degrading agents herein described in an amount of at least 0.01 uM, preferably at least 5 uM and possibly between 5 uM and 20 uM at least one engineered pyocyanin demethylase of the present disclosure and/or a derivative thereof, together with a compatible vehicle. In some embodiments, the composition can comprise one or more phenazine degrading agents and one or more medium components as will be understood by a skilled person.

According to an eleventh aspect, a method and system for inhibiting bacteria biofilm formation and/or disrupting mature biofilm in a medium is described. The method comprises
administering an effective amount of 1-OH-PHZ as metal-chelating agent to the medium comprising the biofilm, alone or in combination with at least one engineered pyocyanin demethylase of the present disclosure and/or a derivative thereof, an antibiotic and/or other an antimicrobial for a time and under conditions to reduce survivability and/or antibiotic resistance of the bacteria.

The system comprises 1-OH-PHZ, one or more phenazine degrading agents herein described one or more antibiotics and/or one or more other antimicrobials.

The phenazine degrading agents and related antimicrobial compositions, methods and systems herein described, in several embodiments are expected to be particularly effective in treating and/or prevent bacterial infection in vitro or in vivo.

The phenazine degrading agents and related antimicrobial compositions, methods and systems herein described can be used in connection with applications wherein reduction of viability of bacteria and/or reduction of antibiotic resistance is desired, which include but are not limited to medical application, drug research, biological analysis and diagnostics including but not limited to clinical applications. Additional exemplary applications include uses of the methods and system and related compositions herein described in several fields including basic biology research, applied biology, bio-engineering, etiology, medical research, medical diagnostics, therapeutics, and in additional fields identifiable by a skilled person upon reading of the present disclosure.

BRIEF DESCRIPTION OF THE DRAWINGS

FIGS. 4B) and 4E) are presented as maximum-intensity XZ-projections and the brightness/contrast in each data set was normalized to the tobramycin only sample, as described in Materials and Methods. FIGS. 4C) and 4F) represent an average pixel intensity (left Y-axis) of PI calculated from images in FIGS. 4B) and 4E). Each data point represents a single aggregate, with a bold lines representing the mean intensity and thin dashed lines representing the 95% confidence interval. Both mean and confidence interval were calculated as described in the Materials and Methods with a bin size of 20. Dotted black line represents average oxygen concentration measured after 24 hours as plotted on right Y-axis; O2 measurements after 12 and 18 hours are found in FIG. 10. Data points (diamonds) are the mean of technical triplicates of biological triplicates and error bars represent standard deviation. FIGS. 4D) and 4G) PodA and tobramycin ABBA treatments were homogenized, diluted in series, and dilutions were plated onto LB agar. Cells were counted if a dilution contained 10-100 colonies. Data represent the mean of biological triplicates with error bars representing the standard error of the mean. FIG. 4D) represents aggregates grown in LB and FIG. 4G) in SCFM. Data represent the mean of biological triplicates with error bars representing the standard error of the mean.

DETAILED DESCRIPTION

Figure 1:
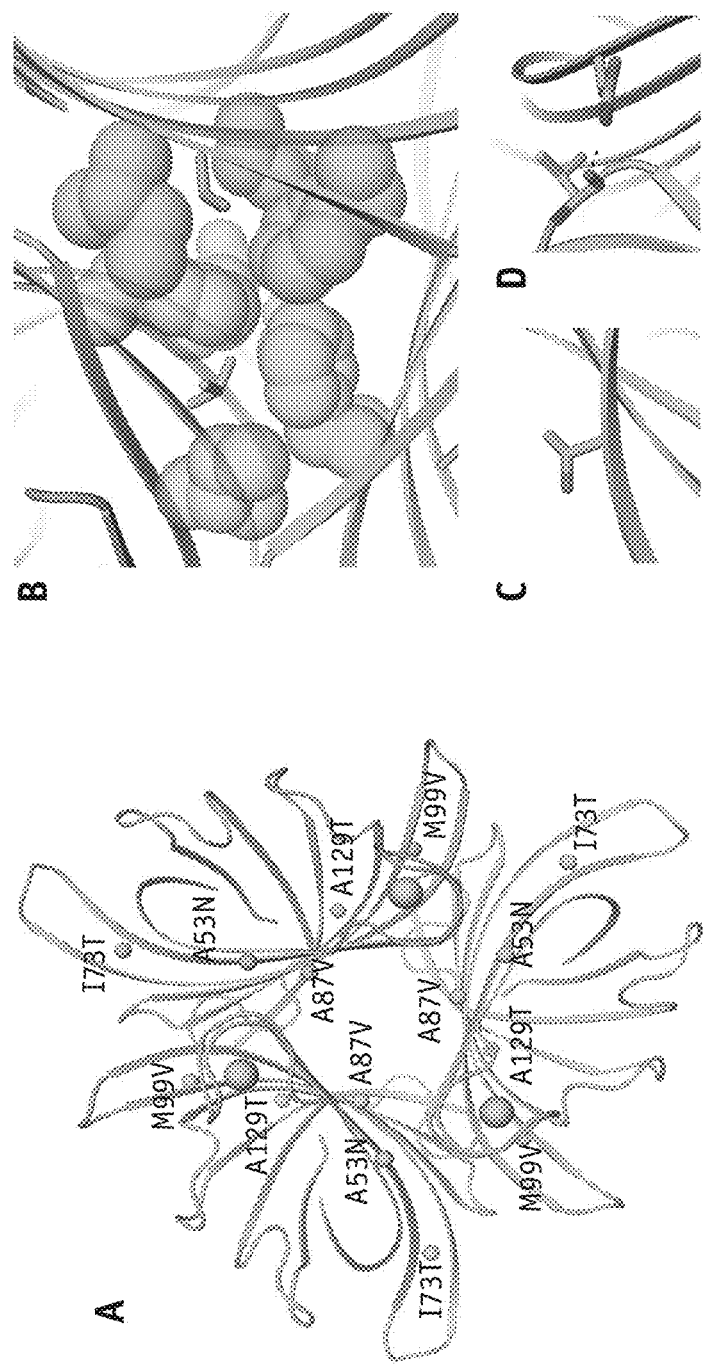
FIG. 1. Structure-based design of stabilized PodA variants. A) PodA forms a symmetric trimer. The structure depicted is a core structure of PodA$_{41-162}$ comprised in PodA$_{30-132}$ and PodA. The positions that were subjected to design are marked by shapes, with each monomer's amino acids subject to replacement indicated in the corresponding positions and each monomer of the trimer indicated with different shades of gray. B) Mutation Ala87Val increases core packing in a hydrophobic region. C) Mutation Ile73Thr improves surface polarity. D) Mutation Ala53Asn form an interfacial hydrogen bond with a Ser. E) Yield of trimer interface variants purified from inclusion bodies per L of overexpression culture. Amino acid residues changed for each variant are listed below yields.

Provided herein are engineered phenazine degrading agents, effective phenazine degrading agents' amounts, as well as related methods, systems and compositions that in several embodiments are configured for effective reduction of antibiotic resistance and/or survivability of phenazine producing bacteria.

The term "phenazine" as used herein indicates small, colorful, redox-active compounds formed by bacteria to perform diverse physiological functions. In particular, "phenazines" in the sense of the disclosure comprise several phenazines of bacterial origin produced by bacteria such as *Pseudomonas* spp., *Streptomyces* spp., *Burkholderia* spp., and *Pantoea agglomerans*. The absorption spectra of phenazines are characteristic, with an intense peak in the range 250-290 nm and a weaker peak at 350-400 nm. At least one main band occurs in the visible region (400-600 nm) to which the phenazines owe their colors. Phenazines in the sense of the disclosure comprise compounds of Formula (I):

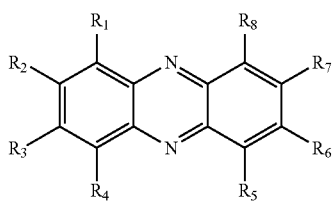
(I)

where $R_1$-$R_8$ are independently selected from hydrogen, hydroxy, alkoxy, alkyl, alkenyl, alkynyl, aryl, heteroaryl, acyl, and other groups identifiable to the skilled person.

Additionally, phenazines can include, but are not limited to, molecules according to the structures and formulas below:

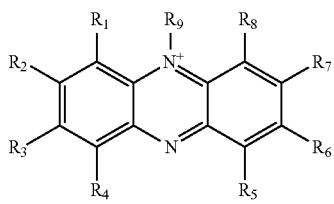
(II)

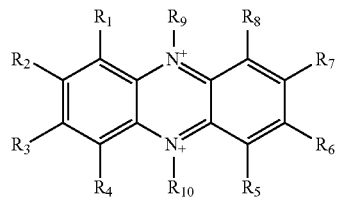
(III)

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

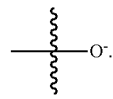

In particular, exemplary phenazine structures comprise:

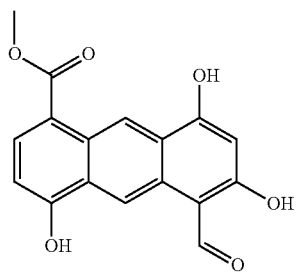
(1)

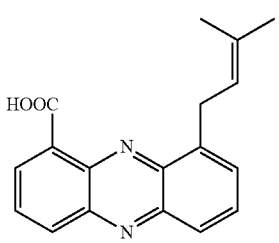
(2)

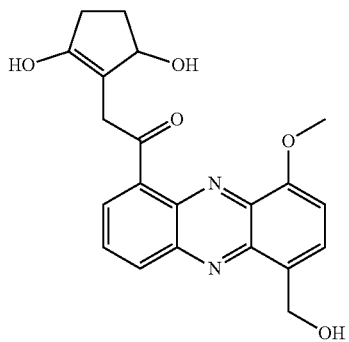
(3)

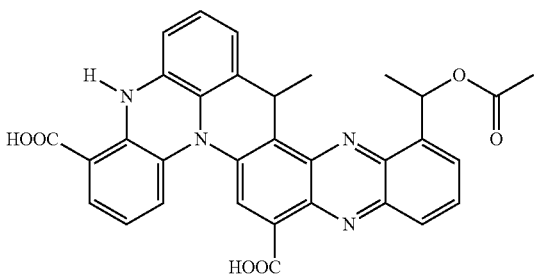
(4)

-continued

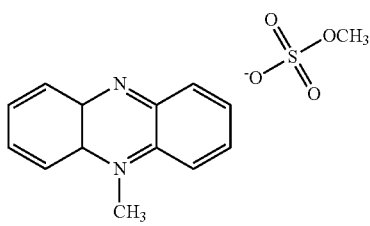
(5)

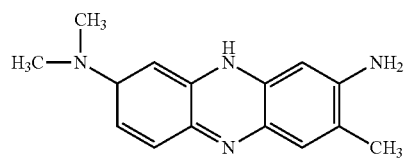
(6)

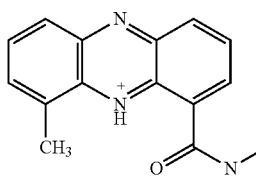

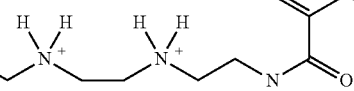
(8)

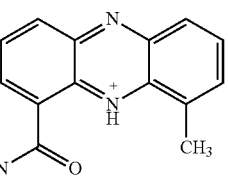
(7)

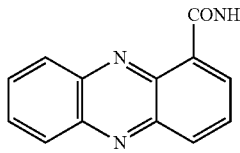
(10)

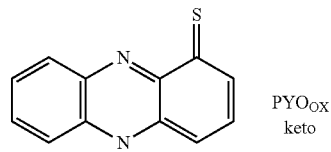
PYO$_{OX}$ keto
(9)

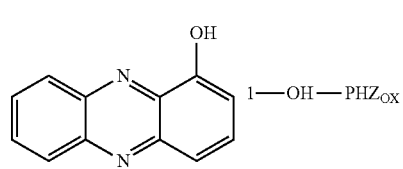
1—OH—PHZ$_{OX}$
(11)

PYO$_{OX}$ enol as well as additional phenazines that can be identified by a skilled person such as the exemplary phenazines described in Mentel et al. (ChemBioChem 2009, 10, 2295-2304) [3] and Pierson et al. (Appl Microbiol. Biotechnol. 2010, 86, 1659-1670) [4] and in other references cited in the instant disclosure which are incorporated herein by reference in their entirety Phenazine pigments are mostly water soluble and are excreted into the medium. For example, pyocyanin produced by *Pseudomonas aeruginosa*, diffuses readily into agar-solidified media which become stained blue. Some phenazines are only sparingly water soluble and precipitate. For examples, chlororaphine, a mixture of phenazine-1-carboxamide (oxychlororaphine) and its dihydro derivative, produced by *Pseudomonas chlororaphis*, accumulate as isolated emerald-green crystals at the base of agar slants. Iodinin crystallizes on the surfaces of old colonies of *Brevibacterium iodinum*, giving them a dark-purple appearance, and phenazine-1-carboxylic acid (PCA) is deposited as golden yellow crystals in colonies of *Pseudomonas aureofaciens* and in the surrounding medium. It is noted, however, that the same pigment can be produced by unrelated bacteria and "achromogenic" strains of many phenazine-producers are common. A number of strains of bacteria produce more than one phenazine. It seems likely that all bacterial phenazines are derived from a common precursor.

Representative phenazines comprise pyocyanin (PYO) and Phenazine-1-carboxylic acid (PCA). Pyocyanin (PYO) is the phenazine characteristically produced by chromogenic strains of the pseudomonad, which is found as the blue pigment occasionally seen on infected wound dressings. More attention has been paid to pyocyanin than to any other phenazine. Pyocyanin is an organic base, blue in alkaline aqueous solutions but red when acidified. The differential solubility of these forms in chloroform and water was exploited for this pigment. Pyocyanin was found to be chemically reduced to a colorless form and spontaneously reoxidized in air, which has led to the discovery, the indicator and redox properties of the compound. Additionally, pyocyanin slowly decomposed to a yellow substance, no longer basic in nature, now known to be 1-hydroxy-phenazine.

PCA is a yellow crystalline compound naturally produced by *P. aureofaciens*. The phenazine produced was readily extracted from acidified cultures with chloroform. Dilute alkali changed the color of the phenazine to orange-red and rendered it insoluble in chloroform. PCA isolated from cultures, in amounts of up to 1 g of pigment litre-1, was shown to have antibacterial activity towards a number of plant pathogens.

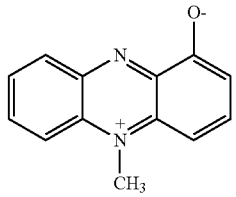
Pycyanin (PYO)

Phenazine-1-carboxylic acid (PCA)

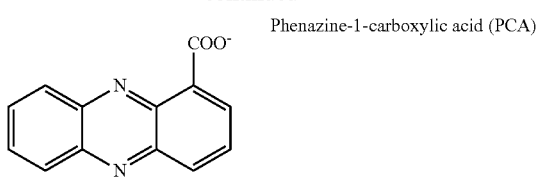

Biosynthesis as well as properties of individual phenazines are identifiable by a skilled person. In particular, phenazine natural products have been implicated in the virulence and competitive fitness of producing organisms. For example, the phenazine pyocyanin produced by *Pseudomonas aeruginosa* contributes to its ability to colonise the lungs of cystic fibrosis (CF) patients. Production of pyocyanin by *P. aeruginosa* is responsible for the bluish tint of sputum and pus associated with *P. aeruginosa* infections in humans. Clear correlation has been demonstrated between phenazine concentration in sputum and lung function decline. Further, phenazines are found to affect bacterial community development for *P. aeruginosa*.

Similarly, phenazine-1-carboxylic acid, produced by a number of *Pseudomonas* spp., increases survival in soil environments and has been shown to be essential for the biological control activity of certain strains. Examples are provided below for two types of phenazines known as pyocyanin and phenazine-1-carboxylic acid, respectively. For more examples of the occurrence, biochemistry and physiology of phenazine production, see Turner et al., 1986, Advances in Microbial Physiology, vol. 27, page 211-275. [5]

Phenazines targeted by phenazines degrading agents, herein described, comprise in particular pyocyanin-like phenazines which are formed by phenazines of formula (III)

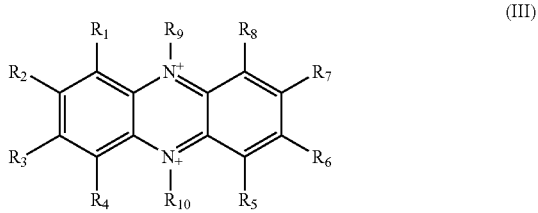

wherein $R_1$-$R_{10}$ are independently selected from hydrogen, hydroxy, alkoxy, alkyl, alkenyl, alkynyl, aryl, heteroaryl, acyl, and one of $R_1$-$R_{10}$ is a negatively charged substituent. In some of those embodiments, $R_1$-$R_8$ are independently selected from hydrogen, hydroxy, C1-C4 alkoxy, C1-C4 alkyl, C2-C4 alkenyl, C2-C4 alkynyl, and other groups identifiable to the skilled person, N+-$R_{10}$ is H and R9 is CH3.

In some embodiments, pyocyanin-like phenazines comprise phenazines of formula III wherein at least one of $R_1$-$R_8$ is hydroxy group. In some embodiments, pyocyanin-like phenazines comprise phenazines of formula (III) wherein at least one of $R_1$-$R_8$ is methoxy group.

In some embodiments, pyocyanin and/or a pyocyanin-like phenazines can be represented by formula (IV)

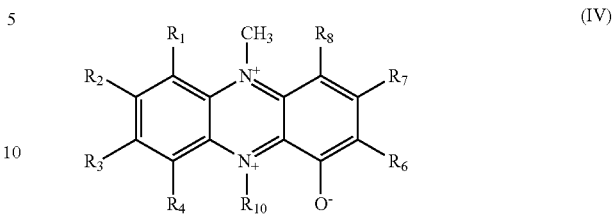

where $R_1$-$R_4$, $R_6$-$R_8$ and $R_{10}$ are independently selected from hydrogen, hydroxy, alkoxy, alkyl, alkenyl, alkynyl, aryl, heteroaryl, acyl, and other groups identifiable to the skilled person.

In some embodiments, pyocyanin-like phenazines comprise-methylphenazinium methyl sulfate or 3,6-diamino-10-methylacridinium or 1,8-dimethoxyphenazine or myxin, 5-methylphenazinium methyl sulfate or 3,6-diamino-10-methylacridinium or 1,8-dimethoxyphenazine or myxin and additional phenazines identifiable by a skilled person.

Embodiments here described are directed to compounds configured to be able to degrade phenazines in the sense of the disclosure, herein also defined as phenazine degrading agents Accordingly, the term "phenazine degrading agent" as used herein indicates any compound capable of breaking down phenazine in the sense of the disclosure into smaller molecules. Phenazine degrading agents comprise proteins from bacteria capable to degrade pyocyanin to 1-OH-phenazine+formaldehyde. Additional features of degraded phenazines can be identified by a skilled person.

In some embodiments, phenazine degrading agents can be naturally produced by a bacterium capable of producing phenazines. Identification of those degrading agents can be performed, for example, by constructing a bacterial "enrichment culture" by defining a minimal growth medium where a phenazine (PCA, PYO, and additional phenazines identifiable by a skilled person) is provided as either (or both) the sole source of carbon or nitrogen. If growth is observed after many rounds of serial dilutions, phenazine-degraders can be isolated by plating the enrichment culture on an agar plate with the same medium composition. Single colonies are picked, and streaked to fresh plates, and visually checked for purity. Once pure, the 16S rDNA is sequenced and the organism can be phenotypically characterized. Other methods for identifying a bacterium capable of phenazine degradation would be identifiable to a skilled person upon reading of the present disclosure. Once a bacterium capable of degrading phenazine is identified, one or more particular enzymes responsible for phenazine degradation in the bacterium can be identified, for example, by biochemical approach and/or genetic approaches identifiable by a skilled person In some embodiments, phenazine degrading agents herein described are synthetic phenazine degrading agents including at least one residue or chemical moiety that differs from naturally produced phenazine degrading agents.

In some embodiments, phenazine degrading agents herein described can be produced following modifications of a naturally occurring or other synthetic pyocyanin degrading agent by biochemical approach, a genetic approach and other approaches identifiable by a skilled person. In particular, a biochemical approach to provide a phenazine degrading agents herein described can comprise performing an activity assay following chemical modification of the pyocyanin demethylase, for example based on absorption or fluorescence a phenazine over time and a subsequent purifying of cell fractions to promote a disappearance of phenazine. A genetic approach to provide a phenazine degrading agents herein described can comprise employing transposition mutagenesis of the pyocyanin demethylase to make a collection of random mutants and screening them for an inability to grow on a minimal medium plus the phenazine, as described, for example, in Gallagher et al. (J. Bacteriol. 2002, 184, 6472-6480). [6] Functionality of a modified pyocyanin demethylase can be tested by a biochemical assay where the enzyme is mixed with the substrate pyocyanin. The loss of blue coloration indicates an active pyocyanin demethylase.

In some embodiments herein described, a phenazine degrading agent comprises or consists of a pyocyanin demethylase.

The term "pyocyanin demethylase" herein described refers to a type of enzymes having the ability to oxidize a methyl group of pyocyanin-like phenazines of formula (III) to formaldehyde and reduce the pyrazine ring of pyocyanin-like phenazines of formula (III) via a tautomerizing demethylation reaction. The pyocyanin demethylase uses an oxidized phenazine substrate as an electron acceptor with a methyl group to produce a reduced phenazine and formaldehyde. In general, the catalytic site of the pyocyanin demethylase contains several charged and polar residues and a nearby disulfide, also referred to as demethylating residues such as histidine, aspartate, glutamate or tyrosine, as these residues contribute to the demethylase capability of the enzyme. A derivative of a pyocyanin demethylase indicates an enzyme having a) at least 30% identity with the pyocyanin demethylase, and b) at least one demethylating residue in the catalytic site of the derivative pyocyanin demethylase, which is i) the same demethylating residue of the catalytic site of the pyocyanin demethylase or a functional equivalent thereof, and is ii) in a position equivalent to the position of the same demethylating residue of the catalytic site of the pyocyanin demethylase. The derivative of the pyocyanin demethylase to maintain a same, reduced or increased an ability to demethylate pyocyanin as will be understood by a skilled person.

An exemplary demethylation by a pyocyanin demethylase is the demethylation of PYO to 1-OH-PHZ$_{re}$ performed by a pyocyanin demethylase herein described. The chemical reaction is shown as follows:

$$C_{13}H_{10}N_2O(PYO_{ox}) + H_2O \rightarrow C_{12}H_{10}N_2O(1\text{-OH-PHZ}_{red}) + CH_2O \quad (1)$$

in which oxidized PYO (PYO$_{ox}$) and water are converted to reduced 1-OH-PHZ and formaldehyde. The reduced 1-OH-PHZ can in turn react with Fe(III) generating Fe(II) and oxidized 1-OH-PHZ (1-OH-PHZ$_{ox}$). The oxidized 1-OH-PHZ is also an iron chelator and can chelate Fe(III), Fe(II) as well as other metals. The generation of 1-OH-PHZ will limit the Fe concentration in pathogens such as *P. aeruginosa*, thus interfering with biofilm formation and/or maintenance.

In particular some embodiments, a pyocyanin demethylase in the sense of the disclosure indicates a protein from *Mycobacterium* fortuitum encoded by MFORT_14352 (NCBI Accession number: EJZ13467) that catalyzes pyocyanin (PYO) degradation (K. C. Costa, M. Bergkessel, S. Saunders, J. Korlach, D. K. Newman, Enzymatic degradation of phenazines can generate energy and protect sensitive organisms from toxicity. *MBio* 6, e01520-01515 (2015) [7] herein also referred to as PodA (pyocyanin: phenazine oxidoreductase demethylating).

In particular, a pyocyanin demethylase in the sense of the disclosure can have sequence MTGKTKPAIIGGVAI-TALAAAGLGVWLFTDGRG-GRSTTEPVTMTLDVKNDQVAKHDFG KPGMDVGD-MDIFSDILSVDGKQVGYDGGACFFTNVTPDNPMT-YCELTIHLDAGEIFARS LTPHTLAPFTMAITGGTGEY-ANSKGELTVSGVATPDEKYELKLTK (SEQ ID NO: 1) herein also indicated as PodA unless otherwise indicated.

In some embodiments, a pyocyanin demethylase according to the present disclosure is an engineered pyocyanin demethylases PodA having sequence (SEQ ID NO: 1)
$M_1T_2G_3K_4T_5K_6P_7A_8I_9I_{10}G_{11}G_{12}V_{13}A_{14}I_{15}T_{16}A_{17}$ $L_{18}A_{19}A_{20}A_{21}G_{22}L_{23}G_{24}V_{25}W_{26}L_{27}F_{28}T_{29}D_{30}G_{31}$ $R_{32}G_{33}G_{34}R_{35}S_{36}T_{37}T_{38}E_{39}P_{40}V_{41}T_{42}M_{43}T_{44}L_{45}$ $D_{46}V_{47}K_{48}N_{49}D_{50}Q_{51}V_{52}\mathbf{A}_{53}K_{54}H_{55}D_{56}F_{57}G_{58}K_{59}$ $P_{60}G_{61}M_{62}D_{63}V_{64}G_{65}D_{66}M_{67}D_{68}I_{69}F_{70}S_{71}D_{72}\mathbf{I}_{73}$ $L_{74}S_{75}V_{76}D_{77}G_{78}K_{79}Q_{80}V_{81}G_{82}Y_{83}D_{84}G_{85}G_{86}\mathbf{A}_{87}$ $C_{88}F_{89}F_{90}T_{91}N_{92}V_{93}T_{94}P_{95}D_{96}N_{97}P_{98}\mathbf{M}_{99}T_{100}$ $Y_{101}C_{102}E_{103}L_{104}T_{105}I_{106}H_{107}L_{108}D_{109}A_{110}$ $G_{111}E_{112}I_{113}F_{114}A_{115}R_{116}S_{117}L_{11}ST_{119}P_{120}$ $H_{121}T_{122}L_{123}A_{124}P_{125}F_{126}T_{127}M_{128}\mathbf{A}_{129}I_{130}$ $T_{131}G_{132}G_{133}T_{134}G_{135}E_{136}Y_{137}A_{138}N_{139}S_{140}$ $\mathbf{K}_{141}G_{142}E_{143}L_{144}T_{145}V_{146}S_{147}G_{148}V_{149}A_{150}$ $T_{151}P_{152}D_{153}E_{154}K_{155}Y_{156}E_{157}L_{158}K_{159}L_{160}$ $T_{161}K_{162}$, having replacement in positions A53, I73, A87, T91, M99, A129 and K141 to increase stability, yield and/or activity of the pyocyanin demethylase in SEQ ID NO: 1 or portions thereof.

In particular the pyocyanin demethylase further modified to include at least two replacements in SEQ ID NO: 1 selected from
A53 with L, N, or V
I73 with I, E, K, L, Q, R, T or V
A87 with C, I, T or V
T91 with V
M99 with M, C, F, I, K, R, V or Y
A129 with A, C, S, T, or V
K141 with K, S or T
and configured to be capable of the engineered pyocyanin demethylase or a derivative thereof to demethylate pyocyanin and/or a pyocyanin-like phenazines of formula (III)

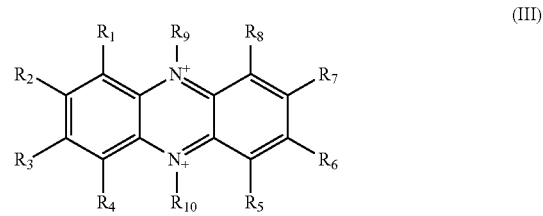

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

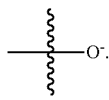

In preferred embodiments, the engineered demethylase in the sense of the present disclosure has replacements in positions 73, 87, 91, 99 and 129, or in positions 73, 87, 99, 129 and 141, or in position 73, 87, 91, 129 and 141, or in positions 53, 73, 87, 99 and 129, as mutations in those residues are expected to result in an increased yield with respect to wild type PodA of SEQ ID NO 1 (see example section reporting data for representative example of SEQ ID NO:3)

In more preferred embodiments, the engineered demethylase in the sense of the disclosure has at least two of a replacement in position 73 selected from I73T, I73K, I73L, I73R, a replacement in position 87 selected from A87V, and A87I, a replacement in position 99 selected from M99V and M99T, a replacement in position 129 selected from A129V and A129T, the replacement K141T, in position 141, the replacement T91V, in position 91 and the replacement A53N, in position 53 of SEQ ID NO: 1.

In additional preferred embodiments, an engineered demethylase in the sense of the disclosure is PodA2 of SEQ ID NO: 1, herein also PodA2 unless otherwise indicated, having replacements I73T, A87V, T91V, M99V and A129V, PodA3 of SEQ ID NO: 1, herein also PodA3 unless otherwise indicated, having replacements I73K, A87V, T91V, M99V, A129V, PodA5 of SEQ ID NO: 1, herein also PodA5 unless otherwise indicated, having replacements I73L, A87I, M99V, A129V, K141T, PodA6 of SEQ ID NO: 1, herein also PodA6 unless otherwise indicated, having replacements I73R, A87V, T91V, M99V, A129T, PodA7 of SEQ ID NO: 1, herein also PodA7 unless otherwise indicated, having replacements I73L, A87I, T91V, M99T, and A129V, PodA8 of SEQ ID NO: 1, herein also PodA8 unless otherwise indicated, having replacements A53N, I73R, A87V, T91V, A129V, PodA9 of SEQ ID NO: 1, herein also PodA9 unless otherwise indicated, having replacements I73K, A87V, T91V, A129V and K141T, and/or PodA10 of SEQ ID NO: 1, herein also PodA10 unless otherwise indicated, having replacements A53N, I73T, A87V, M99V, A129T.

In some embodiments, phenazine degrading agents encompass derivatives of pyocyanin demethylase in the sense of the disclosure and in particular of engineered pyocyanin demethylase in the sense of the disclosure.

A derivative of a pyocyanin demethylase in the sense of the disclosure indicates a variant of a protein that has at least 30% identity with the reference sequence while retaining the ability to demethylate pyocyanin.

The term "percent identity" refers to a quantitative measurement of the similarity between sequences of a polypeptide or a polynucleotide and, in particular, indicates the amount of characters that match between two different sequences. Commonly used similarity searching programs, like BLAST, PSI-BLAST (Altschul S F, M. T., Schäffer AA, Zhang J, Zhang Z, Miller W, Lipman D J., *Gapped BLAST and PSI-BLAST: a new generation of protein database search programs*. Nucleic Acids Res., 1997. 25(17): p. 14), SSEARCH (Smith T F, W. M., *Identification of common molecular subsequences*. J Mol Biol, 1981. 147(1): p. 3, W R, P., *Searching protein sequence libraries: comparison of the sensitivity and selectivity of the Smith-Waterman and FASTA algorithms*. Genomics, 1991. 11(3): p. 16) FASTA (Pearson W R, L. D., *Improved tools for biological sequence comparison*. Proc Natl Acad Sci USA, 1988. 85(8): p. 5) [11] and the HMMER3 9 (Johnson L S, E. S., Portugaly E, *Hidden Markov model speed heuristic and iterative HMM search procedure*. BMC Bioinformatics, 2010. 11(431): p. 8) [12] can produce accurate statistical estimates, ensuring that protein sequences that share significant similarity also have similar structures.

The similarity between sequences is typically measured by a process that comprises the steps of aligning the two polypeptide or polynucleotide sequences to form aligned sequences, then detecting the number of matched characters, i.e. characters similar or identical between the two aligned sequences and calculating the total number of matched characters divided by the total number of aligned characters in each polypeptide or polynucleotide sequence, including gaps. The similarity result is expressed as a percentage of identity.

For example in embodiment wherein the pyocyanin demethylase is, PodA derivatives in the sense of the disclosure encompass homologous proteins of PodA with at least 30% identity with PodA of SEQ ID NO:1 and that possesses the demethylating residues at positions equivalent to D72, E154, and Y156 in PodA.

In some embodiments, a derivative of a pyocyanin demethylase comprise a truncated version the protein encoded by MFORT_14352 (lacking a predicted N-terminal, membrane-spanning helix), hereafter referred to as PodA$_{30-162}$. The gene expressing PodA$_{30-162}$ derived from *Mycobacterium* was heterologously expressed in *E. coli*. from *Escherichia coli*. In particular, PodA$_{30-162}$ in the sense of the disclosure can have sequence MDGRG-GRSTTEPVTMTLDVKNDQ-VAKHDFGKPGMDVGDMDIFSDILSVDGKQVGYD GGACFFTNVTPDNPMTYCELTIHLDAGEIFARSLTPH-TLAPFTMAITGGTGEYANSKGEL TVSG-VATPDEKYELKLTKAENLYFQ (SEQ ID NO: 2) as described in U.S. Pat. No. 10,913,936 filed on Mar. 22, 2017 and issued on Feb. 9, 2021, herein incorporated by reference in its entirety.

In some embodiments, a derivative of a pyocyanin demethylase comprise a truncated version the protein encoded by MFORT_14352 (lacking a predicted N-terminal, membrane-spanning helix), hereafter referred to as PodA$_{41-162}$. The gene expressing PodA$_{41-162}$ derived from *Mycobacterium* was heterologously expressed in *E. coli*. from *Escherichia coli*. In particular, PodA$_{41-162}$ in the sense of the disclosure can have sequence

```
                                          (SEQ ID NO: 3)
VTMTLDVKNDQVAKHDFGKPGMDVGDMDIFSDILSVDG

KQVGYDGGACFFTNVTPDNPMTYCELTIHLDAGEIFAR

SLTPHTLAPFTMAITGGTGEYANSKGELTVSGVATPDE

KYELKLTK.
```

A table indicating the correspondence of the positions of residues A53, I73, A87, M99, A129 and K141 of PodA of SEQ ID NO: 1 in the derivative PodA$_{30-162}$ of SEQ ID NO: 2 and in derivative PodA$_{41-162}$ of SEQ ID NO: 3 is reported in Table 1 below

TABLE 1

Overview PodA residues/positions for stability, yield and/or activity

| PodA-SEQ ID NO: 1 | PodA$_{30-162}$- SEQ ID NO: 2 | PodA$_{41-162}$- SEQ ID NO: 3 |
|---|---|---|
| A53 | A24 | A13 |
| I73 | I44 | I33 |
| A87 | A58 | A47 |
| T91 | T62 | T51 |
| M99 | M70 | M59 |
| A129 | A100 | A89 |
| K141 | K112 | K101 |

Whenever not accompanied by a specific indication of a SEQ ID NO the above residues and position replaceable to increase stability, yield and/or activity of pyocyanin demethylase PodA or a derivative thereof are indicated with respect to the PodA sequence (SEQ ID NO: 1) as customary in the field and would be understood by a skilled person.

A skilled person will also be able to identify the residues and positions reported in Table 1 in sequences of derivatives of pyocyanin demethylases upon review of the present disclosure.

Accordingly, in some embodiments, an engineered pyocyanin demethylase PodA$_{30-162}$ or a derivative thereof are described, the pyocyanin demethylase comprising sequence (SEQ ID NO: 2)
$D_1G_2R_3G_4G_5R_6S_7T_8T_9E_{10}P_{11}V_{12}T_{13}MI_4TI_5LI_6D_{17}$ $V_{18}K_{14}N_{20}D_2I Q_{22}V_{23}\mathbf{A}_{24}K_{25}H_{26}D_{27}F_{28}G_{29}K_{30}P_{31}$ $G_{32}M_{33}D_{34}V_{35}G_{36}D_{37}M_{38}D_{39}I_{40}F_{41}S_{42}D_{43}\mathbf{I}_{44}L_{45}$ $S_{46}V_{47}D_{48}G_{49}K_{50}Q_{51}A_{52}G_{53}Y_{54}D_{55}G_{56}G_{57}\mathbf{A}_{58}C_{59}$ $F_{60}F_{61}\mathbf{T}_{62}N_{63}V_{64}T_{65}P_{66}D_{67}N_6SP_{69}\mathbf{M}_{70}T_{71}Y_{72}C_{73}$ $E_{74}L_{75}T_{76}I_{77}H_{78}L_{79}D_{80}A_{81}G_{82}E_{83}I_{84}F_{85}A_{86}R_{87}$ $S_{88}L_{89}T_{90}P_{91}H_{92}T_{93}L_{94}A_{95}P_{96}F_{97}T_{98}M_{99}\mathbf{A}_{100}$ $I_{101}T_{102}G_{103}G_{104}T_{105}G_1O_6E_{107}Y_{108}AI_{09}N_{110}$ $S_{111}\mathbf{K}_{112}G_{113}E_{114}L_{115}T_{116}V_{117}S_{118}G_{119}V_{120}$ $A_{121}T_{122}P_{123}D_{124}E_{125}K_{126}Y_{127}E_{128}L_{129}K_{130}$ $L_{131}T_{132}K_{133}A_{134}E_{135}N_{136}L_{137}Y_{138}F_{139}Q_{140},$ the pyocyanin demethylase further modified to include at least two replacements in SEQ ID NO: 2 selected from A24 with L, N, or V I44 with I, E, K, L, Q, R, T or V A58 with C, I, T or V T62 with V M70 with M, C, F, I, K, R, V or Y A100 with A, C, S, T, or V K112 with K, S or T and configured to be capable of the engineered pyocyanin demethylase or a derivative thereof to demethylate pyocyanin and/or a pyocyanin-like phenazines of formula (III)

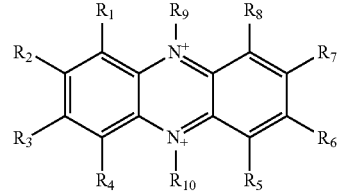

(III)

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of –1) such as

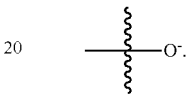

In some preferred embodiments, and engineered pyocyanin demethylase PodA$_{30-162}$ has replacements in positions 44, 58, 62, 70 and 100, or in positions 44, 58, 70, 100 and 112, or in position 44, 58, 62, 100 and 112, or in positions 24, 44, 58, 70 and 100 of SEQ ID NO: 2, as mutations in those residues are expected to result in an increased yield with respect to wild type PodA (see example section reporting data in connection with representative example of SEQ ID NO: 3).

In more preferred embodiments, the engineered demethylase PodA$_{30-162}$ has at least two of a replacement in position 44 selected from I44T, I44K, I44L, I44R, a replacement in position 58 selected from A58 V, and A58 I, a replacement in position 70 selected from M70V and M70T, a replacement in position 100 selected from A100V and A100T, the replacement K112T, in position 112, the replacement T62V, in position 62 and the replacement A24N, in position 24 of SEQ ID NO: 2.

In additional preferred embodiments, the engineered demethylase in the sense of the disclosure is PodA2 of SEQ ID NO: 2, herein also PodA$_{230-162}$ unless otherwise indicated, having replacements I44T, A58V, T62V, M70V and A100V, PodA3 of SEQ ID NO: 2, herein also PodA$_{330-162}$ unless otherwise indicated, having replacements I44K, A58, T62V, M70V, A100V, PodA5 of SEQ ID NO: 2, herein also PodA$_{530-162}$ unless otherwise indicated, having replacements I44L, A58I, M70V, A100V, K112T, PodA6 of SEQ ID NO: 2, herein also PodA$_{630-162}$ unless otherwise indicated, having replacements I44R, A58V, T62V, M70V, A100T, PodA7 of SEQ ID NO: 2, herein also PodA$_{730-162}$ unless otherwise indicated, having replacements I44L, A58I, T62V, M70T, and A100V, PodA8 of SEQ ID NO: 2, herein also PodA$_{830-162}$ unless otherwise indicated, having replacements, A24N, I44R, A58V, T62V, A100V, PodA9 of SEQ ID NO: 2, herein also PodA$_{930-162}$ unless otherwise indicated, having replacements I44K, A58V, T62V, A100V and K112T, and/or PodA10 of SEQ ID NO: 2, herein also PodA$_{230-162}$ unless otherwise indicated, having replacements A24N, 144T, A58V, M70V, A100T.

In some embodiments, an engineered pyocyanin demethylase can be PodA$_{41-162}$ or a derivative thereof, the pyocyanin demethylase comprising sequence (SEQ ID NO: 3)
$V_1T_2M_3T_4L_5D_6V_7K_8N_9D_{10}Q_{11}V_{12}A_{13}K_{14}H_{15}D_{16}F_{17}$ $G_{18}K_{19}P_{20}G_{21}M_{22}D_{23}V_{24}G_{25}D_{26}M_{27}D_{28}I_{29}F_{30}S_{31}$ $D_{32}I_{33}L_{34}S_{35}V_{36}D_{37}G_{38}K_{39}Q_{40}V_{41}G_{42}Y_{43}D_{44}G_{45}$ $G_{46}A_{47}C_{48}F_{49}F_{50}T_{51}N_{52}V_{53}T_{54}P_{55}D_{56}N_{57}P_{58}M_{59}$ $T_{60}Y_{61}C_{62}E_{63}L_{64}T_{65}I_{66}H_{67}L_{68}D_{69}A_{70}G_{71}E_{72}I_{73}$ $F_{74}A_{75}R_{76}S_{77}L_{78}T_{79}P_{80}H_{81}T_{82}L_{83}A_{84}P_{85}F_{86}T_{87}$ $M_{88}A_{89}I_{90}T_{91}G_{92}G_{93}T_{94}G_{95}E_{96}Y_{97}A_{98}N_{99}S_{100}$ $K_{101}G_{102}E_{103}L_{104}T_{105}V_{106}S_{107}G_{108}V_{109}A_{110}$ $T_{111}P_{112}D_{113}E_{114}K_{115}Y_{16}E_{117}L_{118}K_{119}L_{120}$ $T_{121}K_{122}$, the pyocyanin demethylase further modified to include at least two replacements in SEQ ID NO: 3 selected from A13 with L, N, or V
I33 with I, E, K, L, Q, R, T or V
A47 with C, I, T or V
T51 with V
M59 with M, C, F, I, K, R, V or Y
A89 with A, C, S, T, or V
K101 with K, S or T and configured to be capable of the engineered pyocyanin demethylase or a derivative thereof to demethylate pyocyanin and/or a pyocyanin-like phenazines of formula (III)

(III)

where $R_1$-$R_{10}$ are independently selected from hydrogen, hydroxy, alkoxy, alkyl, alkenyl, alkynyl, aryl, heteroaryl, acyl, and other groups identifiable to the skilled person, and one of $R_1$-$R_{10}$ is a negatively charged substituent (formal charge of −1) such as

—O⁻.

In preferred embodiments, the engineered demethylase PodA$_{41-162}$ has replacements in positions 33, 47, 51, 59 and 89, or in positions 33, 47, 59, 89 and 101, or in position 33, 47, 51, 89 and 101, or in positions 13, 33, 47, 59 and 89, as mutations in those residues are expected to result in an increased yield with respect to PodA$_{41-162}$ of SEQ ID NO 3 (see example section)

In more preferred embodiments, the engineered demethylase PodA$_{41-162}$ has at least two of a replacement in position 33 selected from I33T, I33K, I33L, I33R, a replacement in position 47 selected from A47V, and A47I, a replacement in position 59 selected from M59V and M59T, a replacement in position 89 selected from A89V and A89T, the replacement K101T, in position 101, the replacement T51V, in position 51 and the replacement A13N, in position 13 of SEQ ID NO: 3.

In additional preferred embodiments, an engineered demethylase in the sense of the disclosure is PodA2 of SEQ ID NO: 3, herein also PodA2$_{41-162}$ unless otherwise indicated, having replacements I33T, A47V, T51V, M59V and A89V, PodA3 of SEQ ID NO: 3, herein also PodA3$_{41-162}$ unless otherwise indicated, having replacements I33K, A47V, T51V, M59V, A89V, PodA5 of SEQ ID NO: 3, herein also PodA5$_{41-162}$ unless otherwise indicated, having replacements I33L, A47I, M59V, A89V, K101T, PodA6 of SEQ ID NO: 3, herein also PodA6$_{41-162}$ unless otherwise indicated having replacements I33R, A47V, T51V, M59V, A89T, PodA7 of SEQ ID NO: 3, herein also PodA7$_{41-162}$ unless otherwise indicated, having replacements I33L, A47I, T51V, M59T, and A89V, PodA8 of SEQ ID NO: 3, herein also PodA8$_{41-162}$ unless otherwise indicated, having replacements, A13N, I33R, A47V, T51V, A89V, PodA9 of SEQ ID NO: 3, herein also PodA9$_{41-162}$ unless otherwise indicated, having replacements I33K, A47V, T51V, A89V and K101T, and/or PodA10 of SEQ ID NO: 3, herein also PodA10$_{41-162}$ unless otherwise indicated, having replacements A13N, I33T, A47V, M59V, A89T.

In some embodiments, pyocyanin demethylase herein described can include additional sequences at the N-terminus or C-terminus, e.g. typically methionine for the start codon, as will be understood by a skilled person.

In particular, in some embodiments, reported in the Example section PodA10$_{41-162}$ can have sequence, MVTMTLDVKNDQVNKHDFGKPGMDVGDMDIFSD-TLSVDGKQVGYDGGVCFFTNVTP DNPVTYCELT-IHLDAGEIFARSLTPATLAPFTMTITGGTGEYAN-SKGELTVSGVATPDEK YELKLTK (SEQ ID NO: 4) as will be understood by a skilled person.

In some of those embodiments, a PodA derivative can have a 40% identity, a 50% identity or a 60% identity with PodA of SEQ ID NO:1, SEQ ID NO: 2, SEQ ID NO: 3 or SEQ ID NO: 4. In some embodiments, a PodA derivative can have 70% or higher identity with PodA of SEQ ID NO: 1 SEQ ID NO: 2, SEQ ID NO: 3 or SEQ ID NO: 4.

In pyocyanin demethylases and derivatives herein described, the demethylating residues can be identified by first aligning a PodA derivative to SEQ ID NO:1 SEQ ID NO: 2, SEQ ID NO: 3 or SEQ ID NO: 4 and then identifying the residues in the PodA derivative that correspond to the demethylating residues of SEQ ID NO:1, SEQ ID NO: 2, SEQ ID NO: 3 or SEQ ID NO: 4 in the aligned columns as would be understood to a person skilled in the art.

The PodA derivatives in some embodiments encompass homologous proteins of PodA with at least 30% identity, 40% identity, 50% identity or >70% identity with PodA of SEQ ID NO: 1, SEQ ID NO: 2, SEQ ID NO: 3 or SEQ ID NO: 4 while retaining the ability to demethylate pyocyanin.

In some embodiments, derivatives of pyocyanin demethylase comprise homologous proteins of PodA having SEQ ID NO: 1, SEQ ID NO: 2, SEQ ID NO: 3 or SEQ ID NO: 4, with at least 30% identity, in which one or more demethylating residues within the enzyme's catalytic site, such as H121, F70, D68, D72, E154 and Y156 of SEQ ID NO: 1 or corresponding residues in SEQ ID NO: 2, SEQ ID NO: 3 or SEQ ID NO: 4, are replaced with a functionally equivalent residue.

In some embodiments, derivatives of the engineered pyocyanin demethylase comprise homologous proteins of PodA having SEQ ID NO: 1, SEQ ID NO: 2, SEQ ID NO: 3 or SEQ ID NO: 4 in which at least 30% identity, in which one or more demethylating residues within the enzyme's catalytic site, such as H121, F70, D68, D72, E154 and Y156 of SEQ ID NO: 1 or corresponding residues in SEQ ID NO:2, SEQ ID NO:3 and SEQ ID NO:4, are replaced with a functionally equivalent residue.

A functionally equivalent residue of an amino acid used herein typically refers to other amino acid residues having physiochemical and stereochemical characteristics substantially similar to the original amino acid. The physiochemical characteristics include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

In particular, the demethylating residue H121 of PodA can be replaced by a protonating residue such as arginine or lysine; D68, D72, E154 or Y156 can be replaced with a negatively charged residue such as aspartate, glutamate or tyrosine; F70 can be replaced by an aromatic residue such as tyrosine or tryptophan.

In some embodiments, a derivative pyocyanin demethylase herein described can be provided using directed evolution from a pyocyanin demethylase or a derivative thereof herein described.

In some embodiments, a pyocyanin demethylase derivative can be provided by protein engineering methods identifiable by those skilled in the art, such as methods based on rational design of modified pyocyanin demethylase derivatives and/or directed evolution techniques. The term "rational design" indicates a process wherein detailed knowledge of the structure and function of a protein is used to make desired changes, employing site-directed mutagenesis and other methods known to those skilled in the art.

In one exemplary embodiment, a derivative pyocyanin demethylase can be designed and generated using computational strategies by introducing mutations to PodA having SEQ ID: NO: 1 SEQ ID NO: 2, SEQ ID NO: 3 or SEQ ID NO: 4. The designed pyocyanin demethylase derivatives can potentially possess enhanced stability, higher yield, and comparable or even enhanced catalytic efficiency compared to that of PodA having SEQ ID: NO: 1 SEQ ID NO: 2, SEQ ID NO: 3 or SEQ ID NO: 4. Many computational rational design tools can be used for performing such task. For example, automated algorithm based on atomistic Rosetta modeling and phylogenetic sequence information as described in Goldenzweig et. al, Molecular Cell 63, 337-346, 2016 can be used to computationally scan various pyocyanin demethylase variants.

In another exemplary embodiment, the genetic sequence corresponding to the pyocyanin demethylase can be mutated using error-prone PCR or another technique identifiable to the skilled person to produce a library of mutated genetic sequences. The proteins expressed by the mutant sequences can be screened for phenazine degrading activity against specific or broad ranges of phenazines, for example, by the spectrophotometric measurement of phenazine levels over time. The proteins thus identified to be able to degrade a specific phenazine or broad range of phenazines can be synthesized, for example, in a bacterium using recombinant DNA techniques known to the skilled person. The term "directed evolution" indicates a process wherein random mutagenesis is applied to a protein, and a selection regime is used to pick out variants that have one or more desired properties, such as selecting variants with pyocyanin demethylase activity. Directed evolution requires no prior structural knowledge of a protein, nor is it necessary to be able to predict what effect a given mutation will have. Accordingly, the sequence and structure of known pyocyanin demethylases can be modified using protein engineering techniques to provide new pyocyanin demethylase variants.

In some embodiments, a pyocyanin demethylase or a derivative thereof or other phenazine degrading agents herein described, can be obtained from gene expression of an encoding polynucleotide. Polynucleotides encoding pyocyanin demethylase derivatives can be cloned using commercially available reagents from vendors such as Qiagen, Invitrogen, Applied Biosystems, Promega, and others, following standard molecular biology methods known in the art, such as those described in Sambrook and Russell (2001) Molecular Cloning, A Laboratory Manual.

Synthetic DNA. Genomic DNA or cDNA encoding pyocyanin demethylase derivatives can be cloned into an expression vector. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences, as would be understood by a skilled person. Promoters can be constitutively active or inducible. RNA can be isolated from a cell, such as Mycobacterium fortuitum and cDNA produced by reverse transcription using standard techniques and commercial kits. Alternatively, genomic DNA can be purified from the cell, and cDNA or genomic DNA encoding one or more pyocyanin demethylases isolated, following methods known to those in the art. PCR-based amplification of the gene of interest can be performed using appropriately designed primer pairs (e.g. using PrimerDesign or other programs known to those skilled in the art). An encoded tag can be incorporated into the primer design (e.g. encoding a His-tag designed to be fused to the N- or C-terminus of the recombinant enzyme) to facilitate protein purification (e.g. using commercially-available His-tagged protein purification columns/kits), as described below. PCR-based amplification can be followed by ligation (e.g. using T4 DNA ligase) of the amplicon into an appropriate expression cassette in a plasmid suitable for propagation in bacteria or other cells, such as transformation-competent *E. coli*, followed by growth of transformed cell cultures, purification of the plasmid for confirmation of the cloned pyocyanin demethylase by DNA sequence analysis, among other methods known to those skilled in the art.

Cloned recombinant pyocyanin demethylases can be expressed using cell-based methods, or cell-free methods, following standard techniques and using commercially available kits. Cell-based methods for expression of recombinant enzymes can include expression in prokaryotic or eukaryotic cell cultures, such as *E. coli* or other bacterial cells, yeast strains, insect cells, or mammalian cells, among others known to those skilled in the art.

In some embodiments, the pyocyanin demethylase derivatives in the sense of the disclosure encompass a PodA having a SEQ ID NO: 1 SEQ ID NO: 2, SEQ ID NO: 3 or SEQ ID NO: 4, an engineered pyocyanin demethylase or a derivative thereof, further linked to one or more other proteins, polypeptides, or domains to form a recombinant fusion protein.

Recombinant fusion proteins can be created artificially using recombinant DNA technology identifiable by a person skilled in the art of molecular biology. In general, the methods for producing recombinant fusion proteins comprise removing the stop codon from a cDNA or genomic sequence coding for the PodA protein having a SEQ ID NO: 1 SEQ ID NO: 2, SEQ ID NO: 3 or SEQ ID NO: 4 or a derivative thereof, then appending the cDNA or genomic sequence of the second protein in frame through ligation or overlap extension PCR. Optionally, PCR primers can further encode a linker of one or more amino acids residues and/or a PCR primer-encoded protease cleavage site placed between two proteins, polypeptides, or domains or parts thereof. The resulting DNA sequence will then be expressed by a cell or other protein expression system as a single protein. A fusion protein can also comprise a linker of one or more amino acids residues, which can enable the proteins to fold independently and retain functions of the original separate proteins or polypeptides or domains or parts thereof. Linkers in protein or peptide fusions can be engineered with protease cleavage sites that can enable the separation of one or more proteins, polypeptides, domains or parts thereof from the rest of the fusion protein.

In other embodiments, a pyocyanin demethylase fusion protein can be generated using directed evolution approaches such as DNA shuffling and others known to those skilled in the art.

In some embodiments, a pyocyanin demethylase or a derivative thereof can further comprise at least one tag having the ability to tag the pyocyanin demethylase, without affecting the enzyme's ability to degrade phenazine. The tag allows the pyocyanin demethylase to bind to tag-specific antibodies, or other molecules, depending on the tag selection.

The term "tag" as used herein indicates peptide sequences genetically grafted onto a recombinant protein. Tags can be removed by chemical agents or by enzymatic means, such as proteolysis or splicing, as known to a skilled person in the art. Tags can be attached to proteins for various purposes. For example, affinity tags can be appended to proteins so that the tagged protein can be purified from a crude biological source using an affinity technique. Exemplary affinity tags include poly-Histidine (His tag), chitin binding protein (CBP), maltose binding protein (MBP), and glutathione-S-transferase (GST), among others known to those skilled in the art. The poly(His) tag is a commonly used protein tag which binds to metal matrices. Solubilization tags can be used to assist in the proper folding in proteins and keep them from precipitating. Exemplary solubilization tags include thioredoxin (TRX) and poly (NANP). Some affinity tags have a dual role as a solubilization agent, such as MBP, and GST. Chromatography tags can be used to alter chromatographic properties of the protein to afford different resolution across a particular separation technique. Other tags applicable to the current disclosure would be identifiable to a person of ordinary skill in the art.

In some embodiments, a pyocyanin demethylase, an engineered pyocyanin demethylase or a derivative thereof can comprise a His-tag or other tags herein described attached using standard molecular biology techniques known to those skilled in the art. For example, a tag can be added by inserting the polynucleotide encoding a protein of interest in a vector that has the tag configured to fuse at the N-terminus or C-terminus. The tag can also be added using primers encoding the tag then fused to the N-terminus or C-terminus of the gene by PCR. Alternatively or in addition, methods such as overlap extension PCR and infusion HD cloning can be used to insert the tag at a site between the N-terminus and C-terminus of the protein-coding polynucleotide. Optionally, PCR primers can further encode a linker of one or more amino acids residues placed between the protein of interest and the tag to prevent the tag from affecting the activity of the protein being tagged and/or a PCR primer-encoded protease cleavage site. The choice of the location where a tag is inserted to a protein sequence depends mainly on the structural and functional features of the protein and the intended downstream methods employing the use of the tag, as would be understood to a person skilled in the art.

In some embodiments, a tagged pyocyanin demethylase, or derivative thereof is PodA of SEQ ID NO: 1 or $PodA_{30-162}$ of SEQ ID NO: 2, or $PodA_{41-162}$ of SEQ ID NO: 3, or $PodA_{10}$ of SEQ ID NO: 4, further comprising a tag such as a His tag. For example, $PodA_{41-162}$ comprising a C-terminal His tag and a TEV protease cleavage site can facilitate nickel affinity purification of PodA and/or derivatives thereof. Affinity-purified PodA and/or derivatives thereof can be generated by expression in an expression system such as *E. coli* under control of an expression vector, followed by nickel affinity purification followed by cleavage of the 6×-His tag by TEV protease.

Additional phenazine degrading agents and engineered pyocyanin demethylase in the sense of the disclosure can be identified with methods herein described. The method comprises contacting a candidate demethylase protein with a pyocyanin-like phenazine and detecting the ability of the candidate agent to inactivate said pyocyanin-like phenazine and/or a phenazine related pathway in the bacteria. The system comprises one or more phenazine producing bacteria able to produce pyocyanin-like phenazine, and one or more agents capable of detecting phenazine and/or phenazine related pathways. In some embodiments of the methods and systems, the bacteria comprise persister cells.

The terms "detect" or "detection" as used herein indicates the determination of the existence, presence, or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred to as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

In some embodiments, activity of phenazine degrading agents herein described can be detected by detecting difference in the amount of phenazine in bacteria before and after administration of the phenazine degrading agents herein described. The amount of phenazine in the bacteria before and after reduction of the quantity of phenazine according to the methods described herein can be measured by methods identifiable to a skilled person upon reading of the present disclosure. For example, the quantity of phenazine in bacterial culture before and after reduction of the quantity of phenazine can be measured by directly loading the filtrate of the culture onto a HPLC column and analyzing the filtrate as done by Dietrich et al. (Molecular Microbiology 2006, 61, 1308-1321). Additional quantification techniques can be identified by a skilled person and can include, for example, using time-lapsed spectral multiphoton fluorescence microscopy of Sullivan et al., (ACS Chemical Biology 2011, 6, 893-899) to monitor phenazine concentrations within bacterial cells in vivo both before and after reduction of the phenazine levels.

In some embodiments, one or more phenazine degrading agents herein described and in particular one or more engineered pyocyanin demethylase herein described can be used in methods and systems to interfere with viability of bacteria.

The term "bacterium" or "bacteria" as used herein refers to a prokaryotic microbial species of Gram-negative or Gram positive bacteria. The wording "Gram-negative bacteria" refers to bacteria that do not retain crystal violet dye in the Gram staining protocol. In contrast, the wording "Gram-positive bacteria" refers to those that are stained dark blue or violet by Gram staining. Exemplary bacteria in the sense of the disclosure comprise *Pseudomonas, Brevibacterium, Coryneform Bacteria, Nocardia Brevibacterium linens, Brevibacterium, Burkholderia cenocepecia, Methanosarcina mazei, Mycobacterium abscessus, Pantoea agglomerans, Pectobacterium atrosepticum, Pelagio variabilis, Pseudomonas fluorescens, Streptomyces anulatus, Streptomyces cinnamonensis*, and related species that produce phenazines to facilitate various physiological functions identifiable to a skilled person upon reading of the present disclosure.

In particular, in several embodiments, herein described, bacteria in the sense of the disclosure comprise phenazine producing bacteria, which comprise *Pseudomonas aeruginosa* and additional bacteria known or identifiable by a skilled person, and phenazine degrading bacteria which comprise *Sphingomonas* sp. DP58 (see Yang et al. Current Microbiology 2007, 55, 284-287 and Chen et al. Biodegradation 2008, 19, 659-667) and additional bacteria known or identifiable by a skilled person.

Identification of a phenazine degrading bacterium can be performed by various techniques. For example, identification of a phenazine producing bacterium can be performed by constructing a bacterial "enrichment culture" by defining a minimal growth medium where a phenazine (PCA, PYO, and additional phenazines identifiable by a skilled person) is provided as either (or both) the sole source of carbon or nitrogen. If growth is observed after many rounds of serial dilutions, phenazine-degraders can be isolated by plating the enrichment culture on an agar plate with the same medium composition or by dilution to extinction in liquid medium. Single colonies are picked, and streaked to fresh plates, and visually checked for purity. Once pure, the 16S rDNA is sequenced and the organism can be phenotypically characterized. Other methods for identifying a bacterium capable of phenazine degradation would be identifiable to a skilled person upon reading of the present disclosure.

In some embodiments, bacteria comprise persister cells which typically constitute a small portion of a culture which is tolerant to killing by lethal doses of bactericidal antibiotics. Persister bacterial cells can be identified, for example, by exposure of logarithmic or stationary cultures of the bacteria to antibiotics using concentrations exceeding five times the minimum inhibitory concentration for each antibiotic. Persister numbers can be determined by plating the antibiotic-treated cultures on LB agar plates and subsequent counting of colony forming units representing the cell numbers which survived antibiotic exposure. Other methods for identification of persister cells will be known by a skilled person, and can be found, for example, in Möker et al. ("*Pseudomonas aeruginosa* increases formation of multi-drug-tolerant persister cells in response to quorum-sensing signaling molecules." In J Bacteriol. 2010 April; 192(7): 1946-55. Epub 2010 Jan. 22).

In some embodiments, one or more phenazine degrading agents herein described and in particular one or more engineered pyocyanin demethylases herein described can be used in methods and systems for the inactivation of phenazines and/or a phenazine related pathway.

The term "inactivation" as used herein with reference to a pathway refers to a complete or partial inhibition of one or more of the reactions or steps in the pathway.

The terms "inhibit" and "inhibition" as used herein refers to a decrease relative to a baseline level. Accordingly, inhibition of a reaction indicates a decrease in the relative output compared to an output selected as a baseline level. Inhibition of a reaction can be detected by detecting any products or other indicator and/or parameter associated with completion of the reaction and identifiable by a skilled person. Accordingly, an inactivated pathway in the sense of the present disclosure indicates a pathway in which any enzyme controlling a reaction in the pathway is biologically inactive or in which at least one of the reactions or steps of the pathway is otherwise inhibited, e.g. by degrading one or more enzymes of the pathway and/or by subtracting the relevant substrate and/or intermediate through phenazine degradation.

The term "pathway" as used herein refers to a biological process comprising one or more chemical or biological reactions or steps in which at least one substance is transformed, produced, and/or acquired by a bacterium. The one or more reactions or steps comprised in the pathway can involve molecules such as, for example, proteins, enzymes, cofactors, oxidizing/reducing agents, signaling molecules, metal ions, and others identifiable to a skilled person upon reading of the present disclosure that participate in the transformation, production and/or acquisition of the substance by a bacterium. In embodiments wherein pathway involves a bacterial cell signaling molecule, the pathway indicates signal transduction through cascade reactions of a series of signaling molecules as part of a complex system of communication that governs basic cellular activities and coordinates cell actions. Exemplary pathways of the disclosure comprise Fe(III) reduction to Fe(II) comprising the steps of reduction of Fe(III) to Fe(II) through the use of a reducing agent (such as, for example, pyocyanin, and/or other reducing agents), bacterial acquisition of Fe(II) comprising the steps of reduction of Fe(III) to Fe(II) by a reducing agent (such as, for example, pyocyanin, and/or other reducing agents) and importation of Fe(II) into the bacteria by a transporter protein (such as, for example, FeoB), and other pathways identifiable to a skilled person upon reading of the present disclosure.

The term "phenazine-related pathway" as used herein refers to either a pathway in which a phenazine is a starting material, intermediate, or product, or alternatively, any pathway in which at least one of the one or more of the steps comprised in the pathway are mediated by a phenazine. Exemplary pathways in which a phenazine is a starting material, intermediate, or product include, but are not limited to, phenazine biosynthesis, phenazine cycling, quorum sensing, and other pathways identifiable to a skilled person upon reading of the present disclosure. Exemplary pathways in which one or more of the steps of the pathway are promoted or mediated by a phenazine include, but are not limited to, reduction of Fe(III) to Fe(II) by phenazine, bacterial Fe(II) acquisition in which the Fe(II) is obtained, and other processes identifiable to a skilled person upon reading of the present disclosure.

In some embodiments, phenazine related pathways comprise phenazine-mediated bacterial biofilm formation, phenazine-mediated iron acquisition and phenazine mediated intracellular redox balancing of bacteria In some embodiments, a phenazine related pathway comprises a phenazine-mediated signaling pathway of the bacteria. Specifically, in some embodiments, the bacteria have a motile and a sessile state and the signaling pathway triggers a transition from the motile to the sessile state.

In some embodiments, one or more phenazine related pathways comprise central metabolic pathways of the bacteria.

In some embodiments, the one or more phenazine related pathways comprise transportation of phenazines in and/or out of the bacterial cell. In other embodiments, phenazine related pathways comprise intracellular phenazine mediated redox hemostasis of the bacteria.

In some embodiments, a method and system to interfere with viability of bacteria is described, the method comprising contacting bacteria with one or more phenazine degrading agents herein described to reduce survivability and/or antibiotic resistance of the bacteria.

The term "viability" as used here in refers to whether or not a bacterial cell is able to maintain itself or recover its potentiality. Viable cells in the sense of the present disclosure are cells able to, or capable of recover the ability to form colonies and biofilms on or in a solid or liquid medium. In some embodiments, the term "medium" as used herein indicates an environment that is suitable to support growth of microorganisms or cells. In particular, suitable medium comprise growth medium or culture medium in a liquid or gel designed to support the bacteria in vitro, as well as tissues and other suitable environments within a host (including a human host) in vivo. Accordingly, various mediums are formed by or comprise medium components that are chemical compounds and molecules that are used in life-supporting functions and processes of bacteria, which allow bacterial cells to grow and reproduce.

Exemplary medium components comprise at least one redox-active compound in a solvent. In some embodiments, the solvent can comprise water in at least 10% by volume, preferably at least 50% by volume, and most preferably at least 95% by volume.

In some embodiments, the medium solvent can further comprise at least one organic solvent. Exemplary organic solvent includes ethanol, methanol, tetrahydrofuran, dimethylformamide (DMF), dimethyl sulfoxide (DMSO), acetic acid, formic acid, glycerol, glycol, isopropanol and 1-butanol.

In some embodiments, the redox-active compound has at least one oxidation absorption maximum in the wavelength of 400 nm to 700 nm in the oxidized state with a corresponding oxidation extinction coefficient. In some embodiments, the redox-active compound has at least one reduction absorption maximum in the wavelength of 400 nm to 700 nm in the reduced state with a corresponding reduction extinction coefficient.

In some embodiments, the at least one oxidation absorption maximum and the at least one reduction absorption maximum have an absorption shift or difference of at least 5 nm, preferably 50 nm and most preferably 150 nm.

In some embodiments, the ratio of oxidation extinction coefficient to the reduction extinction coefficient is at least 2 to 1, preferably at least 20:1 and most preferably 100:1.

In some embodiments, the ratio of reduction extinction coefficient to the oxidation extinction coefficient is at least 2 to 1, preferably at least 20:1 and most preferably 100:1.

In some embodiments, the at least one redox-active compound has a standard electrode potential $E°$ vs. NHE of $-500$ mV to 500 mV. As used herein, the term redox-active compound refers to a chemical compound that is able to undergo reversible electrochemical conversion between an oxidation state and reduction state. A redox-active compound includes naturally occurring redox-active molecules, organic, inorganic or metal ion complexes. Redox-active natural products include, but are not limited to those produced by the genera *Streptomyces* and *Pseudomonas*, including those redox-active natural products produced by *P. aeruginosa*, *P. oryzihabitans*, and *P. luteola*.

Exemplary redox-active compounds listed in Table 2.

TABLE 2

Exemplary redox-active compounds

| Chemical name (Abbreviation) | Structure (The oxidized form) | $E^{0,}$ (vs. NHE) (mV) | # of Redox cycles over 7 days | Support survival? | Reduction by PA14? |
|---|---|---|---|---|---|
| Pyocyanin (PYO) | | $-40^a$ | 31 | Yes | Yes |
| Phenazine-1-carboxylate (PCA) | | $-114^a$ | 22 | Yes | Yes |

TABLE 2-continued

Exemplary redox-active compounds

| Chemical name (Abbreviation) | Structure (The oxidized form) | $E^{0\prime}$ (vs. NHE) (mV) | # of Redox cycles over 7 days | Support survival? | Reduction by PA14? |
|---|---|---|---|---|---|
| 1-Hydroxyphenazine (1-OHPHZ) | | −174 [a] | 14 | Yes | Yes |
| Methylene blue (MB) | | 0 [b] (+11 [c]) | 3 | No | Yes |
| 2,6-AQDS | | −184 [d] | No cycle | No | Yes (very slowly) |
| Paraquat | | −446 [e] | No cycle | No | No |
| Homogentisic acid (HMA) | | +306 [b] | No cycle | No | — |

[a] Reference [20] [21]
[b] $E^{0\prime}$ values were measured in aqueous solution at pH 7 in this study
[c] Reference (Fultz, M. L., and R. A. Durst. 1982. Mediator Compounds for the Electrochemical Study of Biological Redox Systems - a Compilation. Analytica Chimica Acta 140:1-18) [22]
[d] Reference [23] [24]
[e] References [25, 26] [27]

Additional medium components that can be found in a medium comprise amino acids. salts, polyacrylic acids, polyols, polyglycols, such as Polyethylene Glycols (e.g. PEG 1000, PEG 3000), polysaccharides, polypeptides, polynucleotides as well as other organic polymers with molecular weight between 10,000 to 1,000,000 Da and additional components identifiable by a skilled person. For example medium components can comprise sodium thioglycolate ($HS-CH_2CO_2Na$), sodium dithionite, Organic; simple sugars e.g. glucose, acetate or pyruvate; extracts such as peptone, tryptone, yeast extract etc., hydrogen carbonate salts ($HCO_3^-$), amino acids, $NH_4Cl$, $(NH_4)_2SO_4$, $KNO_3$, KCl, $K_2HPO_4$, $MgCl_2$, $MgSO_4$, $CaCl_2$), $Ca(HCO_3)_2$, $FeCl_3$, $Fe(NH_4)(SO_4)_2$, Fe-chelates, $CoCl_2$, $ZnCl_2$, $Na_2MoO_4$, $CuCl_2$, $MnSO_4$, $NiCl_2$, $Na_2SeO_4$, $Na_2WO_4$, $Na_2VO_4$, Vitamins, amino acids, purines, pyrimidines Methods for evaluating the viability of bacteria after the use of the methods and systems for interference with viability of bacteria described herein include, but are not limited to, measurement of colony forming units, cell counts such as that described by Wang et al. (J. Bacteriol. 2010, 192, 365-369) [28], and other methods identifiable to a skilled person upon the reading of the present disclosure.

In some embodiments, phenazine degrading agents, herein described, can be administered to enhance phenazine degradation endogenously and/or exogenously.

In particular, in some embodiments, enhancing phenazine degradation can be performed by expressing and/or delivering to the bacteria one or more phenazine degrading agents herein described. In an exemplary embodiment, a DNA sequence of a phenazine-degrading agent can be delivered by introduction of the DNA sequence into a bacterium via a vector (e.g. viral or plasmid vector), or other techniques identifiable by a skilled person upon reading of the present disclosure, and the DNA sequence expressed in the bacteria to produce the phenazine-degrading protein. In another embodiment, phenazine-degrading proteins can be expressed in other bacteria and then isolated and purified to afford phenazine-degrading proteins suitable for extracellular degradation of phenazine.

In embodiments wherein the phenazine degrading agent can be administered exogenously, any one of the engineered pyocyanin demethylase or derivative thereof herein described can be administered at suitable concentration to achieve inhibition of a phenazine degrading pathway, and/or to interfere with viability of bacteria and in particular inhibit viability of phenazine producing bacteria identifiable by detecting functionality of the pathway and/or viability of bacteria following contacting the bacteria with one or more of engineered pyocyanin demethylase or derivative thereof herein described. Additional methods to identify suitable concentrations of engineered pyocyanin demethylase or derivative thereof herein described are identifiable by a skilled person upon reading of the disclosure.

In some embodiments inhibition of a phenazine degrading pathway, and/or of viability of phenazine producing bacteria, can be performed in vitro or in vivo. Inhibition in vitro can be detected, by detecting decreased bacterial survival after treatments For in vivo applications, efficacy can be determined by healing rate of a chronic infection or through counts of bacteria in vivo.

In some embodiments concentration of engineered pyocyanin demethylase or derivative thereof herein described, suitable to achieve inhibition of a phenazine degrading pathway, and/or to interfere with viability of bacteria and in particular inhibit viability of phenazine producing bacteria identifiable comprise at least 0.001 uM, at least 0.01 uM, at least 0.1 uM, at least 1.0 uM, and more preferably at least 5.0 uM, at least 10.0 uM, and at least 20 uM.

In some embodiments, concentrations of a pyocyanin demethylase herein described capable of inhibition a phenazine degrading pathway, and/or of viability of phenazine producing bacteria can be in a range from 0.1 uM to 20 uM of PodA and can be combined with clinical concentrations of antimicrobials, which differ depending on the antimicrobial agent. Antimicrobial agents can be defined as any known compound that is being used with the intent to treat infections.

In some embodiments, a pyocyanin demethylase or derivative thereof herein described and in particular of an engineered pyocyanin demethylase or derivative thereof can be used in ranges of at least 0.75 uM at least 1 uM, at least 1.25 uM, at least 1.5 uM, at least 1.75 uM, at least 2 uM, at least 2.25 uM at least 2.5 uM at least 2.75 uM, at least 3 uM, at least 3.25 uM, at least 3.5 µM, at least 3.75 uM at least 4 uM, at least 4.25 uM, at least 4.5 uM, at least 4.75 uM and in additional concentrations identifiable by a skilled person upon reading of the present disclosure.

In embodiments where the inhibition is performed in vivo, the determination of a proper concentration can be performed in combination with clinical concentrations of antimicrobials, which differ depending on the antimicrobial agent.

In some embodiments, inactivating a phenazine or phenazine-related pathway comprises contacting the bacteria with one or more phenazine degrading agents to impair phenazine-mediated bacterial biofilm development in the bacteria.

As used herein the term "biofilm" indicates an aggregate of microorganisms in which cells adhere to each other on a surface. These adherent cells are frequently embedded within a self-produced matrix of extracellular polymeric substance (EPS). Biofilms can form on living or non-living surfaces and can be prevalent in natural, industrial and hospital settings. The microbial cells growing in a biofilm are physiologically distinct from planktonic cells of the same organism, which, by contrast, are single-cells that can float or swim in a liquid medium. Formation of a biofilm begins with the attachment of free-floating microorganisms to a surface. These first colonists adhere to the surface initially through weak, reversible adhesion via van der Waals forces. If the colonists are not immediately separated from the surface, they can anchor themselves more permanently using cell adhesion structures such as pili. When the biofilm growth is balanced with that of biofilm dispersion, the biofilm is considered "mature." Methods to quantify and measure biofilms will be known to a skilled person and can include, for example, the COMSTAT method of Heydorn et al. (Microbiology 2000, 146, 2395-2407) [29].

In some embodiments, the phenazine-mediated bacterial biofilm development comprises phenazine-mediated iron acquisition of bacteria. Iron has been shown to be involved as a signal in bacterial biofilm formation (see, for example, Banin et al. PNAS, 2005, 102, 11076-11081) [30]. Phenazines have been shown to mediate iron acquisition in bacterial biofilm development, for example, by reduction of insoluble Fe(III) to more soluble Fe(II) (See, for example, Wang et al. J. Bacteriol. 2011, 193, 3606-3617) [31].

In some embodiments, one or more phenazine degrading agents herein described and in particular engineered pyocyanin demethylase and/or derivative thereof can be used to inhibit pathogenic microbial biofilm formation as well as to disrupt mature biofilm in vitro and in vivo (see Example 7).

In particular, in some embodiments, herein described phenazine degrading agents herein described can impact early stages in biofilm formation and development by decreasing the biofilm surface coverage.

In some embodiments, phenazine degrading agents herein described can disrupt the mature biofilm by interfering with anoxic growth of pathogens in deeper layers of the biofilm.

A person skilled in the art would understand that as biofilm matures, cells in deeper layers of the biofilm begin to experience oxygen limitation and redox stress, rendering the cells to be slow growing and highly resistant to antibiotics.

Thus, in some embodiments, a method for inhibiting bacteria biofilm formation and/or disrupting mature biofilm in a medium is described, the method comprising administering one or more phenazine degrading agents to the medium comprising the biofilm. The suitable medium comprises growth medium or culture medium in a liquid or gel designed to support the bacteria in vitro, as well as tissues and other suitable environments within a host (including a human host) in vivo.

The phenazine degrading agents such as PodA and a derivative thereof can degrade pyocyanin-like phenazines into 1-Hydroxyphenazine (1-OH-PHZ) which can limit the Fe concentration in pathogens such as *P. aeruginosa* by acting as an iron chelator, thus interfering with biofilm formation and/or maintenance In some embodiments, functional derivative can be determined by assessing the proteins specific activity and kinetic parameters in comparison with a reference pyocyanin demethylase according to the disclosure and the related demethylase and biofilm inhibiting activity can be derived on that basis. For example, if a derivative of a pyocyanin demethylase has a specific activity and kinetic parameters comparable with those of WT PodA or PodA10, the derivative is expected to inhibit biofilms as will be understood by a skilled person upon reading of the present disclosure.

Thus, in some embodiments, another method for inhibiting bacteria biofilm formation and/or disrupting mature biofilm in a medium is described. The method comprises administering 1-hydroxyphenazine (1-OH-PHZ) as metal-chelating agent to the medium comprising the biofilm, alone or in combination with an antibiotic and/or other antimicrobial for a time and under conditions to reduce survivability and/or antibiotic resistance of the bacteria.

The term "chelator" or "chelating agent" as used herein refers to a molecule or ligand capable of binding a metal ion (e.g. iron) by forming multiple bonds to the metal. In particular, chelation involves the formation or presence of two or more separate coordinate bonds between a polydentate (multiple bonded) ligand and a single central metal. These ligands can be organic compounds, and are called chelants, chelators, chelating agents, or sequestering agents. Chelators can be molecules made by the host (such as, hemoglobin, transferrin, lactoferrin, conalbumin and ferritin); or molecules made by other microoorganisms (such as siderophores including Enterobactin, Yersiniabactin, Pyoverdine, Pyochelin, and others identifiable to a skilled person); or synthetic molecules (e.g. deferoxamine, deferiprone, deferasirox, 2,2 dipyridyl, 1,10 phenanthroline, FerroZine, EDTA, diethylenetriamine, ethylene diamine, N,N', N"-tris(2-pyridylmethyl)-1,3,5-cis,cis-triaminocyclohexane (tachpyr), and others identifiable to a skilled person).

In general, a metal chelator is a molecule capable of binding a metal and forming a molecular complex according to the generic reaction:

$$mM + lL + hH^+ = M_mL_lH_h \quad (2)$$

wherein M is the metal, L is the chelator, and H$^+$ is positive hydrogen ions with m, l and h independently equal to or higher than 1, and wherein the equilibrium constant βmlh is determined to be $$\beta mlh(M, L) = \frac{[M_mL_lH_h]}{[M]^m[L]^l[H^+]^h}. \quad (3)$$

Some molecules are capable of binding more than one metal with different binding affinities which are reflected in different equilibrium constant βmlh. In those instances, a molecule is known to a skilled person as a chelator of a particular metal when the molecule is capable of specifically binding that metal. Specific binding of a metal by a chelator is determined by the molecule binding with a highest equilibrium constant βmlh for the metal separately calculated with respect to other metals according to equation (3).

For example, some molecules capable of binding more than one metal. To determine whether a molecule is a Cu or Zn chelator, the equilibrium constant βmlh can be calculated for the molecule with respect to Cu, with respect to Zn and with respect to other metals. The calculated βmlh values can be compared to determine whether the molecule is a Cu) or Zn chelator.

1-hydroxyphenazine (1-OH-PHZ) in the sense of the present disclosure is a metal chelating agent. FIG. 27A of related application to U.S. Non-Provisional application Ser. No. 15/466,839 entitled "Phenazine Degrading Agents And Related Compositions, Methods And Systems For Interfering With Viability Of Bacteria" filed on Mar. 22, 2017 and granted on Feb. 9, 2019 with US patent number U.S. Pat. No. 10,913,936, illustrates a coordination geometry for 1-OH-PHZ metal complexation. 1-OH-PHZ can act as a bivalent metal chelator by forming a stable five-membered, 2:1, chelate compound. For example, 1-OH-PHZ can form metal complexes with bivalent metals such as Cu, Ni, Co, Zn and Cd (Kidani Y. Studies on Metal Chelate Compounds of Phenazine Derivatives. VIII. Metal Complexes of 1-Hydroxyphenazine, Yakugaku Zasshi. 1973 September; 93(9): 1089-93) [33]. The dissociation constant of 1-hydroxyphenazine with metals can be calculated according to equation 3 or determined by spectrophotometry or potentiometry as will be understood by a person skilled in the art. For example, in one exemplary embodiment, 1-hydroxyphenazine (1-OH-PHZ) as a copper chelating agent has a log of the equilibrium constant βmlh of binding copper equal to 8.68. (Kidani Y., Studies on Metal Chelate Compounds of Phenazine Derivatives. I. Spectrophotometric Studies on Copper Chelate Compounds of 1-Hydroxyphenazine and its Di-N-oxide. Chemical and Pharmaceutical Bulletin, Vol. 6 (1958) No. 5, P 556-562) [34])

In some embodiments, antimicrobials used in combination with the pyocyanin demethylase of the disclosure and/or suitable antibiotics, can comprise one or more chelating agents have concentrations ranging from 1 µM to 1000 µM, for example in amounts of 100 µM, 200 µM and in additional concentrations identifiable by a skilled person.

In some embodiments, phenazine degrading agents can be used in methods for treating and/or preventing a bacterial infection by a phenazine producing bacteria in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism, including but not limited to, animals and in particular higher animals and in particular vertebrates such as mammals and in particular human beings.

In some embodiments, the method for treating and/or preventing a bacterial infection in an individual comprises administering to the individual an effective amount of one or more phenazine degrading agents herein described alone or in combination with an antibiotic and/or other antimicrobial. In some embodiments, administering of one or more phenazine degrading agents can be performed in combination with one or more antibiotics and/or other antimicrobials. In particular, the phenazine degrading agents, herein described, will be selected by the skilled person as not interfering in a deleterious manner with the normal biochemical pathways of the individual.

Exemplary antibiotics that can be used in combination with the one or more phenazine degrading agents herein described include Amoxicillin and clavulanic acid (Augmentin®), Methicillin, oxacillin, nafcillin, cloxacillin, dicloxacillin, cabenicillin, ticarcillin, piperacillin, mezlocillin, azlocillin, ticarcillin and clavulanic acid (Timentin®), piperacillin and tazobactam (Zosyn®), cephalexin, cefdinir, cefprozil, cefaclor, cefuroxime, sulfisoxazole, erythromycin/ sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam. As a person of ordinary skill in the art would understand, the antibiotics herein listed can be selected for treating infections or reducing inflammation caused by bacteria including *Staphylococcus aureus, Pseudomonas (P. aeruginosa), Burkholderia cepacia*, some mycobacteria.

The administering to the individual the one or more phenazine degrading agents alone or in combination with an antibiotic and/or other antimicrobial can be performed through various administration routes including oral ingestion, inhalation, intranasal, topical application, intravenous or subcutaneous injections and others as will be recognized by a person skilled in the art. The one or more phenazine degrading agents alone or in combination with an antibiotic and/or other antimicrobial can be in a form of an aqueous solution, cream, solid powder, tablets, aerosols, or other forms as will be understood by a person skilled in the art.

In some embodiments, an antimicrobial is described. The antimicrobial comprises one or more phenazine degrading agents herein described. The one or more phenazine degrading agents are in particular comprised in the antimicrobial in an amount suitable to reduce antibiotic resistance and/or survivability of phenazine producing bacteria. In some embodiments, the antimicrobial comprises a compatible vehicle, which can be a vehicle for effective administrating and/or delivering of the one or more agents to an individual. In some embodiments of the methods and systems, the bacteria comprise persister cells.

An "antimicrobial" as described herein indicates a substance that kills or inhibits the growth of microorganisms such as bacteria, fungi, or protozoans. Antimicrobial either kills microbes (microbiocidal) or prevent the growth of microbes (microbiostatic).

In some embodiments, the antimicrobial comprises one or more phenazine degrading agents optionally a compatible vehicle for effective administrating and/or delivering of the one or more agents to an individual.

The term "vehicle" as used herein indicates any of various media acting usually as solvents, carriers, binders or diluents for phenazine degrading agents comprised in the composition as an active ingredient.

In some embodiments, antimicrobial is a pharmaceutical composition comprising one or more phenazine degrading agents for the treatment of cystic fibrosis and a pharmaceutically acceptable vehicle such as an excipient or diluent.

The term "excipient" as used herein indicates an inactive substance used as a carrier for the active ingredients of a medication. Suitable excipients for the pharmaceutical compositions herein disclosed include any substance that enhances the ability of the body of an individual to absorb the one or more agents. Suitable excipients also include any substance that can be used to bulk up formulations with the one or more agents to allow for convenient and accurate dosage. In addition to their use in the single-dosage quantity, excipients can be used in the manufacturing process to aid in the handling of the one or more agents. Depending on the route of administration, and form of medication, different excipients may be used. Exemplary excipients include but are not limited to anti-adherents, binders, coatings disintegrants, fillers, flavors (such as sweeteners) and colors, glidants, lubricants, preservatives, or sorbents.

The term "diluent" as used herein indicates a diluting agent which is issued to dilute or carry an active ingredient of a composition. Suitable diluents include any substance that can decrease the viscosity of a medicinal preparation.

In particular, in some embodiments, the phenazine degrading agents herein described can be included in pharmaceutical compositions which contain at least one phenazine degrading agents herein described, in combination with one or more compatible and pharmaceutically acceptable vehicles, and in particular with pharmaceutically acceptable diluents or excipients. In those pharmaceutical compositions, the phenazine degrading agents can be administered as an active ingredient for treatment or prevention of a condition in an individual.

In some embodiments, the antimicrobial or pharmaceutical composition comprising one or more phenazine degrading agents herein described further comprises antibiotic and/or an additional antimicrobial.

The term "antibiotics" as used herein refers to a type of antimicrobial used in the treatment and prevention of bacterial infection. Some antibiotics can either kill or inhibit the growth of bacteria. Others can be effective against fungi and protozoans. The term "antibiotics" can be used to refer to any substance used against microbes. Antibiotics are commonly classified based on their mechanism of action, chemical structure, or spectrum of activity. Most antibiotics target bacterial functions or growth processes. Antibiotics having bactericidal activities target the bacterial cell wall, such as penicillins and cephalosporins, or target the cell membrane, such as polymyxins, or interfere with essential bacterial enzymes, such as rifamycins, lipiarmycins, quinolones and sulfonamides. Antibiotics having bacteriostatic properties target protein synthesis, such as macrolides, lincosamides and tetracyclines. Antibiotics can be further categorized based on their target specificity. "Narrow-spectrum" antibacterial antibiotics target specific types of bacteria, such as Gram-negative or Gram-positive bacteria. "Broad-spectrum" antibiotics affect a wide range of bacteria.

In some embodiments, suitable antibiotics that can be used in the antimicrobial in combination with Fe chelators include ampicillin, kanamycin, ofloxacin, Aminoglycosides, Carbapenems, Ceftazidime, Cefepime, Ceftobiprole, Fluoroquinolones, Piperacillin, Ticarcillin, tobramycin, aztreonam, coliston, tazobactam, and others (or combinations of these antibiotics) that can be recognized by a person skilled in the art.

In some embodiments, suitable antibiotics comprise antibiotics effective against pathogen *Pseudomonas aeruginosa* such as Aminoglycosides, Carbapenems, Ceftazidime, Cefepime, Ceftobiprole, Fluoroquinolones, Piperacillin, Ticarcillin, tobramycin, aztreonam, coliston, and others (alone or in combination) that can be recognized by a skilled person.

Additional antibiotics suitable in particular for treatment of cystic fibrosis include Amoxicillin and clavulanic acid (Augmentin®), Methicillin, oxacillin, nafcillin, cloxacillin, dicloxacillin, cabenicillin, ticarcillin, piperacillin, mezlocillin, azlocillin, ticarcillin and clavulanic acid (Timentin®), piperacillin and tazobactam (Zosyn®), cephalexin, cefdinir, cefprozil, cefaclor, cefuroxime, sulfisoxazole, erythromycin/sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam. A person skilled in the art would be able to select appropriate antibiotics for treating cystic fibrosis caused by particular pathogen. An exemplary indication of antibiotic, is shown in Table 3 below From Orenstein, D. *Cystic Fibrosis: A Guide for Patient and Family,* 4th ed. LWW; 2011.

TABLE 3

An exemplary list of antibiotics

| Type and kinds | Bacteria Treated | How Taken |
|---|---|---|
| Penicillins | | |
| Amoxicillin and clavulanic acid (Augmentin ®) | *Staphylococcus aureus* (Staph) | |
| Methicillin, oxacillin and nafcillin | Pseudomonas (*P. aeruginosa*) | Intravenous, intramuscular |
| Cloxacillin and dicloxacillin | Staph | Oral |
| Cabenicillin, ticarcillin, piperacillin, mezlocillin and azlocillin | *P. aeruginosa* | Intravenous |
| Ticarcillin and clavulanic acid (Timentin ®) | Staph, *P. aeruginosa* | intravenous |
| Piperacillin and tazobactam (Zosyn ®) | *P. aeruginosa* | intravenous |
| Cephalosporins | | |
| Cephalexin, cefdinir, cefprozil and cefaclor | Staph, *P. aeruginosa* | oral |
| Cefuroxime | Staph | oral |
| Sulfa | | |
| Sulfisoxazole | *P. aeruginosa* | oral |
| Erythromycin/sulfisoxazole | Staph | oral |
| Aminoglycosides | | |
| Tobramycin, amikacin, gentamicin | *P. aeruginosa* (*in combination* with gentamicin, tobramycin, and amikacin; also work well with anti-Pseudomonas penicillin drug) | Intravenous, inhaled |
| Macrolides | | |
| Erythromycin, clarithromycin and azithromycin | Staph and may help reduce inflammation from *P. aeruginosa* | Oral, intravenous |
| Tetracyclines | | |
| Tetracycline, doxycycline, minocycline, and tigecycline | Formerly *P. aeruginosa*, some *Burkholderia cepacian* and Staph | Oral, intravenous, intramuscular |
| Quinolones | | |
| Ciprofloxacin, levofloxacin | Pseudomonas | Oral, intravenous |
| Vancomycin | | |
| Vancomycin | Staph and methicillin-resistant *Staphylococcus aureus* (MRSA) | intravenous |
| Linezolid | | |
| Linezolid | MRSA and some mycobacteria | Oral, intravenous |
| Imipenem & Meripenem | | |
| Imipenem & Meripenem | *P. aeruginosa*, Staph | intravenous |
| Aztreonam (Cayston ®) | | |
| Aztreonam (Cayston ®) | *P. aeruginosa* | Intravenous, inhaled |

In embodiments herein described concentration of suitable antibiotics that can be used in the antimicrobial against phenazine producing bacteria can identified based on the respective breakpoint Minimum Inhibitory Concentration (MIC)

The wording breakpoint minimum inhibitory concentration (MIC) indicates the concentration that inhibits visible bacterial growth at 24 hours of growth in specific media, at a specific temperature, and at a specific carbon dioxide concentration. Methods that can be used to measure the MIC of a microorganism comprise broth dilution, agar dilution and gradient diffusion (the 'E test'), where twofold serial dilutions of antibiotic are incorporated into tubes of broth, agar plates or on a paper strip, respectively, as will be understood by a person skilled in the art. The disk diffusion method defines an organism as susceptible or resistant based on the extent of its growth around an antibiotic-containing disk. MIC values are influenced by several laboratory factors.

Laboratories follow standard for parameters such as incubation temperature, incubation environment, growth media, as well as inoculum and quality control parameters. In the U.S. Standards for determining breakpoint MIC values for various bacteria can be found in Clinical & Laboratory Standards Institute (CLSI) publications, with an example also provided as Appendix A of U.S. Provisional Application No. 62/722,124 incorporated herein by reference in its entirety, as will be understood by the skilled person. In Europe, standards for determining breakpoint MIC values for bacteria can be found in European Committee on Antimicrobial Susceptibility Testing (EUCAST) see website: www.eucast.org/clinical_breakpoints/at the time of filing of the instant disclosure) as will be understood by the skilled person.

In some embodiments, in methods and systems herein described and related compositions one or more antibiotics can be administered in concentration of at least 0.00005 ug mL, preferably at least 0.002 ug mL, at least 0.01 ug mL, at least 0.025 ug mL, or at least 0.08 ug mL. or at least 0.1 ug mL, and in additional concentrations identifiable by a skilled person upon reading of the present disclosure. The specific concentration of each antibiotic can be determined based on the related MIC as will be understood by a skilled person.

In most preferred embodiments of methods and systems of the present disclosure, one or more antibiotics can be administered at a concentration of at least 2.0 ug mL, at least 10.0 ug mL, at least 25.0 ug mL, at least 50.0 ug mL, and at least 100.0 ug mL-1, in particular in combination with concentration of one or more engineered pyocyanin demethylase in concentration associated with a resulting synergic inhibition of bacteria viability herein described. The specific concentration of each antibiotic can be determined based on the related MIC as will be understood by a skilled person.

In most preferred embodiments, antibiotics used in methods and systems and related compositions of the present disclosure are aminoglycosides. The term "aminoglycosides" as used herein indicates an antibiotic that inhibit protein synthesis and contain an amino-modified glycoside aa portion of the molecule. Aminoglycoside antibiotics are typically used as a Gram-negative antibacterial medication, more typically against Gram-negative aerobes. such as *Pseudomonas, Acinetobacter*, and *Enterobacter* as well as some Mycobacteria, including the bacteria that cause tuberculosis, as well be understood by a skilled person.

Aminoglycosides antibiotics can be categorized based on the molecular structure in 4,6-disubstituted deoxystreptamine sub-class of aminoglycosides, the neomycins are examples of the 4,5-disubstituted sub-class, and a non-deoxystreptamine aminoglycoside subclass. Aminoglycosides antibiotics are typically administered intravenously and intramuscularly, topical preparations for wounds, oral administration for gut decontamination (e.g., in hepatic encephalopathy) and/or a nebulized form Exemplary aminoglycoside antibiotics comprise, Kanamycin A Amikacin, Tobramycin, Dibekacin, Gentamicin, Sisomicin, Netilmicin, Neomycins B, C, Streptomycin and Plazomicin wherein kanamycin A through netilmicin are examples of the 4,6-disubstituted deoxystreptamine sub-class of aminoglycosides, the neomycins are examples of the 4,5-disubstituted sub-class, and streptomycin is an example of a non-deoxystreptamine aminoglycoside. Tobramycin is an exemplary representative of aminoglycosides as will be understood by a skilled person.

In some preferred embodiments methods and systems as well as related compositions according to the disclosure are performed to provide a combined administration of a phenazine degrading agent and an antibiotic at combined concentrations resulting in a synergistic inhibition of one or more target phenazine producing bacteria. In those embodiments, a naturally occurring and isolated pyocyanin demethylase PodA and/or an engineered pyocyanin demethylase PodA can be administered at a concentration of at least 0.01 uM, 0.1 uM, 1.0 uM, 5.0 uM, 10.0 uM, and 20 uM and the antibiotic can be administered at a concentration of at least 2.0, at least 10.0 ug mL-1, at least 25.0 ug mL-1, at least 50.0 ug mL-1, and at least 100.0 ug mL.

As a person skilled in the art would appreciate, pyocyanin-like phenazine as a natural pigment can change its color from blue to yellow upon reduction, thus can be used as bacterial pigments for applications in food, pharmaceutical, cosmetics, paint, and textile industries. Thus, in some embodiments, the phenazine degrading agents herein described can be administered to a medium comprising pyocyanin-like phenazine pigments in absence of bacteria as a color-control agent to control the color of the medium.

In some embodiments, a composition can comprise one or more phenazine degrading agents herein described with one or more medium components.

In some embodiments, the composition can comprise medium components such as sodium thioglycolate (HS-$CH_2CO_2Na$), sodium dithionite, organic molecules such as simple sugars e.g. glucose, acetate or pyruvate; extracts such as peptone, tryptone, yeast extract etc., hydrogen carbonate salts ($HCO_3^-$), amino acids, $NH_4Cl$, $(NH_4)_2SO_4$, $KNO_3$, KCl, $K_2HPO_4$, $MgCl_2$, $MgSO_4$, $CaCl_2$, $Ca(HCO_3)_2$, $FeCl_3$, $Fe(NH_4)(SO_4)_2$, Fe-chelates, $CoCl_2$, $ZnCl_2$, $Na_2MoO_4$, $CuCl^2$, $MnSO_4$, $NiCl_2$, $Na_2SeO_4$, $Na_2WO_4$, $Na_2VO_4$, Vitamins, amino acids, purines, pyrimidines.

In some embodiments, the composition can comprise a basic binder, and an isocyanate compound and in particular an isocyanate pre-polymer. In some embodiments, the composition can comprise an aqueous dispersion of an acryl-modified polyester resin, a blocked polyisocyanate compound having a nonionic hydrophilic group; and an aqueous dispersion of acrylic-based polymer fine particles.

In several embodiments, the composition comprising one or more phenazine degrading agent and one or more medium component can act as a barrier against environmental conditions. Such chemical composition can contain one or more pigments to impact color and opacity, binder polymer forming a matrix to hold the one or more pigments in place, extender to improve adhesion, solvent such as organic solvent or water to reduce the viscosity of the paint, additives to modify the properties of the paint and other ingredients identifiable to a person skilled in the paint industry.

As described herein, the phenazine degrading agents, bacteria, antimicrobial agents or compositions herein described can be provided as a part of systems to perform any methods, including any of the assays described herein. In some embodiments, a system can comprise one or more phenazine degrading agents alone or in combination with pyocyanin-like phenazine in a certain proportion to produce a desired color.

In embodiments of systems where detection can be performed, the systems can be provided in the form of arrays or kits of parts. An array, sometimes referred to as a "microarray", can include any one, two or three dimensional arrangement of addressable regions bearing a particular molecule associated to that region. Usually, the characteristic feature size is micrometers.

In a kit of parts, the phenazine degrading agents, antimicrobial agent, candidate phenazine degrading agents, bacteria and compositions and other reagents to perform the method can be comprised in the kit independently. In particular, the phenazine degrading agents, antimicrobial agent, candidate phenazine degrading agents, bacteria can be included in one or more compositions, and each phenazine degrading agent can be in a composition together with a suitable vehicle. In some embodiments, a kit can comprise a phenazine degrading agent with medium components within a composition herein described.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzyme substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of a viable bacteria can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

The methods, herein described, can be performed in vivo and/or in vitro as will be understood by a skilled person.

EXAMPLES

The stabilized phenazine degrading agents and related compositions, methods and systems herein disclosed are further illustrated in the following examples, which are provided by way of illustration and are not intended to be limiting.

In particular, the following examples illustrate exemplary stabilized PodAs, as well as related methods and protocols for degrading phenazine. A person skilled in the art will appreciate the applicability and the necessary modifications to adapt the features described in detail in the present section, to additional phenazine degrading agents and related compositions, methods and systems according to embodiments of the present disclosure. The following materials and methods were used.

Bacterial strains, culture media, and chemicals. Strains used in this study are listed in Table 4 below

TABLE 4

| Bacterial strains used in this study | | |
|---|---|---|
| Strain | Relative Genotype | Source |
| *E. coli* strains | | |
| *E. coli* DH5α | Φ80dlacZ ΔM15 recA1 endA1 gyrA96 thi-1 hsdR17 ($r_k-$, $m_k^+$) supE44 relA1 deoR Δ(lacZYA-argF) U169 phoA | NEB |
| *E. coli* BL21 (☐DE3) | B F⁻ ompT gal den) ion hsdS ($r_Bm_B$) gal (ΔDE3) | NEB |
| *P. aeruginosa* strains | | |
| DKN263 | Wildtype UCBPP-14 | Lab Collection |

*Escherichia coli* BL21 (λDE3) (41)[36] was used for protein overexpression and *E. coli* DH5α (New England Biolabs) was used for plasmid construction. All *E. coli* strains were grown at 37° C. in lysogeny broth (LB, Difco™) or Terrific Broth (TB, Difco™). Ampicillin for culturing *E. coli* was used at 100 ug mL-1. *Pseudomonas aeruginosa* strain UCBPP-PA14 (hereafter *Pseudomonas aeruginosa aeruginosa*) was used for growth analyses and cultivated on LB. All chemicals were purchased from Sigma-Aldrich unless otherwise noted; glycerol (VWR), HEPES (Gold BioTechnology), sodium chloride (Fisher Scientific).

Plasmid construction. All plasmids used in this work are listed in Table 5, below

TABLE 5

| Plasmids used in this study | | |
|---|---|---|
| Plasmid | Genotype | Source |
| pTEV16 | lad⁺ bla⁺ | (1) |
| Overexpression plasmids | | |
| pET20b(+)-podA D68A | pET20b(+)-podA D68A | pET20b(+)-podA D68A |
| pET20b(+)-podA D72A | pET20b(+)-podA D72A | pET20b(+)-podA D72A |
| pET20b(+)-podA H121A | pET20b(+)-podA H121A | pET20b(+)-podA H121A |
| pET20b(+)-podA E154A | pET20b(+)-podA E154A | pET20b(+)-podA E154A |
| pET20b(+)-podA Y156A | *M. fortuitum* PodA$^{Y156A}$ in pET20b(+) | (2) |
| pPodA1 | *Mycobacterium fortuitum* podA$_{41-162}$ + cloned into pTEV16 with a TEV cleavable 6X-His tag | This study |
| pPodA2 | *Mycobacterium fortuitum* podA designed variant cloned into pTEV16 with a TEV cleavable 6X-His tag: I73K, A87V, T91V, M99T, A128V | This study |

TABLE 5-continued

Plasmids used in this study

| Plasmid | Genotype | Source |
|---|---|---|
| pPodA3 | Mycobacterium fortuitum podA designed variant cloned into pTEV16 with a TEV cleavable 6X-His tag: I73T, A87V, T91V, M99V, A128V | This study |
| pPodA4 | Mycobacterium fortuitum podA designed variant cloned into pTEV16 with a TEV cleavable 6X-His tag: I73K, A87V, M99T, A129V, K141T | This study |
| pPodA5 | Mycobacterium fortuitum podA designed variant cloned into pTEV16 with a TEV cleavable 6X-His tag: I73E, A87V, M99I, A129V, K141T | This study |
| pPodA6 | Mycobacterium fortuitum podA designed variant cloned into pTEV16 with a TEV cleavable 6X-His tag: I73L, A87I, M99V, A129V, K141T | This study |
| pPodA7 | Mycobacterium fortuitum podA designed variant cloned into pTEV16 with a TEV cleavable 6X-His tag: I73R, A87V, T91V, M99V, A129T | This study |
| pPodA8 | Mycobacterium fortuitum podA Sarel designed variant cloned into pTEV16 with a TEV cleavable 6X-His tag: I73L, A87I, T91V, M99T, A129V | This study |
| pPodA9 | Mycobacterium fortuitum podA designed variant cloned into pTEV16 with a TEV cleavable 6X-His tag: A53N, I73R, A87V, T91V, A129V | This study |
| pPodA10 | Mycobacterium fortuitum podA designed variant cloned into pTEV16 with a TEV cleavable 6X-His tag: I73K, A87V, T91V, A129V, K141T | This study |
| pPodA11 | Mycobacterium fortuitum podA designed variant cloned into pTEV16 with a TEV cleavable 6X-His tag: A53N, I73T, A87V, M99V, A129T | This study |

Primers were synthesized by Integrated DNA Technologies, Inc. (IDT [San Diego, CA]) and are listed in Table 6, below.

TABLE 6

Primers used in this study

| Primer Name | Primer Sequence 5' → 3' | SEQ ID NO |
|---|---|---|
| Overexpression primers | | |
| 5' pod A pTEV 16 | NNGCTCTTCNTTCATGGACGGTCGCGGCGGCCCGGAGTACAA | 5 |
| 3' podA pTEV16 | NNGCTCTTCNTAATCATTTCGTCAGTTTCAATTCGTACTTCTC | 6 |
| 5' pTEV16 gibson | GCCCTGAAAATACAGGTTTTCACTAGTTG | 7 |
| 3' pTEV16 gibson | TAAGAATTCTCGAGCTCCCGGGATC | 8 |
| 5' podA gBlock gibson | ATTACGATATCCCAACTAGTGAAAACCTGTATTTTCAGGGC | 9 |
| 3' podA gBlock gibson | TGCTCAGCGGCCGCGGATCCCGGGAGCTCGAGAATTCTTA | 10 |

For heterologous protein expression, the gene coding for PodA was amplified from Mycobacterium fortuitum strain ATCC 6841 using Phusion™ High Fidelity DNA Polymerase (ThermoFisher Scientific) per manufactures instructions and cloned into an IPTG inducible overexpression vector, pTEV16 (42), using Type II-Restriction BspQI cloning (43) [38]. The resulting plasmid was referred to as pPodA1. Catalytic PodA variants were utilized from a previous study (12) [1]. For designed proteins gBlocks® were synthesized from IDT to code for relevant amino acid substitutions, with 5' and 3' basepairs corresponding to the MCS of pTEV16. One set of primers was used to amplify each gBlock® and another set to amplify pTEV16. PCR constructs were isolated using the Monarch® PCR & DNA Cleanup Kit (NEB). Genes were then cloned into pTEV16 using Gibson Assembly® Master Mix (NEB) per manufacturer protocol. The resulting plasmids pPodA2-pPodAllare listed in Table 5.

Protein overproduction and purification of soluble and inclusion body fractions. Plasmids coding for proteins of interest were transformed into *E. coli* BL21 (2DE3). Overnight cultures (10 mL) of transformants were sub-cultured (1% [v/v]) into 10 L of TB containing ampicillin. Cultures were grown at 37° C. with shaking to an optical density of 0.4 ($OD_{600\ nm}$) and plasmid expression was induced with IPTG (50 μM) and shaken overnight at 16° C. Cells were harvested by centrifugation at 5,000×g for 10 min in a Beckman Coulter Avanti J-20 XOI refrigerated centrifuge using a JLA-8.1000 rotor at 4° C. Cell pellets were stored at −80° C. until used.

For purification, cell pellets were thawed and re-suspended in 30 mL Buffer A (HEPES [50 mM, pH 7.5], NaCl [500 mM], and imidazole [20 mM]) containing lysozyme (1 mg/mL) DNase (5 μg $mL^{-1}$), and protease inhibitor (PMSF, 0.5 mM). Cells were lysed by four passages through an Avestin Emulsiflex C3 (ATA Scientific) at 15,000 psi. Due to difficulties filtering lysate in subsequent steps, additional DNase (5 ug mL-1) was added before centrifugation. Clarified lysates were obtained via centrifugation at 40,000×g for 30 min at 4° C. in a Beckman Coulter Avanti centrifuge with the JA-25.50 rotor and filtered through a 0.45 μm filter (Millipore). Using an AKTA FPLC, lysate was applied to a pre-equilibrated 5 mL HisTrap™ FF (Sigma-Aldrich) after which the column was washed with 10 CV of Buffer A, 7 CV of 8% Buffer B (HEPES [50 mM, pH 7.5], NaCl [500 mM], and imidazole [500 mM]), and a gradient to 100% Buffer B over 10 CV. Fractions were run on an SDS-PAGE gel and fractions containing PodA were combined and cleaved for 3 h at 25° C. with TEV protease (1:50 mg:mg ratio of TEV to PodA). TEV was purified and stored as described previously (44) [39]. Cleaved protein was dialyzed at 4° C. for 3 h in HEPES (50 mM, pH 7.5), NaCl (500 mM), EDTA (1 mM), followed by dialysis against HEPES (50 mM, pH 7.5), NaCl (500 mM), and imidazole (20 mM). Cleaved PodA was separated from TEV and contaminates by passage over a HisTrap™ FF that was equilibrated with Buffer A. For the final dialysis, PodA was dialyzed against 50 mM HEPES (pH 7.5), 100 mM NaCl, and 20% glycerol (v/v).

For purification of PodA from inclusion bodies, the pellets remaining following lysis and centrifugation at 40,000×g were resuspended in 20 mL of detergent buffer [50 mM HEPES (pH 7.5) and 1% Triton-X (v/v)] using a Bio-gen PRO200 cell homogenizer (PRO Scientific). Sample was spun for 15 min at 40,000×g at 4° C. in a Beckman Coulter Avanti centrifuge with a JA-25.50 rotor. Supernatant was discarded and the remaining cell pellet was resuspended in 5 mL of buffer [50 mM HEPES (pH 7.5), 500 mM NaCl] using a cell homogenizer, supplemented with lysozyme (200 μg $mL^{-1}$), and incubated for 10 min. Volume was increased to 20 mL with HEPES (50 mM, pH 7) and sample was spun for 40,000×g at 4° C. for 15 min. Supernatant was discarded and pellet was homogenized in 10 mL of denaturing buffer 50 mM HEPES (pH 7.5), 500 mM NaCl, and 8M urea) and incubating rocking overnight. The sample was spun at for 40,000×g at 25° C. for 30 min and supernatant was incubated with 1 mL HisPur Ni-NTA resin (Thermo Fisher Scientific) on a rocking platform for 10 min. Beads were allowed to settle without shaking, supernatant was discarded, and resin was pipetted into glass gravity columns. Resin was washed with 15 mL of denaturing buffer, followed by an elution with denaturing buffer supplemented with imidazole (500 mM). Fractions were analyzed by SDS-PAGE and those containing protein were combined into SnakeSkin 3.5 K MWCO dialysis tubing (Thermo Fisher Scientific). Urea was slowly dialyzed out in HEPES (50 mM, pH 7.5) and NaCl (500 mM) by lowing urea concentrations by 1 M increments. Each step was dialyzed at RT for 30 min. Protein was dialyzed in HEPES (50 mM, pH 7.5), NaCl (500 mM), and imidazole (20 mM) overnight at 4° C. The following day, protein was cleaved for 3 h at 25° C. with TEV protease (1:50 mg:mg ratio of TEV to PodA). The sample was applied to a HisPur gravity column and cleaved protein in the flow thru was confirmed by SDS-PAGE. Cleaved PodA protein was then dialyzed for storage for 3 h at 4° C. in HEPES (50 mM pH 7.5), NaCl (250 mM) and finally in HEPES (50 mM, pH 7.5), NaCl (100 mM), and glycerol (20%, v/v). Protein concentration was established on a NanoDrop™ using the extinction coefficient and MW of each protein. Protein was drop frozen in $LN_2$ and stored at −80° C. until use.

Protein design calculations. Using the PodA structure as a starting point (PDB entry 5k21), 13 positions was selected in the homotrimeric interfaces for design: 53Ala, 64Val, 67Met, 73Ile, 87Ala, 91Thr, 92Asn, 99Met, 112Glu, 118Leu, 129Ala, 134Thr, 141Lys. As previously described (24, 25), a Position Specific Scoring Matrix (PSSM) was generated using the default parameters and calculated the tolerated sequence identities at each of the 13 positions with PSSM cutoff ≥−2 and Rosetta ΔΔG<6 R.e.u. Next, it was enumerated, modeled and refined in Rosetta all the possible combinations of mutations allowed by the tolerated sequence space that differed from the WT protein by 3 to 5 mutations (a total of 118,424 combinations of mutations). During all Rosetta modeling and design calculations, the structure was modeled with the $Ca^{2+}$ ions and their ligating residues unchanged and subject to C3 symmetry constraints. The designs were ranked according to Rosetta energy and clustered them, retaining the low-energy designs that exhibited at least two mutations relative to one another. For experimental screening 10 mutants out of the top 35 were chosen by visual inspection.

A web-accessible version of AffiLib (for non-symmetric design) is available at the web page (//AffiLib.weizmann.ac.il) for academic users.

Synthesis of Pyocyanin (PYO). PYO was synthesized from phenazine methosulfate using a protocol described previously (45) [42]. Deviations included eliminating purification of PYO via TLC plates and utilizing dichloromethane in the place of chloroform. PYO was analyzed for purity via HPLC analysis and was found to be >95% pure. Lyophilized PYO was stored at 4° C. until use, after which it was resuspended in 20 mM HCl to make a 5 mM PYO stock, filtered to rid of insoluble particulate, and PYO stock concentration was calculated by measuring the absorbance at 690 nm and using the extinction coefficient of PYO (4130 $M^{-1}$ $cm^{-1}$) in combination with Beer's Law (A=εcl).

Specific activity and kinetics of PodA. To determine specific activity and kinetic parameters of PodA for PYO, a continuous spectrophotometric assay monitoring the absorbance of PYO (690 nm) was utilized. Briefly, assays were performed at 25° C. in 100 μL reaction volumes in 96-well plates and reactions were monitored at 690 nm over 10 min. Reaction mixtures contained Phosphate buffer (50 mM, pH 6.0), ethylene glycol (1%, v/v), protein (3 µM) and substrate (for specific activity, 100 µM, for kinetics, varying). Data were acquired using the SpectraMax® M3 Microplate Reader (Molecular Devices) using the Soft Max Pro software every 10 s over 10 min. Path lengths for each well were calculated using Soft Max Pro endpoint readings and slopes were corrected for path lengths of 1 cm.

Specific activity was calculated from the slope of the linear range of ($\Delta OD_{690}$ min$^{-1}$) using Beer's Law (A=εcl) with a path length of 1 cm and the molar extinction coefficient of PYO (4,130 M$^{-1}$ cm$^{-1}$). Equation was solved for c, giving specific activity in nmol min$^{-1}$ mg$^{-1}$ of PodA. For kinetic parameters, graphs of initial velocity (µM s$^{-1}$) versus substrate concentration (µM) were plotted using Prism v8 (GraphPad). The Michaelis-Menten kinetics model was used to determine $K_m$ and $V_{max}$. The turnover number ($k_{cat}$) was determined using the following equation: $V_{max}=k_{cat}[E]$, where [E] was the concentration of PodA added. All spectrophotometric assays mentioned above were completed thrice, each in technical triplicate with a representative data set shown. Error bars represent standard deviation as calculated by Prism v8 (GraphPad). Standard deviation for $k_{cat}$ and $K_{cat} K_M^{-1}$ was calculated using standard formulas for propagation of error.

*Pseudomonas aeruginosa* PodA and tobramycin liquid synergy experiments. For planktonic synergy experiments, starter cultures were grown 24 h at 37° C. shaking in LB. Stationary phase cultures (usually between $OD_{500}$ 4-6) were aliquoted (100 µL) into 96-well clear bottom flat well plates (VWR). Antibiotics and PodA were diluted into stock concentrations to pipette 5 µL antibiotic and 2 µL PodA per well. Antibiotics were diluted into water and PodA was diluted into 50 mM HEPES (pH 7.5). Plates were incubated in a humidity Tupperware chamber lined with wet paper towel at 37° C. for 10 h. After incubation, wells were pipetted to resuspend, and each well was diluted 1:10 into fresh LB. From that mixture, 10 µL of diluted cells were pipetted into 90 µL fresh LB in 96-well flat bottom plates. Mineral Oil, light (65 µL undiluted, Sigma-Aldrich) was pipetted onto top of cultures to prevent dehydration and allow for oxygen diffusion. Microtiter plates were incubated at 37° C. inside a temperature-controlled chamber of a BioTek Synergy 4 plate reader. Plates were continuously shaken (medium setting) and time points ($OD_{500}$) were taken for 24 h every 30 min. Data were plotted using Prism v8. Growth studies were completed thrice, with a representation from one experiment shown. For concentrations that led to an increase in lag times, the same experiment was set up but rather than an outgrowth step, cells were diluted over a dilution series and seven dilutions (10 µL each) were plated on LB agar to determine CFUs mL$^{-1}$. Cells were plated in biological triplicate to obtain an average number of CFUs mL$^{-1}$ to calculate a standard deviation. Cells from each 10 µL drips dilution were counted if colonies were between 10-100.

PodA$_{10}$ and tobramycin cell treatments (same samples from FIG. 8) were diluted in series and dilutions were plated onto LB agar. Cells were counted if a dilution contained 10-100 colonies.

Crystal violet assay. *Pseudomonas aeruginosa* grown overnight in LB were inoculated (1.5%, v/v) and grown for 24 h at 37° C. in 96-well round bottom plates in minimal medium (100 µL) with arginine (40 mM) as the sole carbon source. PodA was added with cells simultaneously and was present during growth and biofilm development. Planktonic cells were removed and attached cells were quantified with crystal violet staining (125 µL. 0.1% v/v), followed by washes with water and de-staining with an acetic acid (30%, v/v) mixture in water. Crystal violet was measured using a SpectraMax® M3 Microplate Reader (Molecular Devices) at an absorbance of 550 nm. Details of procedure were published previously (28)[43].

*Pseudomonas aeruginosa* PodA and tobramycin agar block biofilm assay (ABBA) synergy experiments. Starter *Pseudomonas aeruginosa* cultures were grown 24 h at 37° C. shaking in LB and the $OD_{500}$ was determined by diluting cells 1:10. For inoculation into agar, cells were first diluted to an OD of 1.0, followed by a 1:10 dilution for a final OD of 0.1. Molten LB agar (1% w/v) or SCFM agar (1% w/v, made by mixing premade 2× SCFM and 2% agar) was incubated at 44° C., after which 10 µL of OD 0.1 culture was added and mixed into 1 mL of agar, for a final starting OD of 0.001. A portion of the mixture (200 µL) was pipetted into a well of an 8-well glass chamber slide for microscopy (Thermo Fisher Scientific #155409) or into a 2 mL Eppendorf tube for cell viability experiments. ABBAs were incubated at 37° C. for 24 h in a Tupperware lined with wet paper towels. Following growth, ABBAs were washed with 200 µL of HEPES (20 mM, pH 7) to rid planktonic cells growing on the surface of the agar. Treatment stocks (100 µL each) were made by diluting PodA10 and/or tobramycin into HEPES (final concentration of 20 mM, pH 7), with the no treatment control consisting of solely HEPES. Final concentrations of PodA (5 µM) and tobramycin (50 ug mL$^{-1}$) were calculated accounting for the total volume of the agar+liquid. ABBAs were treated overnight (14 h), treatment mixture was decanted, and agar blocks were washed with HEPES (400 µL).

For microscopy experiments, cells were incubated for 30 min with 125 µL of diluted propidium iodide (final concentration of 490 µM when added to ABBA, taking into account volume of the agar) and SYTO-9 (final concentration of 16 µM), after which 50 µL of a 1:50 dilution of 5-µm fluorescent beads (Spherotech; CFP-5045-2) was added to each agar block. ABBAs were imaged with a Leica TCS SPE confocal microscope as described elsewhere using 512×512-pixel format (29)[44], with the exception of imaging with a 6 µm step-size in the Z-direction.

For cell viability experiments, 300 µL of HEPES (20 mM, pH 7) was pipetted into each Eppendorf ABBA tube and samples were homogenized on speed 3 of a Bio-Gen PRO200 Homogenizer (PRO Scientific). Samples were briefly spun to rid of air bubbles (<1,000×g) and diluted in series and plated as described above in liquid synergy experiments. Experiments were completed with biological triplicates and was repeated thrice, with a representative figure shown.

ABBA microscopy image analysis. Images were analyzed in FIJI by re-slicing the data set in the XZ dimension followed by a max-intensity Z-projection. The brightness/contrast was auto-normalized in FIJI to the sample treated with only tobramycin. These LUT values were then applied to the other images in the corresponding data sets. Average pixel intensities along the Z-dimensions were found using the "Plot Profile" function in FIJI. Experiments were completed in a minimum of biological triplicate with a representative replicate shown in figures.

To determine mean pixel intensity and aggregate volume of each ABBA, channels 1 (SYTO-9) and 2 (Propidium Iodide) were combined into a single channel using FIJI. Images were analyzed in Imaris and aggregate masks were created using the "surface" module of the software. Using the surface Imaris wizard, all options under algorithm settings were unchecked. For surface channel settings, channel 3 (representing combined channels) was chosen and default settings were maintained. For threshold settings, the no treatment ABBA sample was analyzed for proper data inclusion and a value of 60 was used for all LB samples, with a threshold value of 40 for all SCFM samples. Lastly, data were excluded 0.1 µm from the XY edges, to exclude aggregates that were cut off due to imaging field. Data were not excluded from the top edge of the ABBA, as images were collected from the surface of the agar using fluorescent beads as described above. Exported statistics were used to plot aggregate volume or mean PI intensity against position of aggregates in the Z-dimension.

To determine mean and 95% confidence intervals of PI staining of ABBAs, collections of aggregates were binned by 25 µm through the depth of the agar. Then 10,000 bootstrap replicates per bin were produced, took the mean of each of those replicates, then calculated the 2.5 and 97.5 percentiles of those collections to calculate the 95% confidence interval.

Oxygen probe measurements. ABBAs were inoculated and set-up identically as in the section titled "*Pseudomonas aeruginosa* PodA and tobramycin agar block biofilm assay (ABBA) synergy experiments." ABBAs were incubated for 24 h at 37° C. in a humidity chamber and were incubated in a 37° C. sand bath during oxygen probe measurements. Oxygen concentrations were measured using a Clark-type amperometric electrode with a 10 µm tip diameter, which was connected to an amplifier of a multimeter (Unisense, Denmark). A two-step calibration was performed using an oxygen free solution (0.1 M NaOH, 0.1 M sodium ascorbate) and an oxygen saturated LB solution (with 1% w/v salinity). The agar surface was found by decreasing the tip depth by 25 µm until oxygen measurements declined by 2 µmol L$^{-1}$. The oxygen sensor was positioned 100 µm above the agar interface, and data were collected in 25 µm steps for a total of 700 µm. Technical triplicate measurements were made at each depth, with each measurement taking 3 s, with 2 s between measurements. Oxygen profile data are averages from one experiment of technical triplicates of biological triplicates, with each experiment done in triplicate on different days. Data were collected using SensorTrace Pro 3.1.3 software and were plotted using Prism v8 (GraphPad).

Example 1. Characterization of PodA Activity and Kinetics

To assess PodA's activity of therapeutic relevance in the context of human chronic infections, PodA activity was quantified and its kinetic parameters determined under a spectrum of physiologically relevant variables (i.e. pH, viscosity, sodium and potassium concentrations).

As done previously to facilitate PodA purification (12) [1], a predicted N-terminal transmembrane domain was excluded, resulting in a wild type variant called WT PodA$_{41-162}$.

In particular, PodA$_{41-162}$ is a truncated version the protein encoded by MFORT_14352 (lacking a predicted N-terminal, membrane-spanning helix), The gene expressing PodA$_{41-162}$ derived from *Mycobacterium* was heterologously expressed in *E. coli*. from *Escherichia coli*. In particular, PodA$_{41-162}$ in the sense of the disclosure can have sequence (SEQ ID NO: 3)

Moving forward in the present and subsequent examples, all PodA purified proteins maintained this deletion.

Figure 5:
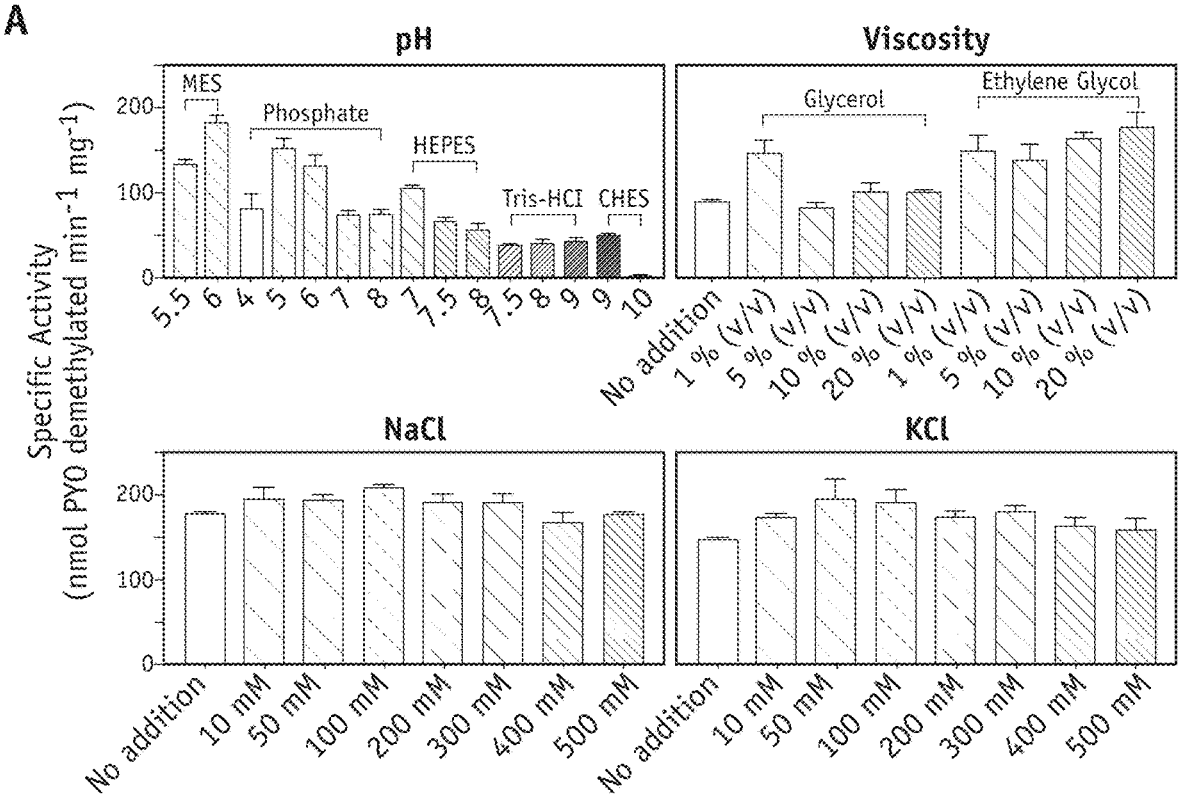
FIG. 5. Characterization of WT PodA$_{41-162}$ and active site mutant variants. (A) Specific activity of WT PodA$_{41-162}$ under varying conditions. WT PodA$_{41-162}$ (3 μM) was incubated with PYO (100 μM) and activity was monitored by measuring absorbance of PYO over time. Activity was analyzed by changing pH, viscosity, or salt concentrations. Error bars represent standard deviation of triplicates. (B) PodA (3 µM) and PYO (concentrations indicated on x-axis) were incubated and monitored at 690 nm. $V_{max}$ values were plotted against [PYO] and an $K_M$ was calculated by fitting data to the Michaelis-Menten equation as indicated by black line. Each data point represents the mean of three replicates and error bars represent standard deviation.
Figure 5:
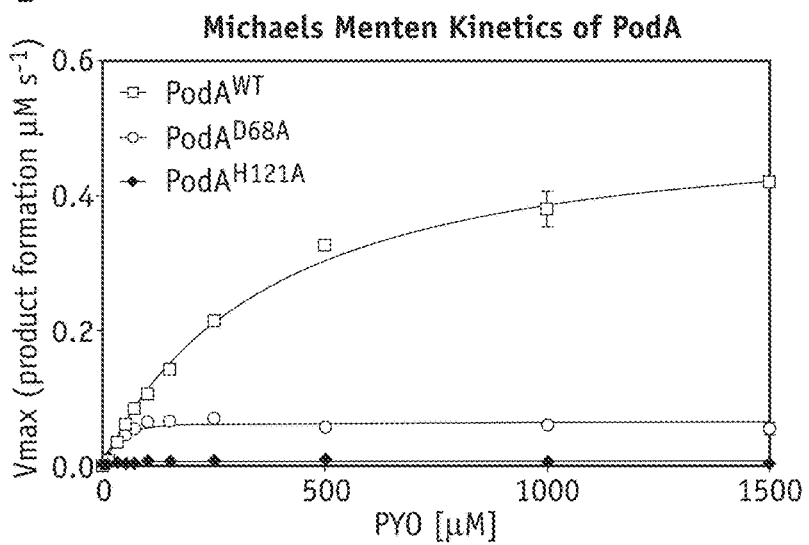

WT PodA$_{41-162}$ demethylation activity was measured and compared with active site variants, using a spectrophotometric assay that monitors the absorbance of PYO over time In particular the specific activity of WT PodA$_{41-162}$ under varying conditions. WT PodA$_{41}$-162 (3 µM) was incubated with PYO (100 µM) and activity was monitored by measuring absorbance of PYO over time. Activity was analyzed by changing pH, viscosity, or salt concentrations. The results are shown in FIG. 5.

Using a variety of buffers to analyze activity from pH 5.5-10.0, it was found that WT PodA$_{41-162}$ had optimal activity at pH 6 as shown in the illustration of FIG. 5A.

Activity of WT PodA$_{41-162}$ below pH 5.5 was not established due to the pK$_a$ of PYO (4.9), which changes the chemical and therefore absorptive properties of the substrate. Using a reaction condition with a pH of 6, a slight increase in viscosity with ethylene glycol or glycerol (1% v/v) enhanced WT PodA$_{41-162}$ activity (FIG. 5A).

In the case of glycerol, higher concentrations (5%-20%) reverted this activity increase.

Average ion concentrations of potassium and sodium in cystic fibrosis sputum are 15 mM (K$^+$) and 66 mM (Na$^+$) (15) [45]. Addition of these ions in salt form (NaCl and KCl) in this concentration range did not inhibit or enhance WT PodA$_{41-162}$ activity (FIG. 5A).

For these reasons, conditions were established for kinetic analyses to be carried out at a pH of 6 with 1% ethylene glycol.

WT PodA$_{41-132}$ was also characterized in comparison with selected variants PodA$^{D68A}$, PodA$^{D72A}$, PodA$^{H121A}$, PodA$^{H121K}$, PodA$^{H12IR}$, PodA$^{E154A}$, PodA$^{Y156A}$, and PodA$^{Y156F}$.

In particular, WT PodA$_{41-132}$ or related variants (3 µM) and PYO (concentrations indicated on x-axis) were incubated and monitored at 690 nm. V$_{max}$ values were plotted against [PYO] and an K$_M$ was calculated by fitting data to the Michaelis-Menten equation Using Michaelis-Menten parameters, WT PodA$_{41-162}$ exhibited a K$_M$ of 0.372 mM±0.018, a k$_{cat}$ of 0.176±0.003 s$^{-1}$, and a catalytic efficiency of 4.74±0.24×10$^2$ M$^{-1}$ s$^{-1}$ (FIG. 5B).

WT PodA$_{41-162}$ active site variants PodA$^{D72A}$, PodA$^{H121A}$, PodA$^{H121K}$, PodA$^{H121R}$, PodA$^{E154A}$, PodA$^{Y156A}$, and PodA$^{Y156F}$ did not have measurable activity compared to controls. A variant inhibiting product release, PodA$^{D68A}$, maintained similar Michaelis-Menten trends for concentrations of PYO under 100 µM, after which V$_{max}$ leveled off (FIG. 5B).

Example 2. Identification of PodA Variants with Mutated Trimer Interface

Although the characterization of WT PodA$_{41-162}$ reported win Example 1 confirmed the enzyme's activity under a broad range of conditions, it also revealed limitation in the related protein yields (typically ~0.3 mg L$^{-1}$ of bacterial culture).

Furthermore, that PodA purification demands laborious refolding experiments argued against using protein-optimization methods that require high or even medium-throughput experimental screening such as in vitro evolution or deep mutational scanning.

Accordingly, protein design was applied to attempt to identify possible variants with increased stability with the aim of improving yield while maintaining or improving activity.

The AffiLib protein-design method and a related method, called AbLIFT, were used. AffiLib was shown to improve protein binding affinity by almost two orders of magnitude (24) AbLIFT, led to dramatic improvement in antibody stability, expressibility and binding affinity through the design of mutations in the variable domain's light-heavy chain obligatory interface (26)[46].

The AffiLib design approach is especially relevant for the design of small-to-large mutations, since it uses Rosetta atomistic design calculations to enumerate all of the combinations of mutations that are observed in a phylogenetic analysis of sequence homologs and are individually tolerated according to computational mutation scanning. Each combination of mutations is allowed to relax, including through backbone and rigid-body minimization to promote the introduction of small-to-large mutations.

Figure 6:
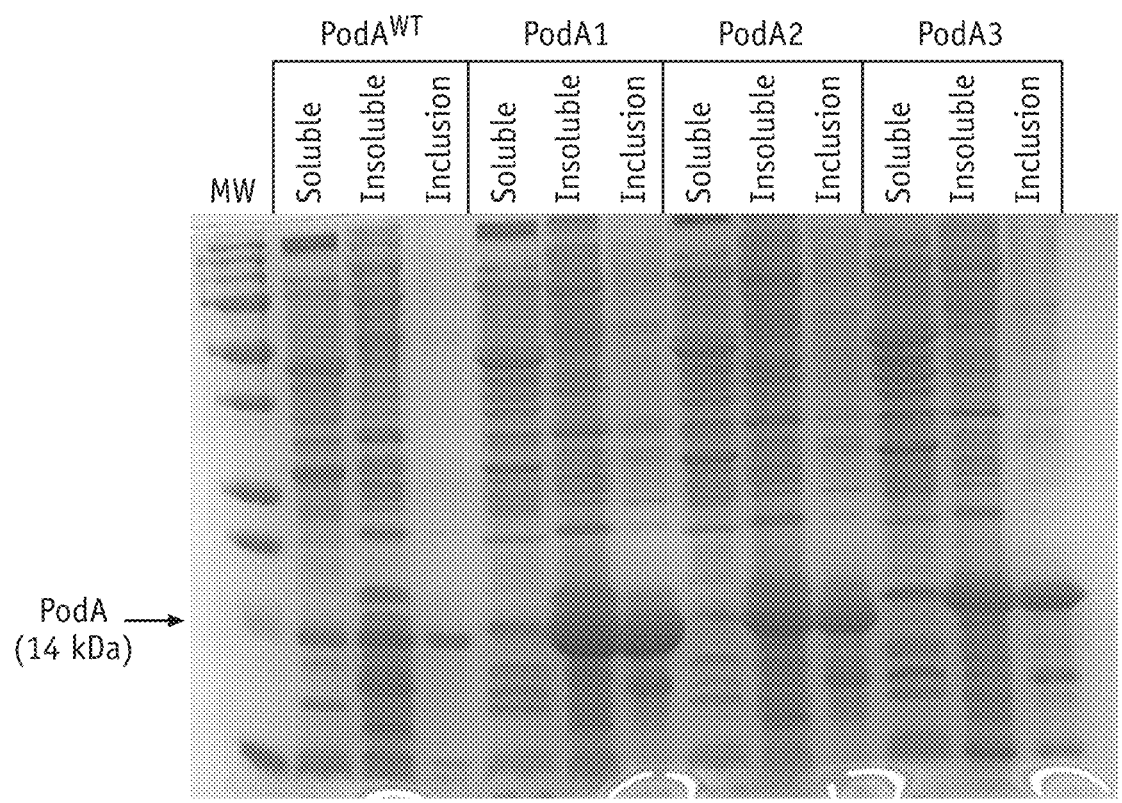
FIG. 6. Protein design of PodA trimer interface. Inclusion bodies from overexpression cultures of designed variants were analyzed using BugBuster™. A representative SDS-PAGE gel is shown for $PodA_1$-PodA3. Precision Plus Protein™ used as a MW marker (lane 1).

AffiLib was applied to PodA to increase its yield during heterologous overexpression. Since PodA is a homotrimer, all modeling and design simulations used symmetric sequence, backbone and rigid-body sampling. Furthermore, each PodA monomer binds a structural $Ca^{2+}$ ion and any change in amino acid identity or conformation at the ion-ligation sites were disallowed.

Since PodA forms symmetric homotrimers, residues were selected to improve the interactions within these obligatory interfaces as well as complex stability and expressibility.

In particular, because PodA forms symmetric homotrimers, it was hypothesized that improving the interactions at these obligatory interfaces will similarly improve complex stability and expressibility.

In particular in view of the results of structural analysis of these obligatory interfaces, residues and positions in the interface were selected also based on the observation that the related sites may be under-packed due to the presence of three alanine amino acids.

The AffiLib design approach is especially relevant for the design of small-to-large mutations, since it uses Rosetta atomistic design calculations to enumerate all of the combinations of mutations that are observed in a phylogenetic analysis of sequence homologs and are individually tolerated according to computational mutation scanning. Each of the enumerated mutants is allowed to relax, including through backbone and rigid-body minimization, to enable the entire trimeric structure to accommodate the introduction of small-to-large mutations.

examples section to denature and purify WT $PodA_{30-162}$ from inclusion bodies, followed by a refolding procedure.

Residues and positions were selected in view of the results of the above analysis performed with respect to $PodA_{41-162}$ and tested in $PodA_{41-162}$. The selected residues and positions are reported in FIG. 1 panel A with numbering referred to PodA of SEQ ID NO: 1.

In particular the illustration of FIG. 1 panel A and through the examples of the disclosure, the residue numbers for the selected position are indicated with respect the full protein sequence of PodA SEQ ID NO: 1, as that is the norm within the field, even if the experiments reported in the Examples were performed with $PodA_{41-162}$.

Accordingly in the set of examples of the present disclosure

- the residue indicated as A53 corresponds to residue A13 of SEQ ID NO: 3,
- the residue indicated as I73 corresponds to residue 133, of SEQ ID NO: 3,
- the residue indicated as T87 corresponds to residue A47 of SEQ ID NO: 3,
- the residue indicated as M99 corresponds to residue M59 of SEQ ID NO: 3,
- the residue indicated as A129 corresponds to residue A89 of SEQ ID NO: 3, and
- the residue indicated as K141 corresponds to residue K101 of SEQ ID NO: 3 as will be understood by a skilled person upon reading of the present disclosure.

In particular, positions corresponding to A53, I73, A87, T91, M99, A129 and K141 of PodA of SEQ ID NO: 1 were chosen (See FIG. 1 panel A where positions that were subjected to design are marked by spheres).

Mutations were designed and the resulting designs were ranked according to their computed energies and the top 35 designs were visually inspected.

From those, for experimental testing a diverse set of 10 mutants that exhibited improved packing or hydrogen-bonding interactions across the obligatory interfaces the variants reported in the following Table 7 and in FIG. 1 panels A-D were chosen.

TABLE 7

| Protein | WT PodA | PodA1 | PodA2 | PodA3 | PodA4 | PodA5 | PodA6 | PodA7 | PodA8 | PodA9 | PodA10 |
|---|---|---|---|---|---|---|---|---|---|---|---|
| Residue Changes | (–) | I73K<br>A87V<br>T91V<br>M99T<br>A129V | I73T<br>A87V<br>T91V<br>M99V<br>A129V | I73K<br>A87V<br>T91V<br>M99V<br>129V | I73E<br>A87V<br>M99I<br>A129V<br>K141T | I73L<br>A87I<br>M99V<br>A129V<br>K141T | I73R<br>A87V<br>T91V<br>M99V<br>A129T | I73L<br>A87I<br>T91V<br>M99T<br>A129V | A53N<br>I73R<br>A87V<br>T91V<br>A129V | I73K<br>A87V<br>T91V<br>A129V<br>K141T | A53N<br>I73T<br>A87V<br>M99V<br>A129T |

Because PodA is a homotrimer, all modeling and design simulations used symmetric sequence, backbone, and rigid-body sampling. Furthermore, because the available crystallographic structure of PodA shows that each monomer binds a $Ca^{2+}$ ion (FIG. 12), any change in amino acid identity or conformation at the ion-ligation sites was disallowed.

The designs were ranked according to their computed energies, and the top 35 designs were visually inspected. From those a diverse set of 10 mutants that exhibited improved core packing or hydrogen-bonding interactions across the obligatory interfaces was chosen Induction studies showed that a majority of the PodA variants were shuttled into inclusion bodies. A protocol was developed reflected in the material and methods reported in this In particular, testing indicated that mutations Ala87Val and A129V increase core packing in a hydrophobic region (see FIG. 1 panel B), mutations Ile73Thr, Ile73K, Ile73R, and Ile73E improves surface polarity (see FIG. 1 panel C), mutation Ala53Asn forms an interfacial hydrogen bond with a Ser (see FIG. 1 panel D) K14T contributes to the maintenance of a stable configuration.

Example 3: Characterization of Yields in Production of PodA Variants in Comparison with WT PodA Induction studies were performed by providing overexpression cultures of designed variants were analyzed using BugBuster™. The results illustrated by a representative SDS-PAGE gel for PodA1-PodA3 shown in FIG. 6 indicated that a majority of the PodA variants were shuttled into inclusion bodies (FIG. 6).

A protocol was developed (see Materials and Methods) to denature and purify WT PodA$_{41\text{-}162}$ from inclusion bodies, followed by a refolding procedure. Before moving forward using the inclusion body purification exclusively for the designed variants, it was verified that WT PodA$_{41\text{-}162}$ activity and kinetics were not altered after denaturing and refolding the enzyme. Soluble fraction WT PodA$_{41\text{-}162}$ had a catalytic efficiency of $1.05\pm0.093\times10^2$ M$^{-1}$ s$^{-1}$ and WT PodA$_{41\text{-}162}$ purified from inclusion bodies had a catalytic efficiency of $1.14\pm0.25\times10^2$ M$^{-1}$ s$^{-1}$.

Remarkably, eight PodA designs exhibited increased protein yields relative to the wild-type protein as shown by the yield reported in Table 8 and FIG. 1 panel E.

Figure 2:
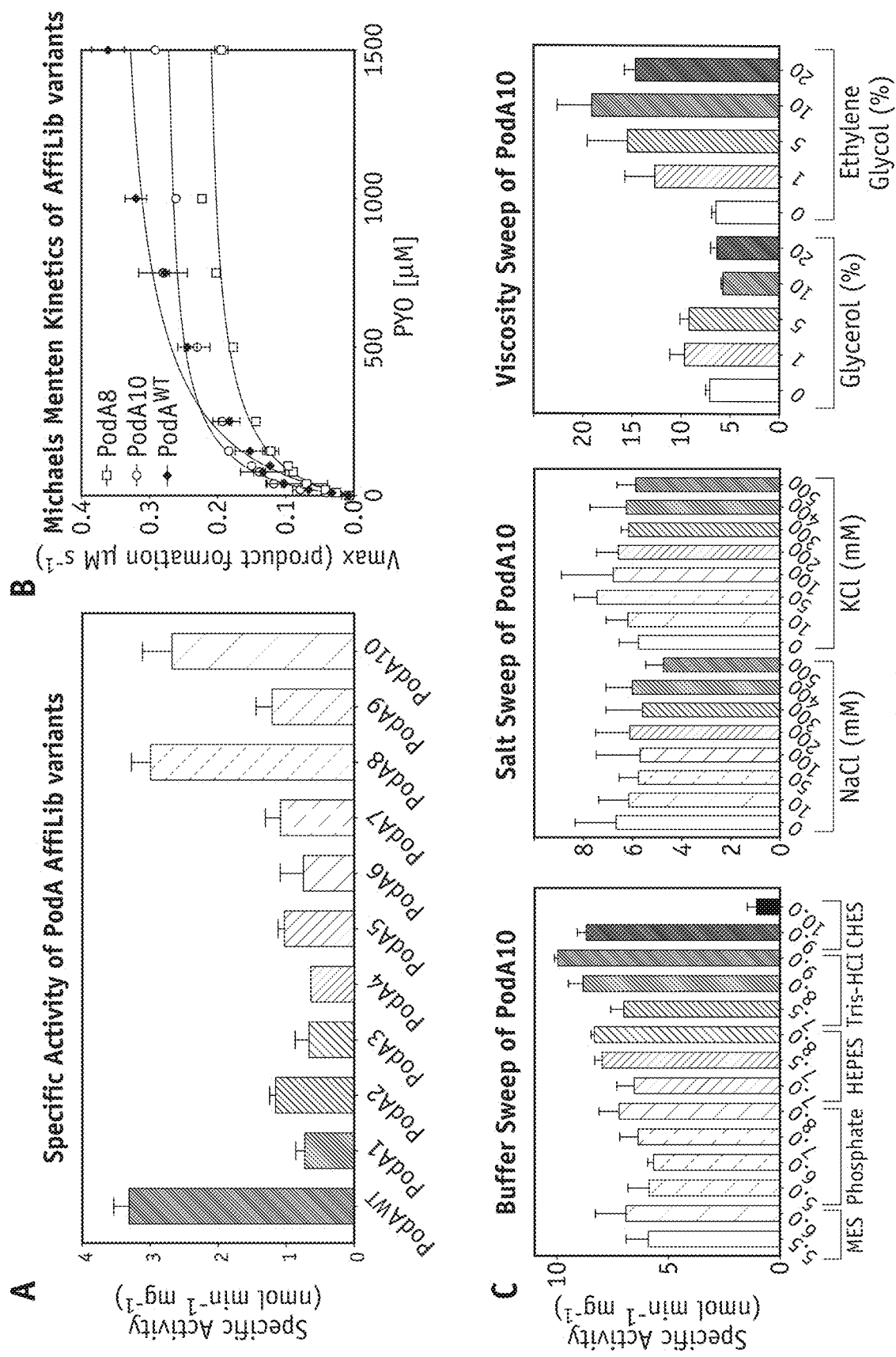
FIG. 2. Characterization of PodA$_{10}$. A) PYO (50 uM) demethylation activity of PodA variants (3 uM) was determined using a spectrophotometric assay described in the Materials and Methods. Error bars represent standard deviation of the mean of triplicates. B) Michaelis-Menten kinetics of PodA8 and PodA10 (3 μM) were found by plotting $V_{max}$ values against [PYO], as indicated on x-axis. Error bars represent standard deviation of the mean of triplicates. C) PodA10 specific activity under varying conditions. PodA10 (3 μM) was incubated with PYO (100 μM) and activity was monitored by measuring absorbance of PYO over time. Activity was analyzed by changing pH, viscosity, or salt concentrations. Error bars represent standard deviation of triplicates.

Kinetics of these proteins were compared. In particular Michaelis-Menten kinetics of PodA8 and PodA10 (3 µM) were found by plotting V$_{max}$ values against [PYO], as indicated on x-axis of the chart shown in FIG. 2 panel B and it was found no change in catalytic efficiency between PodA$^{WT}$ and PodA8 and a slight increase in efficiency for PodA10 (FIG. 2 panel B). Due to the slight increased efficiency combined with a higher yield, it was decided to utilize PodA10 for in studies of PodA effects on *P. aeruginosa*.

As in FIG. 5 panel A with WT PodA$_{41\text{-}162}$, PodA10 activity was analyzed across a broad range of buffers, salts, and viscosity agents.

In particular, PodA10 specific activity under varying conditions. PodA10 (3 µM) was incubated with PYO (100 µM) and activity was monitored by measuring absorbance of PYO over time.

TABLE 8

| Protein | WT PodA | PodA1 | PodA2 | PodA3 | PodA4 | PodA5 | PodA6 | PodA7 | PodA8 | PodA9 | PodA10 |
|---|---|---|---|---|---|---|---|---|---|---|---|
| Yield mg/L$^{-1}$ | 0.33 | 0.20 | 16.1 | 9.45 | 0.38 | 9.9 | 4.4 | 4.1 | 2.1 | 1.28 | 5.92 |
| Residue Changes | (—) | I73K | I73T | I73K | I73E | I73L | I73R | I73L | A53N | I73K | A53N |
| | | A87V | A87V | A87V | A87V | A87I | A87V | I73R | I73T | A87V | I73T |
| | | T91V | 791V | T91V | M99I | M99V | T91V | T91V | A87V | T91V | A87V |
| | | M99T | M99V | M99V | A129V | A129V | M99V | M99T | T91V | A129V | M99V |
| | | A129V | A129V | 129V | K141T | K141T | A129T | A129V | A129V | K141T | A129T |

The above results are consistent with the expectation that the trimeric interfaces in the wild-type PodA were unstable and that improving packing at these interfaces might improve protein production yields.

In particular, the eight variants PodA2, PodA3, PodA5, PodA6, PodA7, PodA8, PodA9 and PodA10, showed a significant increase in yield with respect to WT PodA and the production yields of was successfully increased by optimizing contacts across the obligatory homotrimeric interfaces with selected positions and replacements.

In particular, variants PodA3, PodA5, PodA6, PodA7, and PodA10, showed an increase in yield of one order of magnitude with respect to the wild type.

In general the variants allow production yields of PodA 20-fold increased. This enabled the study of the physiological effects of PodA on planktonic and biofilm-grown *P. aeruginosa* cells under conditions relevant to human infections, revealing significant synergistic killing with the commonly used clinical antibiotic, tobramycin.

Example 4. Characterization of PodA Variants Stability Activity and Kinetics in Comparison with WT PodA The same continuous spectrophotometric assay used to characterize WT PodA$_{41\text{-}132}$ in Example 1 was used to determine enzyme kinetics of PodA and the variants identified in Example 2 for PYO.

The eight variants PodA2, PodA3, PodA5, PodA6, PodA7, PodA8, PodA9 and PodA10 were tested for kinetics and the results are reported in FIG. 2)

In particular, PYO (50 µM) demethylation activity of PodA variants (3 µM) was determined using a spectrophotometric assay described in the Materials and Methods. As can be seen by the illustration of FIG. 2 panel A, of the eight variants tested, wild-type activity was maintained for PodA8 and PodA10 (FIG. 2 panel A).

Unlike WT PodA$_{41\text{-}162}$, PodA10$_{41\text{-}162}$ maintained activity over a large range of pH, with no observable preference between a pH of 5.5 and 9 (FIG. 1 panel D), indicating that the design was also more stable to environmental conditions than the wild-type enzyme. PodA10 activity was not altered with addition of salts, and a slight ad-vantage was seen with addition of ethylene glycol (FIG. 2 panel D), similar to WT PodA$_{41\text{-}162}$.

Activity was analyzed by changing pH, viscosity, or salt concentrations. The results are shown in FIG. 2C As shown in FIG. 2 panel C. PodA$_{10}$ maintained activity over a large range of pH, with no observable preference between a pH of 5-9 (FIG. 2 panel C). PodA$_{10}$ activity was not altered with addition of salts, and a slight advantage was seen with addition of ethylene glycol (FIG. 2 panel C), similar to WT PodA$_{41\text{-}162}$.

Figure 13:
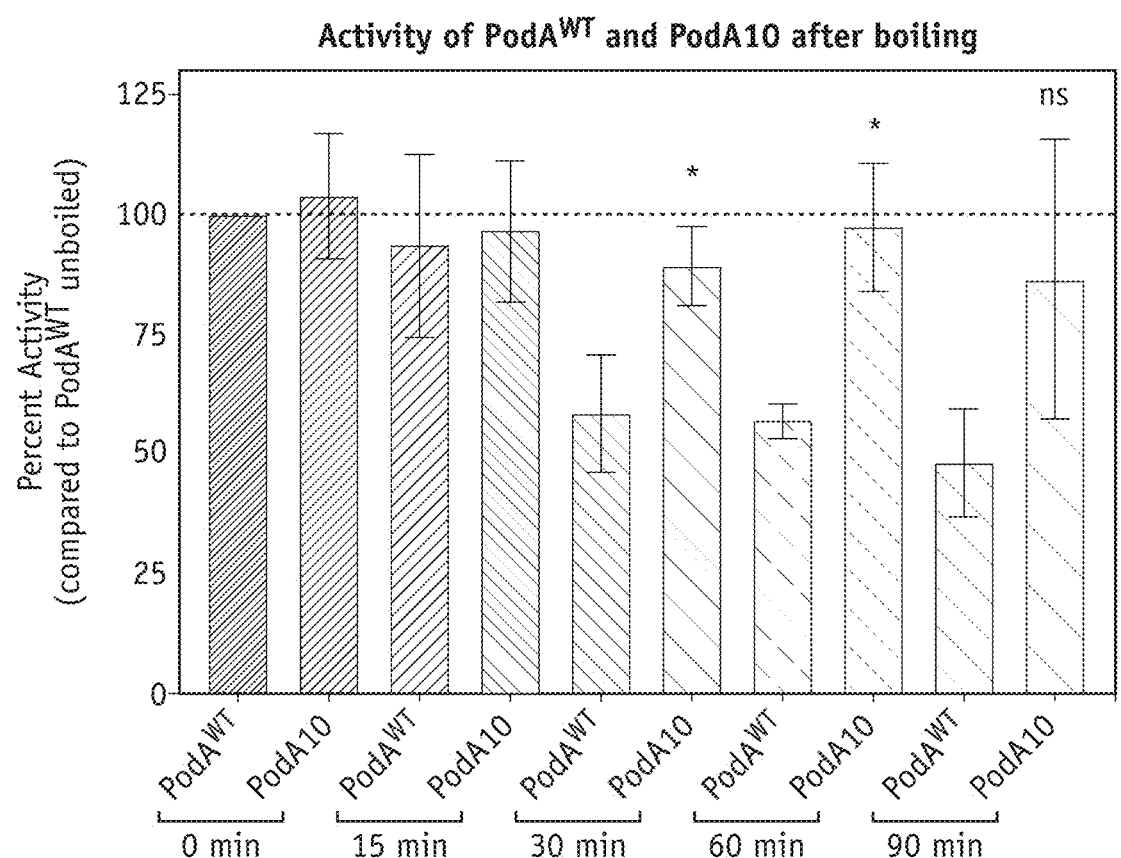
FIG. 13. Activity of WT $PodA_{30-162}$ and $PodA_{10}$ after boiling. Protein was boiled as described in Materials and Methods, followed by an activity assay with PodA (3 µM) and PYO (100 µM) in a Spectramax M3 plate reader monitoring PYO absorbance (690 nm) overtime. Specific activity (nmol min-1 mg-1) was calculated for each sample. Replicates of $PodA^{WT}$ un-boiled were averaged and set to 100% activity (dashed line). All other activities of boiled samples were compared to this value and presented as a percentage. Data represent technical triplicates and error bars represent standard deviation. A t-test was completed, with * representing a p-value<0.05 and ns representing not significant.
Figure 14:
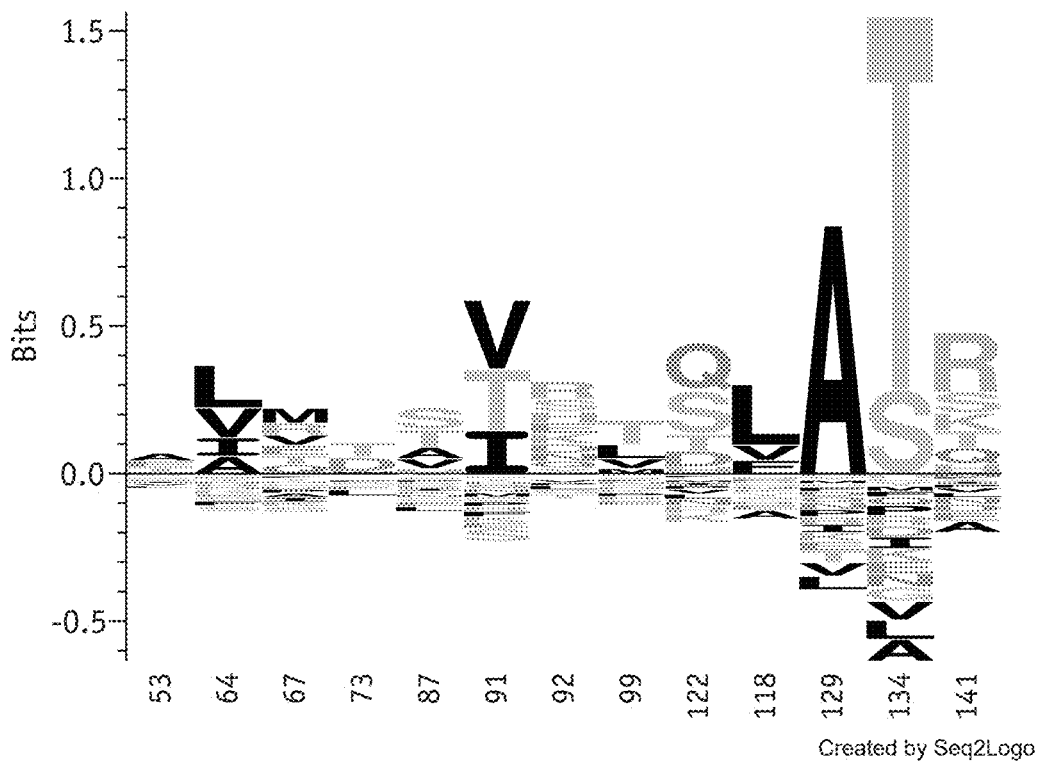
FIG. 14. Sequence logo of diversified positions. Sequence logo representing residue observations in evolutionary analysis, generated with default parameters using the indications in the web page_.cbs.dtu.dk/biotools/Seq2Logo/. [2] Most successful designs did not use the most conserved residue in each position. For example, both PodA8 and PodA10 incorporated A53N, although Ala, Glu and Thr are evolutionarily more likely for this position. In addition, in position 129 the only preferable amino acid is Ala, but PodA8 and PodA10 mutated to A129V and A129T, respectively.
Figure 15:
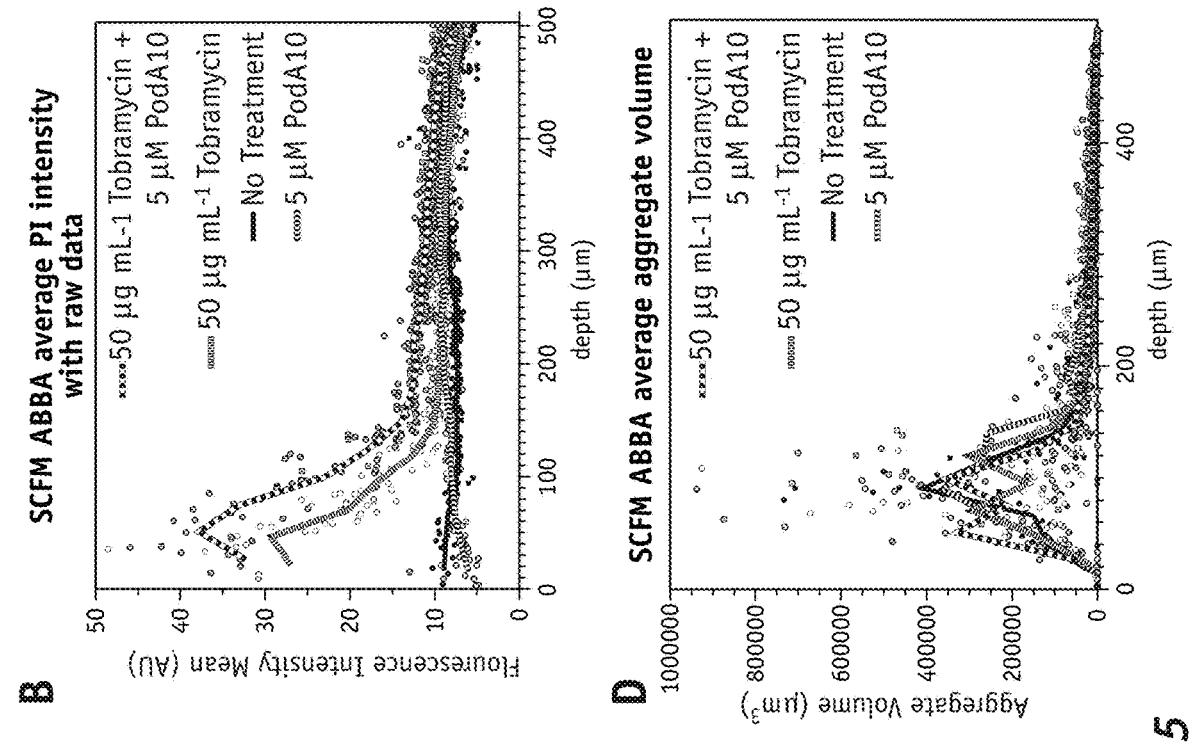
FIG. 15. *Pseudomonas* LB and SCFM ABBA aggregate volume analyses. ABBA data from FIGS. 4A-4G were analyzed in Imaris to obtain PI mean intensity for LB (A) and SCFM (B), along with the volume of each aggregate for LB (C) and SCFM (D). Each point represents a single aggregate. Mean aggregate volume was calculated with a bin size of 20 (every 25 µm) and plotted as a solid line. Propidium Iodide intensity from FIGS. 4A-4G was plotted against each aggregate volume for LB (E) and SCFM (F).
Figure 15:
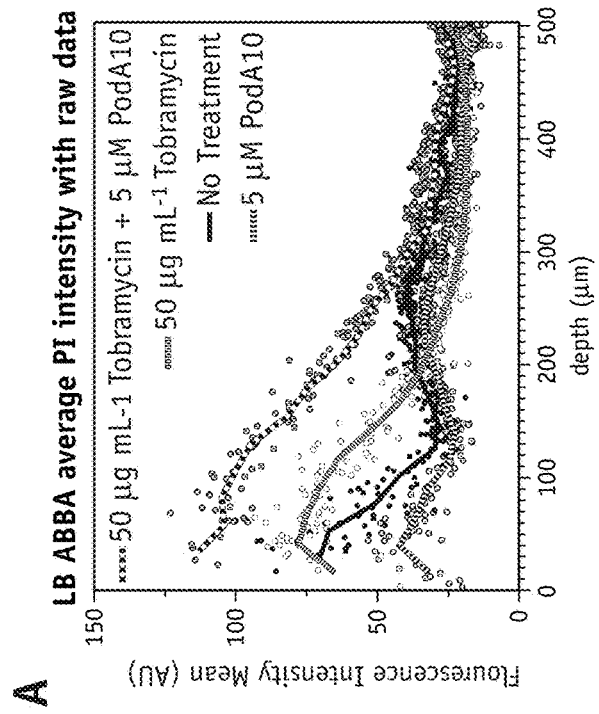
Figure 15:
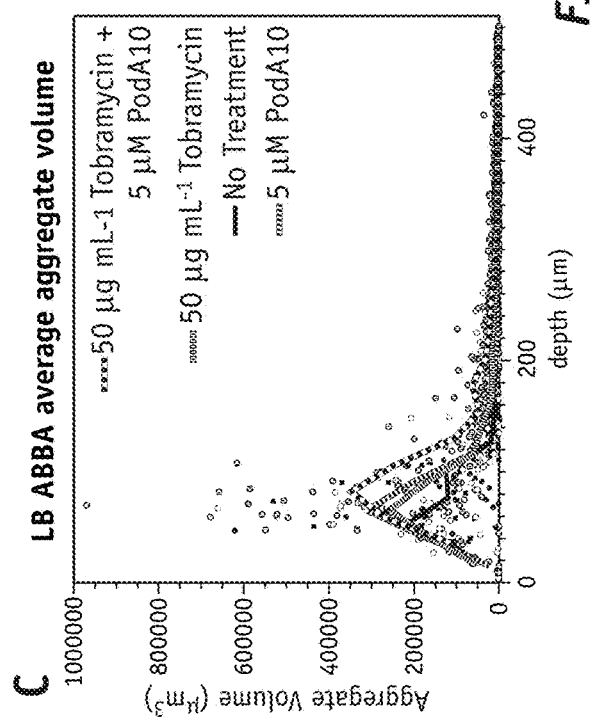
Figure 15:
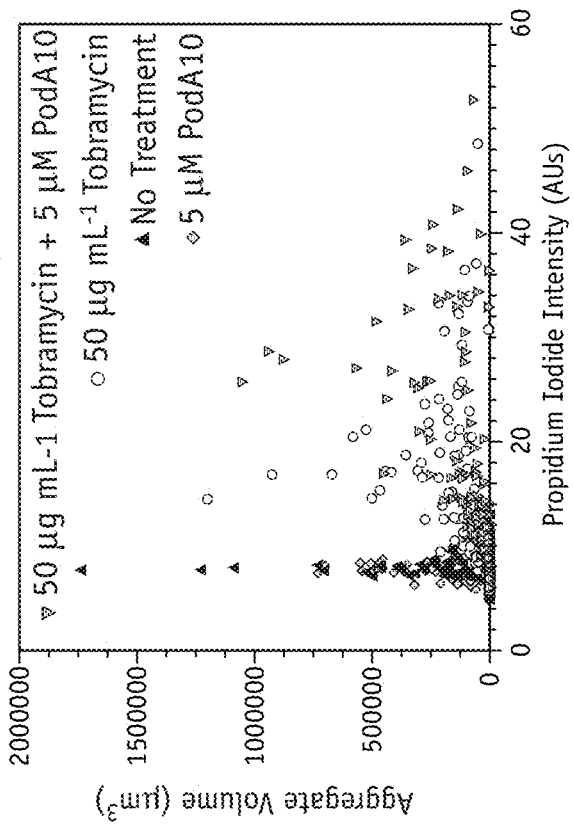
Figure 15:
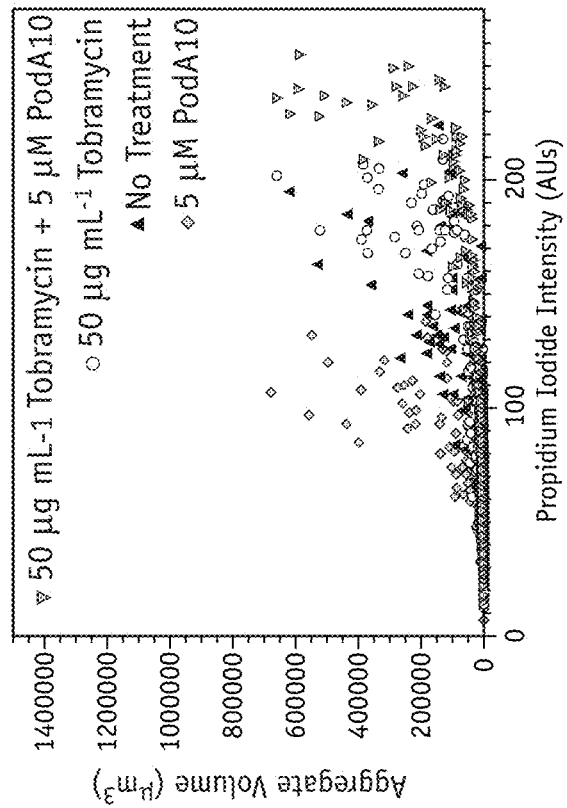

Due to the high thermal stability of PodA, stability assays that rely on monitoring protein unfolding over a temperature gradient were not suitable for the related testing. Therefore the enzyme's kinetic stability were analyzed by boiling WT PodA$_{41\text{-}162}$ and PodA$_{10}$ and measuring activity of each protein after specified boiling times. After 30 and 60 min of boiling, PodA10 had significantly higher activity compared to WT PodA$_{30\text{-}162}$ (FIG. 13). Thus, the optimized inter-subunit interactions in the designed PodA$_{10}$ resulted in significantly higher *Escherichia coli* expression levels and kinetic stability compared to the parental enzyme. We also noted that several designed mutations in PodA8 and PodA10 were not prevalent in a multiple-sequence alignment of PodA homologs (FIG. 14), indicating the importance of the atomistic calculations to design success Even if activity of PodA2, PodA3, PodA5, PodA6, PodA7 PodA8 and PodA9, have not been tested it is expected that in view of the higher stability during overexpression those variants will have a higher stability in pH, viscosity, and salinity. Accordingly, PodA3, PodA5, PodA6, PodA7 PodA8 and PodA9 are expected to have an activity

Example 5. Addition of PodA10 to P. Aeruginosa Cultures in Combination with Antibiotics Enhances Planktonic Killing and Blocks Biofilm Development Prior to testing the impact of PodA10 on biofilms, it was sought to determine its effects on P. aeruginosa grown planktonically.

To ensure its activity and kinetics would not be compromised in physiologically relevant growth medium, PodA10 PYO demethylation activity was tested in lysogeny broth (LB) and Synthetic Cystic Fibrosis Medium (SCFM1, (15)) [45].

In particular, Using a continuous spectrophotometric assay as described in the Material and Methods, PodA (3 µM) and PYO (concentrations indicated on x-axis) were incubated and monitored at 690 nm. $V_{max}$ values were plotted against [PYO] and an $K_M$ was calculated by fitting data to the Michaelis-Menten equation.

Figure 7:
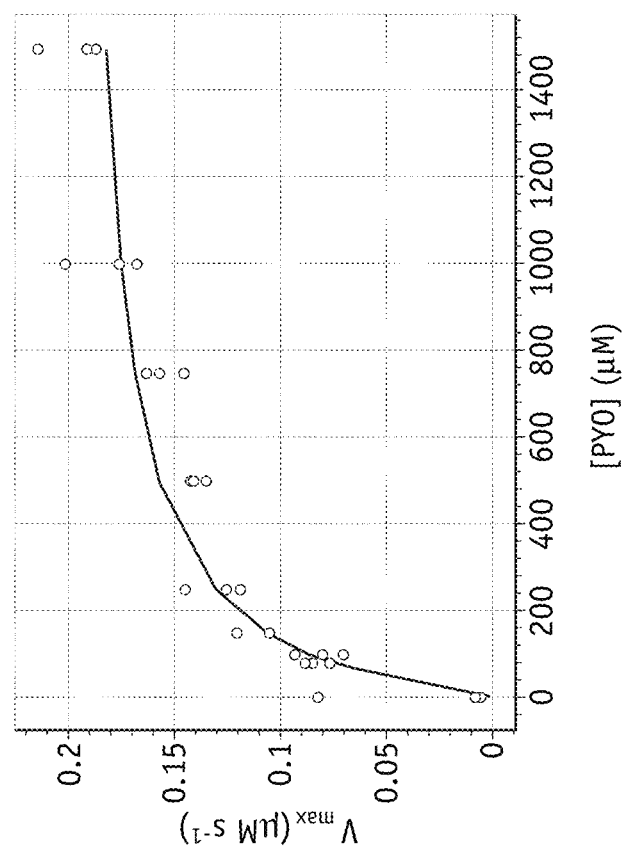
FIG. 7. Kinetics of PodA in growth media. Using a continuous spectrophotometric assay as described in the Material and Methods, PodA (3 µM) and PYO (concentrations indicated on x-axis) were incubated and monitored at 690 nm. $V_{max}$ values were plotted against [PYO] and an $K_M$ was calculated by fitting data to the Michaelis-Menten equation as indicated by black line. Each data point represents the mean of three replicates and error bars represent standard deviation. LB; lysogeny broth, SCFM; synthetic cystic fibrosis medium.
Figure 7:
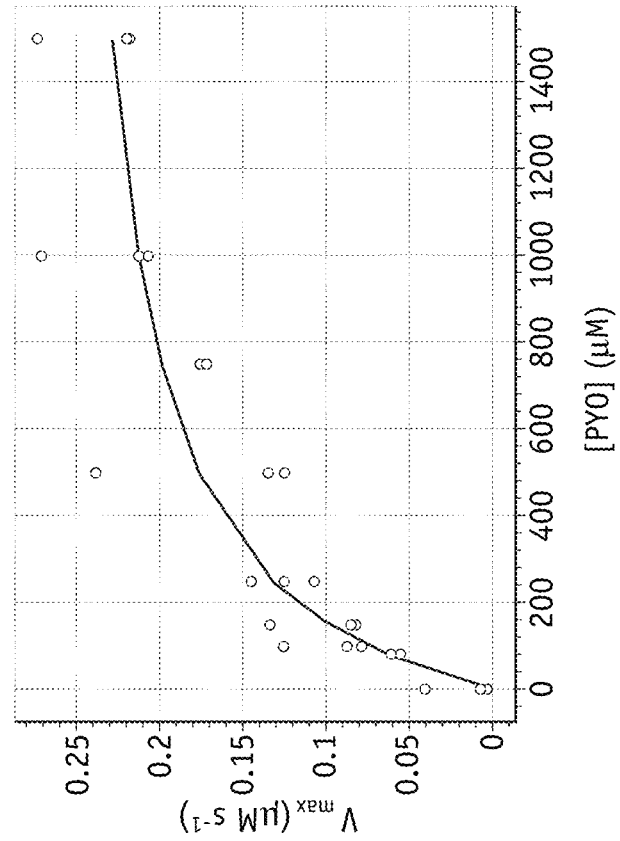

The results are shown in FIG. 7. No change was observed in catalytic efficiency in either medium compared to the kinetic experiments performed in buffer (FIG. 7), allowing moving forward with studying PodA10 effects on P. aeruginosa.

Planktonic cultures of P. aeruginosa strain PA14 were therefore grown to high densities in LB or SCFM over a range of concentrations of PodA10 (0-20 µM) and tobramycin (0-100 ug mL$^{-1}$). Cells were incubated statically to reduce access to oxygen and require P. aeruginosa to utilize PYO to sustain viability.

After incubation, cells were resuspended and reinoculated into fresh medium. Lag times were calculated for each well and it was hypothesized those with increased lag times reflected increased cell death from the treatment.

The same experiments in SCFM were repeated, a minimal medium whose composition is based upon that of sputum from cystic fibrosis patients (15)[45] and which elicits a similar response from P. aeruginosa grown in vitro compared to the in vivo environment (27)[47].

Figure 3:
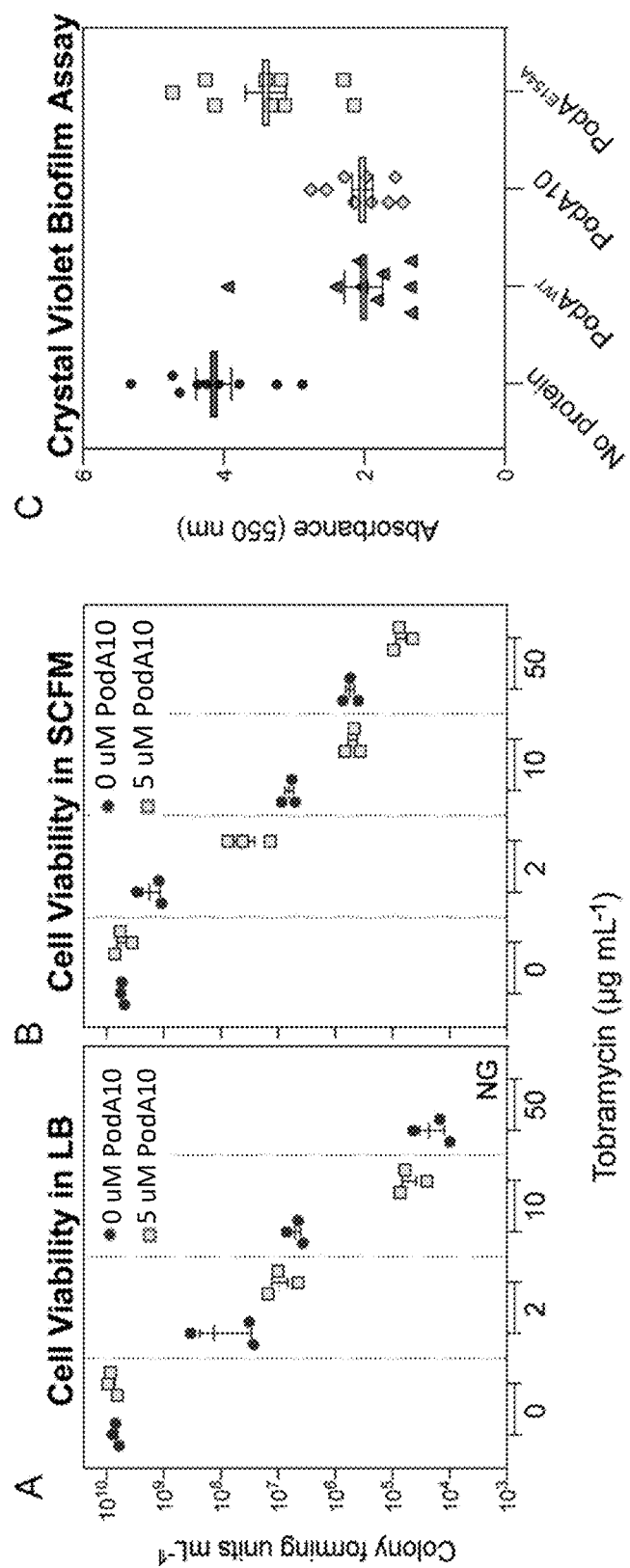
FIG. 3. Effects of PodA10 on planktonic viability and crude biofilm development. Cell viability counts of P. aeruginosa liquid medium synergy experiments with PodA10 (0 μM or 5 μM) and tobramycin (concentrations indicated on x-axis) for LB (A) and SCFM (B). Data represent the mean of biological triplicates with error bars representing the standard error of the mean. NG; No Growth. (C) P. aeruginosa cells were inoculated in a 96-well polystyrene plate containing minimal medium with arginine (40 mM) and either no PodA, WT PodA$_{41-162}$, or PodA$_{10}$, or inactive PodA$^{E154A}$, followed by incubation at 37° C. After 24 h of growth, planktonic cells were washed away, and sessile cells were stained with crystal violet. Cells were de-stained with an acetic acid and methanol mixture, after which sessile cells were quantified with relation to crystal violet absorbance at 550 nm. Error bars represent standard error of the mean.
Figure 8:
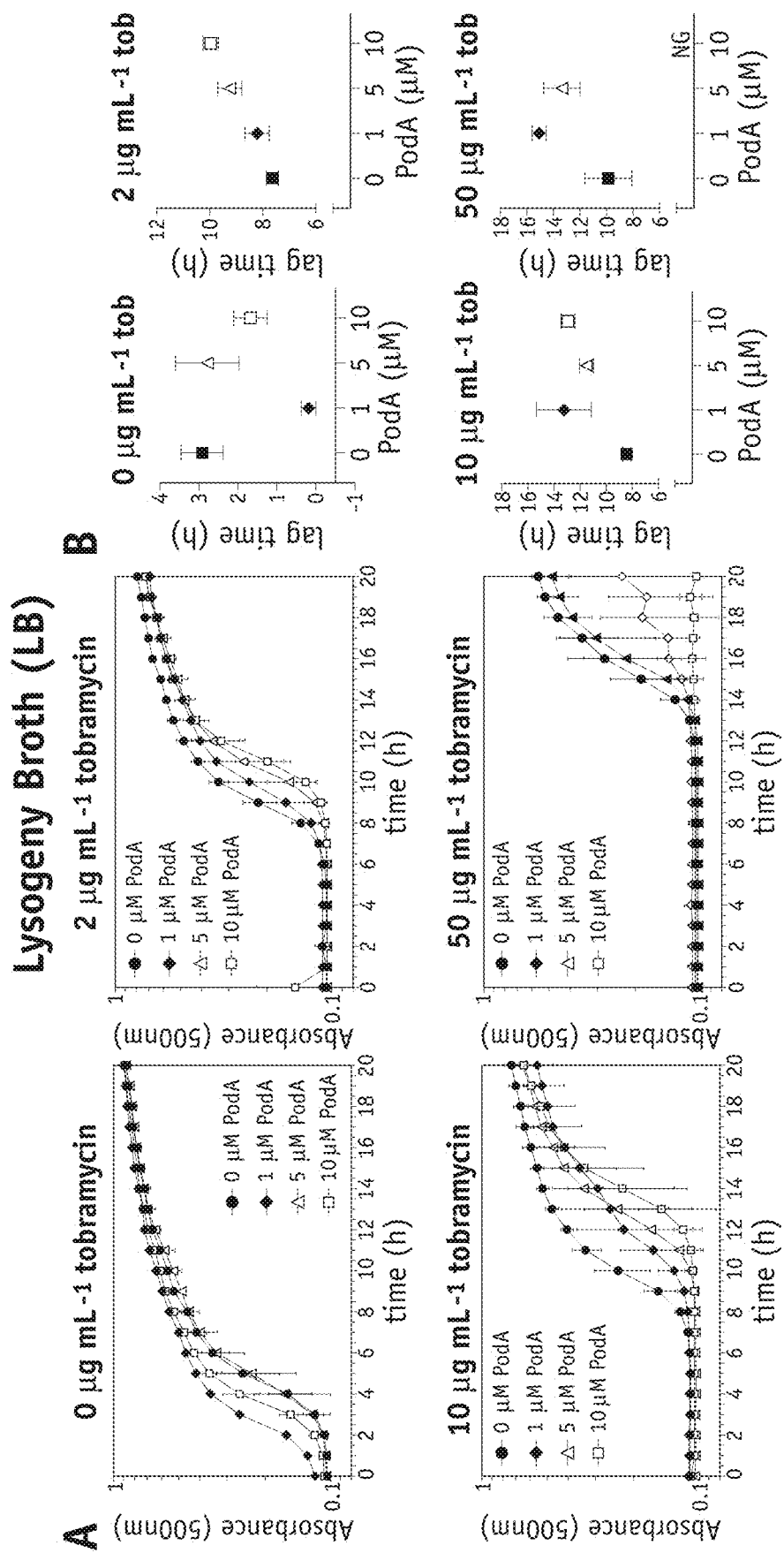
FIG. 8. *Pseudomonas* PodA and antibiotic synergy experiments in LB and SCFM. Growth curves represent outgrowth of cells that were incubated in LB (A) or SCFM (C) with PodA and no tobramycin (top left), or varying amounts of tobramycin (indicated in titles). Buffer was added in lieu of protein for 0 µM PodA controls. Growth was monitored at $OD_{500}$ over time using a BioTek Plate Reader. Experiment was repeated in triplicate with a representative graph is shown. Error bars represent the standard error of the mean of triplicates. B) and D) Lag times of cultures were calculated from growth curves in respective panels. Data were fit to the Gompertz curve-fitting model using Growth Curve Fitting program in R (see website: webpage scott-h-saunders.shinyapps.io/gompertz_fitting_0v2/). Data represent the mean and standard error of triplicates. NG; no growth.
Figure 8:
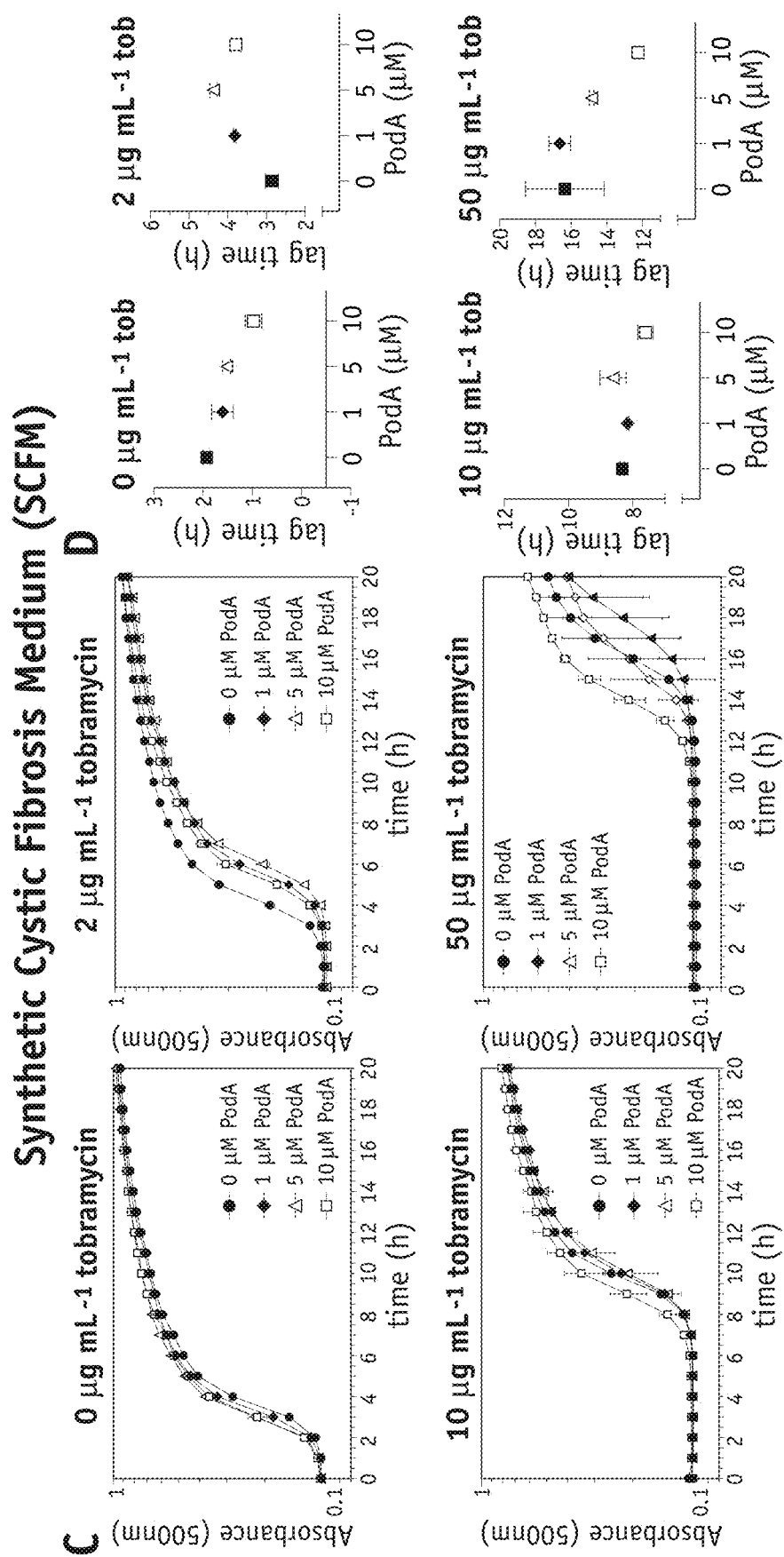

The results of the experiments are shown in FIG. 3 panel A (LB), FIG. 3 panel B (SCFM) and FIG. 8 (LB and SCFM).

A review of the results indicates that while slight differences were seen in lag times when PodA$_{10}$ was added with tobramycin in SCFM, the effects were not as dramatic as seen in our experiments with LB (FIG. 8).

However, when plating the same SCFM cultures to calculate viability via CFUs, there was a significant decrease in survival when PodA10 (5 µM) was added with tobramycin (FIG. 3 panel B). It was speculated that the inconsistent lag times observed in our experiments (FIG. 8) were due to cells adjusting from being treated in SCFM and then grown in LB. This indicates that direct cell counts are a better test for analyzing PodA10 and tobramycin synergistic killing. Contrary to lag times, synergy between PodA and tobramycin in SCFM was clear from directly counting cells (FIG. 3 panel A) and that lag times were not a good universal analysis of synergy (FIG. 8).

Other variants were not tested, but it expected that if activity of a PodA variant is comparable PodA10, then the efficacy for ability to kill Pseudomonas will be similar.

Example 6. Effects of PodA10 in Combination with Antibiotic on Planktonic Viability and Crude Biofilm Development After it was established that PodA10 enhances killing of planktonic P. aeruginosa, experiments were performed to verify that the designed variant could also inhibit biofilm formation as shown previously for WT PodA$_{41-162}$ (12)[1].

In particular for the first biofilm test, the classic biofilm crystal violet microtiter plate assay was to measure the amount of biomass attached to microtiter plate wells after a defined period of time (28)[43]. Incubation for 24 h with addition of designed variant PodA$_{10}$ from the beginning of the assay led to a biofilm attachment defect that was comparable to that achieved by WT PodA$_{41-162}$ (FIG. 3 panel C).

Similarly what indicated for Example 5, also in this case other variants were not tested, but it expected that if activity of a PodA variant is comparable PodA$_{10}$, then the efficacy for ability to kill Pseudomonas will be similar.

Example 7. Addition of PodA10 to Aggregate Biofilms Together with Conventional Antibiotics Leads to Synergistic Killing Based on the results of the experiments in Example 5 and Example 6, synergistic concentrations of PodA and tobramycin to be analyzed in triplicate were identified.

Prior to testing the im-pact of PodA10 on biofilms, we sought to determine its effects on P. aeruginosa grown planktonically. To ensure that its activity and kinetics would not be compromised in physiologically relevant growth medium, we tested PodA10 PYO demethylation activity in lysogeny broth (LB) and synthetic cystic fibrosis medium (SCFM). No change in catalytic efficiency was detected in either medium compared to experiments performed in buffer (FIG. 7), which allowed moving forward with studying PodA10 effects on P. aeruginosa.

Accordingly the next assessment was directed to verify whether PodA is synergistic with tobramycin (an antibiotic commonly used to treat P. aeruginosa infections in the clinic). Tobramycin is an aminoglycoside that targets the ribosome, and its efficacy requires a sufficient proton motive force for entry. [48] [49] The minimum inhibitory concentration (50%) for tobramycin on Pseudomonas ranges from 1 to 3 µg·mL$^{-1}$ (31), with the target tobramycin concentration in sputum of cystic fibrosis infections being ~130 µg·mL$^{-1}$ [50].

To assess whether PodA10 is synergistic with tobramycin, planktonic cultures of P. aeruginosa strain PA14 were grown to high densities in LB or SCFM over a range of concentrations of PodA10 (0 to 20 µM) and tobramycin (0 to 100 µg·mL$^{-1}$). Cells were incubated statically. After incubation, cells were resus-pended and reinoculated into fresh medium. Lag times were calculated for each well, and we hypothesize that increased lag times reflect increased cell death from the treatment. Based on the results of these screens, synergistic concentrations of PodA and tobramycin were identified to be analyzed in triplicate.

In particular, to complete preliminary experiments in triplicate, and perform targeted experiments in biological triplicate with technical triplicate in LB and SCFM, a minimum of 10 mg of PodA was needed. To perform these studies, instead of purifying protein from over 30 L of culture for WT PodA$_{41-162}$ but, due to the improvements in yield observed for PodA$_{10}$, the goals were achieved using only 1.6 L of culture—a substantial improvement in experimental efficiency.

In LB, addition of PodA10 (>1 µM) together with tobramycin increased lag times compared to PodA (-) controls (FIG. 8).

When PodA10 was added with tobramycin, lag times increased by 1.5-2.0 h compared to no PodA controls (FIG. 8)

To verify that lag times were due to increased cell death, in the same experimental set up, cells were plated for colony forming units (CFUs). PodA10 (5 µM) alone did not increase cell death, but when PodA10 was added with tobramycin, cell viability greatly decreased compared to the individual antibiotic controls (FIG. 3 panel A).

The same experiments were repeated in SCFM, a minimal medium whose composition is based upon that of sputum from cystic fibrosis patients and which elicits a similar response from P. aeruginosa grown in vitro compared to the in vivo CF lung environment [47]. While slight differences were seen in lag times when PodA10 was added with tobramycin, the effects were not as dramatic as seen in our experiments with LB (FIG. 8). However, when plating the same SCFM cultures to calculate viability via CFUs, there was a significant decrease in survival when PodA10 (5 µM) was added with tobramycin com-pared to no protein or inactive PodA10 controls (FIG. 3 panel B). It is expected that the inconsistent lag times observed in our experiments (FIG. 8) were due to cells adjusting from being treated in minimal defined medium (SCFM) and then grown in rich medium (LB), an observation that is common in microbiological growth experiments. This indicates that direct cell counts are a better test for analyzing PodA10 and tobramycin synergistic killing. impacts mature biofilms and their viability.

In planning additional experiments, it was noted that while the crystal violet assay permits biofilm phenotypes to be rapidly screened, it only provides a crude measurement of a biofilm defect related to attachment. To better understand how PodA10 impacts biofilm development and longevity, the agar block biofilm assay (ABBA) was used, which was designed to enable the experimental study (12, 29) of the type of aggregate biofilms that characterize human chronic infections (30)[51].

Due to the ABBA assay being less high throughput than experiments in liquid cultures, it was chosen to test a single concentration of tobramycin (50 µg mL$^{-1}$) with PodA10 (5 µM) in LB and SCFM, as these concentrations showed the most dramatic synergistic effects in previous experiments (FIG. 3, FIG. 8).

Previous ABBA experiments performed in succinate-minimal medium with WT PodA41-162 showed that addition of PodA led to smaller aggregates in anoxic regions of the agar after 27 hours of incubation (12) [1].

These experiments also showed that inactive PodA$_{41-162}$ had no effect on P. aeruginosa aggregate development. Given this, and the low protein yield for expression of this inactive PodA variant (which was not redesigned with AffiLib), it was opted to use buffer as a negative control for these experiments.

Figure 4A:
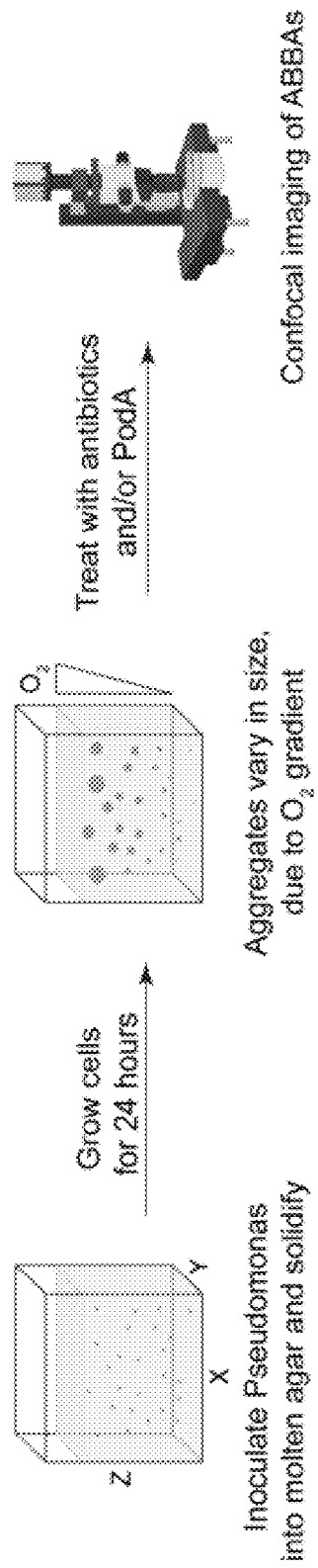
FIGS. 4A-4G. Microscopy imaging of propidium iodine stained ABBAs treated with PodA10 and tobramycin. Cells were incubated in an ABBA as described in Materials and Methods, followed by treatment with PodA10 (5 μM), tobramycin (50 ug mL-1), or PodA10 and tobramycin. For no treatment conditions, buffer was added in lieu of protein. Cells were either grown in FIG. 4B) LB or FIG. 4E) SCFM.

Cells were inoculated into the agar and allowed to grow into aggregates for 24 hours, after which PodA$_{10}$ and tobramycin were added simultaneously and allowed to incubate for 12 hours (FIG. 4A). Samples were then stained with propidium iodide (PI), a fluorescent DNA binding dye that is incapable of passing through the membrane of viable cells, and imaged. Generally, higher PI staining indicates lower cell viability due to the compromised membranes of these cells. Aggregates were analyzed via confocal microscopy throughout the depth of the ABBA.

Figure 17:
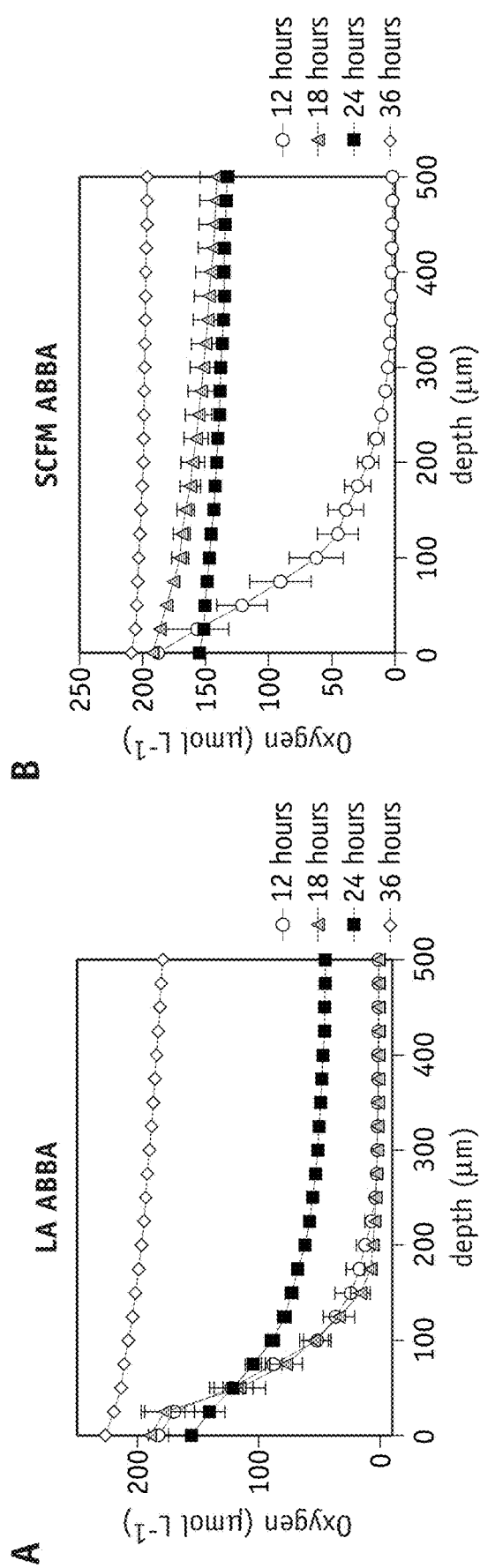
FIG. 17. *Pseudomonas* LB and SCFM ABBA oxygen profiles. Cells were inoculated in LB or SCFM ABBAs and grown for the time indicated in graph legends. Oxygen profiles were determined using a micrometer oxygen sensor (UniSense). All time points consisted of biological triplicates with technical triplicate readings of each ABBA block with error bars representing standard deviation. A) Oxygen profile time course of LB ABBA. B) Oxygen profile time course of SCFM ABBA.

Addition of PodA10 and tobramycin for LB and SCFM was administered at the latest time point for which an oxygen gradient was present (24 h for LB; 12 h for SCFM) (FIG. 17). This ensured that biofilms were at their most mature state, while still exhibiting metabolic stratification. After treatment, samples were stained with propidium iodide (PI), a fluorescent DNA-binding dye that is incapable of passing through the membrane of highly energized cells and imaged. Generally, higher PI staining indicates lower cell viability due to the com-promised membranes of these cells.

Aggregates were analyzed via confocal microscopy throughout the depth of the ABBA, with each aggregate representing a distinctly growing Pseudomonas biofilm. Incubation of LB-grown aggregates with tobramycin and PodA10 led to PI staining intensity that was significantly greater than PodA10 or tobramycin alone (FIG. 4B).

Figure 4B:
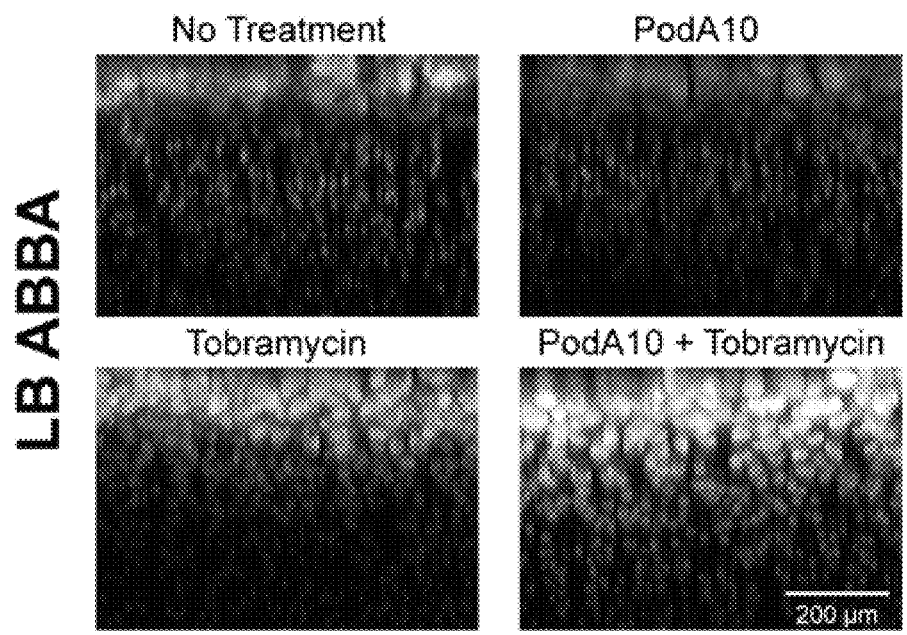

In particular Incubation of LB-grown aggregates with tobramycin and PodA10 led to a PI staining intensity that was visibly higher than PodA10 or tobramycin alone (FIG. 4B).

Figure 4C:
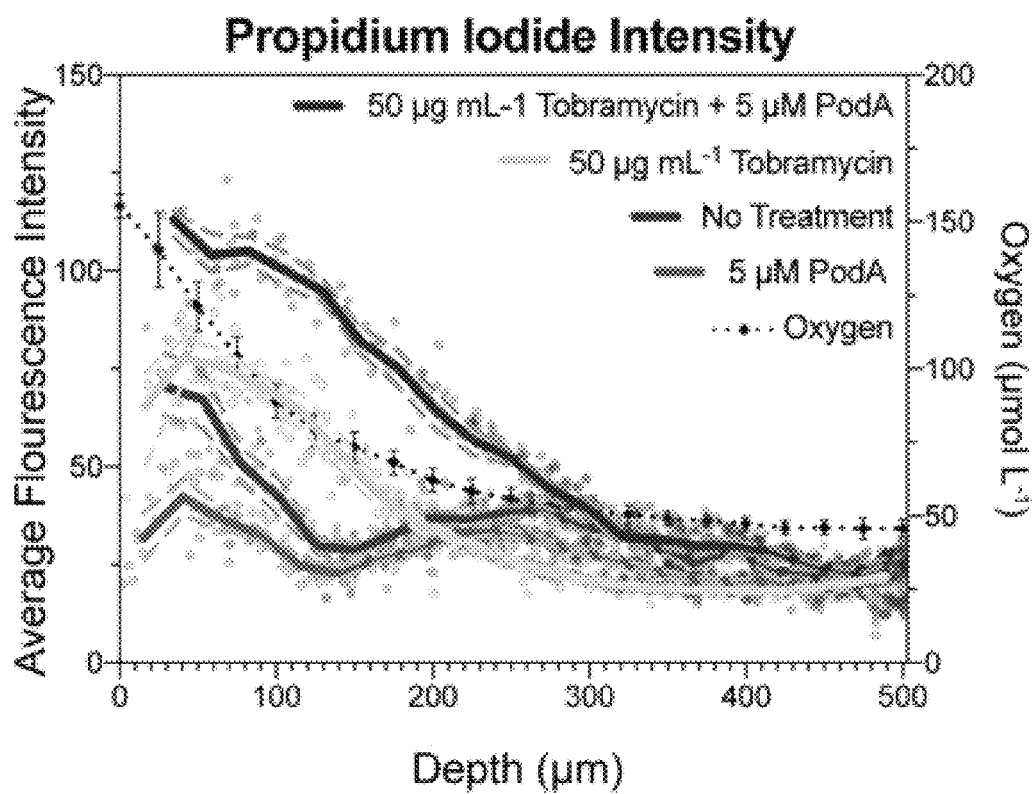

To quantify this visual effect, the average fluorescence intensity of PI in each sample was measured through the XZ-plane of the ABBA (FIG. 4C). In LB, the peak PI intensity with PodA10 and tobramycin was higher than the peak intensity of tobramycin alone (193.3 AUs vs. 151.0 AUs, respectively). To ensure higher intensities were not due to differing aggregate sizes, the average volume of each aggregate was plotted over depth and saw no significant differences in volumes between treatments (FIG. 9).

Figure 4D:
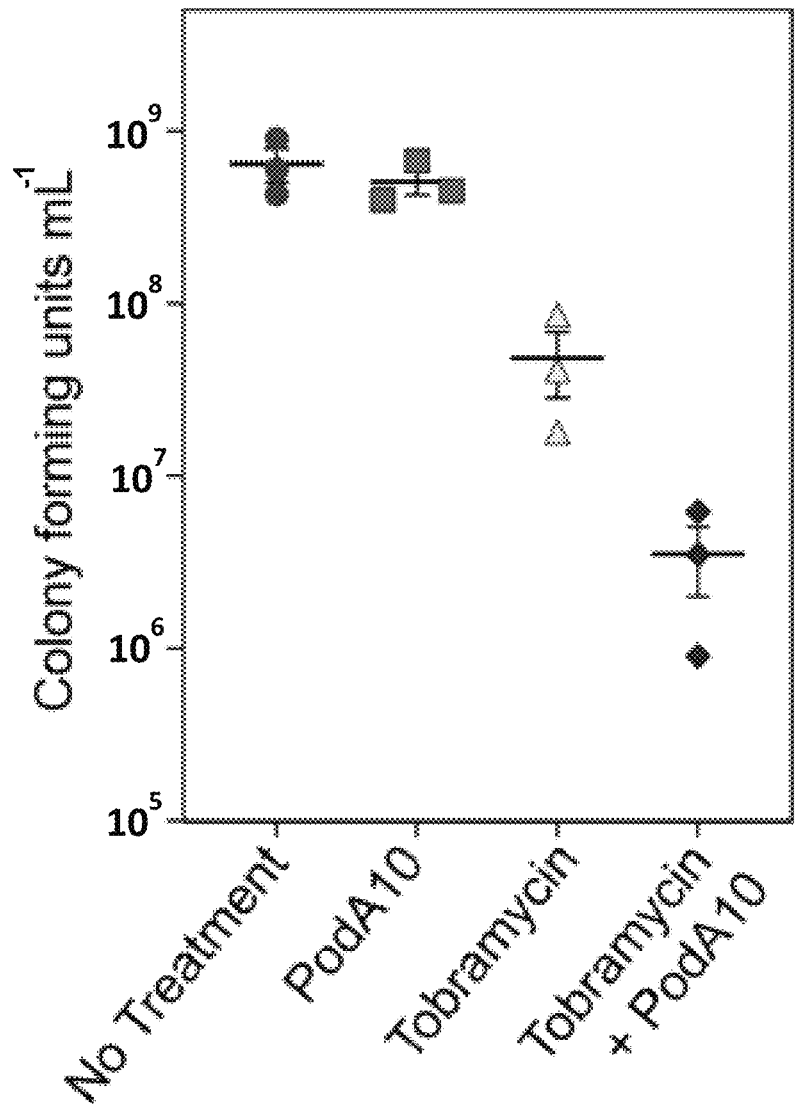
Figure 9:
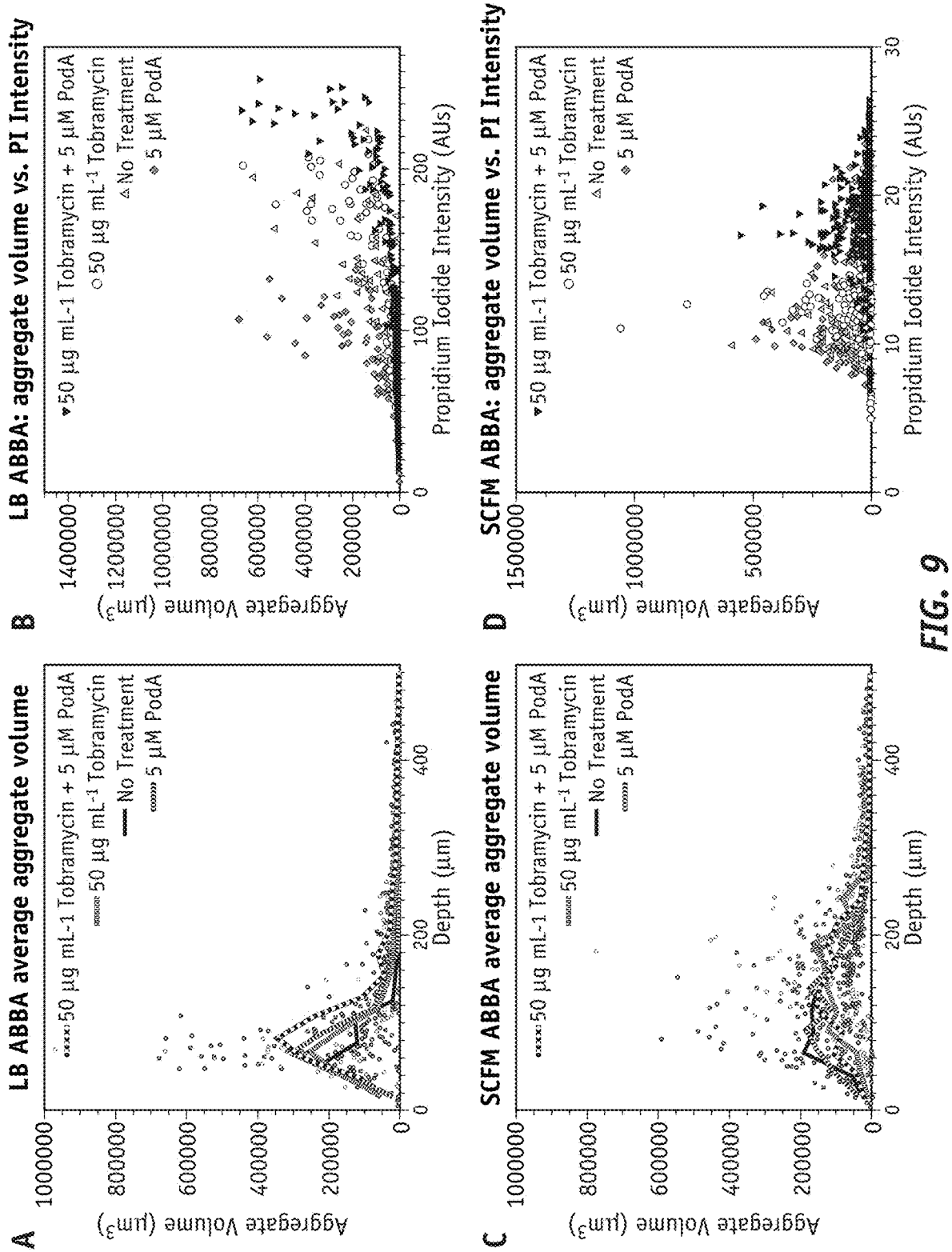
FIG. 9. *Pseudomonas* LB and SCFM ABBA aggregate volume analyses. ABBA data from FIGS. 4A-4G_were analyzed in Imaris to obtain volume of each aggregate for LB (A) and SCFM (C). Mean aggregate volume was calculated with a bin size of 20 (every 25 µm) and plotted as a solid line (legend in each graph). Propidium Iodide intensity from FIGS. 4A-4G was plotted against each aggregate volume for LB (B) and SCFM (D).

Plotting the aggregate volume vs. PI intensity of each aggregate further showed that PI staining was highest in the PodA10+tobramycin treated samples (FIG. 9). These staining results correlated with cell viability, which was determined by homogenizing ABBAs and plating for CFUs. ABBAs that were incubated with PodA10 and tobramycin had the lowest viable cell counts compared to controls (FIG. 4D).

For the LB ABBA, the largest differences in PI staining between tobramycin and tobramycin+PodA11 (FIGS. 4C and 4F) were between 0 and 300 µm, a region previously characterized as the oxic-hypoxic zone within the agar (12) [1]. To confirm this, parallel experiments were set up identically and microelectrodes were used to measure the oxygen profiles in our ABBA system.

Figure 10:
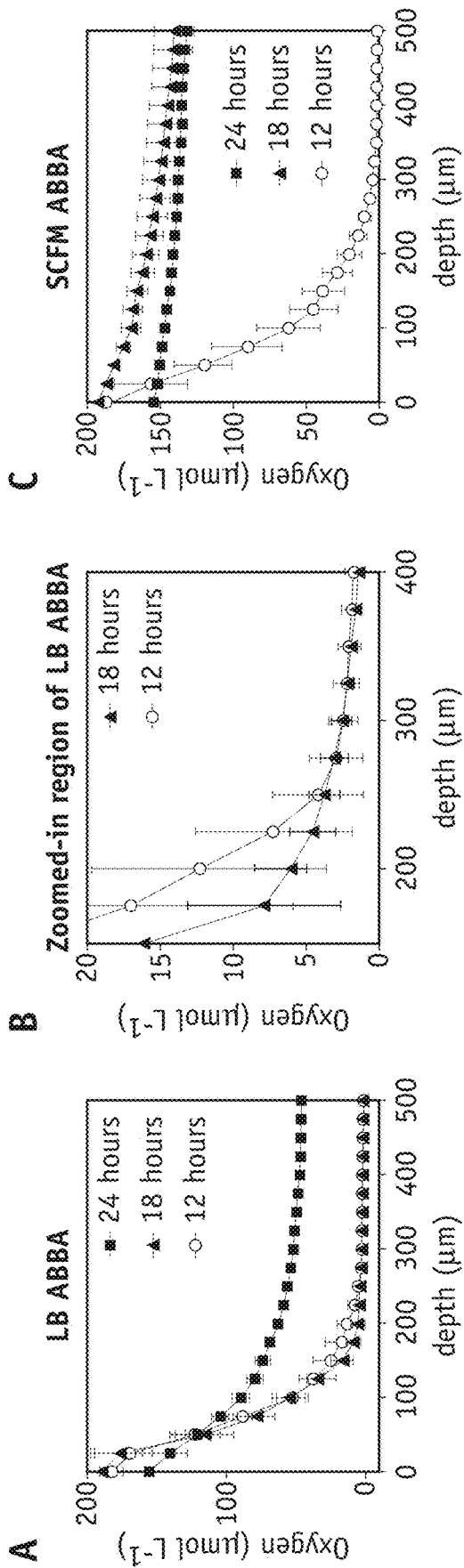
FIG. 10. *Pseudomonas* LB and SCFM ABBA oxygen profiles. Cells were inoculated in LB or SCFM ABBAs and grown for the time indicated in graph legends. Oxygen profiles were determined using a micrometer oxygen sensor (UniSense). All time points consisted of biological triplicates with technical triplicate readings of each ABBA block with error bars representing standard deviation. A) Oxygen profile time course of LB ABBA. B) A zoomed in region of A) to display the transition from oxic to hypoxic (between 300-400 µm depths). C) Oxygen profile time course of SCFM ABBA.

An oxygen gradient existed through the depth of the LB ABBA and correlated with the viability patterns observed (FIG. 4C, FIG. 17). Importantly, the oxygen gradient changes over time: at 12 hours, no oxygen is present at a depth of ~350 µm (FIG. 10, FIG. 17); however, by 24 hours, oxygen is again detected. These dynamics likely a change in what is limiting metabolism at these different timepoints: first oxygen, and then carbon. The expectation which is not intended to be limiting is that these dynamics reflect a change in the limiting nutrient at these different time points: first oxygen, then carbon. Once carbon is depleted, oxygen concentrations rise again due to diffusion and a lack of cellular consumption.

Figure 11:
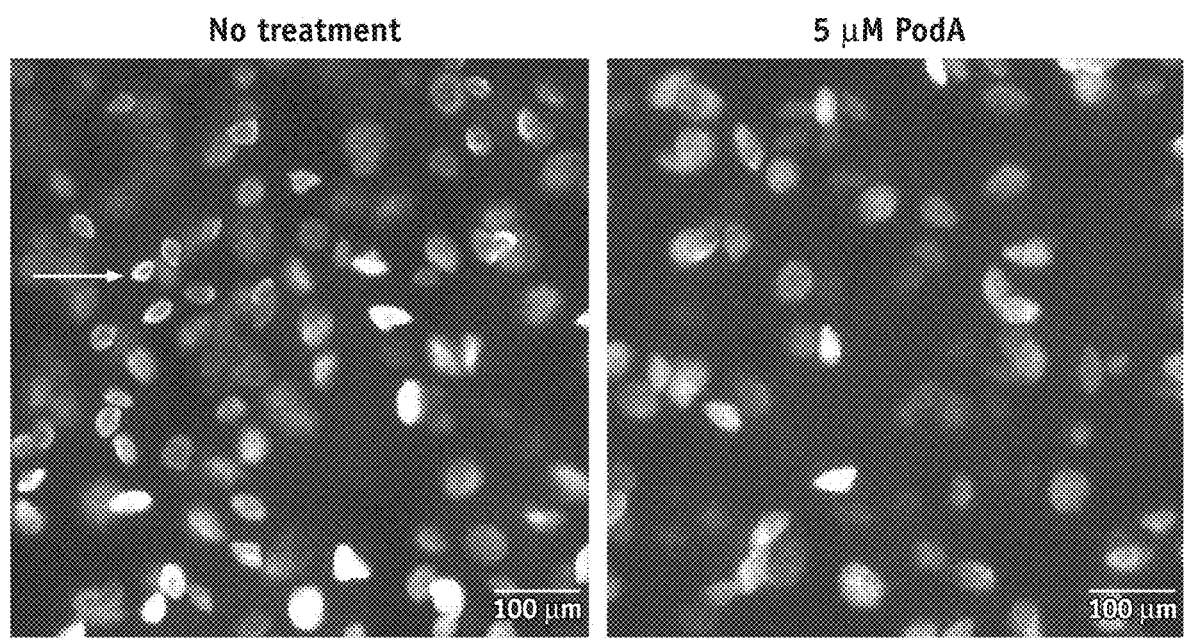
FIG. 11. Differences of PI staining in LB between untreated and PodA treated ABBAs. Microscopy data LB ABBAs were analyzed in the XY-plane at 90 µm depth (stack 15/84), with brightness contrast normalized to the no treatment control. Example of ring staining pattern indicated by red arrow.
Figure 12:
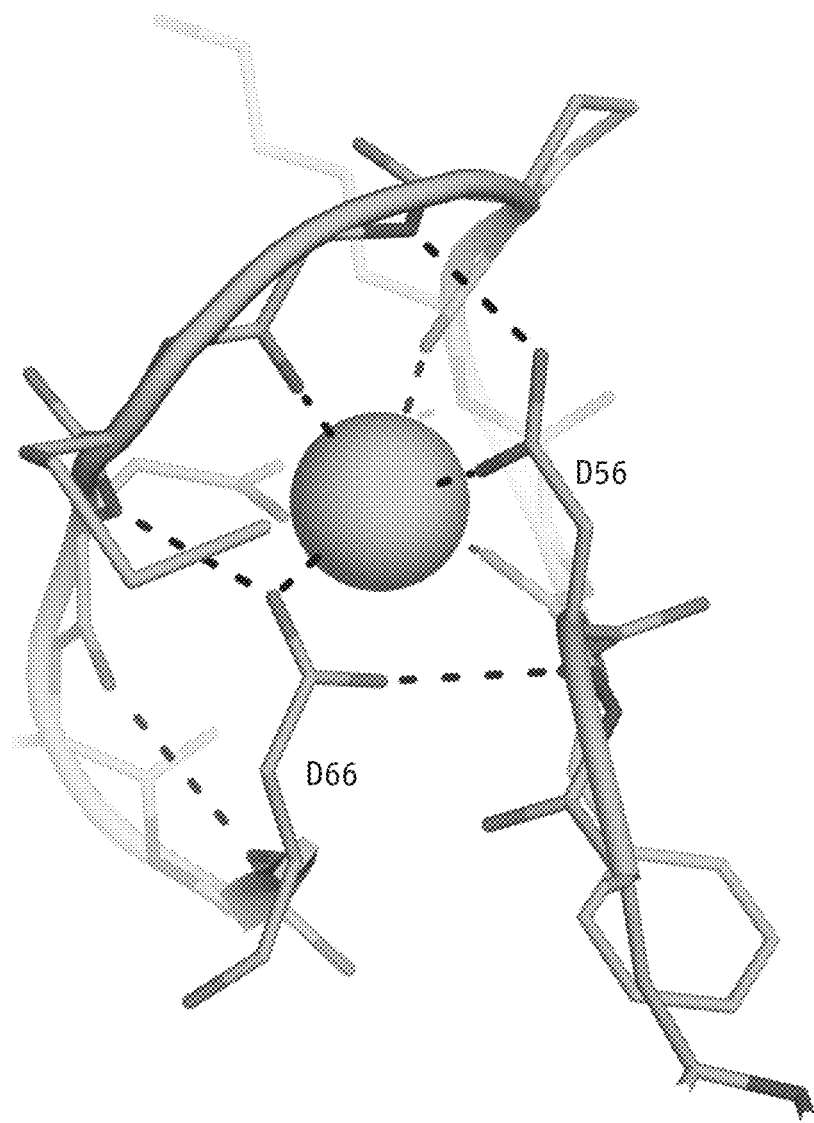
FIG. 12 (S2 PP). $Ca^{2+}$ ion binding site of PodA. The loop between residues 56-66 connecting the ends of anti-parallel β-strands is stabilized through multiple bonds between a $Ca^{2+}$ ion and loop backbone atoms and sidechains, mainly through Asp56 and Asp66. This $Ca^{2+}$ ion was present in the crystal structure upon which our design calculations were based, likely due to the crystal having formed in a buffer that contained calcium [1].
Figure 16:
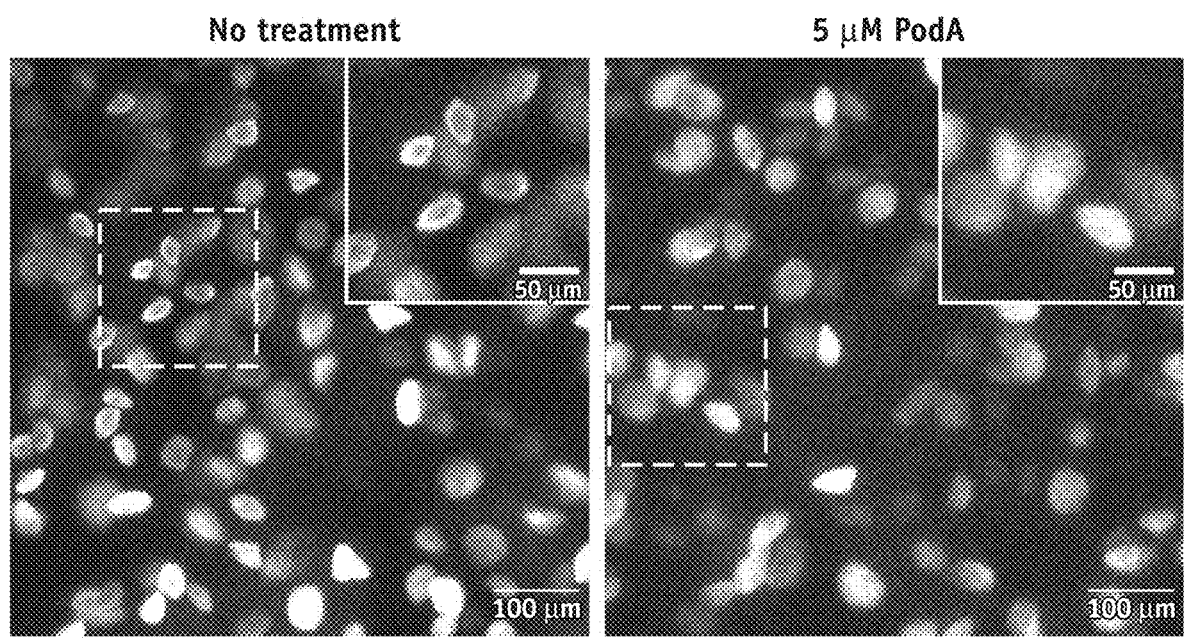
FIG. 16. Differences of PI staining in LB between untreated and PodA treated ABBAs. Microscopy data LB ABBAs were analyzed in the XY-plane at 90 µm depth (stack 15/84), with brightness contrast normalized to the no treatment control. Example of ring staining pattern indicated by zooming in on dashed boxes, with zoomed in images in the upper right corner. Look up table (LUT) settings were normalized to no treatment condition.

At smaller scales, an oxygen gradient also exists within each single aggregate, due to cellular oxygen consumption outpacing its diffusion (31) [52]. Additionally, gradients of phenazines have been shown to exist within biofilms, with PYO being localized to the periphery (32), reflecting its requirement for molecular oxygen for its biosynthesis. Analyzing data from FIG. 4B in a XY-plane (top-view) rather than a XZ-plane (side view) a staining pattern consistent with such gradients was found: untreated aggregates grown in LB show an outside ring PI staining pattern that is abolished upon PodA addition (FIG. 11 and FIG. 16).

Figure 4E:
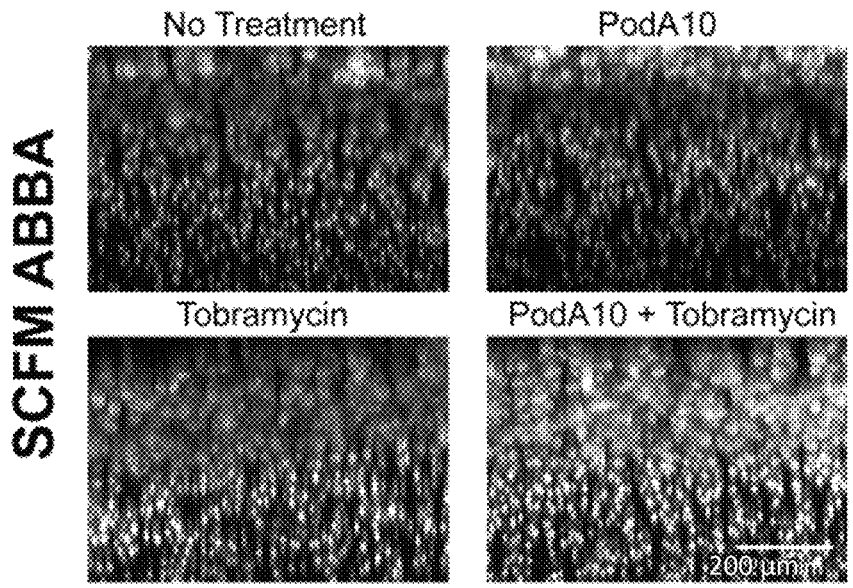
Figure 4F:
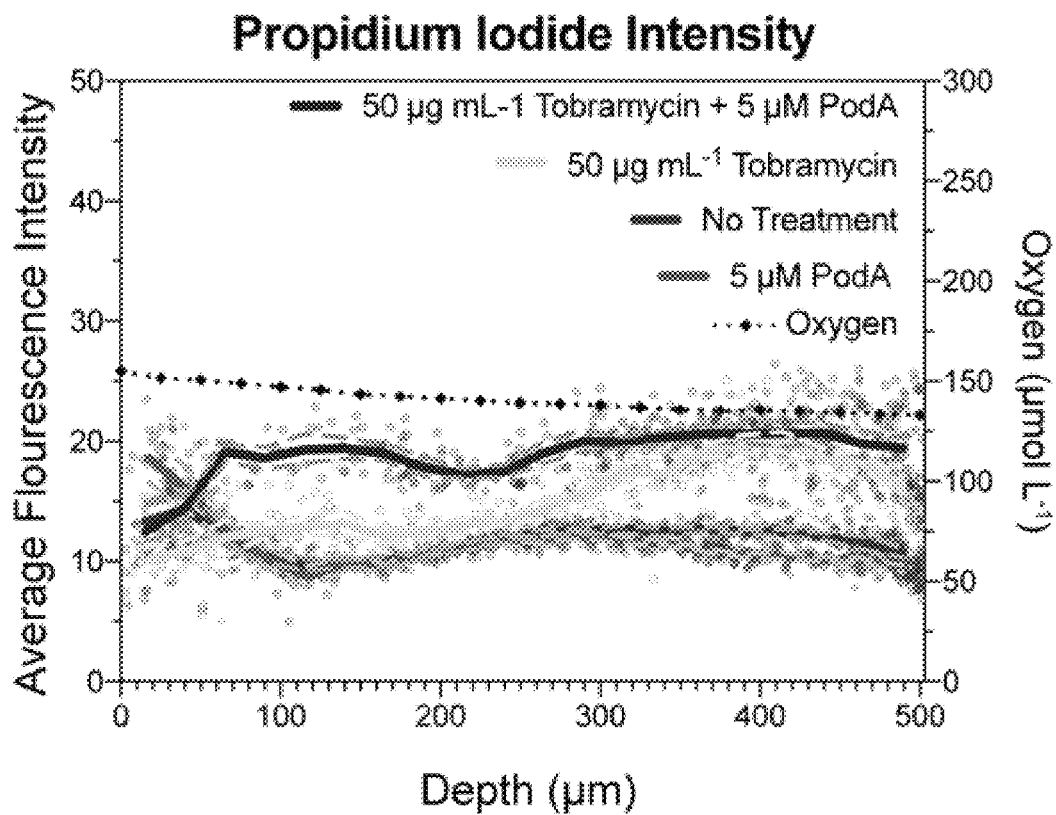
Figure 4G:
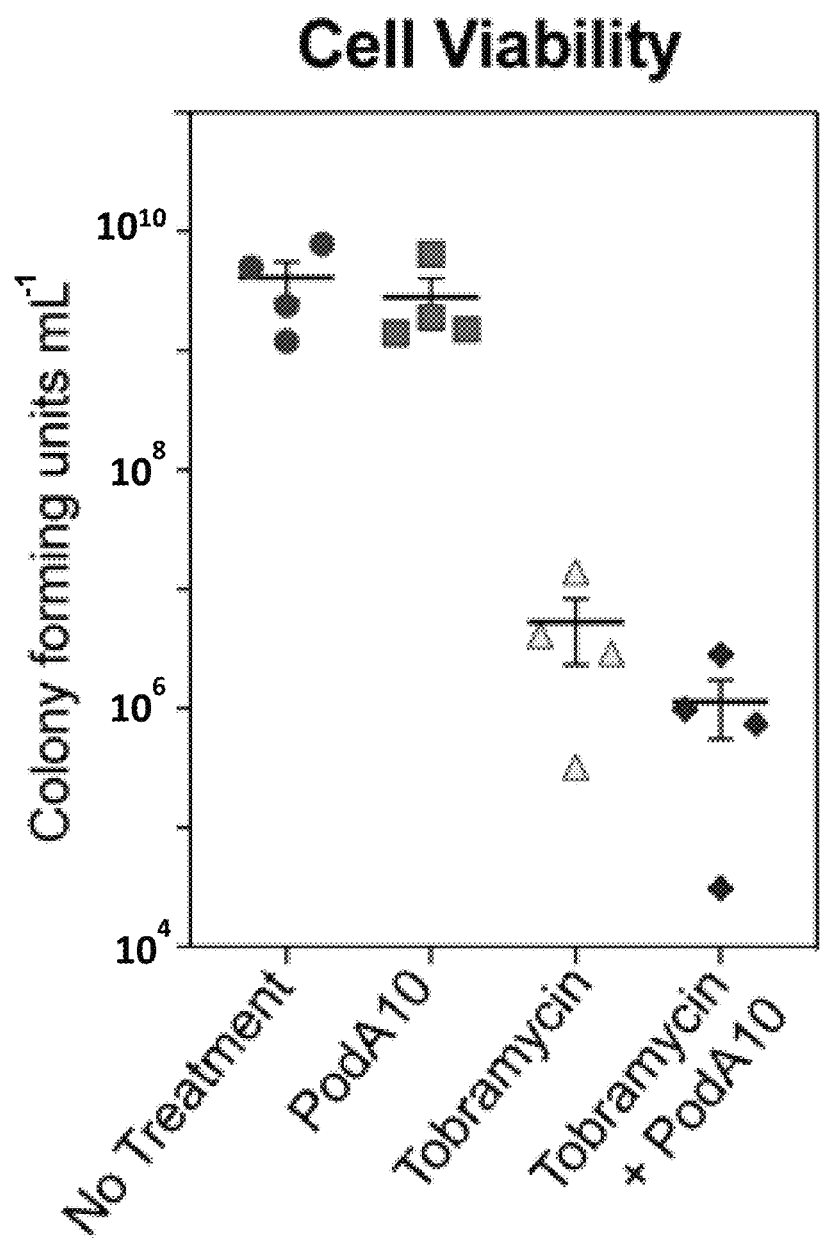

Similar synergistic effects of PodA and tobramycin treatment were observed for biofilm aggregates grown in SCFM. Qualitative differences in PI staining trends were also seen in this medium (FIG. 4E), with the peak PI intensity of PodA10 with tobramycin being higher than tobramycin alone (31.2 AUs vs. 22.6 AUs, respectively) (FIG. 4F). This difference was lower compared to that seen in LB, as reflected in the viability counts (FIG. 4G). While the differences were not as dramatic in SCFM as in LB, this was expected given that SCFM aggregates are smaller in size and therefore exhibit lower PI uptake (FIG. 9). In microelectrode experiments in 24 h grown SCFM ABBAs, no significant oxygen gradient decline was found, mirroring the higher PI staining intensity throughout the entire depths of the ABBA in the presence of tobramycin (FIG. 4F).

It is expected that antibiotics effective against phenazine producing bacteria will have comparable effect comparable to the one illustrated in this example. In particular a comparable efficacy is expected when PodA variant herein described are combined with one or more aminoglycosides (same antibiotic class as tobramycin).

Example 8. Effects of Concentration on PodA Ability to Perform Synergistic Killing with Tobramycin and Other Antibiotics PodA and antibiotics will be combined and applied to *Pseudomonas* cultures and cell viability will be calculated by counting alive cells after treatments. Treatments that have the highest killing compared to antibiotic or PodA only controls will be used for future PodA applications.

In order to determine synergistic effects of PodA and antibiotics, concentrations of PodA or engineered PodA can be tested at 0.01 μM, 0.1 μM, 1.0 μM, 5.0 μM, 10.0 μM, and 20.0 μM.

For antibiotics, concentrations are tested ranging from 100× below the MIC to 10× above the MIC. To determine synergy all possible combinations of PodA and tobramycin can be combined with a dense culture of bacterial cells and incubated for 12 hours.

Afterwards, cell viability can be determined by diluting cells and plating to calculate colony forming units.

Any combinations that lead to further killing compared to the sum of either compound alone, will be considered synergistic. Combinations of PodA and antibiotics that are equal to the sum or less of each compound alone, are considered non-synergistic.

Specific PodA concentrations that were tested were: 0.001 μM, 0.01 μM, 0.1 μM, 1.0 μM, 5.0 μM, 10.0 μM, and 20 μM.

Concentrations of the exemplary antibiotics tobramycin tested: 0.00005, 0.002, 0.01, 0.025, 0.08. 0.1, 2.0, 10.0, 25.0, 50.0, and 100.0 ug mL−1.

The concentration indicated in bold were shown to have synergic effect and are known or expected to be able to provide synergic effects in any combinations one with another.

The PodA concentrations were tested on $PodA10_{41-162}$, are expected to be effective for $PodA_{1032-162}$, $PodA10_{wt}$ and also for the other variants exemplified herein as well as for PodA wild type and any other PodA derivatives as will be understood by a skilled person upon reading of the present disclosure.

Example 9. $PodA_{30-162}$ Activity is Stable Across Conditions Relevant to Cystic Fibrosis Sputum in a Manner Equivalent to $PodA_{41-162}$ To assess PodA's potential for therapeutic relevance in the context of human chronic infections, such as those in the cystic fibrosis (CF) airways, PodA activity was quantified and its kinetic parameters determined under a spectrum of physiologically relevant variables (i.e., pH, viscosity, and sodium and potassium concentrations). As done previously to facilitate PodA purification [1], A predicted N-terminal transmembrane domain, resulting in a wild-type (WT) variant called WT $PodA_{30-162}$ which includes the structure of $PodA_{41-162}$.

Experiments performed proved that $PodA_{30-162}$ variants had activity and behavior substantially identical to the variants of $PodA_{41-162}$ whose activity has been tested with experiments reported in the previous examples.

Using a variety of buffers to analyze activity from pH 5.5 to 10.0, we found that WT $PodA_{30-162}$ had optimal activity at pH 6. Activity of WT $PodA_{30-162}$ below pH 5.5 was not established due to the $pK_a$ of PYO ($pK_a$=4.9), which changes the chemical and therefore absorptive proper-ties of the substrate. The pH of CF airway surface liquid is acidic and is thought to increase viscosity of CF mucus by influencing mucin electrostatic interactions [54]. Using a reaction condition with a pH of 6, a slight increase in viscosity with ethylene glycol or glycerol (1% vol/vol) enhanced WT $PodA_{30-162}$ activity.

In the case of glycerol, higher concentrations (5 to 20%) reversed this activity increase. Average ion concentrations of potassium and sodium in cystic fibrosis sputum are 66 mM ($Na^+$) and 15 mM (K+) (16). Addition of these ions in salt form (NaCl and KCl) in this concentration range did not inhibit or enhance WT $PodA_{30-162}$ activity For these reasons, we established conditions for kinetic analyses to be carried out at a pH of 6 with 1% ethylene glycol.

The same continuous spectrophotometric assay was used to determine enzyme kinetics of PodA for PYO. Using Michaelis-Menten parameters, WT $PodA_{30-162}$ exhibited a $K_M$ of 0.372 mM±0.018, a $k_{cat}$ of 0.176±0.003 s$^{-1}$, and a catalytic efficiency of 4.73±0.24×10² M$^{-1}$ s$^{-1}$. The WT $PodA_{30-162}$ active-site variants $PodA^{D72A}$, $PodA^{H121A}$, $PodA^{H121K}$, $PodA^{H12IR}$, $PodA^{E154A}$, $PodA^{Y156A}$, and $PodA^{Y156F}$ did not have measurable activity compared to controls, as previously seen [1]. A variant inhibiting product release (13), $PodA^{D68A}$, maintained similar Michaelis-Menten trends for concentrations of PYO under 100 μM, after which $V_{max}$ leveled off.

Therefore similarly to what indicated for $PodA_{41-162}$ also for $PodA_{30-162}$ Stabilizing the PodA Trimer Interface Increased the yield by 20-Fold.

Before moving forward using the inclusion body purification exclusively for the designed variants, we verified that WT $PodA_{30-162}$ activity and kinetics were not altered after denaturing and refolding the enzyme. Soluble fraction WT $PodA_{30-162}$ had a catalytic efficiency of 1.05±0.093×10² M$^{-1}$·s$^{-1}$ and WT $PodA_{30-162}$ purified from inclusion bodies of the same prep had a catalytic efficiency of 1.14±0.25× 10² M$^{-1}$·s$^{-1}$.

Remarkably, also for $PodA_{30-162}$ the eight PodA designs discussed in the preceding example with reference to $PodA_{41-162}$ exhibited increased protein yields relative to the wild-type protein when purified from inclusion bodies. Also for PodA 30-162 there is no change in the kinetics of these proteins and in catalytic efficiency between PodA WT and $PodA_{830-162}$ and a slight increase in efficiency for $PodA10_{30-162}$ substantially the same of the ones shown for the variant of $PodA_{41-162}$. Similar considerations apply to the results reporting yields and stability as well as planktonic killing and synergic results confirming the key importance of the positions and the replacements to obtain increased stability, activity and yield for stabilized PodA and related derivatives.

Example 10. Stabilized PodA Variants are Expected to be Effective Therapeutics Alone or Preferably in Combination with Antibiotics The phenazine PYO is beneficial to *P. aeruginosa* biofilm development and metabolic activity (13, 14)[55, 56], and cells that cannot synthesize phenazines have lowered rates of anoxic survival without added terminal electron acceptors (8, 33) [55, 57]. Phenazines are in an oxidized form when acting as electron acceptors, so it was wondered whether the conversion of $PYO_{ox}$ to $1\text{-}OH\text{-}PHZ_{red}$ via PodA would be detrimental to *P. aeruginosa* metabolic vitality within the anoxic zone. Because oxygen was present throughout our SCFM samples, only such an effect in LB-grown ABBA aggregates was looked for.

Because PYO and other phenazines permit *P. aeruginosa* to adopt metabolic strategies that lead to evasion of antibiotic treatments (9-11) [60], it stands to reason that removal of these metabolites is expected to offer an attractive new therapeutic approach.

A review of the results provided in the preceding examples indicated that, PodA addition alone did not significantly change PI staining at depth (>300 μm in LB, where the anoxic zone begins after 12 hours). Three possible explanations for this phenotype which are not intended to be limiting comprise: 1) conversion of $PYO_{ox}$ to $1\text{-}OH\text{-}PHZ_{red}$ still permits sufficient metabolic activity to persist over the time period of our assay (12 hours between PodA addition and PI staining) because $1\text{-}OH\text{-}PHZ_{red}$ can be oxidized and recycled; 2) given the low energetic state previously measured for *P. aeruginosa* surviving anaerobically by cycling phenazines (6), the membrane potential of cells at this depth of the ABBA system is sufficiently low that PI can be taken up as efficiently by metabolically active cells as dead cells, thus obscuring a viability readout; and/or 3) PYO is not the primary phenazine sustaining metabolic activity in the anoxic zones-rather, another phenazine, such as phenazine carboxamide (which can also sustain anaerobic survival (34) and localizes to the interior of large anoxic colony biofilms grown on 1% tryptone (32) [53]), may maintain viability under these conditions.

In contrast to the anoxic zone in LB, PodA addition alone or in combination with tobramycin produced striking effects in the oxic/hypoxic zones of the ABBA assay in both LB and SCFM (FIGS. 4A-4G). Importantly, while PYO is beneficial to cells when they are electron-donor replete but oxidant-limited, PYO is toxic to *P. aeruginosa* under regimes where electron donors are limited but oxidants are replete, such as in the oxic/hypoxic zone, where PYO can react with oxygen and cause oxidative stress (35) [62].

This fact, combined with the knowledge that PYO is maximally concentrated in the outer regions of large colony biofilms grown on 1% tryptone (32), supports the conclusion that for untreated cells in LB, PYO causes localized toxicity at the oxic interface of biofilm aggregates. Addition of PodA alone removes PYO from oxic regions, leading to greater metabolic activity of aggregates in these zones, as well as in the outer rings of large aggregates (reflected by lower PI staining).

In contrast, when PodA is added together with tobramycin, this enhancement of metabolic activity is a double-edged sword. Greater metabolic activity—specifically, having an inner membrane that is sufficiently energized to be able to take up to bramycin—has been shown to be correlated with greater tobramycin susceptibility (36) [48]. Accordingly, in ABBA regions that have both oxygen and PYO, the depletion of PYO by PodA sensitizes these cells to tobramycin treatment. Supportive of this hypothesis is the fact that SCFM ABBA was completely oxic and PI staining patterns of tobramycin or tobramycin+$PodA_{10}$ treated samples were considerably higher than no treatment controls at all depths (FIG. 4F). In the LB ABBA, the switch to hypoxia/anoxia occurred around 300 μm leading to metabolic restriction, correlating with no significant differences in PI staining between non-treated and tobramycin-treated samples (FIG. 4C).

It is expected that the differences in effects observed for PodA treatment (in the presence or absence of tobramycin) in LB and SCFM reflect differences in media composition, with varying electron donor:electron acceptor abundance. Indeed, SCFM has 3 mM glucose and 9 mM lactate as a carbon source, in contrast to LB which only has amino acids as carbon sources (37) [63]—it is therefore possible that in the oxic zone, cells in SCFM are more protected from PYO toxicity due to a high electron donor:electron acceptor ratio (35) [62]. Moreover, metabolic flux through the TCA-cycle is known to promote antibiotic susceptibility due to proton-motive force production, which subsequently facilitates the import of tobramycin (38) [49]. It is possible that the presence of sugars in SCFM alters metabolic flux and PMF production in *P. aeruginosa* in such a way that, relative to LB, cells are generally less sensitive to tobramycin. Finally, the ratios and production of different phenazines (e.g. PYO, PCA, PCN) in *P. aeruginosa* are known to vary depending on the carbon source in the growth medium (39) [64]; such variation could also explain the differences that was observed in PodA effects between our media.

Overall, the experiments demonstrates that a combined use of stabilized variants of PodA with tobramycin results in an enhancement of synergistic killing by a designed PodA and the antibiotic.

In this respect, the results obtained for PodA10 are expected to be representative of the activity of additional stabilized PodAs and that the activity can be regulated by modulating PodA concentration to be administered.

Accordingly, the results of the experiments provided in the instant application support the conclusion that stabilized PodA's having increased yield over WT PodA can be used as a biologic therapeutic for treating chronic *P. aeruginosa* infections a phenazine containing bacteria in combination with antibiotics such as tobramycin.

In summary, provided herein are engineered pyocyanin demethylases having replacements in in positions A53, I73, A87, T91, M99, A129 and K141 of pyocyanin demethylase PodA of SEQ ID NO: 1 or a derivative thereof and related phenazine degrading agents, compositions methods and systems. Preferred embodiments comprise $PodA_{30\text{-}162}$ (SEQ ID NO: 2) and more preferably $PodA_{41\text{-}162}$ (SEQ ID NO: 3) having replacements in positions corresponding to A53, I73, A87, T91, M99, A129 and K14 of SEQ ID NO: 1 as will be understood by a skilled person upon reading of the disclosure, or a derivative thereof. Also provided herein is a combined administration of one or more pyocyanin demethylases and antibiotics and/or antibiotics resulting in a synergic inhibition of viability of phenazine producing bacteria, and related phenazine degrading agents, compositions methods and systems.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art upon the reading of the present disclosure, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all sub-ranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which are not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Costa, K. C., et al., *Pyocyanin degradation by a tautomerizing demethylase inhibits Pseudomonas aeruginosa biofilms.* Science, 2017. 355(6321): p. 170-173.
2. Thomsen, M. C. F. and M. Nielsen, *Seq2Logo: a method for construction and visualization of amino acid binding motifs and sequence profiles including sequence weighting, pseudo counts and two-sided representation of amino acid enrichment and depletion.* Nucleic acids research, 2012. 40(W1): p. W281-W287.
3. Mentel, M., et al., *Of two make one: the biosynthesis of phenazines.* ChemBioChem, 2009. 10(14): p. 2295-2304.
4. Pierson, L. S. and E. A. Pierson, *Metabolism and function of phenazines in bacteria: impacts on the behavior of bacteria in the environment and biotechnological processes.* Applied microbiology and biotechnology, 2010. 86(6): p. 1659-1670.
5. Turner, J. M. and A. J. Messenger, *Occurrence, biochemistry and physiology of phenazine pigment production.* Advances in microbial physiology, 1986. 27: p. 211-275.
6. Gallagher, L. A., et al., *Functions required for extracellular quinolone signaling by Pseudomonas aeruginosa.* Journal of bacteriology, 2002. 184(23): p. 6472-6480.
7. Costa, K. C., et al., *Enzymatic degradation of phenazines can generate energy and protect sensitive organisms from toxicity.* MBio, 2015. 6(6): p. e01520-15.
8. Altschul, S. F., et al., *Gapped BLAST and PSI-BLAST: a new generation of protein database search programs.* Nucleic acids research, 1997. 25(17): p. 3389-3402.
9. Smith, T. F. and M. S. Waterman, *Identification of common molecular subsequences.* Journal of molecular biology, 1981. 147(1): p. 195-197.
10. Pearson, W. R., *Searching protein sequence libraries: comparison of the sensitivity and selectivity of the Smith-Waterman and FASTA algorithms.* Genomics, 1991. 11(3): p. 635-650.
11. Pearson, W. R. and D. J. Lipman, *Improved tools for biological sequence comparison.* Proceedings of the National Academy of Sciences, 1988. 85(8): p. 2444-2448.
12. Johnson, L. S., S. R. Eddy, and E. Portugaly, *Hidden Markov model speed heuristic and iterative HMM search procedure.* BMC bioinformatics, 2010. 11(1): p. 1-8.
13. Goldenzweig, A., et al., *Automated structure-and sequence-based design of proteins for high bacterial expression and stability.* Molecular cell, 2016. 63(2): p. 337-346.
14. Sambrook, J. and D. Russell, *Molecular cloning: A laboratory manual.* Mol. Cloning A Lab. Man, 2001.
15. Dietrich, L. E., et al., *The phenazine pyocyanin is a terminal signalling factor in the quorum sensing network of Pseudomonas aeruginosa.* Molecular microbiology, 2006. 61(5): p. 1308-1321.
16. Sullivan, N. L., et al., *Quantifying the dynamics of bacterial secondary metabolites by spectral multiphoton microscopy.* ACS chemical biology, 2011. 6(9): p. 893-899.

17. Yang, Z.-J., et al., *Isolation, identification, and degradation characteristics of phenazine-1-carboxylic acid-degrading strain Sphingomonas sp. DP58*. Current microbiology, 2007. 55(4): p. 284-287.
18. Chen, K., et al., *Metabolic degradation of phenazine-1-carboxylic acid by the strain Sphingomonas sp. DP58: the identification of two metabolites*. Biodegradation, 2008. 19(5): p. 659-667.
19. Möker, N., C. R. Dean, and J. Tao, *Pseudomonas aeruginosa increases formation of multidrug-tolerant persister cells in response to quorum-sensing signaling molecules*. Journal of bacteriology, 2010. 192(7): p. 1946-1955.
20. Wang, Y. and D. K. Newman, *Redox reactions of phenazine antibiotics with ferric (hydr)oxides and molecular oxygen*. Environmental Science & Technology, 2008. 42(7): p. 2380-2386.
21. Wang, Y. and D. K. Newman, *Redox reactions of phenazine antibiotics with ferric (hydr) oxides and molecular oxygen*. Environmental science & technology, 2008. 42(7): p. 2380-2386.
22. Fultz, M. L. and R. A. Durst, *Mediator compounds for the electrochemical study of biological redox systems: a compilation*. Analytica Chimica Acta, 1982. 140(1): p. 1-18.
23. Hernandez, M. E. and D. K. Newman, *Extracellular electron transfer*. Cellular and Molecular Life Sciences, 2001. 58(11): p. 1562-1571.
24. Hernandez, M. and D. Newman, *Extracellular electron transfer*. Cellular and Molecular Life Sciences CMLS, 2001. 58(11): p. 1562-1571.
25. Michaelis, L. and E. S. Hill, *POTENTIOMETRIC STUDIES ON SEMIQUINONES*. Journal of the American Chemical Society, 1933. 55: p. 1481-1494.
26. Michaelis, L. and E. S. Hill, *THE VIOLOGEN INDICATORS*. THE JOURNAL OF GENERAL PHYSIOLOGY, 1933. 16: p. 859-873.
27. Michaelis, L. and E. S. Hill, *The viologen indicators*. Journal of General Physiology, 1933. 16(6): p. 859-873.
28. Wang, Y., S. E. Kern, and D. K. Newman, *Endogenous phenazine antibiotics promote anaerobic survival of Pseudomonas aeruginosa via extracellular electron transfer*. Journal of bacteriology, 2010. 192(1): p. 365-369.
29. Heydorn, A., et al., *Quantification of biofilm structures by the novel computer program COMSTAT*. Microbiology, 2000. 146(10): p. 2395-2407.
30. Banin, E., M. L. Vasil, and E. P. Greenberg, *Iron and Pseudomonas aeruginosa biofilm formation*. Proceedings of the National Academy of Sciences, 2005. 102(31): p. 11076-11081.
31. Wang, Y., et al., *Phenazine-1-carboxylic acid promotes bacterial biofilm development via ferrous iron acquisition*. Journal of bacteriology, 2011. 193(14): p. 3606-3617.
32. Friedheim, E. A., *Pyocyanin, an accessory respiratory enzyme*. The Journal of experimental medicine, 1931. 54(2): p. 207.
33. Kidani, Y., K. Inagaki, and H. Koike, *Studies on metal chelate compounds of phenazine derivatives. 8. Metal complex of 1-hydroxyphenazine (author's transl)*. Yakugaku zasshi: Journal of the Pharmaceutical Society of Japan, 1973. 93(9): p. 1089-1093.
34. Kidani, Y., *Studies on Metal Chelate Compounds of Phenazine Derivatives. I. Spectrophotometric Studies on Copper Chelate Compounds of 1-Hydroxyphenazine and its Di-N-oxide*. Chemical and Pharmaceutical Bulletin, 1958. 6(5): p. 556-562.
35. Orenstein, D. M., *Cystic fibrosis: A guide for patient and family 4th ed.* 4th ed. 2011: Lippincott Williams & Wilkins.
36. Miroux, B. and J. E. Walker, *Over-production of proteins in Escherichia coli: mutant hosts that allow synthesis of some membrane proteins and globular proteins at high levels*. Journal of molecular biology, 1996. 260(3): p. 289-298.
37. VanDrisse, C. and J. Escalante-Semerena, *New high-cloning-efficiency vectors for complementation studies and recombinant protein overproduction in Escherichia coli and Salmonella enterica*. Plasmid, 2016. 86: p. 1-6.
38. Galloway, N. R., et al., *Rapid cloning for protein crystallography using type IIS restriction enzymes*. Crystal growth & design, 2013. 13(7): p. 2833-2839.
39. Blommel, P. G., et al., *Enhanced bacterial protein expression during auto-induction obtained by alteration of lac repressor dosage and medium composition*. Biotechnology progress, 2007. 23(3): p. 585-598.
40. Netzer, R., et al., *Ultrahigh specificity in a network of computationally designed protein-interaction pairs*. Nature communications, 2018. 9(1): p. 1-13.
41. Khersonsky, O., et al., *Automated design of efficient and functionally diverse enzyme repertoires*. Molecular cell, 2018. 72(1): p. 178-186. e5.
42. Cheluvappa, R., *Standardized chemical synthesis of Pseudomonas aeruginosa pyocyanin*. MethodsX, 2014. 1: p. 67-73.
43. O'Toole, G. A., *Microtiter dish biofilm formation assay*. Journal of visualized experiments: JOVE, 2011(47).
44. Spero, M. A. and D. K. Newman, *Chlorate specifically targets oxidant-starved, antibiotic-tolerant populations of Pseudomonas aeruginosa biofilms*. MBio, 2018. 9(5): p. e01400-18.
45. Palmer, K. L., L. M. Aye, and M. Whiteley, *Nutritional cues control Pseudomonas aeruginosa multicellular behavior in cystic fibrosis sputum*. Journal of bacteriology, 2007. 189(22): p. 8079-8087.
46. Warszawski, S., et al., *Optimizing antibody affinity and stability by the automated design of the variable light-heavy chain interfaces*. PLOS computational biology, 2019. 15(8): p. e1007207.
47. Cornforth, D. M., et al., *Quantitative framework for model evaluation in microbiology research using Pseudomonas aeruginosa and cystic fibrosis infection as a test case*. MBio, 2020. 11(1): p. e03042-19.
48. Walters III, M. C., et al., *Contributions of antibiotic penetration, oxygen limitation, and low metabolic activity to tolerance of Pseudomonas aeruginosa biofilms to ciprofloxacin and tobramycin*. Antimicrobial agents and chemotherapy, 2003. 47(1): p. 317-323.
49. Meylan, S., et al., *Carbon sources tune antibiotic susceptibility in Pseudomonas aeruginosa via tricarboxylic acid cycle control*. Cell chemical biology, 2017. 24(2): p. 195-206.
50. Ruddy, J., et al., *Sputum tobramycin concentrations in cystic fibrosis patients with repeated administration of inhaled tobramycin*. Journal of aerosol medicine and pulmonary drug delivery, 2013. 26(2): p. 69-75.
51. Kragh, K. N., et al., *Role of multicellular aggregates in biofilm formation*. MBio, 2016. 7(2): p. e00237-16.
52. Stewart, P. S., *Diffusion in biofilms*. Journal of bacteriology, 2003. 185(5): p. 1485-1491.

53. Bellin, D. L., et al., *Electrochemical camera chip for simultaneous imaging of multiple metabolites in biofilms*. Nature communications, 2016. 7(1): p. 1-10.
54. Tang, X. X., et al., *Acidic pH increases airway surface liquid viscosity in cystic fibrosis*. The Journal of clinical investigation, 2016. 126(3): p. 879-891.
55. Ramos, I., et al., *Phenazines affect biofilm formation by Pseudomonas aeruginosa in similar ways at various scales*. Research in microbiology, 2010. 161(3): p. 187-191.
56. Saunders, S. H., et al., *Extracellular DNA promotes efficient extracellular electron transfer by pyocyanin in Pseudomonas aeruginosa biofilms*. Cell, 2020. 182(4): p. 919-932. e19.
57. Dietrich, L. E., et al., *Bacterial community morphogenesis is intimately linked to the intracellular redox state*. Journal of bacteriology, 2013. 195(7): p. 1371-1380.
58. Schiessl, K. T., et al., *Phenazine production promotes antibiotic tolerance and metabolic heterogeneity in Pseudomonas aeruginosa biofilms*. Nature communications, 2019. 10(1): p. 1-10.
59. Zhu, K., et al., *Universal antibiotic tolerance arising from antibiotic-triggered accumulation of pyocyanin in Pseudomonas aeruginosa*. PLOS biology, 2019. 17(12): p. e3000573.
60. Meirelles, L. A., et al., *Bacterial defenses against a natural antibiotic promote collateral resilience to clinical antibiotics*. PLOS biology, 2021. 19(3): p. e3001093.
61. Glasser, N. R., S. E. Kern, and D. K. Newman, *Phenazine redox cycling enhances anaerobic survival in Pseudomonas aeruginosa by facilitating generation of ATP and a proton-motive force*. Molecular microbiology, 2014. 92(2): p. 399-412.
62. Meirelles, L. A. and D. K. Newman, *Both toxic and beneficial effects of pyocyanin contribute to the lifecycle of Pseudomonas aeruginosa*. Molecular microbiology, 2018. 110(6): p. 995-1010.
63. Sezonov, G., D. Joseleau-Petit, and R. d'Ari, *Escherichia coli physiology in Luria-Bertani broth*. Journal of bacteriology, 2007. 189(23): p. 8746-8749.
64. Jo, J., et al., *Interdependency of respiratory metabolism and phenazine-associated physiology in Pseudomonas aeruginosa PA14*. Journal of bacteriology, 2020. 202(4): p. e00700-19.

The invention claimed is:

1. An engineered pyocyanin demethylase or a derivative thereof, the pyocyanin demethylase having the sequence of SEQ ID NO:1, modified to include at least two replacements in SEQ ID NO: 1 selected from:

A53 with L, N, or V
I73 with E, K, L, Q, R, T or V
A87 with C, I, T or V
T91 with V
M99 with C, F, I, K, R, V or Y
A129 with C, S, T, or V
K141 with S or T
the engineered pyocyanin demethylase or a derivative thereof configured to be capable of demethylating pyocyanin and/or a pyocyanin-like phenazine of formula (III)

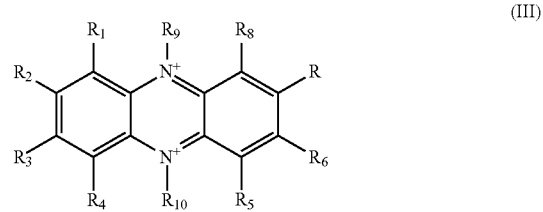

(III)

where R1-R9 are independently selected from hydrogen, hydroxy, alkoxy, alkyl, alkenyl, alkynyl, aryl, heteroaryl, and acyl, R10 is a methyl group, and one of R1-R9 is a negatively charged substituent,
wherein the amino acid sequence of SEQ ID NO: 1 has demethylating residues D68, D72, H121, E154, and Y156,
wherein the derivative has at least 40% identity with SEQ ID NO:1, and comprises demethylating residues:
D, E, or Y at position 68;
D, E, or Y at position 72;
H, R, or K at position 121;
D, E, or Y at position 154; and
D, E, or Y at position 156, and
wherein the derivative has the ability to demethylate the pyocyanin-like phenazines of formula (III).

2. The engineered pyocyanin demethylase or derivative thereof of claim 1, wherein the engineered pyocyanin demethylase has replacements in positions 73, 87, 91, 99 and 129 of SEQ ID NO: 1, or replacements in positions 73, 87, 99, 129 and 141 of SEQ ID NO: 1, or replacements in positions 73, 87, 91, 129 and 141 of SEQ ID NO: 1, or replacements in positions 53, 73, 87, 99 and 129 of SEQ ID NO: 1.

3. The engineered pyocyanin demethylase or derivative thereof of claim 1, wherein the engineered pyocyanin demethylase has at least two of a replacement in position 73 selected from I73T, I73K, I73L, and I73R, a replacement in position 87 selected from A87V and A87I, a replacement in position 99 selected from M99V and M99T, a replacement in position 129 selected from A129V and A129T, the replacement K141T in position 141, the replacement T91V in position 91 and the replacement A53N in position 53.

4. The engineered pyocyanin demethylase or derivative thereof of claim 1, wherein the engineered pyocyanin demethylase is PodA₂ having SEQ ID NO: 1 including replacements I73T, A87V, T91V, M99V and A129V, or a derivative thereof, PodA3 having SEQ ID NO: 1 including replacements I73K, A87V, T91V, M99V, and A129V, or a derivative thereof, PodA5 having SEQ ID NO: 1 including replacements I73L, A87I, M99V, A129V, and K141T, or a derivative thereof, PodA6 having SEQ ID NO: 1 including replacements I73R, A87V, T91V, M99V, and A129T, or a derivative thereof, PodA7 having SEQ ID NO: 1 including replacements I73L, A87I, T91V, M99T and A129V, or a derivative thereof, PodA8 having SEQ ID NO: 1 including replacements A53N, I73R, A87V, T91V, and A129V, or a derivative thereof, PodA9 having SEQ ID NO: 1 including replacements I73K, A87V, T91V, A129V and K141T, or a derivative thereof, or PodA10 having SEQ ID NO: 1 including replacements A53N, I73T, A87V, M99V, and A129T, or a derivative thereof.

5. The engineered pyocyanin demethylase or derivative thereof of claim 1, wherein the derivative comprises a protein having at least 70% identity with SEQ ID NO: 1.

6. A phenazine degrading agent comprising the engineered pyocyanin demethylase or derivative thereof according to claim 1.

7. A method to interfere with viability of phenazine producing bacteria, the method comprising
contacting the phenazine producing bacteria with one or more pyocyanin demethylases or derivative thereof of claim 1, alone or in combination with an antibiotic and/or other antimicrobial for a time and under conditions to reduce survivability and/or antibiotic resistance of the bacteria.

8. The method of claim 7, wherein the engineered pyocyanin demethylase comprises the engineered pyocyanin demethylase having:
the replacements in positions 73, 87, 91, 99 and 129 of SEQ ID NO: 1,
the replacements in positions 73, 87, 99, 129 and 141 of SEQ ID NO: 1,
the replacements in positions 73, 87, 91, 129 and 141 of SEQ ID NO: 1, or
the replacements in positions 53, 73, 87, 99 and 129, of SEQ ID NO: 1.

9. The method of claim 7, wherein the one or more phenazine degrading agents are capable of degrading pyocyanin-like phenazine of formula III, wherein pyocyanin-like phenazines comprise phenazines of formula III wherein at least one of $R_1$-$R_8$ is hydroxy group or a methoxy group.

10. The method of claim 7, wherein the antibiotic comprises one or more aminoglycosides.

11. The method of claim 10, wherein the antibiotic comprises one or more of an aminoglycoside of 4,6-disubstituted deoxystreptamine sub-class of aminoglycosides, an aminoglycoside of 4,5-disubstituted sub-class, and a non-deoxystreptamine aminoglycoside.

12. The method of claim 10, wherein the antibiotic comprises one or more of Kanamycin A, Amikacin, Tobramycin, Dibekacin, Gentamicin, Sisomicin, Netilmicin, Neomycins B and C, Streptomycin and Plazomicin.

13. The method of claim 7, wherein the antibiotic is selected from the group consisting of Amoxicillin and clavulanic acid, Methicillin, oxacillin, nafcillin, cloxacillin, dicloxacillin, cabenicillin, ticarcillin, piperacillin, mezlocillin, azlocillin, ticarcillin and clavulanic acid, piperacillin and tazobactam, cephalexin, cefdinir, cefprozil, cefaclor, cefuroxime, sulfisoxazole, erythromycin/sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam.

14. The method of claim 7, wherein the phenazine producing bacteria is selected from the group consisting of *Staphylococcus aureus, Pseudomonas, Burkholderia cepacia*, and mycobacteria.

15. The method of claim 7, wherein the phenazine producing bacteria is in a biofilm.

16. A method for inhibiting bacterial biofilm formation and/or disrupting mature biofilm in a medium, the method comprising:
contacting the bacterial biofilm with one or more pyocyanin demethylases or derivatives thereof of claim 1, alone or in combination with an antibiotic and/or other antimicrobial for a time and under conditions thus reducing survivability and/or antibiotic resistance of the bacterial biofilm.

17. The method of claim 16, wherein the bacterial biofilm comprises one or more of *Staphylococcus aureus, Pseudomonas, Burkholderia cepacia*, and mycobacteria.

18. A system to interfere with viability of phenazine producing bacteria, the system comprising:
1) one or more pyocyanin demethylases or derivatives thereof of claim 1; and
2) one or more antibiotics, and/or one or more other antimicrobials;
for simultaneous or sequential use in a method for inhibiting bacterial biofilm formation and/or disrupting mature biofilm in a medium.

19. A method for treating and/or preventing a bacterial infection by phenazine producing bacteria in an individual, the method comprising
administering to the individual an effective amount of one or more pyocyanin demethylases or derivative thereof of claim 1, alone or in combination with an antibiotic and/or other antimicrobial.

20. A system for treating and/or preventing a bacterial infection by a phenazine producing bacteria in an individual, the system comprising:
1) one or more pyocyanin demethylases or derivatives thereof of claim 1; and
2) one or more antibiotics, and/or one or more other antimicrobials;
for simultaneous or sequential use in a method for treating and/or preventing a bacterial infection by phenazine producing bacteria in the individual.

21. An antimicrobial comprising one or more pyocyanin demethylases of claim 1, in an amount suitable to reduce antibiotic resistance and/or survivability of phenazine producing bacteria.

22. A composition comprising one or more pyocyanin demethylases of claim 1 together with a compatible vehicle.

23. The composition of claim 22, wherein the vehicle is a pharmaceutically acceptable vehicle and the composition is a pharmaceutical composition.

24. A method for inhibiting bacterial biofilm formation and/or disrupting mature biofilm in a medium, the method comprising:
administering to the medium comprising the bacterial biofilm an effective amount of:
1) 1-hydroxyphenazine in combination with one or more pyocyanin demethylase or derivatives thereof of claim 1; and
2) one or more antibiotic and/or one or more other antimicrobial;
for a time and under conditions thus reducing survivability and/or antibiotic resistance of the bacterial biofilm.

\* \* \* \* \*